(12) United States Patent
Tawada et al.

(10) Patent No.: US 6,680,312 B2
(45) Date of Patent: Jan. 20, 2004

(54) SULFONAMIDE DERIVATIVES, THEIR PRODUCTION AND USE

(75) Inventors: Hiroyuki Tawada, Takatsuki (JP); Fumio Itoh, Toyonaka (JP); Hiroshi Banno, Ikeda (JP); Zen-ichi Terashita, Toyonaka (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/128,809

(22) Filed: Apr. 24, 2002

(65) Prior Publication Data

US 2002/0193382 A1 Dec. 19, 2002

Related U.S. Application Data

(62) Division of application No. 09/601,660, filed on Aug. 3, 2000, now Pat. No. 6,403,595.

(30) Foreign Application Priority Data

Feb. 5, 1998 (JP) .............................. 10-24833
Nov. 9, 1998 (JP) ........................... 10-317205

(51) Int. Cl.$^7$ ...................... A61K 31/33; A61K 31/352; A61K 31/445; C07D 341/04; C07D 401/00

(52) U.S. Cl. ............. 514/183; 514/255.02; 514/255.05; 514/402; 514/456; 514/326; 514/331; 544/252; 544/360; 544/362; 544/386; 544/383; 544/402; 544/405; 544/374

(58) Field of Search ............................ 514/183, 255.02, 514/255.05, 402, 456, 326, 331; 544/360, 362, 386, 383, 402, 405

(56) References Cited

U.S. PATENT DOCUMENTS 5,559,232 A 9/1996 Ackermann et al.

FOREIGN PATENT DOCUMENTS

| EP | 0203743 | 12/1986 |
|----|---------|---------|
| EP | 0299493 | 1/1989 |
| EP | 0529858 A | 3/1993 |
| EP | WO96/10022 | 4/1996 |
| EP | 0739886 | 10/1996 |
| EP | WO96/40679 | 12/1996 |
| EP | 0805149 | 5/1997 |
| EP | 0805149 A | 11/1997 |
| EP | 0838460 | 4/1998 |
| EP | WO98/54164 | 12/1998 |
| JP | 49-110680 | 10/1974 |
| JP | 62/502339 | 3/1986 |
| WO | WO90/05523 | 5/1990 |
| WO | WO94/18185 | 8/1994 |
| WO | WO96/05189 | 2/1996 |
| WO | WO96/33982 | 10/1996 |
| WO | 9640679 | * 12/1996 |
| WO | WO96/40737 | 12/1996 |
| WO | WO97/03060 | 1/1997 |
| WO | WO97/19919 | 5/1997 |
| WO | WO97/40023 | 10/1997 |
| WO | WO98/21188 | 5/1998 |
| WO | WO99/06395 | 2/1999 |
| WO | 9937304 | * 7/1999 |

OTHER PUBLICATIONS

CAS Abstract Nr. 131:130007–1999:487215 also cited as WO 9937304 and claiming priority to U.S. Application Sr. Nr. 60072707 dated Jan. 27, 1998.*

Sturzebecher, et al. "Synthesis and Structure—Activity Relationships of Potent Thrombin Inhibitors: Piperazides of 3–Amidinophenylalanine" J. Med. Chem 40:3091–3099 (1997).

* cited by examiner

*Primary Examiner*—Mukund J. Shah
*Assistant Examiner*—Sudhaker B. Patel
(74) *Attorney, Agent, or Firm*—Mark Chao; Elaine M. Ramesh

(57) ABSTRACT

The present invention is to provide a compound or a salt thereof represented by the formula:

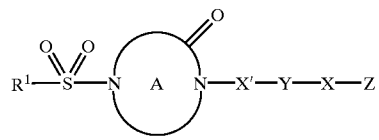

wherein $R^1$ is an optionally substituted hydrocarbon group or an optionally substituted heterocyclic group, the ring A is an optionally substituted divalent nitrogen-containing heterocyclic group, X' is an optionally substituted alkylene chain, Y is an optionally substituted divalent cyclic group, X is a chemical bond or an optionally substituted alkylene chain, and Z is (1) an optionally substituted amino group, (2) an optionally substituted imidoyl group or (3) an optionally substituted nitrogen-containing heterocyclic group, or a prodrug thereof, which has activated coagulation factor X inhibitory activity and which are useful as anti-coagulants.

26 Claims, No Drawings

SULFONAMIDE DERIVATIVES, THEIR PRODUCTION AND USE

This application is a divisional application of U.S. patent application Ser. No. 09/601,660, filed on Aug. 3, 2000; now U.S. Pat. No. 6,403,595 which was the National Stage of International Application No. PCT/JP99/00470, filed Feb. 4, 1999.

TECHNICAL FIELD

The present invention relates to novel sulfonamide derivatives which are useful as a medicine and which inhibit activated coagulation factor X (FXa) to show anti-coagulant activity, their production and use.

BACKGROUND ART

For the purpose of the prevention and treatment of cardiac infarction, cerebral thrombosis, etc., it is important to inhibit formation of thrombus and various investigations and developments of thrombus inhibitors such as anti-thrombin agents, platelet aggregation inhibitors, etc. have been carried out. However, anti-thrombin agents as well as platelet aggregation inhibitors have side effects such as bleeding and safety problems. On the other hand, FXa inhibitors specifically inhibit the coagulation factor and are useful as anti-coagulants.

So far, compounds having FXa inhibitory activity are disclosed in e.g. Japanese Unexamined Patent Publication No. 1995 (H7)-112970, Japanese Unexamined Patent Publication No. 1993 (H5)-208946, WO 96/16940, WO 96/40679 and WO 96/10022, etc.

However, the above compounds having FXa inhibitory activity do not have sufficient FXa inhibitory activity and, in particular, do not show sufficient action when orally administered, therefore, they are not practically useful as a medicine.

DISCLOSURE OF INVENTION

The present invention is to provide novel sulfonamide derivatives which specifically inhibit FXa, which are effective when orally administered and which are useful as safe medicine for the prevention (prophylaxis) or treatment (therapy) of diseases caused by thrombus or infarction.

The present inventors diligently made extensive studies and, as a result, they succeeded in synthesizing a compound or a salt thereof [hereinafter, referred to as Compound (I)], whose characteristic feature in the chemical structure lies in having (1) an oxo group on the ring A and (2) an optionally substituted amino group, an optionally substituted imidoyl group or an optionally substituted nitrogen-containing heterocyclic group at the end of a substituent on the ring A, represented by the formula (I):

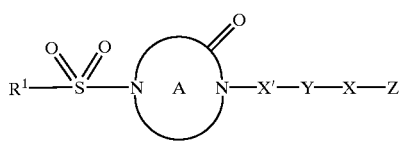

(I)

wherein $R^1$ is an optionally substituted hydrocarbon group or an optionally substituted heterocyclic group; the ring A is an optionally substituted divalent nitrogen-containing heterocyclic group; X' is a chemical bond or an optionally substituted alkylene chain; Y is an optionally substituted divalent cyclic group; X is a chemical bond or an optionally substituted alkylene chain; and Z is (1) an optionally substituted amino group, (2) an optionally substituted imidoyl group or (3) an optionally substituted nitrogen-containing heterocyclic group; or a salt thereof, and further found that the compound (I) unexpectedly possesses potent FXa inhibitory activity based on its specific chemical structure and that the compound (I) can be safely and orally administered as a medicine for the prevention or treatment of diseases such as thrombus and infarction. Based on these findings, the present invention was accomplished.

More specifically, the present invention relates to (1) the Compound (I) or a salt thereof;
(2) a pro-drug of the Compound (I) or a salt thereof;
(3) a compound of the above (1) wherein $R^1$ is an optionally substituted hydrocarbon group;
(4) a compound of the above (1) wherein $R^1$ is an optionally substituted heterocyclic group;
(5) a compound of the above (1) wherein $R^1$ is an aryl group optionally substituted with a halogen atom or C24 alkenyl group;
(6) a compound of the above (1) wherein $R^1$ is a benzopyranyl group optionally substituted with a halogen atom;
(7) a compound of the above (1) wherein the ring A is

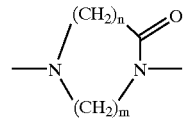

wherein n is 1 or 2, and m is 2 or 3;
(8) a compound of the above (1) wherein X' is an optionally substituted alkylene chain which may be substituted with 1–3 substituents selected from an optionally substituted lower alkyl group, an optionally substituted carbamoyl group, cyano group, hydroxy group and an optionally esterified carboxyl group;
(9) a compound of the above (1) wherein Y is an optionally substituted divalent cyclic hydrocarbon group, and Z is an optionally substituted amino group or an optionally substituted imidoyl group;
(10) a compound of the above (1) wherein Y is an optionally substituted divalent heterocyclic group;
(11) a compound of the above (1) wherein Y is an optionally substituted divalent heterocyclic group, and Z is an optionally substituted nitrogen-containing heterocyclic group;
(12) a compound of the above (1) wherein Y is an optionally substituted phenylene;
(13) a compound of the above (1) wherein Y is an optionally substituted piperidine;
(14) a compound of the above (1) wherein Z is an optionally substituted amidino group;
(15) a compound of the above (1) wherein Z is an optionally substituted nitrogen-containing heterocyclic group;
(16) A compound selected from the class consisting of 1-(4-amidinobenzyl)-4-(6-chloronaphthanlene-2-sulfonyl)-2-piperazinone, 1-(4-amidinobenzyl)-4-(7-chloro-2H-benzopyran-3-sulfonyl)-2-piperazinone, 4-(6-chloronaphthanlene-2-sulfonyl)-1-[1-(4-pyridyl)piperidin-4-ylmethyl]-2-piperazinone, 4-(7-chloro-2H-benzopyran-3-sulfonyl)-1-[1-(4-pyridyl)piperidin-4-ylmethyl]-2-piperazinone, 1-[1-(4-pyridyl)piperidin-4-ylmethyl]-4-(4-vinylbenzenesulfonyl)-2-piperazinone, 4-(6-chloronaphthanlene-2-sulfonyl)-1-[4-hydroxy-1-(4-pyridyl)piperidin-4-ylmethyl]-2-piperazinone, 4-(7-chloro-2H-benzopyran-3-sulfonyl)-1-[4-hydroxy-1-(4- pyridyl)piperidin-4-ylmethyl]-2-piperazinone and 1-[4-hydroxy-1-(4-pyridyl)piperidin-4-ylmethyl]-4-(4-vinylbenzenesulfonyl)-2-piperazinone or a salt thereof,

(17) a pro-drug of the compound as described in the above (16) or a salt thereof;
(18) a pharmaceutical composition comprising the compound (I) of the above (1) or a salt thereof;
(19) a composition of the above (18) which is an anti-coagulant;
(20) a composition of the above (18) which is an inhibitor of activated coagulation factor X;
(21) a composition of the above (18) which is for the prevention or treatment of cardiac infarction, cerebral thrombosis or deep vein thrombosis;
(22) use of the compound (I) of the above (1) or a salt thereof for manufacturing an anti-coagulant;
(23) use of the compound (I) of the above (1) or a salt thereof for manufacturing a pharmaceutical composition for inhibiting activated coagulation factor X;
(24) use of the compound (I) of the above (1) or a salt thereof for manufacturing a pharmaceutical composition for the prevention or treatment of cardiac infarction, cerebral thrombosis or deep vein thrombosis;
(25) a method for inhibiting coagulation in a mammal which comprises administering an effective amount of the compound (I) of the above (1) or a salt thereof;
(26) a method for inhibiting activated coagulation factor X in a mammal which comprises administering an effective amount of the compound (I) of the above (1) or a salt thereof;
(27) a method for preventing or treating cardiac infarction, cerebral thrombosis or deep vein thrombosis in a mammal which comprises administering an effective amount of the compound (I) of the above (1) or a salt thereof;
(28) A method for producing Compound (I) as described in the above (1) or a salt thereof by reacting Compound (II) or a salt thereof represented by the formula: $R^1SO_2Q$ (II) wherein Q is a halogen atom, and the other symbol is as defined in the above (1)
with Compound (III) or a salt thereof represented by the formula:

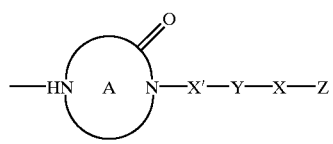
(III)

wherein each symbol is as defined in the above (1); or producing Compound (I) as described in the above (1) or a salt thereof by reacting Compound (IV) or a salt thereof represented by the formula:

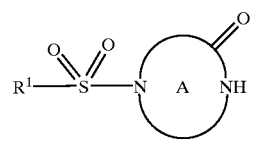
(IV)

wherein each symbol is as defined in the above (1) with Compound (V) or a salt thereof represented by the formula:

$Q^1$—X'—Y—X—Z  (V)

wherein $Q^1$ is a halogen atom or a group of the formula: $R^2$—$SO^2$—O— (wherein $R^2$ is a lower alkyl group optionally substituted with a halogen atom or an optionally substituted phenyl group), and the other symbols are as defined in the above (1); or producing Compound (Ia) as described in the above (1) or a salt thereof represented by the formula:

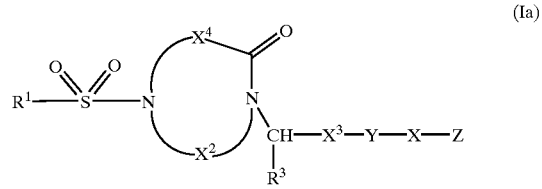
(Ia)

wherein each symbol is as defined above by subjecting Compound (X) or a salt thereof represented by the formula:

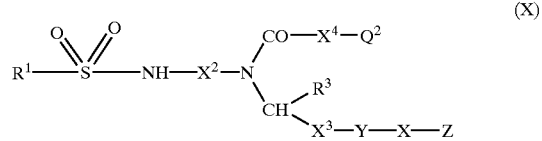
(X)

wherein $X^2$ and $X^4$ are respectively an optionally substituted alkylene chain, $X^3$ is a chemical bond or an optionally substituted alkylene chain, $R^3$ is a hydrogen atom or an optionally substituted hydrocarbon group, $Q^2$ is a halogen atom or a group of the formula: $R^4$—$SO^2$—O— (wherein $R^4$ is a lower alkyl group optionally substituted with a halogen atom or an optionally substituted phenyl group), and the other symbols are as defined in the above (1) to ring closure reaction; or producing Compound (Ib) as described in the above (1) or a salt thereof represented by the formula:

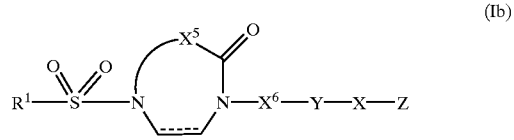
(Ib)

wherein a combination of a broken line and a full line is a single bond or a double bond, and the other symbols are as defined above by subjecting Compound (XIII) or a salt thereof represented by the formula:

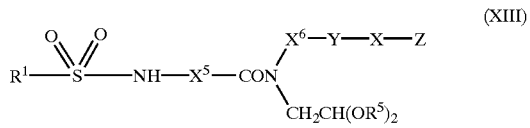
(XIII)

wherein $X^5$ is an optionally substituted alkylene chain, $X^6$ is a chemical bond or an optionally substituted alkylene chain, $R^5$ is a lower alkyl group, and the other symbols are as defined in the above (1) to ring closure reaction, and if desired, subjecting the obtained product to reduction; or producing Compound (Ia) or a salt thereof represented by the formula:

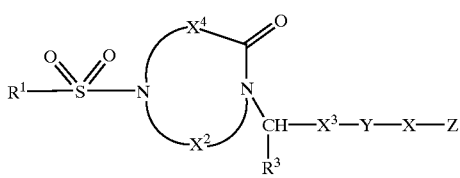

(Ia)

wherein each symbol is as defined above
by subjecting Compound (VI) or a salt thereof represented by the formula:

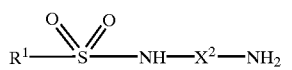

(VI)

wherein $X^2$ is an optionally substituted alkylene chain, and the other symbols are as defined in the above (1) and Compound (VII) or a salt thereof represented by the formula:

$$R^3-(C=O)-X^3-Y-X-Z \quad \text{(VII)}$$

wherein $X^3$ is a chemical bond or an optionally substituted alkylene chain, $R^3$ is a hydrogen atom or an optionally substituted hydrocarbon group, and the other symbols are as defined in the above (1)
to reductive amination to produce Compound (VIII) or a salt thereof represented by the formula:

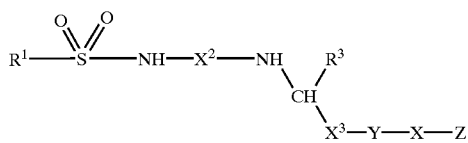

(VIII)

wherein each symbol is as defined above, and
reacting the obtained Compound (VIII) or a salt thereof with Compound (IX) represented by the formula:

$$Q^2-X^4-COOH \quad \text{(IX)}$$

wherein $X^4$ is an optionally substituted alkylene chain, $Q^2$ is a halogen atom or a group of the formula: $R^4-SO_2-O-$ (wherein $R^4$ is a lower alkyl group optionally substituted with a halogen atom or an optionally substituted phenyl group), and the other symbols are as defined above or a salt thereof or its reactive derivative
to produce Compound (X) or a salt thereof represented by the formula:

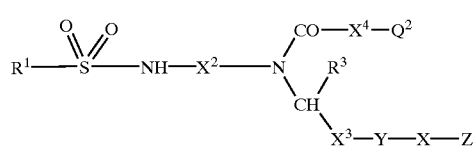

(X)

wherein each symbol is as defined above,
which is subjected to ring-closure reaction; or
producing Compound (Ib) or a salt thereof by reacting Compound (XI)
or a salt thereof or its reactive derivative represented by the formula:

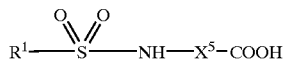

(XI)

wherein $X^5$ is an optionally substituted alkylene chain, and the other symbols are as defined in the above (1)
with Compound (XII) or a salt thereof represented by the formula:

$$Z-X-Y-X^6-NHCH_2CH(OR5)_2 \quad \text{(XII)}$$

wherein $X^6$ is a chemical bond or an optionally substituted alkylene chain, $R^5$ is a lower alkyl group, and the other symbols are as defined in the above (1) to produce Compound (XIII) or a salt thereof represented by the formula:

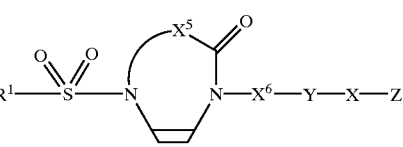

(XIII)

wherein each symbol is as defined above, and
subjecting the obtained Compound (XIII) or a salt thereof to ring-closure reaction with an acid to produce Compound (XIV) or a salt thereof represented by the formula:

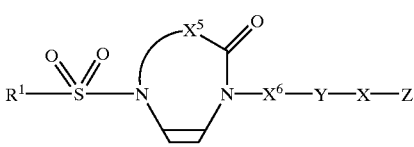

(XIV)

wherein each symbol is as defined above, and, if desired, reducing a double bond of the obtained Compound (XIV) or a salt thereof; or producing Compound (I) as described in the above (1) or a salt thereof by reacting Compound (XX) or a salt thereof represented by the formula:

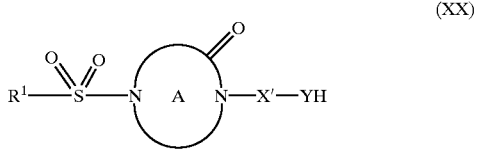

(XX)

wherein each symbol is as defined in the above (1)
with Compound (XXI) or a salt thereof represented by the formula:

$$Z-X^7-Q^3$$

wherein $X^7$ is a chemical bond or an optionally substituted alkylene chain, $Q^3$ is a halogen atom or a group of the formula: $R^6-SO_2-O-$ (wherein $R^6$ is a lower alkyl group optionally substituted with a halogen atom or an optionally substituted phenyl group), and the other symbol is as defined in the above (1); or producing Compound (XXV) or a salt thereof represented by the formula:

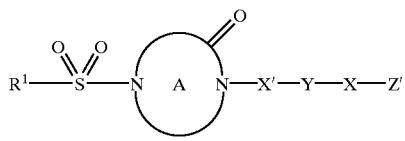

(XXV)

wherein Z' is an optionally substituted amidino group, and the other symbols are as defined above
by reacting Compound (XXII) or a salt thereof represented by the formula:

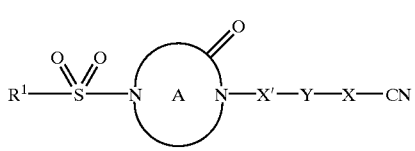

(XXII)

wherein each symbol is as defined in the above (1)
with Compound (XXIII) or a salt thereof represented by the formula:

$R^7OH$

wherein $R^7$ is a lower alkyl group
to produce Compound (XXIV) or a salt thereof represented by the formula:

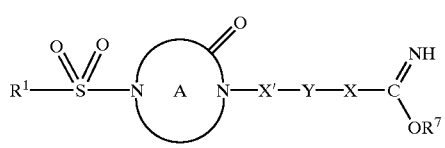

(XXIV)

wherein each symbol is as defined above, and
reacting the obtained Compound (XXIV) or a salt thereof with an amine, etc.

In the above formula, $R^1$ is an optionally substituted hydrocarbon group or an optionally substituted heterocyclic group.

Examples of the hydrocarbon group in the "optionally substituted hydrocarbon group" represented by $R^1$ includes an aliphatic hydrocarbon group, an alicyclic hydrocarbon group, an aryl group, etc. Among others, an aryl group, etc. is preferable.

Examples of the "aliphatic hydrocarbon group" exemplified by the hydrocarbon group include e.g. a straight-chain or branched aliphatic hydrocarbon group such as an alkyl group, an alkenyl group, an alkynyl group, etc.

Examples of the alkyl group include e.g. $C_{1-10}$ alkyl group (preferably $C_{1-6}$ alkyl, etc.), etc. such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl, nheptyl, 1-methylheptyl, 1-ethylhexyl, n-octyl, 1-methyl-heptyl, nonyl, etc.

Examples of the alkyl group include e.g. a $C_{1-10}$ alkyl group (preferably $C_{1-6}$ alkyl, etc.), etc. such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl, n-heptyl, 1-methyiheptyl, 1-ethylhexyl, n-octyl, 1-methyl-heptyl, nonyl, etc.

Examples of the alkynyl group include e.g. a $C_{2-6}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, etc.

Examples of the "alicyclic hydrocarbon group" exemplified by the hydrocarbon group include e.g. a saturated or unsaturated alicyclic hydrocarbon group such as a cycloalkyl group, a cycloalkenyl group, a cycloalkanedienyl group, etc.

Examples of the "cycloalkyl group" include e.g. $C_{3-9}$ cycloalkyl, etc. such as cyclopropyl, cyclobutyl, cyclopentyl, cyclohexyl, cycloheptyl, cyclooctyl, cyclononyl, etc.

Examples of the "cycloalkenyl group" include e.g. $C_{3-6}$ cycloalkenyl group, etc. such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl, etc.

Examples of the "cycloalkanedienyl group" include e.g. $C_{4-6}$ cycloalkanedienyl group, etc. such as 2,4-cyclopentadien-1-yl, 2,4-cyclohexadien-1-yl, 2,5-cyclohexadien-1-yl, etc.

Examples of the "aryl group" exemplified by the hydrocarbon group include e.g. a monocyclic or fused aromatic hydrocarbon group. Among others, $C_{6-14}$ aryl group, etc. such as phenyl, naphthyl, anthryl, phenathryl, acenaphthyl, etc. is preferable. In particular, phenyl, 1-naphthyl, 2-naphthyl, etc. are preferable.

Examples of the heterocyclic group in the "optionally substituted heterocyclic group" represented by $R^1$ include e.g. an aromatic heterocyclic group, saturated or unsaturated non-aromatic heterocyclic group (alicyclic heterocyclic group) etc., which contains, besides carbon atoms, at least one hetero-atom (preferably 1 to 4 hetero-atoms, more preferably 1 to 2 hetero-atoms) consisting of 1 to 3 kinds of hetero-atoms (preferably 1 to 2 kinds of hetero-atoms) selected from oxygen atom, sulfur atom, nitrogen atom, etc.

Examples of the "aromatic heterocyclic group" include an aromatic monocyclic heterocyclic group such as 5- to 6-membered aromaticmonocyclicheterocyclicgroup, etc. (e.g. furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.); an aromatic fused heterocyclic group such as 8- to 12-membered aromatic fused heterocyclic group (preferably, heterocyclic group consisting of the above-mentioned 5- or 6-membered aromatic monocyclic heterocyclic group fused with a benzene ring or heterocyclic group consisting of the above-mentioned 5- or 6-membered aromatic monocyclic heterocyclic group fused with the same or different above-mentioned 5- or 6-membered aromatic monocyclic heterocyclic group), etc. (e.g. benzofuranyl, isobenzofuranyl, benzo[b]thienyl, indolyl, isoindolyl, 1H-indazolyl, benzindazolyl, benzoxazolyl, 1,2-benzoisooxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.); etc.

Examples of the "non-aromatic heterocyclic group" include a 3- to 8-membered (preferably 5- or 6-membered) saturated or unsaturated (preferably saturated) non-aromatic heterocyclic group (alicyclic heterocyclic group), etc. such as oxiranyl, azetidinyl, oxetanyl, thiethanyl, pyrrolidinyl, tetrahydrofuryl, thiolanyl, piperidyl, tetrahydropyranyl, morpholinyl, thiomorpholinyl, piperazinyl, etc., or non-aromatic heterocyclic group wherein a part or all of the double bonds in the above-mentioned aromatic monocyclic heterocyclic group or aromatic fused heterocyclic group are saturated, etc. such as 1,2,3,4-tetrahydroquinolyl, 1,2,3,4-tetrahydroisoquinolyl, etc.

Examples of the "non-aromatic heterocyclic group" include a 3-to 8-membered (preferably 5- or 6-membered) saturated or unsaturated (preferably saturated) non-aromatic heterocyclic group (alicyclic heterocyclic group), etc. such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, etc., or non-aromatic heterocyclic group wherein a part or all of the double bonds in the above-mentioned aromatic monocyclic heterocyclic group or aromatic fused heterocyclic group are saturated, etc. such as 1,2,3,4-tetrahydroquinolyl, 1,2,3,4-tetrahydroisoquinolyl, etc.

The "optionally substituted hydrocarbon group" and "optionally substituted heterocyclic group" may have 1 to 5 substituents as described above (preferably 1 to 3 substituents) at any possible position.

In addition, the "optionally substituted hydrocarbon group" and "optionally substituted heterocyclic group" represented by $R^1$ may have an oxo group. For example, when $R^1$ is abenzopyranyl, $R^1$ may formbenzo-α-pyronyl, benzo-γ-pyronyl, etc.

Examples of the aryl group in the "optionally substituted aryl group" as the substituent include $C_{6-14}$ aryl group, etc. such as phenyl, naphthyl, anthryl, phenathryl, acenaphthyl, etc. Said aryl groups may have 1 to 3 substituents at any possible positions. Examples of the substituent include a lower alkoxy group (e.g. $C_{1-6}$alkoxy group, etc. such as methoxy, ethoxy, propoxy, etc.), a halogen atom (e.g. fluorine, chlorine, bromine, iodine, etc.), a lower alkyl group (e.g. $C_{1-6}$ alkyl group, etc. such as methyl, ethyl, propyl, etc.), a lower alkenyl group (e.g. $C_{2-6}$ alkenyl, etc. such as vinyl, allyl, etc.), a lower alkynyl group (e.g. $C_{2-6}$ alkynyl group, etc. such as ethynyl, propargyl, etc.), an optionally substituted amino group, an optionally substituted hydroxy group, a cyano group, an optionally substituted amidino group, etc.

The "optionally substituted amino group", "optionally substituted hydroxy group" and "optionally substituted amidino group" as the substituent are similar to those exemplified by the "optionally substituted amino group", "optionally substituted hydroxy group" and "optionally substituted amidino group", which the "optionally substituted hydrocarbon group" and "optionally substituted heterocyclic group" represented by $R^1$ may have.

Examples of the cycloalkyl group in the "optionally substituted cycloalkyl group" as the substituent include $C_{3-7}$ cycloalkyl group, etc. such as cyclopropyl, cyclobutyl, cyclopentyl, cyclohexyl, cycloheptyl, etc. Said cycloalkyl groups may have the same kind and number of substituents as those of the above described "optionally substituted aryl group".

Examples of the cycloalkenyl group in the "optionally substituted cycloalkenyl group" as the substituent include e.g. $C_{3-6}$ cycloalkenyl group, etc. such as cyclopropenyl, cyclobutenyl) cyclopentenyl, cyclohexenyl, etc. Said cycloalkenyl groups may have the same kind and number of substituents as those of the above described "optionally substituted aryl group".

Examples of the alkyl group in the "optionally substituted alkyl group" as the substituent include e.g. $C_{1-6}$ alkyl, etc. such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, etc. Said alkyl groups may have the same kind and number of substituents as those of the above described "optionally substituted aryl group".

Examples of the alkenyl group in the "optionally substituted alkenyl group" as the substituent include e.g. $C_{2-6}$ alkenyl group, etc. such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, etc. Said alkenyl groups may have the same kind and number of substituents as those of the above described "optionally substituted aryl group".

Examples of the alkynyl group in the "optionally substituted alkynyl group" as the substituent include e.g. a $C_{2-6}$ alkynyl group, etc. such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, etc. Said alkynyl groups may have the same kind and number of substituents as those of the above described "optionally substituted aryl group".

Examples of the heterocyclic group in the "optionally substituted heterocyclic group" as the substituent include e.g. an aromatic heterocyclic group, saturated or unsaturated non-aromatic heterocyclic group (alicyclic heterocyclic group) etc., which contains, besides carbon atoms, at least one hetero-atom (preferably 1 to 4 hetero-atoms, more preferably 1 to 2 hetero-atoms) consisting of 1 to 3 kinds of hetero-atoms (preferably 1 to 2 kinds of hetero-atoms) selected from oxygen atom, sulfur atom, nitrogen atom, etc.

Examples of the "aromatic heterocyclic group" include an aromatic monocyclic heterocyclic group such as a 5- to 6-membered aromatic monocyclic heterocyclic group, etc. (e.g. furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.); an aromatic fused heterocyclic group such as 8- to 12-membered aromatic fused heterocyclic group (preferably, heterocyclic group consisting of the above-mentioned 5- or 6-membered aromatic monocyclic heterocyclic group fused with a benzene ring or heterocyclic group consisting of the above-mentioned 5- or 6-membered aromatic monocyclic heterocyclic group fused with the same or different above-mentioned 5- or 6-membered aromatic monocyclic heterocyclic group), etc. (e.g. benzofuranyl, isobenzofuranyl, benzothienyl, indolyl, isoindolyl, 1H-indazolyl, benzindazolyl, benzoxazolyl, 1,2-benzoisooxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolizinyl, pyrrolo[1,2- b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.); etc.

Examples of the "non-aromatic heterocyclic group" include a 3-to 8-membered (preferably 5- or 6-membered) saturated or unsaturated (preferably saturated) non-aromatic heterocyclic group (alicyclic heterocyclic group), etc. such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, etc., or non-aromatic heterocyclic group wherein a part or all of the double bonds in the above-mentioned aromatic monocyclic heterocyclic group or aromatic fused heterocyclic group are saturated, etc. such as 1,2,3,4-tetrahydroquinolyl, 1,2,3,4-tetrahydroisoquinolyl, etc.

Examples of the substituent of the "optionally substituted heterocyclic group" as the substituent include a lower alkyl group (e.g. $C_{1-6}$alkyl group, etc. such as methyl, ethyl, propyl, etc.), a lower alkenyl group (e.g. $C_{2-6}$ alkenyl group, etc. such as vinyl, allyl, etc.), a lower alkynyl group (e.g. $C_{2-6}$ alkynyl group, etc. such as ethynyl, propargyl, etc.), an acyl group (e.g. $C_{1-6}$ alkanoyl such as formyl, acetyl, propionyl, pivaloyl, etc., benzoyl, etc.), an optionally substituted amino group, an optionally substituted hydroxy group, a halogen atom (e.g. fluorine, chlorine, bromine, iodine, etc., preferably chlorine, bromine, etc.), an optionally substituted imidoyl group, an optionally substituted amidino group, etc.

The "optionally substituted amino group", "optionally substituted hydroxy group", "an optionally substituted imidoyl group" and "optionally substituted amidino group", which the "optionally substituted heterocyclic group" as the substituent may have, are similar to those exemplified by the "optionally substituted amino group", "optionally substituted hydroxy group", "an optionally substituted imidoyl group" and "optionally substituted amidino group", which the "optionally substituted hydrocarbon group" and "optionally substituted heterocyclic group" represented by $R^1$ may have.

Examples of the substituent in the "optionally substituted amino group", "optionally substituted imidoyl group", "optionally substituted amidino group", "optionally substituted hydroxy group" and "optionally substituted thiol group" as the substituent, which "the optionally substituted hydrocarbon group" and "the heterocyclic group" represented by may have, include e.g. a lower alkyl group (e.g. $C_{1-6}$ alkyl group, etc. such as methyl, ethyl, propyl, isopropyl, butyl, isobutyl, an acyl group such as $C_{1-6}$ alkanoyl (e.g. formyl, acetyl, propionyl, pivaloyl, etc.), beuzoyl, etc., an optionally halogenated $C_{1-6}$ alkoxy-carbonyl (e.g. methoxycarbonyl, ethoxycarbonyl, trifluoromethoxy-carbonyl, 2,2,2-trifluoroethoxycarbonyl, trichloro-methoxycarbonyl, 2,2,2-trichloroethoxycarbonyl, etc.), a heterocyclic group (e.g. the above described "heterocyclic group" similar to "optionally substituted hydrocarbon group" in the "optionally substituted hydrocarbon group" represented by $R^1$; preferably, pyridyl; more preferably, 4-pyridyl; etc.), etc. In addition, the "amino group" in the "optionally substituted amino group" as the substituent may be substituted with an optionally substituted imidoyl group (e.g., $C_{1-6}$ alkylimidoyl, $C_{1-6}$ alkanoylimidoyl (e.g. formimidoyl, etc.), amidino, etc.), an amino group optionally substituted with 1–2 C16 alkyl groups, etc. and two substituents of the "amino group" may form a cyclic amino group together with a nitrogen atom. Examples of said cyclic amino group include e.g. 3- to 8-membered (preferably 5- to 6-membered)cyclic amino group, etc. such as 1-azetidinyl, 1-pyrrolidinyl, piperidino, morpholino, 1-piperazinyl and 1-piperazinyl which may have at the 4-position a lower alkyl group (e.g. $C_{1-6}$ alkyl group, etc. such as methyl, ethyl, propyl, isopropyl, butyl, t-butyl, pentyl, hexyl, etc.), an aralkyl group (e.g. $C_{7-10}$ aralkyl group, etc. such as benzyl, phenethyl, etc.), an aryl group (e.g. $C_{6-10}$ aryl group, etc. such as phenyl, 1-naphthyl, 2-naphthyl, etc.), etc.

Examples of the "optionally substituted carbamoyl group" include unsubstituted carbamoyl, N-mono-substituted carbamoyl group and N,N-di-substituted carbamoyl group.

The "N-mono-substituted carbamoyl group" is a carbamoyl group having one substituent on the nitrogen atom and said substituent include e.g. a lower alkyl group (e.g. $C_{1-6}$ alkyl group, etc. such as methyl, ethyl, propyl, isopropyl, butyl, isobutyl, t-butyl, pentyl, hexyl, etc.), a lower alkenyl group (e.g. $C_{2-6}$ alkenyl group, etc. such as vinyl, allyl, isopropenyl, propenyl, butenyl, pentenyl, hexenyl, etc.), a cycloalkyl group (e.g. $C_{3-6}$ cycloalkyl group, etc. such as cyclopropyl, cyclobutyl, cyclopentyl, cyclohexyl, etc.), an aryl group (e.g. $C_{6-10}$ aryl group, etc. such as phenyl, 1-naphthyl, 2-naphthyl, etc.), an aralkyl group (e.g. $C_{1-10}$ aralkyl group, preferably phenyl-$C_{1-4}$ alkyl group, etc. such as benzyl, phenethyl, etc.), arylalkenyl group (e.g., $C_{8-10}$ arylalkenyl group such as cinnamyl, etc., preferably phenyl-$C_{2-4}$ alkenyl group, etc.), a heterocyclic group (e.g. the above described "heterocyclic group" as the substituent of the "optionally substituted hydrocarbon group" represented by $R^1$, etc.), etc.

Said lower alkyl group, lower alkenyl group, cycloalkyl group, aryl group, aralkyl group, aralkenyl group and heterocyclic group may have a substituent and examples of the substituent include e.g. a hydroxy group, an optionally substituted amino group [said amino group may have 1 to 2 substituents (e.g. a lower alkyl group (e.g. $C_{1-6}$ alkyl group, etc. such as methyl, ethyl, propyl, isopropyl, butyl, isobutyl, t-butyl, pentyl, hexyl, etc.), an acyl group (e.g. $C_{1-6}$ alkanoyl such as formyl, acetyl, propionyl, pivaloyl, etc., benzoyl, etc.), a carboxyl group, $C_{1-6}$ alkoxy-carbonyl group, etc.)], a halogen atom (e.g. fluorine, chlorine, bromine, iodine, etc.), a nitro group, a cyano group, a lower alkyl group optionally substituted with 1 to 5 halogen atoms (e.g. fluorine, chlorine, bromine, iodine, etc.), a lower alkoxy group optionally substituted with 1 to 5 halogen atoms (e.g. fluorine, chlorine, bromine, iodine, etc.), etc.

Said lower alkyl group include e.g. $C_{1-6}$ alkyl group, etc. such as methyl, ethyl, n-propyl, isopropyl, n-butyl, isobutyl, sec-butyl, tert-butyl, pentyl, hexyl, etc. and in particular methyl, ethyl, etc. are preferable. Said lower alkoxy group include e.g. $C_{1-6}$ alkoxy group, etc. such as methoxy, ethoxy, n-propoxy, isopropoxy, n-butoxy, isobutoxy, sec-butoxy, tert-butoxy, etc. and in particular methoxy, ethoxy, etc. are preferable.

These substituents may be same or different and the number of the substituents is preferably 1 or 2 to 3 (more preferably 1 or 2).

The "N,N-di-substituted carbamoyl group" is a carbamoyl group having two substituents on the nitrogen atom. Examples of one of the substituents include the same as those of the above described "N-mono-substituted carbamoyl group" and examples of the other substituent include e.g. a lower alkyl group (e.g. $C_{1-6}$ alkyl group, etc. such as methyl, ethyl, propyl, isopropyl, butyl, t-butyl, pentyl, hexyl, etc.), $C_{3-6}$ cycloalkyl group (e.g. cyclopropyl, cyclobutyl, cyclopentyl, cyclohexyl, etc.), $C_{7-10}$ aralkyl group (e.g. benzyl, phenethyl, etc., preferably phenyl-$C_{1-4}$ alkyl group, etc.), etc. In addition, two substituents of the "N,N-di-substituted carbamoyl group may form a cyclic amino-carbamoyl group together with a nitrogen atom. Examples of said cyclic amino-carbamoyl group include e.g. 3 to 8-membered (preferably 5- to 6-membered)cyclic amino-carbamoyl group, etc. such as 1-azetidinylcarbonyl, 1-pyrrolidinylcarbonyl, piperidinocarbonyl, morpholinocarbonyl, 1-piperazinylcarbonyl and 1-piperazinylcarbonyl which may have at the 4-position a lower alkyl group (e.g. $C_{1-6}$ alkyl group, etc. such as methyl, ethyl, propyl, isopropyl, hutyl, t-butyl, pentyl, hexyl, etc.), an aralkyl group (e.g. $C_{7-10}$ aralkyl group, etc. such as benzyl, phenethyl, etc.), an aryl group (e.g. $C_{6-10}$ aryl group, etc. such as phenyl, 1-naphthyl, 2-naphthyl, etc.), etc.

Examples of the substituent in the "optionally substituted thiocarbamoyl group" include the same substituent as those in the above described "optionally substituted carbamoyl group".

Examples of the "optionally esterified carboxyl group" in the present specification include a carboxyl group as well as a lower alkoxycarbonyl group, an aryloxycarbonyl group, aralkyloxycarbonyl group, etc.

Examples of the "lower alkoxycarbonyl group" include e.g. $C_{1-6}$ alkoxy-carbonyl group, etc. methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, etc. Among others, $C_{1-3}$ alkoxy-carbonyl group, etc. such as methoxycarbonyl, ethoxycarbonyl, propoxycarbonyl, etc. are preferable.

Examples of the "aryloxycarbonyl group" include e.g. $C_{7-12}$ aryloxy-carbonyl group, etc. such as phenoxycarbonyl, 1-naphthoxycarbonyl, 2-naphthoxycarbonyl, etc.

Examples of the "aralkyloxycarbonyl group" include e.g. $C_{7-10}$ aralkyloxy-carbonyl group, etc. (preferably, $C_{6-10}$ aryl-$C_{1-4}$ alkoxy-carbonyl, etc.) such as benzyloxycarbonyl, phenethyloxycarbonyl, etc.

Said "aryloxycarbonyl group" and "aralkyloxycarbonyl group" may have a substituent. Examples of the substituent include the same kind and number of the substituents of the aryl group and aralkyl group as the substituent for the above described N-mono-substituted carbamoyl group.

Examples of the "acyl group derived from a sulfonic acid" as the substituent include a sulfonyl group having one substituent which the above described "N-mono-substituted carbamoyl group" have on the nitrogen atom, etc., preferably, $C_{1-6}$ alkylsulfonyl, etc. such as methanesulfonyl, ethane-sulfonyl, etc.

Examples of the "acyl group derived from a carboxylic acid" as the substituent include a carbonyl group having a hydrogen atom or one substituent which the above described "N-mono-substituted carbamoyl group" have on the nitrogen atom, etc., preferably, $C_{1-6}$ alkanoyl such as formyl, acetyl, propionyl, pivaloyl, etc. benzoyl, etc.

As $R^1$, an optionally substituted hydrocarbon group is preferable. Among others, an aryl group (preferably, $C_{6-14}$ aryl group, etc. such as phenyl, 1-naphthyl, 2-naphthyl, etc.) optionally substituted with a halogen atom or $C_{2-4}$ alkenyl group.

Also, as $R^1$, an optionally substituted heterocyclic group is preferable. Among others, a heterocyclic group (preferably, benzofuranyl group, benzopyranyl group, etc., more preferably benzopyranyl group) optionally substituted with a halogen atom.

In the above formula, the ring A is an optionally substituted divalent nitrogen-containing heterocyclic group. That is, the ring A is a divalent nitrogen-containing heterocyclic group which may have an optional substituent at any possible position, in addition to one oxo group clearly described as a substituent on the ring A. Said oxo group may be present at any possible position, preferably on the carbon atom next to the nitrogen atom to which the group of the formula: —X'—Y—X—Z binds.

Examples of the "divalent nitrogen-containing heterocyclic group" in the "optionally substituted divalent nitrogen-containing heterocyclic group" represented by the ring A include a divalent 6- to 8-membered nitrogen-containing heterocyclic group having an oxo group at any possible position and which contains, besides carbon atoms, at least two nitrogen atoms and which may contain 1 to 3 heteroatoms selected from oxygen atom, sulfur atom, etc. and preferably a divalent 6- to 8-membered nitrogen-containing heterocyclic group having an oxo group at any possible position and which contains, besides carbon atoms, at least two nitrogen atoms.

Examples of the "divalent 6- to 8-membered nitrogen-containing heterocyclic group" include e.g. a divalent 6-membered nitrogen-containing heterocyclic group which contains 2 to 4 nitrogen atoms such as piperazinediyl (piperazine-1,4-diyl, etc.), tetrahydropyrazinediyl, triazacyclohexanediyl, tetraazacyclohexanediyl, tetrahydrotriazinediyl, etc.; a divalent 7-membered nitrogen-containing heterocyclic group which contains 2 to 4 nitrogen atoms such as homopiperazinediyl (piperazine-1,4-diyl, etc.), 2,3-dehydrohomopiperazinediyl, etc.; a divalent 8-membered nitrogen-containing heterocyclic group which contains 2 to 4 nitrogen atoms such as 1,4-diazacyclooctanediyl (1,4-diazacyclooctane-1,4-diyl, etc.), 1,5-diazacyclo-octanediyl (1,5-diazacyclooctane-1,5-diyl, etc.) etc.; etc.

These "divalent nitrogen-containing heterocyclic groups" have an oxo group at any possible position. Among others, "divalent 6–8 membered nitrogen-containing cyclic amide group" having an oxo group on the carbon atom next to the nitrogen atom to which the group of the formula: —X'—Y—X—Z binds is preferable.

Examples of the "divalent 6–8 membered nitrogen-containing cyclic amide group" include 2-oxopiperazine-1,4-diyl, 2-oxo-1,2,3,4-tetrahydropyrazine-1,4-diyl, 2-oxohomopiperazine-1,4-diyl, 5-oxohomopiperazine-1,4-diyl, 2-oxo-1,4-diazacyclooctane-1,4-diyl, 5-oxo-1,4-diazacyclooctane-1,4-diyl, 2-oxo-1,5-diazacyclooctane-1,5-diyl, 5-oxo-2,3-dehydrohomopiperazine-1,4-diyl, 3-oxo-1,2,4-triazacyclohexane-1,4-diyl, 3-oxo-1,2,3,4-tetrahydro-1,2,4-triazine-1,4-diyl, 6-oxo-1,2,4-triazacyclohexane-1,4-diyl, 3-oxo-1,2,4,5-tetraazacyclohexane-1,4-diyl, etc.

Examples of the substituents of the "divalent nitrogen-containing heterocyclic group" in the "optionally substituted divalent nitrogen-containing heterocyclic group" represented by the ring A include, in addition to one oxo group, e.g. an optionally substituted hydroxy group, an optionally substituted thiol group, a halogen atom (e.g. fluorine, chlorine, bromine, iodine, etc.), a nitro group, a cyano group, an optionally substituted amino group, an optionally substituted lower alkyl group, an optionally substituted lower alkylidene group, an optionally substituted lower aralkylidene group, a lower alkoxy group optionally substituted with 1 to 5 halogen atoms (e.g. fluorine, chlorine, bromine, iodine, etc.), an optionally esterified carboxyl group, an optionally substituted carbamoyl group, an optionally substituted thiocarbamoyl group, an optionally substituted sulfurmoyl group, etc. Said "divalent nitrogen-containing heterocyclic group" may have 1 to 3 (preferably 1 to 2) of these substituents at any possible position.

Examples of the substituents of the "optionally substituted amino group" include 1–2 substituents selected from an optionally substituted alkyl group, an optionally substituted carbamoyl group, an optionally substituted thiocarbamoyl group, an optionally substituted sulfurmoyl group, an optionally esterified carboxyl, an acyl group derived from a sulfonic acid, an acyl group derived from a carboxylic acid, etc. Examples of said "optionally substituted alkyl group", "optionally substituted carbamoyl group", "an optionally substituted thiocarbamoyl group", "an optionally substituted sulfurmoyl group", "an optionally esterified carboxyl group", "an acyl group derived from a sulfonic acid" and "an acyl group derived from a carboxylic acid" include the "optionally substituted alkyl group", "optionally substituted carbamoyl group", "an optionally substituted thiocarbamoyl group", "an optionally substituted sulfurmoyl group", "an optionally esterified carboxyl group", "an acyl group derived from a sulfonic acid" and "an acyl group derived from a carboxylic acid" as exemplified by the substituents for the above described "optionally substituted hydrocarbon group" represented by $R^1$.

Preferable examples of the "optionally substituted amino group" include an amino group optionally substituted by 1–2 substituents selected from (1) a lower ($C_{1-6}$) alkyl group such as methyl, ethyl, n-propyl, isopropyl, n-butyl, isobutyl, sec-butyl, tert-butyl, etc., (2) mono- or di-lower ($C_{1-6}$) alkylcarbamoyl group, (3) $C_{1-6}$ alkylsulfonyl such as methanesulfonyl, ethanesulfonyl, etc., (4) $C_{1-6}$ alkanoyl such as formyl, acetyl, propionyl, pivaloyl, etc. and (5) benzoyl.

Examples of the "lower alkyl group" in the "the optionally substituted a lower alkyl group" include e.g. $C_{1-6}$ alkyl group, etc. such as methyl, ethyl, n-propyl, isopropyl, n-butyl, isobutyl, sec-butyl, tert-butyl, etc., and in particular methyl, ethyl, etc. are preferable.

Examples of the substituents for the "lower alkyl group" include e.g. a halogen atom (e.g. fluorine, chlorine, bromine, iodine, etc.), an amino group, a carboxyl group, hydroxy group, $C_{6-10}$ aryl, $C_{6-10}$ aryloxy, etc. Said "lower alkyl group" may have 1 to 5 (preferably 1 or 2) substituents at any possible position.

Examples of the "optionally substituted lower alkylidene group" include e.g. $C_{1-6}$ alkylidene, etc. such as methylidene, ethylidene, etc. Examples of the substituents for the "lower alkylidene group" include e.g. a halogen atom (e.g. fluorine, chlorine, bromine, iodine, etc.), an amino group, a carboxyl group, a hydroxy group, etc. Said "lower alkylidene group" may have 1 to 5 (preferably 1 to 2) of these substituents at any possible position.

Examples of the "optionally substituted lower aralkylidene group" include e.g. $C_{6-10}$ aryl-$C_{1-4}$ alkylidene, etc. such as benzylidene, etc. Examples of the substituents for the "lower aralkylidene group" include e.g. a halogen atom (e.g. fluorine, chlorine, bromine, iodine, etc.), an amino group, a carboxyl group, a hydroxy group, etc. Said "lower aralkylidene group" may have 1 to 5 (preferably 1 to 2) of these substituents at any possible position.

Examples of the "lower alkoxy group" in the "lower alkoxy group optionally substituted with 1 to 5 halogen atoms" include e.g. $C_{1-6}$ alkoxy group, etc. such as methoxy, ethoxy, n-propoxy, isopropoxy, n-butoxy, isobutoxy, sec-butoxy, tert-butoxy, etc. and in particular methoxy, ethoxy, etc. are preferable.

Examples of the "optionally esterified carboxyl group" include the optionally esterified carboxyl group as exemplified by the substituents for the above described "optionally substituted hydrocarbon group" represented by $R^1$.

Examples of the "optionally substituted carbamoyl group", "an optionally substituted thiocarbamoyl group" and "an optionally substituted sulfurmoyl group "include the optionally substituted carbamoyl group, an optionally substituted thiocarbamoyl group and an optionally substituted sulfurmoyl group as exemplified by the substituents for the above described "optionally substituted hydrocarbon group" represented by $R^1$.

Examples of the substituents for the "hydroxy group" and "mercapto group" in the "optionally substituted hydroxy group" and "optionally substituted mercapto group" as a substituent, which the "divalent nitrogen-containing heterocyclic group" represented by the ring A may have, include an optionally substituted lower alkyl group, an optionally esterified carboxyl group, an optionally substituted carbamoyl group, an optionally substituted thiocarbamoyl group, an optionally substituted sulfurmoyl group, an acyl group derived from a sulfonic acid, an acyl group derived from a carboxylic acid, etc.

Examples of the lower alkyl group include e.g. $C_{1-6}$ alkyl group, etc. such as methyl, ethyl, n-propyl, isopropyl, n-butyl, isobutyl, sec-butyl, tert-butyl, pentyl, hexyl, etc. Examples of the substituents, which said lower alkyl group may have, include a halogen atom (e.g., fluorine, chlorine, bromine, iodine, etc.), an optionally substituted aryl group [e.g. phenyl or naphthyl, each of which may be substituted with a halogen atom (e.g., fluorine, chlorine, bromine, iodine, etc.), a lower alkyl group (e.g., $C_{1-6}$ alkyl group, etc. such as methyl, ethyl, n-propyl, isopropyl, n-butyl, isobutyl, sec-butyl, tert-butyl, pentyl, hexyl, etc.), a lower alkoxy group (e.g., $C_{1-6}$ alkoxy group, etc. such as methoxy, ethoxy, n-propoxy, isopropoxy, n-butoxy, isobutoxy, sec-butoxy, tert-butoxy, etc.), etc.], an optionally substituted hydroxy group (e.g., similar to the optionally substituted hydroxy group as a substituent for the "optionally substituted hydrocarbon group" represented by the above-mentioned $R^1$, etc.), an optionally substituted thiol group (e.g., similar to the optionally substituted thiol group as a substituent for the "optionally substituted hydrocarbon group" represented by the above-mentioned $R^1$, etc.), an optionally substituted amino group (e.g., similar to the optionally substituted amino group as a substituent for the "optionally substituted hydrocarbon group" represented by the above-mentioned $R^1$, etc.), an optionally esterified carboxyl group (e.g., similar to the optionally esterified carboxyl group as a substituent for the "optionally substituted hydrocarbon group" represented by the above-mentioned $R^1$, etc.), etc. In addition, a sulfur atom in the "optionally substituted mercapto group" may be oxidized. For example, the sulfur atom may be in the form of the formula: $S(O)_k$ [k is an integer of 0 to 2].

Examples of the "optionally esterified carboxyl group", "optionally substituted carbamoyl group", "optionally substituted thiocarbamoyl group", "optionally substituted sulfurmoyl group", "acyl group derived from a sulfonic acid" and "acyl group derived from a carboxylic acid" as a substituent for the "hydroxy group" and "mercapto group" in the "optionally substitutedhydroxy group" and "optionally substitutedmercapto group", which the "divalent nitrogen-containing heterocyclic group" represented by the ring A may have, are similar to the "optionally esterified carboxyl group", "optionally substituted carbamoyl group", "optionally substituted thiocarbamoyl group", "optionally substituted sulfurmoyl group", "acyl group derived from a sulfonic acid" and "acyl group derived from a carboxylic acid" as a substituent for the "optionally substituted hydrocarbon group" represented by the above-mentioned $R^1$.

As the ring A, a group of the formula:

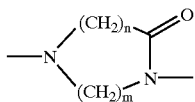

wherein n is 1 or 2, and m is 2 or 3, etc. is preferable.

In the above formula, m is preferably 2, and n is preferably 1.

In particular, the ring A is preferably 2-oxopiperazine-1,4-diyl.

In the above formula, Y is an optionally substituted divalent cyclic group.

Examples of the substituents for the "optionally substituted divalent cyclic group" represented by Y include the same substituents as those of the above described "divalent nitrogen-containing heterocyclic group" represented by the ring A.

As a substituent for the "divalent cyclic group" represented by Y, an optionally substituted hydroxy group is preferable and, among others, hydroxy group and $C_{1-6}$ alkanoyloxy (e.g., acetoxy, etc.) are preferable.

When Y is a divalent saturated nitrogen-containing heterocyclic group (in particular, piperidine-1,4-diyl), the substituent for Y is preferably present on the carbon atom to which the group X' binds.

Examples of the "divalent cyclic group" in the "optionally substituted divalent cyclic group" include a divalent cyclic hydrocarbon group or a divalent heterocyclic group (preferably, a divalent heterocyclic group).

Examples of the "divalent cyclic hydrocarbon group" in the "divalent cyclic group" of the "optionally substituted divalent hydrocarbon group" represented by Y include a saturated or unsaturated cyclic divalent hydrocarbon group, etc.

Examples of the saturated cyclic divalent hydrocarbon group include a divalent group formed by removing a hydrogen atom at an optional position (preferably a hydrogen atom on a carbon atom which is different from the carbon atom at the 1-position, more preferably a hydrogen atom on a carbon atom which is farthest from the carbon atom at the 1-position) from a cycloalkyl group (e.g. $C_{3-9}$ cycloalkyl (preferably $C_{5-7}$ cycloalkyl, more preferably cyclohexyl, etc.), etc. such as cyclopropyl, cyclobutyl, cyclopentyl, cyclohexyl, cyclo-heptyl, cyclooctyl, cyclononyl, etc.). Preferable examples of the saturated cyclic divalent hydrocarbon group include $C_{5-7}$ cycloalkylene (more preferably 1,4-cyclohexylene, etc.), etc.

Examples of the unsaturated cyclic divalent hydrocarbon group include a divalent group formed by removing a hydrogen atom at an optional position (preferably a hydrogen atom on a carbon atom which is different from the carbon atom at the 1-position, more preferably a hydrogen atom on a carbon atom which is farthest from the carbon atom at the 1-position) from a cycloalkenyl group (e.g. $C_{3-6}$ cycloalkenyl group, etc. such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl, etc.), a cycloalkanedienyl group (e.g. $C_{4-6}$ cycloalkanedienyl group, etc. such as 2,4-cyclopentadien-1-yl, 2,4-cyclohexadien-1-yl, 2,5-cyclohexadien-1-yl, etc.), an aryl group (e.g. $C_{6-10}$ aryl group, etc. such as phenyl, naphthyl, etc., preferably phenyl), etc. Among others, phenylene is preferable and in particular 1,4-phenylene is preferable.

As the "divalent hydrocarbon group", $C_{5-7}$ cycloalkylene (preferably 1,4-cyclohexylene, etc.), phenylene (preferably 1,4-phenylene, etc.), etc. are preferable.

Examples of the "divalent heterocyclic group" in the "optionally substituted divalent heterocyclic group" represented by Y include a 5- to 6-membered divalent aromatic heterocyclic group, a 5- to 6-membered divalent saturated or unsaturated non-aromatic heterocyclic group (alicyclic heterocyclic group), etc., which contains, besides carbon atoms, at least one hetero-atom (preferably 1 to 3 hetero-atoms, more preferably 1 to 2 hetero-atoms) consisting of 1 to 3 kinds of hetero-atoms (preferably 1 to 2 kinds of hetero-atoms) selected from oxygen atom, sulfur atom, nitrogen atom, etc.

Examples of the "divalent aromatic heterocyclic group" include a divalent group formed by removing two hydrogen atoms at different positions from a 5-membered heterocyclic ring such as furan, thiophene, pyrrole, oxazole, isoxazole, thiazole, isothiazole, imidazole, pyrazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, etc., a 6-membered heterocyclic ring such as pyridine, pyridazine, pyrimidine, 1,2,4-triazine, 1,3,5-triazine, etc.

Examples of the "divalent non-aromatic heterocyclic group" include a 5- to 6-membered saturated or unsaturated (preferably saturated) non-aromatic heterocyclic group (alicyclic heterocyclic group), etc. such as pyrrolidine, tetrahydrofuran, piperidine, tetrahydropyran, morpholine, thiomorpholine, piperazine, etc.

Among others, Y is preferably an optionally substituted phenylene, an optionally substituted piperidine, etc.

In addition, when the "divalent cyclic group" in the "optionally substituted divalent cyclic group" represented by Y is a divalent cyclic hydrocarbon group, Z is preferably an optionally substituted amino group or an optionally substituted imidoyl group. When the "divalent cyclic group" in the "optionally substituted divalent cyclic group" represented by Y is a divalent heterocyclic group, Z is preferably an optionally substituted nitrogen-containing heterocyclic group.

In the above formula, X and X' are independently a chemical bond or an optionally substituted alkylene chain.

Examples of the "alkylene chain" in the "optionally substituted alkylene chain" represented by X and X' include a straight-chain lower ($C_{1-6}$) alkylene, etc. such as methylene, ethylene, propylene, butylene, pentylene, etc. Among others, $C_{1-4}$ alkylene, etc. such as methylene, ethylene, etc. is preferable.

Examples of the substituents for the "alkylene chain" include a lower alkyl group [similar to the "optionally substituted lower alkyl group" as a substituent for the "optionally substituted divalent nitrogen-containing heterocyclic group" for the above-mentioned the ring A, etc.; preferably, lower alkyl group (e.g. $C_{1-6}$alkyl, etc. such as methyl, ethyl, n-propyl, isopropyl, n-butyl, isobutyl, sec-butyl, tert-butyl, etc.)], an optionally substituted carbamoyl group [similar to the "optionally substituted carbamoyl group" as a substituent for the "optionally substituted divalent nitrogen-containing heterocyclic group" for the above-mentioned the ring A, etc.; preferably, carbamoyl group, N-mono-lower ($C_{1-6}$) alkylcarbamoyl group, N,N-di-lower ($C_{1-6}$)alkylcarbamoyl group, etc.], cyano group, a halogen atom (e.g. fluorine, chlorine, bromine, iodine, etc.), hydroxy group, an optionally esterified carboxyl group (the same "optionally esterified carboxyl group" as exemplified by the substituents for the above described "optionally substituted hydrocarbon group" represented by $R^1$), etc. Said "alkylene chain" may have 1 to 3 of these substituents at any possible position.

In the above formula, Z is (1) an optionally substituted amino group, (2) an optionally substituted imidoyl group or (3) an optionally substituted nitrogen-containing heterocyclic group.

Examples of the substituents for the "optionally substituted amino group" represented by Z are similar to those for the "optionally substituted hydrocarbon group" represented by the above-mentioned $R^1$. Two of the substituents for the "optionally substituted amino group" may bind to each other to form a cyclic amino group together with a nitrogen atom. Examples of said cyclic amino group include 3–8 membered (preferably 5–6 membered) cyclic amino, etc. such as 1-azetidinyl, 1-pyrrolidinyl, piperidino, morpholino, 1-piperazinyl and 1-piperazinyl which may have at the 4-position a lower alkyl group (e.g. $C_{1-6}$ alkyl group, etc. such as methyl, ethyl, propyl, isopropyl, butyl, t-butyl, pentyl, hexyl, etc.), aralkyl group (e.g. $C_{7-10}$ aralkyl group, etc. such as benzyl, phenethyl, etc.), aryl group (e.g. $C_{6-10}$ aryl group, etc. such as phenyl, 1-naphthyl, 2-naphthyl, etc.), etc., etc. Said cyclic amino group may have similar number and kinds of the substituents to those for the "optionally substituted hydrocarbon group" represented by the above-mentioned $R^1$.

When the "optionally substituted hydrocarbon group" as a substituent in the "amino group substituted with optionally substituted hydrocarbon group" represented by Z include "an optionally substituted imino group" in its α-position, the "optionally substituted amino group" represented by Z forms an amino group substituted with "an optionally substituted imidoyl group" exemplified below as Z. For example, a group of the formula: —N(R")—C(R')=N—R [wherein R" is a hydrogen atom or an optionally substituted hydrocarbon group, R is a hydrogen atom, an optionally substituted hydroxy group, an optionally substituted hydrocarbon group or an acyl group derived from a carboxylic acid, and R' is a hydrogen atom, an optionally substituted hydrocarbon group, an acyl group derived from a carboxylic acid, an optionally substituted amino group, an optionally substituted mercapto group or an optionally substituted hydroxy group], etc. is also included by the "optionally substituted amino group" represented by Z.

In addition, when R' is a mercapto group or a hydroxy group and R is a hydrogen atom in the "optionally substituted imidoyl group", said "optionally substituted imidoyl group" may be in the form of a group of the formula: —C(=O)—NH$_2$ or —C(=S)—NH$_2$.

In the above formula, the "optionally substituted hydrocarbon group" represented by R, R' and R" are the same as the above-mentioned "optionally substituted hydrocarbon group" represented by $R^1$. Examples of the "acyl group derived from a carboxylic acid" represented by R and R' include that exemplified by the "acyl group derived from a carboxylic acid" as the substituent for the above-mentioned "optionally substituted hydrocarbon group" represented by $R^1$. Examples of the "optionally substituted hydroxy group" represented by R include that exemplified by the "optionally substituted hydroxy group" as the substituent for the above-mentioned "optionally substituted hydrocarbon group" represented by $R^1$. Examples of the "optionally substituted amino group" represented by R' include that exemplified by the "optionally substituted amino group" as the substituent for the above-mentioned "optionally substituted hydrocarbon group" represented by $R^1$; or an amino group which may have 1–2 " optionally substituted hydrocarbon groups" represented by the above-mentioned $R^1$; etc.

In the compound represented by the formula (I), compounds wherein R is an acyl group derived from a carboxylic acid is useful as a pro-drug for compounds wherein R is a hydrogen atom.

Examples of the "acyl group derived from a carboxylic acid" represented by R include that exemplified by the "acyl group derived from a carboxylic acid" as the substituent for the above-mentioned "optionally substituted hydrocarbon group" represented by $R^1$. In addition, the "acyl group derived from a carboxylic acid" represented by R may be, for example, a group of the formula: —COOR'" wherein R'" is an optionally substituted hydrocarbon group, etc., such as an optionally esterified carboxyl group, etc. Examples of the "optionally substituted hydrocarbon group" represented by R'" include that exemplified by the above-mentioned "optionally substituted hydrocarbon group" represented by $R^1$.

Preferred examples of the "hydrocarbon group" in the "optionally substituted hydrocarbon group" represented by R'" include $C_{1-6}$ alkyl, $C_{2-6}$ alkenyl, $C_{3-6}$ cycloalkyl, $C_{6-10}$ aryl, $C_{6-10}$ aryl-$C_{1-4}$ alkyl, etc. Said "hydrocarbon group" may have similar number and kinds of the substituents to those for the above-mentioned "optionally substituted hydrocarbon group" represented by $R^1$.

Among others, specific examples of the group represented by the formula: —COOR'" include $C_{1-6}$ alkoxy-carbonyl group (e.g., methoxycarbonyl, ethoxycarbonyl, isopropoxycarbonyl, etc.), $C_{1-6}$ alkanoyloxy-$C_{1-6}$ alkoxy-carbonyl group (e.g., pivaloyloxymethoxycarbonyl, 1-(acetoxy)ethoxycarbonyl, acetoxy-tert-butoxycarbonyl, etc.), $C_{1-6}$ alkoxy-carbonyloxy-$C_{1-6}$ alkoxy-carbonyl group (e.g., ethoxycarbonyloxymethoxycarbonyl, etc.), 5-$C_{1-4}$ alkyl-2-oxo-dioxolen-4-yl-$C_{1-6}$ alkoxy-carbonyl group (e.g., 5-methyl-2-oxo-dioxolen-4-ylmethoxycarbonyl, etc.), etc.

More specific examples of the "optionally substituted amino group" represented by Z include a mono- or di-lower ($C_{1-6}$) alkylamino group (e.g. methylamino, ethylamino, benzylmethylamino, dimethylamino, diethylamino, diisobutylamino, diisopropylamino, N-ethyl-t-butylamino, benzylmethylamino, etc.) which may be further substituted with an amino group, a $C_{6-10}$ aryl group (preferably, phenyl), etc.; a group of the formula: —N(R")—C(R')=N—R [wherein R" is a hydrogen atom or an optionally substituted hydrocarbon group (preferably, a hydrogen atom or a lower ($C_{1-6}$) alkyl group), R is a hydrogen atom, an optionally substituted hydroxy group, an optionally substituted hydrocarbon group or an acyl group derived from a carboxylic acid (preferably, a hydrogen atom or an acyl group derived from a carboxylic acid), and R' is a hydrogen atom, an optionally substituted hydrocarbon group, an optionally substituted amino group, an optionally substituted mercapto group or an optionally substituted hydroxy group (preferably, a hydrogen atom, a lower ($C_{1-6}$)alkyl group, an amino group or a mono-or di-lower ($C_{1-6}$) alkylamino group)] (e.g., guanidino group, formimidoylamino group, acetimidoylamino group, etc.); 5–6 membered cyclic amino group (e.g., piperidino group, etc.); etc.

Examples of the "optionally substituted imidoyl group" represented by Z include a group of the formula: —C(R')=N—R wherein each symbol is as defined above, etc.

Here, when R' is an optionally substituted amino group (preferably, amino, methylamino, ethylamino, propylamino, dimethylamino, diethylamino, hydrazino, piperidino, piperazino, morpholino, thiomorpholino, etc.), the "optionally substituted imidoyl group" represented by Z forms an optionally substituted amidino group. Examples of said optionally substituted amidino group include an amidino group optionally substituted with 1–2 lower ($C_{1-6}$) alkyl groups, lower ($C_{1-6}$) alkanoyl groups, benzoyl groups, etc.

(e.g., amidino, N-methylamidino, N-ethylamidino, N-propylamidino, N,N'-dimethylamidino, N,N'-diethylamidino, N-methyl-N'-diethylamidino, N-formylamidino, N-acetylamidino, etc.), etc.

In the above formula, preferred examples of R" include a hydrogen, a lower alkyl group (e.g. $C_{1-6}$ alkyl group such as methyl, ethyl, propyl, isopropyl, butyl, isobutyl, etc.), etc. Preferred examples of R include a hydrogen, a lower alkyl group (e.g. $C_{1-6}$ alkyl group such as methyl, ethyl, propyl, isopropyl, butyl, isobutyl, etc.), an acyl group (e.g. $C_{1-6}$ alkanoyl such as formyl, acetyl, propionyl, pivaloyl, etc.; benzoyl; $C_{1-8}$ alkoxycarbonyl, etc. such as methoxycarbonyl, ethoxycarbonyl, propoxycarbonyl, isopropoxycarbonyl, butoxycarbonyl, isobutoxycarbonyl, etc.; $C_{7-10}$ aralkyloxycarbonyl, etc. such as benzyloxycarbonyl, phenethyloxycarbonyl, etc.), a hydroxy group, etc. Preferred examples of R' include a hydrogen, a lower alkyl group (e.g. $C_{1-6}$ alkyl group such as methyl, ethyl, propyl, isopropyl, butyl, isobutyl, etc.), an optionally substituted amino group (e.g., an amino group optionally substituted with 1–2 same or different substituents selected from a lower alkyl group (e.g. $C_{1-6}$ alkyl group such as methyl, ethyl, propyl, isopropyl, butyl, isobutyl, etc.) or an acyl group (e.g. $C_{1-6}$ alkanoyl such as formyl, acetyl, propionyl, pivaloyl, etc.; benzoyl, etc.), a hydrazino group, a 5–6 membered cyclic amino group (e.g., piperidino, thiomorpholino, morpholino, piperazino, etc.), etc.), a hydroxy group, a lower alkoxy group (e.g. $C_{1-6}$ alkoxy group such as methoxy, ethoxy, propoxy, isopropoxy, butoxy, isobutoxy, etc.), etc.

In the above formula, R" and R are preferably hydrogen.

In the above formula, R' is preferably hydrogen, a lower alkyl group or an optionally substituted amino group. Among others, R' is preferably a lower alkyl group or an optionally substituted amino group, and in particular, an optionally substituted amino group (preferably, amino optionally substituted with $C_{1-4}$ alkyl, etc.).

Examples of the "nitrogen-containing heterocyclic group" in the "optionally substituted nitrogen-containing heterocyclic group" represented by Z include an aromatic nitrogen-containing heterocyclic group and a saturated or unsaturated non-aromatic nitrogen-containing heterocyclic group (aliphatic heterocyclic group), each of which contains, besides carbon atoms, at least one nitrogen atom (preferably 1 to 3 nitrogen atoms) as an atom constituting a ring system (ring atom) and may contain 1 to 3 hetero-atoms selected from oxygen atom, sulfur atom, etc.

Example of the "aromatic nitrogen-containing heterocyclic group" include an aromatic mono cyclic nitrogen-containing heterocyclic group such as pyrrolyl, oxazolyl, isooxazolyl, thiazolyl, isothiazolyl, imidazolyl (1H-imidazol-1-yl, 1H-imidazole-4-yl, etc.), pyrazolyl, 1,2,3-oxadiazolyl, 1,2,4-oxadiazolyl, 1,3,4-oxadiazolyl, furazanyl, 1,2,3-thiadiazolyl, 1,2,4-thidiazolyl, 1,3,4-thiadiazolyl, 1,2,3-triazolyl, 1,2,4-triazolyl (1,2,4-triazolyl-1-yl, 1,2,4-triazolyl-4-yl, etc.), tetrazolyl, pyridyl (2-, 3-or 4-pyridyl), pyridazinyl, pyrimidinyl, pyrazinyl, triazinyl, etc. and N-oxide derivative thereof, etc. Among others, a 5–6 membered aromatic mono cyclic nitrogen-containing heterocyclic group is preferable. In particular, imidazolyl, pyridyl, etc. are preferable.

Examples of the "non-aromatic nitrogen-containing heterocyclic group" include a group formed by partially reducing the above-mentioned "aromatic nitrogen-containing heterocyclic group" (e.g., imidazolinyl, tetrahydropyrimidinyl, etc.), and also azetidinyl, pyrrolidinyl, piperidyl (2-, 3- or 4-piperidyl), morpholinyl, thiomorpholinyl, piperazinyl (1-piperazinyl, etc.), homopiperazinyl, etc. Among others, a 5–6 membered non-aromatic monocyclic nitrogen-containing heterocyclic group is preferable.

As the substituents for the "nitrogen-containing heterocyclic group" represented by Z, the same substituents for the "heterocyclic group" represented by the above-mentioned $R^1$ can be employed. Also, a nitrogen atom constituting the nitrogen-containing heterocyclic group may be oxidized.

As Z, an amidino group or an optionally substituted nitrogen-containing heterocyclic group, etc. are preferable, and in particular, an optionally substituted aromatic nitrogen-containing heterocyclic group, etc. are preferable.

As Compound (I), 1-(4-amidinobenzyl)-4-(6-chloronaphthanlene-2-sulfonyl)-2-piperazinone, 1-(4-amidinobenzyl)-4-(7-chloro-2H-benzopyran-3-sulfonyl)-2-piperazinone, 4-(6-chloronaphthanlene-2-sulfonyl)-1-[1-(4-pyridyl)piperidin-4-ylmethyl]-2-piperazinone, 4-(7-chloro-2H-benzopyran-3-sulfonyl)-1-[1-(4-pyridyl)piperidin-4-ylmethyl]-2-piperazinone, 1-[1-(4-pyridyl)piperidin-4-ylmethyl]-4-(4-vinylbenzenesulfonyl)-2-piperazinone, 4-(6-chloronaphthanlene-2-sulfonyl)-1-[4-hydroxy-1-(4-pyridyl)piperidin-4-ylmethyl]-2-piperazinone, 4-(7-chloro-2H-benzopyran-3-sulfonyl)-1-[4-hydroxy-1-(4-pyridyl)piperidin-4-ylmethyl]-2-piperazinone, 1-[4-hydroxy-1-(4-pyridyl)piperidin-4-ylmethyl]-4-(4-vinylbenzenesulfonyl)-2-piperazinone, or a salt there of, etc. are preferable.

The pro-drug of the Compound (I) means a compound which is converted to Compound (I) under physiological conditions or with a reaction due to an enzyme, gastric acid, etc. in the living body, that is, a compound which is converted to Compound (I) with oxidation, reduction, hydrolysis, etc. according to an enzyme; a compound which is converted to Compound (I) with gastric acid, etc.; etc.

Examples of the pro-drug of Compound (I) include a compound wherein an amino group of Compound (I) is substituted with acyl, alkyl, phosphoric acid, etc. (e.g. a compound wherein an amino group of Compound (I) is substituted with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, tert-butyl, etc.); a compound wherein an hydroxy group of Compound (I) is substituted with acyl, alkyl, phosphoric acid, boric acid, etc. (e.g. a compound wherein an hydroxy group of Compound (I) is substituted with acetyl, palmitoyl, propanoyl, pivaloyl, succinyl, fumaryl, alanyl, dimethylaminomethylcarbonyl, etc.); a compound wherein a carboxyl group of Compound (I) is modified with ester, amide, etc. (e.g. a compound wherein a carboxyl group of Compound (I) is modified with ethylester, phenylester, carboxymethylester, dimethylaminomethylester, pivaloyloxymethylester, ethoxycarbonyloxyethylester, phthalidylester, (5-methyl-2-oxo-1,3-dioxolen-4-yl)methylester, cyclohexyloxycarbonylethylester, methylamide, etc.); etc. These pro-drugs can be produced by per se known methods from Compound (I).

The pro-drug of Compound (I) may be a compound which is converted into Compound (I) under the physiological conditions as described in "Pharmaceutical Research and Development", Vol. 7 (Drug Design), pages 163–198 published in 1990 by Hirokawa Publishing Co. (Tokyo, Japan).

Examples of the salts of the compound (I) include a pharmaceutically acceptable salt, etc. such as an acid addition salt (e.g. a salt with acetic acid, lactic acid, succinic acid, maleic acid, tartaric acid, citric acid, gluconic acid, ascorbic acid, benzoic acid, methanesulfonic acid, p-toluenesulfonic acid, cinnamic acid, fumaric acid, phosphoric acid, hydrochloric acid, nitric acid, hydrobromic acid, hydriodic atom acid, sulfamic acid, sulfuric acid, etc.), a metal salt (e.g. a salt with sodium, potassium, magnesium, calcium, etc.), an organic base (e.g. trimethylamine, triethylamine, pyridine, picoline, N-methyl-pyrrolidine, N-methylpiperidine, N-methylmorpholine, etc.), etc.

The compounds (I) of this invention can be produced by, for example, methods as described below.

Each compound described in the following reaction schemes may be in the form of a salt, unless it inhibits the reaction and examples of the salts are the same as those of the compound (I).

Method A

A compound (II) or a salt thereof represented by the formula:

$$R^1SO_2Q \qquad (II)$$

wherein Q is a halogen atom, and the other symbol is as defined above is reacted with a compound (II) or a salt thereof represented by the formula:

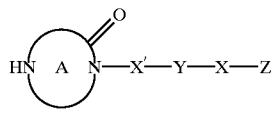

(III)

wherein each symbol is as defined above to produce the compound (I).

In the formula (II), Q is a halogen atom. Examples of the halogen atom represented by Q include fluorine, chlorine, bromine, iodine, etc.

This production method is carried out by reacting a compound (II) or a salt thereof with a compound (III) or a salt thereof. Examples of the salt of the compound (II) or (III) include an acid addition salt with an acid which can form an acid addition salt with the above described compound (I).

This production method is usually carried out in a solvent. Any solvent can be used unless it inhibits this production method.

Examples of the solvent include alcohols such as methanol, ethanol, propanol, isopropanol, butanol, tert-butanol, etc., ethers such as dioxane, tetrahydrofuran, diethylether, tert-butylmethylether, diisopropylether, ethyleneglycol-dimethylether, etc., esters such as ethyl formate, ethyl acetate, n-butyl acetate, etc., halogenated hydrocarbons such as dichloromethane, chloroform, carbon tetrachloride, trichloroethylene, 1,2-dichloroethane etc., hydrocarbons such as n-hexane, benzene, toluene, etc., amides such as formamide, N,N-dimethylformamide, N,N-dimethylacetamide, etc., ketones such as acetone, methylethylketone, methylisobutylketone, etc., nitriles such as acetonitrile, propionitrile, etc., etc., and additionally dimethylsulfoxide, sulfolane (tetramethylene-sulfone), hexamethylphosphorylamide, water, etc., and these can be used singly or as a mixture.

If necessary, this production method can be carried out in the presence of a base. Examples of the base include an inorganic base such as lithium hydroxide, potassium hydroxide, sodium hydroxide, sodium carbonate, potassium carbonate, sodium hydrogen carbonate, etc., a tertiary amine such as triethylamine, tri(n-propyl)amine, tri(n-butyl)-amine, diisopropylethylamine, cyclohexyldimethylamine, pyridine, lutidine, γ-collidine, N,N-dimethylaniline, N-methylpiperidine, N-methylpyrrolidine, N-methylmorpholine, etc.

In the reaction, about 1 to about 5 moles (preferably about 1 to about 3 moles) of the compound (II) is used per 1 mole of compound (III).

The reaction temperature ranges from about −80% to about 100 C., preferably about −50° C. to about 80%.

The reaction time varies depending on the kind of compound (II) or (III), kind of the solvent, the reaction temperature, etc. and usually ranges from about 1 minute to about 72 hours, preferably about 15 minutes to about 24 hours.

Method B

A compound (IV) or a salt thereof represented by the formula:

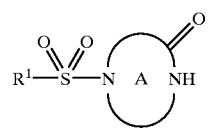

(IV)

wherein each symbol is as defined above is reacted with a compound (V) or a salt thereof represented by the formula:

$$Q^1—X'—Y—X—Z \qquad (V)$$

wherein $Q^1$ is a halogen atom or a group of the formula: $R^2—SO_2—O—$ (wherein $R^2$ is a lower alkyl group optionally substituted with a halogen atom or an optionally substituted phenyl group), and the other symbols are as defined above to produce a compound (I) or a salt thereof.

This production method is carried out by reacting Compound (IV) with Compound (V).

In the above formula (V), examples of the halogen atom represented by $Q^1$ include chlorine, bromine, iodine, etc.

In the above formula, examples of the lower alkyl group optionally substituted with a halogen atom represented by $R^2$ include $C_{1-6}$ alkyl groups such as methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl, etc. Among others, $C_{1-4}$ alkyl groups such as methyl, ethyl, propyl, isopropyl, butyl, isobutyl, etc. are preferable.

Examples of the lower alkyl group substituted with a halogen atom (e.g. fluorine, chlorine, bromine, iodine, etc.), which is represented by $R^2$ include trichloromethyl, trifluoromethyl, etc.

Examples of the substituents for the phenyl group represented by $R^2$ include a lower alkyl group (same as the lower alkyl group represented by the above-mentioned $R^2$), a lower alkoxy group (e.g. $C_{1-6}$ alkoxy group such as methoxy, ethoxy, propoxy, isopropoxy, butoxy, etc.), a halogen atom (e.g. fluorine, chlorine, bromine, iodine, etc.), nitro group, cyano group, carboxyl group, etc.

This production method is carried out by reacting Compound (IV) with Compound (V).

This production method is usually carried out in a solvent. Any solvent can be used unless it inhibits this production method.

Examples of the solvent include alcohols such as methanol, ethanol, propanol, isopropanol, butanol, tert-butanol, etc., ethers such as dioxane, tetrahydrofuran, diethylether, tert-butylmethylether, diisopropylether, ethyleneglycol-dimethylether, etc., esters such as ethyl formate, ethyl acetate, n-butyl acetate, etc., halogenated hydrocarbons such as dichloromethane, chloroform, carbon tetrachloride, trichloroethylene, 1,2-dichloroethane etc., hydrocarbons such as n-hexane, benzene, toluene, etc., amides such as formamide, N,N-dimethylformamide, N,N-dimethylacetamide, etc., ketones such as acetone, methylethylketone, methylisobutylketone, etc., nitriles such as acetonitrile, propionitrile, etc., etc., and additionally dimethylsulfoxide, sulfolane (tetramethylene-sulfone), hexamethylphosphorylamide, water, etc., and these can be used singly or as a mixture.

If necessary, this production method can be carried out in the presence of a base. Examples of the base include an inorganic base such as alkali metal hydrides (e.g. potassium hydride, sodium hydride, etc.), metal alkoxides having 1 to 6 carbon atoms (e.g. lithium-ethoxide, lithium-tert-butoxide, sodium methoxide, sodium ethoxide, carboxyl-tert-butoxide, etc.), lithium hydroxide, potassium hydroxide, sodium hydroxide, sodium carbonate, potassium carbonate, sodium hydrogen carbonate, etc., a tertiary amine such as triethylamine, tri(n-propyl)amine, tri(n-butyl)-amine, diisopropylethylamine, cyclohexyldimethylamine, pyridine, lutidine, γ-collidine, N,N-dimethylaniline, N-methylpiperidine, N-methylpyrrolidine, N-methylmorpholine, etc.

In the reaction, about 1 to about 100 moles (preferably about 1 to about 50 moles) of the compound (V) is used per 1 mole of compound (IV).

The reaction temperature ranges from about −3° C. to about 250%, preferably about −10° C. to about 200° C.

The reaction time varies depending on the kind of the compound (IV) or (V), kind of the solvent, the reaction temperature, etc. and usually ranges from about 1 minute to about 72 hours, preferably about 15 minutes to about 24 hours.

Method C

A compound (VI) or a salt thereof represented by the formula:

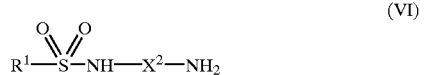

(VI)

wherein $X^2$ is an optionally substituted alkylene chain, and the other symbols are as defined above and
a compound (VII) or a salt thereof represented by the formula:

$R^3$—(C=O)—$X^3$—Y—X—Z (VII)

wherein $X^3$ is an optionally substituted alkylene chain, $R^3$ is a hydrogen atom or an optionally substituted hydrocarbon group, and the other symbols are as defined above are subjected to reductive amination to give a compound (VIII) or a salt thereof represented by the formula:

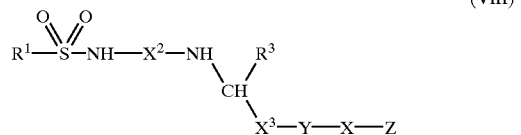

(VIII)

wherein each symbol is as defined above.

In the above formula (VIII), definition of the optionally substituted hydrocarbon group represented by $R^3$ is the same as that shown by $R^1$.

Definition of the substituent for the optionally substituted alkylene chain represented by $X^2$ and $X^3$ is the same as that shown by $R^1$.

Preferred examples of the reducing agent employed in this reductive alkylation include metal hydride complexes such as lithium aluminum hydride, trimethoxy lithium aluminum hydride, tri-tert-butoxy lithium aluminum hydride, aluminum sodium hydride, triethoxy aluminum sodium hydride, sodium boron hydride, trimethoxy sodium boron hydride, sodium boron cyanide hydride, triacetoxy sodium boron hydride, lithium boron hydride, lithium boron cyanide hydride, triethyl lithium boron hydride, etc. In addition, catalytic reduction (catalytic hydrogenation) can be employed. Examples of the catalyst include palladium catalysts such as palladium black, palladium carbon, palladium-silica gel, palladium-barium sulfate, etc., platinum catalysts such as oxidized platinum, platinum carbon, platinum black, etc., rhodium catalysts such as rhodium carbon, rhodium alumina, etc., ruthenium catalysts such as oxidized ruthenium, ruthenium carbon, etc., Raney nickel, etc. Said catalytic reduction is carried out under a hydrogen atmosphere. The amount of the catalyst to be employed ranges from about 0.0001 to about 2 mole, preferably about 0.001 to about 1 mole per mole of Compound (VI). The reduction reaction is usually carried out under atmospheric pressure but, if necessary, can be carried out under high pressure. Said pressure ranges from about 1 to about 150 times atmospheric pressure, preferably about 1 to about 100 times atmospheric pressure.

The reaction is usually carried out in a solvent. Any solvent can be used unless it inhibits this production method.

Examples of the solvent include alcohols such as methanol, ethanol, propanol, isopropanol, butanol, tert-butanol, etc., ethers such as dioxane, tetrahydrofuran, diethylether, tert-butylmethylether, diisopropylether, ethyleneglycol-dimethylether, etc., esters such as ethyl formate, ethyl acetate, n-butyl acetate, etc., halogenated hydrocarbons such as dichloromethane, chloroform, carbon tetrachloride, trichloroethylene, 1,2-dichloroethane etc., hydrocarbons such as n-hexane, benzene, toluene, etc., amides such as formamide, N,N-dimethylformamide, N,N-dimethylacetamide, etc., and additionally dimethylsulfoxide, sulfolane (tetramethylene-sulfone), hexamethylphosphorylamide, water, etc., and these can be used singly or as a mixture.

If necessary, this production method can be carried out in the presence of an acid. Examples of the acid include a mineral acid such as hydrochloric acid, hydrobromic acid, sulfuric acid, phosphoric acid, perchlorate, etc., a sulfonic acid such as methanesulfonic acid, ethanesulfonic acid, benzenesulfonic acid, toluenesulfonic acid, camphor sulfonic acid, etc., an organic acid such as formic acid, acetic acid, propionic acid, etc.

In the reaction, about 0.01 to about 20 moles (preferably about 0.1 to about 10 moles) of the acid is used per 1 mole of Compound (VI), and about 1 to about 2 moles of Compound (VII) is used per 1 mole of Compound (VI).

The reaction temperature ranges from about −30% to about 150° C., preferably about −10° C. to about 120° C.

The reaction time varies depending on the kind of compound (VI) or (VII), kind of solvent, the reaction temperature, etc. and usually ranges from about 10 minute to about 72 hours, preferably about 15 minutes to about 48 hours.

Compound (VIII) is further reacted with Compound (IX) represented by the formula:

$Q^2$—$X^4$—COOH (IX)

wherein $X^4$ is an optionally substituted alkylene chain, $Q^2$ is a halogen atom or a group of the formula: $R^4$—$SO_2$—O—

(wherein $R^4$ is a lower alkyl group optionally substituted with a halogen atom or an optionally substituted phenyl group), and the other symbols are as defined above to produce Compound (X) represented by the formula:

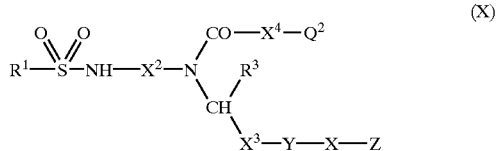

(X)

wherein each symbol is as defined above.

In the above formula, $Q^2$ is a halogen atom or a group of the formula: $R^4—S_2—O—$.

In the above formula, example of the halogen atom represented by $Q^2$ includes chlorine, bromine, iodine, etc. $R^4$ is a lower alkyl group optionally substituted with a halogen atom or an optionally substituted phenyl group. Example of the lower alkyl group represented by $R^4$ include methyl, ethyl, propyl, isopropyl, butyl, isobutyl, sec-butyl, tert-butyl, pentyl, isopentyl, neopentyl, hexyl, etc. Among others, methyl, ethyl, propyl, isopropyl, butyl, etc. are preferable. Examples of the halogen atom include fluorine, chlorine, bromine, iodine, etc. At any possible position, 1 to 9 (preferably 1 to 5) of these halogen atoms may be substituted.

Examples of the substituents for the optionally substituted phenyl group include lower alkyl (e.g., $C_{1-6}$ alkyl group such as methyl, ethyl, propyl, butyl, etc.), lower alkoxy group (e.g., $C_{1-6}$ alkoxy group such as methoxy, ethoxy, propoxy, butoxy, etc.), a halogen atom (e.g., fluorine, chlorine, bromine, iodine, etc.), nitro group, cyano group, carboxyl group, etc.

This production method is carried out by reacting a compound (VIII) or a salt thereof with a free acid (IX) or a salt thereof (inorganic salt, organic salt, etc.) or its reactive derivatives (e.g. acid halide, acid azide, acid anhydride, mixed acid anhydride, active amide, active ester, active thioester, etc.). Examples of the salt of the compound (VIII) include an acid addition salt with an acid which can form an acid addition salt with the above described compound (I).

Examples of the inorganic salt of the compound (IX) include a salt with alkali metal (e.g. a salt with sodium, potassium, etc.), a salt with alkaline earth metal (e.g. a salt with calcium, etc.), etc. Examples of the organic salt of the compound (IX) include a salt with trimethylamine, triethylamine, tert-butyldimethylamine, dibenzylmethylamine, benzyl-dimethylamine, N,N-dimethylaniline, pyridine, quinoline, etc.

Examples of the acid halide include acid chloride, acid bromide, etc. Examples of the mixed acid anhydride include mono-$C_{1-4}$alkyl carbonate mixed acid anhydride (e.g. a mixed acid anhydride of a free acid (IX) with monomethylcarbonate, monoethylcarbonate, monoisopropyl-carbonate, monoisobutylcarbonate, mono-(tert-butyl)carbonate, mono-benzylcarbonate, mono (p-nitrobenzyl) carbonate, monoallylcarbonate, etc.), $C_{1-6}$ alicyclic carboxylic acid mixed acid anhydride (e.g. a mixed acid anhydride of a free acid (IX) with acetic acid, cyanoacetic acid, propionic acid, butyric acid, isobutyric acid, valeric acid, isovaleric acid, pivalic acid, trifluoroacetic acid, trichloroacetic acid, acetoacetic acid, etc.), $C_{7-11}$ aromatic carboxylic acid mixed acid anhydride (e.g. a mixed acid anhydride of a free acid (IX) with benzoic acid, p-toluic acid, p-chlorobenzoic acid, etc.), organic sulfonic acid mixed acid anhydride (e.g. a mixed acid anhydride with methanesulfonic acid, ethanesulfonic acid, benzenesulfonic acid, p-toluenesulfonic acid, etc.), etc. Examples of the active amide include an amide with nitrogen-containing heterocyclic compound (e.g. an acid amide of a free acid (IX) with pyrazole, imidazole, benzotriazole, etc.; Said nitrogen-containing heterocyclic compound is optionally substituted with $C_{1-6}$ alkyl (e.g. methyl, ethyl, propyl, isopropyl, butyl, isobutyl, sec-butyl, tert-butyl, etc.), $C_{1-6}$ (alkoxy (e.g. methoxy, ethoxy, propoxy, isopropoxy, butoxy, tert-butoxy, etc.), a halogen atom (e.g. fluorine, chlorine, bromine, etc.), oxo, thioxo, $C_{1-6}$ alkylthio (e.g. methylthio, ethylthio, propylthio, butylthio, etc.), etc.), etc.

Examples of the active ester include organic phosphoric acid ester (e.g. diethoxyphosphoric acid ester, diphenoxyphosphoric acid ester, etc.), p-nitrophenylester, 2,4-dinitrophenylester, cyanomethylester, pentachlorophenylester, N-hydroxysuccinimide ester, N-hydroxy-phthalimide ester, 1-hydroxybenzotriazole ester, 6-chloro-1-hydroxy-benzotriazole ester, 1-hydroxy-1H-2-pyridone ester, etc.

Examples of the active thioester include ester with aromatic heterocyclic thiol compound (e.g. 2-pyridylthiol ester, 2-benzo-thiazolylthiol ester), etc., said heterocyclic group being optionally substituted with $C_{1-6}$ alkyl (e.g. methyl, ethyl, propyl, isopropyl, butyl, isobutyl, sec-butyl, tert-butyl, etc.), $C_{1-6}$ alkoxy (e.g. methoxy, ethoxy, propoxy, isopropoxy, butoxy, tert-butoxy, etc.), a halogen atom (e.g. fluorine, chlorine, bromine, etc.), $C_{1-6}$ alkylthio (e.g. methylthio, ethylthio, propylthio, butylthio, etc.), etc.

This production method is usually carried out in a solvent and, if necessary, in the presence of a base or a condensing agent (e.g. carbodiimides (e.g. DCC, WSC, DIC, etc.), phosphoric acid derivatives (e.g. cyanophosphorate diethyl, DPPA, BOP-Cl, etc.), etc.).

Examples of the solvent are the same as those described in the above Method A.

In the reaction, about 1 to about 5 moles (preferably about 1 to about 2 moles) of Compound (IX) is used per 1 mole of Compound (VIII).

The reaction temperature ranges about −50° C. to about 150° C., preferably about −20° C. to about 10%.

The reaction time varies depending on the kind of compound (VIII) or (TX), kind of the solvent and the base, the reaction temperature, etc. and usually ranges from about 1 minute to about 100 hours, preferably about 15 minutes to about 48 hours.

Compound (X) is subjected to ring-closure reaction to produce Compound (Ia) or a salt thereof represented by the formula:

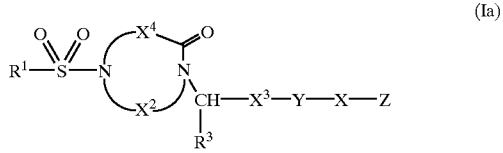

(Ia)

wherein each symbol is as defined above.

This ring-closure reaction is usually carried out in the presence of a base. Preferred examples of the base include an inorganic base such as alkali metal hydride (e.g. sodium hydride, potassium hydride, etc.), alkali metal hydroxide (e.g. lithium hydroxide, sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkali metal hydrogen carbonate (e.g. sodium hydrogen carbonate, potassium hydrogen carbonate, etc.), etc.,; an organic acid such as trimethylamine, triethylamine, diisopropylethylamine, pyridine, picoline, N-methylpyrrolidine, N-methylmorpholine, 1,5-diazabicyclo[4.3.0]non-5-ene, 1,4-diazabicyclo[2.2.2] octane, 1,8-diazabicyclo[5.4.0]-7-undecene, etc.; a lithium salt such as methyl lithium, n-butyl lithium, sec-butyl lithium, tert-butyl lithium, etc., a lithium amide such as lithium diisopropylamide, etc.

This reaction is usually carried out in a solvent. Examples of the solvent are the same as those described in the above Method A.

In the reaction, about 1 to about 100 moles (preferably about 1 to about 20 moles) of the base is used per 1 mole of the compound (I). If necessary, the base can be used as a solvent.

The reaction temperature ranges about −100 C. to about 200 C., preferably about −78 C. to about 150° C.

The reaction time varies depending on the kind of the compound (X), kind of solvent and the base, the reaction temperature, etc. and usually ranges from about 1 minute to about 200 hours, preferably about 5 minutes to about 100 hours.

Method D

A compound (XI) or a salt thereof represented by the formula:

wherein $X^5$ is an optionally substituted alkylene chain, and the other symbols are as defined in the above (1) is reacted with a compound (XII) or a salt thereof represented by the formula:

$$Z—X—Y—X^6—NHCH_2CH(OR^5)_2 \quad (XII)$$

wherein $X^6$ is an optionally substituted alkylene chain, $R^5$ is lower alkyl group, and the other symbols are as defined above to produce Compound (XIII) represented by the formula:

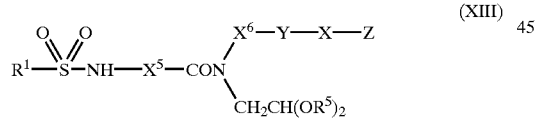

wherein each symbol is as defined above.

In the above formula, as the substituents in the optionally substituted alkylene chain represented by $X^5$ and $X^6$, those exemplified in the optionally substituted hydrocarbon group represented by $R^1$ can be employed.

Examples of the lower alkyl group represented by $R^5$ include methyl, ethyl, propyl, isopropyl, butyl, isobutyl, sec-butyl, tert-butyl, pentyl, isopentyl, neopentyl, hexyl, etc. Among others, methyl, ethyl, propyl, isopropyl, butyl, etc. are preferable.

In this reaction, reactive derivatives, reaction condition, reaction solvent, reaction time, etc. to be employed are the same as reactive derivatives, reaction condition, etc. exemplified in the reaction between Compound (VIII) and Compound (IX) in the method C or an analogous method thereto.

Compound (XIII) is subjected to ring-closure reaction to convert Compound (XIV) represented by the formula;

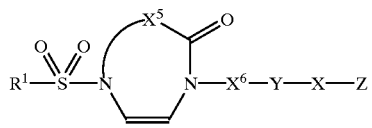

wherein each symbol is as defined above.

This ring-closure reaction is usually carried out in the presence of an acid. Examples of such an acid catalyst include carboxylic acid such as formic acid, acetic acid, propionic acid, benzoic acid, etc., sulfonic acid such as methanesulfonic acid, ethanesulfonic acid, camphor-sulfonic acid, benzenesulfonic acid, toluenesulfonic acid, etc., inorganic acid such as hydrochloric acid, hydrobromic acid, sulfuric acid, etc. Also, polyphosphoric acid, polyphosphoric acid ester, etc. can be used as the acid, and in some cases, Lewis acid can be used. Examples of the Lewis include tin chloride, zinc chloride, aluminum chloride, titanium chloride, tin bromide, zinc bromide, aluminum bromide, titanium bromide, and additionally, boron fluoride, etc.

This reaction is usually carried out in a solvent. As the solvent, any solvent can be selected as far as it does not inhibit the reaction. Examples of the solvent are the same as those described in the above Method A.

In the reaction, about 0.001 to about 100 moles of the acid is used per 1 mole of the compound (XIV). If necessary, the acid can be used as a solvent.

The reaction temperature ranges about −50° C. to about 200° C., preferably about −30° C. to about 15° C.

The reaction time varies depending on the kind of compound (XIV) or the acid, kind of solvent, the reaction temperature, etc. and usually ranges from bout about 10 minutes to about 48 hours, preferably about 20 minutes to about 24 hours.

If desired, Compound (XVI) is subjected to reduction of a double bond to produce Compound (Ib) or a salt thereof represented by the formula:

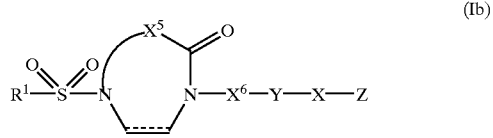

wherein a combination of a broken line and a full line is a single bond or a double bond, and the other symbols are as defined above.

Examples of the reduction agent to be employed for this reduction reaction include metal and acid. Examples of the metal include zinc, tin, iron, etc., Examples of the acid include carboxylic acids such as formic acid, acetic acid, propionic acid, etc., inorganic such as hydrochloric acid, hydrobromic acid, sulfuric acid, phosphoric acid, etc., etc. Also, reduction method mentioned in method C or an analogous method thereto can be employed, and any other reduction method may be employed as long as it does not inhibit the reaction.

This reaction is usually carried out in a solvent. As the solvent, any solvent can be selected as long as it does not inhibit the reaction. Examples of the solvent are the same as those described in the above Method C.

In the reaction, about 0.1 to about 100 moles of the reduction agent is used per 1 mole of the compound (XIV).

The reaction temperature ranges about −30° C. to about 150° C., preferably about −10° C. to about 120° C.

The reaction time varies depending on the kind of compound (XIV), kind of reduction agent, kind of solvent, the reaction temperature, etc. and usually ranges from about 10 minutes to about 72 hours, preferably about 15 minutes to about 48 hours.

Method E

Compound (XX) or a salt thereof represented by the formula:

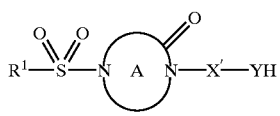

(XX)

wherein each symbol is as defined above is reacted with Compound (XXI) or a salt thereof represented by the formula:

Z—X$^7$—Q$^3$ wherein X$^7$ is a chemical bond or an optionally substituted alkylene chain, Q$^3$ is a halogen atom or a group of the formula: R$^6$—SO$_2$—O— (wherein R$^6$ is a lower alkyl group optionally substituted with a halogen atom or an optionally substituted phenyl group), and the other symbol is as defined above to produce Compound (I).

In the above formula, as the substituents for the optionally substituted alkylene chain represented by X$^7$, those exemplified in the optionally substituted hydrocarbon group represented by R" can be employed.

In the above formula, examples of the halogen atom represented by Q$^3$ include chlorine, bromine, iodine, etc.

In the above formula, R$^6$ is a lower alkyl group optionally substituted with a halogen atom or an optionally substituted phenyl group. Examples of the lower alkyl group represented by R$^6$ include methyl, ethyl, propyl, isopropyl, butyl, isobutyl, sec-butyl, tert-butyl, pentyl, isopentyl, neopentyl, hexyl, etc., and among others, methyl, ethyl, propyl, isopropyl, butyl, etc. are preferable. Examples of the halogen atom include fluorine, chlorine, bromine, iodine, etc. Said lower alkyl group may have at optional position 1 to 9, preferably 1 to 5 halogen atoms. Examples of the substituents in the optionally substituted phenyl group include lower alkyl (e.g., C$_{1-6}$ alkyl group such as methyl, ethyl, propyl, butyl, etc.), lower alkoxy group (e.g., C$_{1-6}$ alkoxy group such as methoxy, ethoxy, propoxy, butoxy, etc.), a halogen atom (e.g., fluorine, chlorine, bromine, iodine, etc.), nitro group, cyano group, carboxyl group, etc.

This method is to produce Compound (I) by reacting compound (XX) or a salt thereof with Compound (XXI) or a salt thereof.

This reaction is usually carried out in the presence of a base. Preferred examples of the base include an inorganic base such as alkali metal hydride (e.g. sodium hydride, potassium hydride, etc.), alkali metal hydroxide (e.g. lithium hydroxide, sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkali metal hydrogen carbonate (e.g. sodium hydrogen carbonate, potassium hydrogen carbonate, etc.), etc.; an organic acid such as trimethylamine, triethylamine, diisopropylethylamine, pyridine, picoline, N-methylpyrrolidine, N-methylmorpholine, 1,5-diazabicyclo[4.3.0]non-5-ene, 1,4-diazabicyclo[2.2.2]octane, 1,8-diazabicyclo[5.4.0]-7-undecene, etc.; a lithium salt such as methyl lithium, n-butyl lithium, sec-butyl lithium, tert-butyl lithium, etc., a lithium amide such as lithium diisopropylamide, etc.

This reaction is usually carried out in a solvent. Examples of the solvent are the same as those described in the above Method A.

In the reaction, about 0.8 to 10 moles (preferably about 0.9 to 5 moles) of Compound (XXI) and about 1 to about 100 moles (preferably about 1 to about 20 moles) of the base are used per 1 mole of the compound (XX). If necessary, the base can be used as a solvent.

The reaction temperature ranges from about −50° C. to about 150° C., preferably about −20° C. to about 100° C.

The reaction time varies depending on kind of Compound (XX), Compound (XXI), base or solvent, the reaction temperature, etc. and usually ranges from about 1 minute to about 200 hours, preferably about 5 minutes to about 100 hours.

This reaction can be promoted, in some cases, by using metal catalyst. Examples of the catalyst include palladium compound [e.g., palladium acetate, tetrakis(triphenylphosphine)palladium, bis(triphenylphosphine)palladium chloride, dichlorobis(triethylphosphine)palladium, tris(dibenzylideneacetone)dipalladium-2,2'-bis(diphenylphosphino)-1,1'-binaphthyl, etc.], nickel compound [e.g., tetrakis(triphenylphosphine)nickel, bis(triethylphosphine)nickel chloride, bis(triphenylphosphine)nickel chloride, etc.], rhodium compound [e.g., tri(triphenylphosphine)rhodium chloride, etc.], etc. Among others, palladium compound is preferable. The amount of the catalyst is about 1 to 0.000001 mole, preferably about 0.1 to 0.00001 mole per 1 mole of the compound (XX).

Also, this reaction may be carried out in a sealed tube.

Method F (Production of Compound (I) Wherein Z is an Optionally Substituted Amidino Group)

Compound (XXII) or a salt thereof represented by the formula:

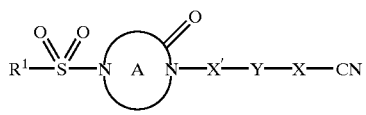

(XXII)

wherein each symbol is as defined above is reacted with Compound (XXIII) or a salt thereof represented by the formula:

R$^7$OH wherein R$^7$ is lower alkyl group to produce Compound (XXIV) or a salt thereof represented by the formula:

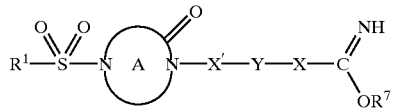

(XXIV)

wherein each symbol is as defined above, followed by reacting Compound (XXIV) or a salt thereof with amine to produce Compound (XXV) or a salt thereof represented by the formula:

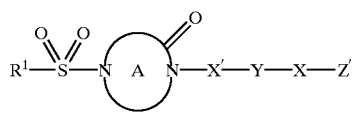

wherein Z' is an optionally substituted amidino group, and the other symbols are as defined above.

In the above formula, examples of the lower alkyl group represented by $R^7$ include $C_{1-4}$ alkyl group such as methyl, ethyl, propyl, isopropyl, butyl, isobutyl, sec-butyl, tert-butyl, etc., etc.

The reaction between Compound (XXII) and Compound (XXIII) is usually carried out in a solvent. Examples of the solvent are the same as those described in the above Method A. Compound (XXIII) itself may be used as the solvent.

This reaction is usually carried out in the presence of an acid (e.g., inorganic acid such as hydrochloric acid, hydrobromic acid, sulfuric acid, phosphoric acid, etc., organic acid such as methanesulfonic acid, toluenesulfonic acid, trifluoromethanesulfonic acid, acetic acid, trifluoroacetic acid, etc., etc.) and an base (e.g., potassium methoxide, sodium methoxide, sodium ethoxide, potassium-tert-butoxide, etc.). The amount of the acid and the base varies catalytic amount (about 0.001 mole) to excess amount.

The reaction temperature ranges from about −50° C. to about 150° C., preferably about −20° C. to about 100° C.

The reaction time varies depending on kind of Compound (XXII), acid, base or solvent, etc. and usually ranges from bout 30 minutes to about 240 hours, preferably about 1 hour to about 120 hours.

Compound (XXIV) is reacted with amine (e.g., primary amine such as ammonia; methylamine, ethylamine, propylamine, etc.; secondary amine such as dimethylamine, diethylamine, methylethylamine, di-n-propylamine, pyrrolidine, piperidine, morpholine, piperazine, 1-methylpiperazine, etc.; aromatic amine such as aniline, N-methylaniline, etc.; etc.) to produce Compound (XXV).

This reaction is usually carried out in a solvent. As the solvent, any solvent can be employed as long as it does not inhibit the reaction. The solvent exemplified in the above Method A is preferably employed, and also amine itself may be employed as the solvent.

The reaction temperature ranges about −20° C. to about 200° C., preferably about −10° C. to about 150° C.

The reaction time varies depending on kind of Compound (XXIV), amine and solvent, and reaction temperature and usually ranges from bout about 30 minutes to about 240 hours, preferably about 1 hour to about 120 hours.

If necessary, this reaction may be carried out in a sealed tube.

Compounds (II), (III), (IV), (V), (VI), (VII), (IX), (XI), (XII), (XX) and (XXII) employed as starting materials in the above-mentioned production methods A to F can be produced per se known methods or a similar method thereto.

a) Production Method of Compound (II)

i)

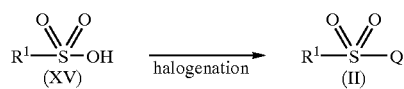

wherein each symbol is as defined above

This production method is carried out by halogenation of the compound (XV) or a salt thereof (inorganic salt, organic salt, etc.). Examples of the inorganic salt of the compound (XV) include a salt with alkali metal (e.g. a salt with sodium, a salt with potassium, etc.), a salt with alkaline earth metal (e.g. a salt with calcium, etc.). Examples of the organic salt of the compound (XV) include a salt with trialkylamine (e.g. a salt with trimethylamine, triethylamine, tert-butyldimethylamine, diisopropylethylamine, etc.), a salt with an aromatic tertiary amine (e.g. N,N-dimethylaniline, pyridine, quinoline, etc.). Examples of a halogenating agent include e.g. phosphorous trichloride, phosphorous tribromide, phosphorous pentachloride, phosphorylchloride, phosphorylbromide, thionylchloride, thionyl-bromide, etc.

The reaction can be carried out by reacting the compound (XV) with the halogenating agent as a solvent in the presence of no other solvent. The reaction can be carried out in the presence of a solvent other than the halogenating agent. Examples of the solvent include ethers such as dioxane, tetrahydrofuran, diethylether, diisopropyl-ether, dimethoxyethane, etc., halogenated hydrocarbons such as dichloromethane, chloroform, carbon tetrachloride, etc., aromatic hydrocarbons such as benzene, toluene, chlorobenzene, etc., amides such as N,N-dimethylformamide, N,N-dimethylacetamide, etc., and these can be used singly or as a mixture.

In the reaction, about 1 to about 100 moles (preferably about 1 to about 50 moles) of the halogenating agent is used per 1 mole of the compound (XV). The reaction temperature ranges from about −30° C. to about 250° C., preferably about −20° C. to about 200° C. The reaction time varies depending on the kind of compound (XV) or the halogenating agent, kind of solvent, the reaction temperature, etc. and usually ranges from about 1 minute to about 72 hours, preferably about 10 minutes to about 24 hours.

ii)

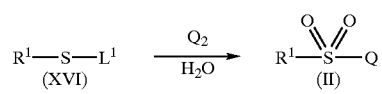

wherein $L^1$ is a hydrogen atom or a leaving group, and the other symbols are as defined above.

This production method is carried out by reacting the compound (XVI) with chlorine or bromine in the presence of water to produce the compound (II). Examples of the leaving group represented by L1 include —CN, —SO$_3$Na, —C(=NH)NH$_2$, etc.

The reaction is usually carried out in a solvent and preferable examples of the solvent include that exemplified in the above described Method C. In the reaction, about 1 to about 100 moles, preferably about 1 to about 30 moles of the chlorine or bromine is used per 1 mole of the compound (XVI). The reaction temperature ranges from about −50° C. to about 180° C., preferably about −30° C. to about 120° C.

There are many known methods for producing a sulfonyl chloride or a sulfonyl bromide of the compound (II) and the compound (II) can be produced by the above method i) or ii) as well as known methods or a method similar thereto.

b) Production Method of the Compound (III)

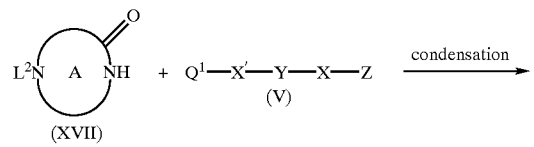

$$\text{(XVIII)} \xrightarrow{\text{deprotection}}$$

$$\text{(III)}$$

wherein $L^2$ is a protective group for an amino group, and other symbols are as defined above.

In the above formulas (XVII) and (XVIII), examples of the protective group represented by $L^2$ include formyl group, $C_{1-6}$ alkyl-carbonyl group (e.g. acetyl, ethylcarbonyl, etc.), benzyl group, tert-butyloxycarbonyl group, benzyloxy-carbonyl group, allyloxycarbonyl group, phenyl-carbonyl group, $C_{1-6}$ alkoxy-carbonyl group (e.g. methoxycarbonyl, ethoxycarbonyl, etc.), $C_{7-10}$ aralkyl-carbonyl group (e.g. benzylcarbonyl, etc.), trityl group, etc. These protective groups may be substituted with 1 to 3 halogen atoms (e.g. fluorine, chlorine, bromine, etc.), nitro group, etc.

This production method is carried out by reacting the compound (XVII) with a compound (V) or its reactive derivatives to produce the compound (XVIII).

The reaction conditions of this production method is the same as described in the above Method B. The compound (III) can be produced by removing the protective group of the compound (XVIII).

Examples of the method for removing the protective group include per se known methods or a similar method thereto such as a method using acid, base, reduction, ultraviolet light, palladium acetate, etc.

c) Production Method of the Compound (IV)

$$\text{(II)} + \text{(XIX)} \xrightarrow{\text{condensation}} \text{(IV)}$$

wherein each symbol is as defined above.

This production method is carried out by reacting the compound (II) with the compound (XIX) to produce the compound (IV). The reaction conditions of this production method are the same as described in the above Method A.

Compounds (V), (VI), (VII), (IX), (XI) and (XII) can be produced by per se known methods or a similar method thereto.

When a free form of the compound is obtained according to the above described reaction of the present invention, it can be transformed into a salt thereof according to per se methods. When a salt of the compound is obtained according to the above described reaction of the present invention, it can be transformed into a free form or the other salt thereof according to per se methods.

The compound (I) of this invention can be isolated from the reaction mixture by a conventional methods separation and purification means such as extraction, concentration, neutralization, filtration, recrystallization, column chromatography and thin-layer chromatography, etc.

Salts of the compound (I) can be obtained by per se known methods, e.g. by adding an inorganic acid or an organic acid to the compound (I).

When stereoisomers are present in the compounds (I), individual isomers or a mixture thereof are included in the scope of the present invention. And, it is also possible to produce these isomers individually. The compounds (I) may be hydrated.

The compounds (I) of the present invention or a salt thereof are low in toxicity, inhibit FXa and have anti-coagulant activity, therefore, they are useful for the prevention or treatment of the following diseases of animals, especially mammals (e.g. human, monkey, cat, pig, horse, cow, mouse, rat, guinea pig, dog, rabbit, etc.). Among others, they are preferably used for the prevention or treatment of cerebral infarction (especially due to atrial fibrillation or auricular fibrillation), deep vein thrombosis, etc.

brain:

cerebral infarction due to atrial fibrillation or auricular fibrillation, acute ischemic cerebral apoplexy, acute phase cerebral thrombosis, cerebral vasospasm after subarachnoid hemorrhage, Alzheimer's disease, transient ischemic attack (TIA), mixed dementia, cerebrovascular dementia, multiple sclerosis dementia, heart:

acute cardiac infarction, sequela of cardiac infarction, unstable angina, angina pectoris, reobturation or restenosis after coronary intervention such as stent-indwelling or PTCA (percutaneous transluminol coronary angioplasty) and atherectomy, periphery:

deep vein thrombosis, peripheral arterial obstruction, adult respiratory distress syndrome (ARDS), chronic renal disease (e.g. diabetic nephropathy, chronic glomerulonephritis, IgA nephropathy, etc.), diabetic cardiovascular disorder, diabetic pain, diabetic nerve disturbance, others:

thrombocytopenia due to dialysis, thrombocytopenia due to operation, arteriosclerosis, cancer metastasis, systemic inflammation reaction syndrome (SIRS) or disseminated intravascular coagulation (DIC) in cases of pancreatitis, sepsis or cancer, rejection after transplantation, protecting organs or ameliorating function of organs after transplantation, various organ failures (e.g. pulmonary failure, hepatic insufficiency, renal insufficiency, heart failure, etc.) due to shock or DIC.

The compound (I) of the present invention or a salt thereof, alone or in combination with a pharmaceutically acceptable carrier, can be administered orally or non-orally.

Examples of a pharmaceutical composition for oral administration of the compound (I) or a salt thereof of the present invention include tablets (including sugar-coated tablet, film coating tablet), pills, granules, powders, capsules (including soft capsules), syrups, emulsions, suspensions, etc. Examples of a pharmaceutical composition for non-oral administration of the compound (I) or a salt thereof of the present invention include injections, inhalants, drops, suppositories, etc.

The content of the compound (I) or a salt thereof in the pharmaceutical composition of this invention varies depending on the kind of formulation and is usually about 2 to about 85 weight %, preferably about 5 to about 70 weight % based on the total weight of the composition.

Examples of the method for preparing the pharmaceutical compositions containing the compound (I) or a salt thereof include conventional methods generally used in this field. In addition, when the above pharmaceutical compositions are prepared, if desired, an appropriate amount of an additive which is generally used in this field such as an excipient, a binder, an disintegrating agent, a lubricant, a sweetener, a surfactant, a suspending agent, an emulsifier, etc. can be added to the compositions.

For example, a tablet of the compound (I) or a salt thereof may contain an excipient, a binder, an disintegrating agent, a lubricant, etc.; a pill and a granulate may contain an excipient, a binder, an disintegrating agent, etc.; a powder and a capsule may contain an excipient, etc.; a syrup may contain a sweetener, etc.; and an emulsion or a suspension may contain a surfactant, a suspending agent, an emulsifier, etc.

Examples of the excipient include lactose, sucrose, glucose, starch, fine crystalline cellulose, powdered glycyrrhiza, mannitol, sodium hydrogen carbonate, calcium phosphorate, calcium sulfate, etc.

Examples of the binder include 5 to 10 weight % of starch solution, 10 to 20 weight % of gum arabic or gelatin solution, 1 to 5 weight % of traganth solution, carboxymethylcellulose solution, sodium alginate solution, glycerin, etc.

Examples of the disintegrating agent include starch, calcium carbonate, etc.

Examples of the lubricant include magnesium stearate, stearic acid, calcium stearate, purified talc, etc.

Examples of the sweetener include glucose, fructose, invert sugar, sorbitol, xylitol, glycerin, simple syrup, etc.

Examples of the surfactant include sodium lauryl sulfate, polysorbate 80, sorbitan mono fatty acid ester, stearic acid polyoxyl 40, etc.

Examples of the suspending agent include gum arabic, sodium alginate, sodium carboxymethylcellulose, methylcellulose, bentonite, etc.

Examples of the emulsifier include gum arabic, traganth, gelatin, polysorbate 80, etc.

In addition, when the above described compositions are prepared, if desired, an appropriate amount of a colorant, a preservative, an aromatic, a flavoring, a stabilizer, a viscous liquid, etc. which is generally used in this field can be added to the compositions.

The compound (I) or a salt thereof is low in toxicity and stable, therefore, it can be used safely. While the dosage of the compound (I) can vary with condition or body weight of patients, kind of the compound and administration routes, etc., when administered orally to a patient of e.g. thrombosis, a dose of about 1 to 1000 mg, preferably about 3 to 300 mg, more preferably about 10 to 200 mg of the active ingredient [compound (I)], per day for an adult (body weight: about 60 kg), divided into one to three times, is appropriate.

When Compound (I) or a salt thereof of the present invention is non-orally administered, it is usually administered in the form of a liquid preparation (e.g. injection). Unit dosage varies depending on subject or organ to be administered to, symptom, administration route, etc. For example, when administered in the form of injection, the preferred unit dosage of intravenous injection usually ranges from about 0.01 mg to about 100 mg, preferably about 0.01 to about 50 mg, and more preferably about 0.01 to about 20 mg per 1 kg body weight. Examples of the injection include subcutaneous injection, intracutaneous injection, intramuscular injection, drip, etc. Examples of the sustained release preparation include iontophoresis transdermal agent, etc.

Said injection is prepared by a per se known method, that is, by dissolving, suspending or emulsifying Compound (I) or a salt thereof of the present invention in sterilized aqueous or oily solution.

Examples of the aqueous solution for injection include isotonic solution comprising isotonic sodium chloride solution brine, glucose or the other additive (e.g., D-sorbitol, D-mannitol, sodium chloride, etc.), etc., and an appropriate solubilizing agent such as alcohol (e.g. ethanol), polyalcohol (e.g. propyleneglycol, polyethyleneglycol), non-ionic surfactant (e.g. polysorbate 80, HCO-50), etc. may be combined. Examples of the oily solution for injection include sesame oil, soybean oil, etc., and an solubilizing agent such as benzyl benzoate, benzylalcohol, etc. may be combined. In addition, buffer solution (e.g., phosphoric acid buffer solution, sodium acetate buffer solution), soothing agent (e.g., benzalkonium chloride, procaine hydrochlide, etc.), stabilizing agent (e.g., human serum albumin, polyethyleneglycol, etc.), preservative (e.g., benzylalcohol, phenol, etc.), etc. maybe combined. Thus prepared injection is usually filled in ampoules.

The pharmaceutical composition of the present invention can be used in combination with thrombolytic drug (e.g. tPA, heparin, urokinase, etc.), drug for treating Alzheimer's disease (e.g. Avan, Calan, etc.), drug for treating cholesterol (e.g. HMG-CoA reductase inhibitor such as Simvastatin, Pravastatin, etc., etc.), TG (triglyceride) decreasing drug (antihyperlipoproteinemic agent) (e.g. Clofibrate, etc.), AII antagonist (e.g. Blopress, etc.), anti-thrombocyte drug (e.g. aspirin, etc.), Ca antagonist (e.g. Calsiot, Amlodipine, etc.) etc., or the active ingredient of these drugs can be added to the pharmaceutical composition of the present invention.

BEST MODE FOR CARRYING OUT THE INVENTION

The present invention is hereinafter described in more detail by means of the following Reference Examples, Working Examples, Formulation Examples and Experimental Examples which are not to be construed as limitative. Also, the following embodiments may be modified within the scope of the present invention.

Elution in column chromatography in Reference Examples and Working Examples was observed under TLC (Thin Layer Chromatography). In the TLC observation, silica gel $60F_{254}$ (Merck) was used as a TLC plate, a solvent used for eluting the column chromatography was used as a mobile phase, and UV detector was employed for detection. Kiesel gel 60 (70 to 230 mesh; Merck) was used for a silica gel column chromatography.

The proton nuclear magnetic resonance (1H-NMR) spectra were recorded on a Varian Gemini-200 (200 MHz) spectrometer using tetramethylsilane as the internal or external standard and chemical shifts are given in δ values (ppm). Infrared (IR) spectra were recorded on a Shimazu FTIR-8200 spectrometer. In the mixture of solvents, the value indicated in the parentheses means the ratio of volume of each solvent. The symbol % for the solution stands for grams per 100 ml solution. The following abbreviations were used in Reference Examples and Working Examples:

| | |
|---|---|
| s | singlet |
| d | doublet |
| t | triplet |
| q | quartet |
| quint | quintet |
| Abq | AB type quartet |

| | |
|---|---|
| dd | double doublet |
| m | multiplet |
| br | broad |
| brs | broad singlet |
| J | coupling constant |
| WSC | water soluble carbodiimide |
| THF | tetrahydrofuran |
| DMF | dimethylformamide |
| DMSO | dimethylsulfoxide |
| Fmoc | 9-fluorenylmethoxycarbonyl |
| HOBt | 1-hydroxybenzotriazole |
| DBU | 1,8-diazabicyclo[5.4.0]-7-undecene |

WORKING EXAMPLE

Reference Example 1
4-(naphthalene-2-sulfonyl)-2-piperazinone

In THF (30 ml) and DMF (30 ml) was dissolved 2-piperazinone (3.00 g), and to the solution was added triethylamine (5.02 ml). Under ice-cooling, to the mixture was added dropwise a solution of naphthalene-2-sulfonyl chloride (8.16 g) in THF (30 ml), and the mixture was stirred at room temperature overnight. The reaction solution was concentrated under reduced pressure. The residue was washed with sodium hydrogen carbonate solution, water and ethanol to give pale brown crystals of the title compound (7.15 g).
$^1$H-NMR (CDCl$_3$) δ: 3.33–3.50 (4H, m), 3.79 (2H, s), 6.05 (1H, brs), 7.63–7.80 (3H, m), 7.90–8.07 (3H, m), 8.38 (1H, s).
IR (KBr): 1680, 1651, 1342, 1323, 1165 cm$^{-1}$.

Reference Example 2
1-(4-cyanobenzyl)-4-(naphthalene-2-sulfonyl)-2-piperazinone

In THF (8 ml) and DMF (2 ml) was dissolved 4-(naphthalene-2-sulfonyl)-2-piperazinone (290 mg), and to the mixture was added sodium hydride (60% in oil, 40 mg) at 0° C. The mixture was stirred for 20 minutes, to which was added 4-cyanobenzylchloride (182 mg), and the mixture was stirred at room temperature overnight. The reaction solution was concentrated under reduced pressure. To the residue was added water, and the mixture was extracted with ethyl acetate. The extract was washed with saturated brine, dried (MgSO$_4$) and concentrated. The residue was purified with silica gel column chromatography (hexane:ethyl acetate=1:2) to give colorless crystals of the title compound (220 mg).
$^1$H-NMR (CDCl$_3$) δ: 3.30–3.42 (4H, m), 3.89 (2H, s), 4.58 (2H, s), 7.24 (2H, d, J=8.5 Hz), 7.53 (2H, d, J=8.5 Hz), 7.68–7.80 (3H, m), 7.92–8.04 (3H, m), 8.38 (1H, d, J=1.6 Hz).
IR (KBr): 2228, 1649, 1346, 1171 cm$^{-1}$.

Reference Example 3
4-(tert-butoxycarbonyl)-2-piperazinone

To a mixture of 2-piperazinone (3.00 g) and acetonitrile (50 ml) was added dropwise di-tert-butylbicarbonate (7.20 g), and the mixture was stirred at room temperature for 2 hours. The reaction solution was concentrated under reduced pressure, and precipitated crystals were washed with ether to give colorless crystals of the title compound (4.77 g).
$^1$H-NMR (CDCl$_3$) δ: 1.48 (9H, s), 3.33–3.43 (2H, m), 3.64 (2H, t, J=5.3 Hz), 4.09 (2H, s), 6.40–6.70 (1H, br).
IR (KBr): 1696, 1667, 1400, 1341, 1130 cm$^{-1}$.

Reference Example 4
4-(tert-butoxycarbonyl)-1-(4-cyanobenzyl)-2-piperazinone

According to a similar method described in Reference Example 2, the title compound of colorless crystals was obtained from 4-(tert-butoxycarbonyl)-2-piperazinone and 4-cyanobenzylchloride.
$^1$H-NMR (CDCl$_3$) δ: 1.47 (9H, s), 3.28 (2H, t, J=5.2 Hz), 3.63 (2H, t, J=5.5 Hz), 4.18 (2H, s), 4.66 (2H, s), 7.37 (2H, d, J=8.0 Hz), 7.64 (2H, d, J=8.0 Hz).
IR (KBr): 2224, 1690, 1651, 1424, 1341, 1246 cm$^{-1}$.

Reference Example 5
1-(4-cyanobenzyl)-2-piperazinone Hydrochloride A solution of 4 N hydrochloric acid in ethyl acetate (20 ml) was added to 4-(tert-butoxycarbonyl)-1-(4-cyanobenzyl)-2-piperazinone (1.10 g), and the mixture was stirred at room temperature for 1 hour. The reaction solution was concentrated. The residue was crystallized from ethanol to give colorless crystals of the title compound (812 mg).
$^1$H-NMR (DMSO-d$_6$) δ: 3.35–3.55 (4H, m), 3.81 (2H, s), 4.67 (2H, s), 7.51 (2H, d, J=8.2 Hz), 7.82 (2H, d, J=8.2 Hz), 9.75 (2H, brs).
IR (KBr): 2928, 2238, 1657, 1491, 1414, 1350 cm$^{-1}$.

Reference Example 6
4-(6-chloronaphthalene-2-sulfonyl)-1-(4-cyanobenzyl)-2-piperazinone A mixture of 1-(4-cyanobenzyl)-2-piperazinone hydrochloride (201 mg), 6-chloronaphthalene-2-sulfonyl chloride (205 mg), sodium carbonate (254 mg), ethyl acetate (10 ml) and water (5 ml) was stirred at room temperature for 2 hours. The organic layer was separated, washed with saturated brine, dried (MgSO$_4$) and concentrated. The residue was purified with silica gel column chromatography (hexane:ethyl acetate=1:2) to give pale pink crystals of the title compound (239 mg).
$^1$H-NMR (CDCl$_3$) δ: 3.37 (4H, s), 3.87 (2H, s), 4.59 (2H, s), 7.28 (2H, d, J=7.9 Hz), 7.57 (2H, d, J=7.9 Hz), 7.58–7.66 (1H, m), 7.78 (1H, dd, J=8.5, 1.9 Hz), 7.90–7.98 (3H, m), 8.35 (1H, d, J=1.4 Hz).
IR (KBr): 2232, 1651, 1346, 1167, 698 cm$^{-1}$.

Reference Example 7
4-(tert-butoxycarbonyl)-1-(3-cyanobenzyl)-2-piperazinone

According to a similar method described in Reference Example 2, the title compound of colorless crystals was obtained from 4-(tert-butoxycarbonyl)-2-piperazinone and 3-cyanobenzylchloride.
$^1$H-NMR (CDCl$_3$) δ: 1.47 (9H, s), 3.28 (2H, t, J=5.4 Hz), 3.64 (2H, t, J=5.4 Hz), 4.18 (2H, s), 4.64 (2H, s), 7.42–7.68 (4H, m).
IR (KBr): 2230, 1705, 1653, 1420, 1342, 1240 cm$^{-1}$.

Reference Example 8
1-(3-cyanobenzyl)-2-piperazinone hydrochloride

According to a similar method described in Reference Example 5, the title compound of colorless crystals was obtained from 4-(tert-butoxycarbonyl)-1-(3-cyanobenzyl)-2-piperazinone.
$^1$H-NMR (DMSO-d$_6$) δ: 3.37–3.57 (4H, m), 3.81 (2H, s), 4.65 (2H, s), 7.52–7.80 (4H, m), 9.85 (2H, brs).
IR (KBr): 2926, 2230, 1659, 1497, 1429, 1354, 693 cm$^{-1}$.

Reference Example 9
4-(6-chloronaphthalene-2-sulfonyl)-1-(3-cyanobenzyl)-2-piperazinone According to a similar method described in Reference Example 6, the title compound of pale pink crystals was obtained from 1-(3-cyanobenzyl)-2-piperazinone hydrochloride and 6-chloronaphthalene-2-sulfonyl chloride.

$^1$H-NMR (CDCl$_3$) δ: 3.37 (4H, s), 3.86 (2H, s), 4.56 (2H, s), 7.38–7.49 (3H, m), 7.52–7.65 (2H, m), 7.78 (1H, dd, J=8.8, 1.8 Hz), 7.90–7.98 (3H, m), 8.35 (1H, s).

IR (KBr): 2230, 1647, 1350, 1165, 963, 698 cm$^{-1}$.

Reference Example 10
4-(tert-butoxycarbonyl)-1-(trans-4-cyanocyclohexan-1-ylmethyl)-2-piperazinone According to a similar method described in Reference Example 2, the title compound of colorless crystals was obtained from 4-(tert-butoxycarbonyl)-2-piperazinone and trans-4-cyano-1-methanesulfonyloxymethylcyclohexane.

$^1$H-NMR (CDCl$_3$) δ: 0.98–1.07 (2H, m), 1.47 (9H, s), 1.42–1.86 (5H, m), 2.06–2.22 (2H, m), 2.32–2.49 (1H, m), 3.24–3.37 (4H, m), 3.64 (2H, t, J=5.4 Hz), 4.08 (2H, s).

IR (KBr): 2238, 1678, 1647, 1426, 1289, 1171 cm$^{-1}$.

Reference Example 11
4-(6-chloronaphthalene-2-sulfonyl)-1-(trans-4-cyanocyclohexan-1-ylmethyl)-2-piperazinone A solution of 4 N hydrochloric acid in ethyl acetate (20 ml) was added to 4-(tert-butoxycarbonyl)-1-(trans-4-cyanocyclohexan-1-ylmethyl)-2-piperazinone (386 mg), and the mixture was stirred at room temperature for 2 hours. The reaction solution was concentrated. To the residue were added 6-chloronaphthalene-2-sulfonyl chloride (313 mg), sodium carbonate (318 mg), ethyl acetate (10 ml) and water (10 ml), and the mixture was stirred at room temperature for 2 hours. The organic layer was separated, washed with saturated brine, dried (MgSO$_4$) and concentrated. The residue was purified with silica gel column chromatography (hexane:ethyl acetate=1:2) to give colorless crystals of the title compound (574 mg).

$^1$H-NMR (CDCl$_3$) δ: 0.85–1.10 (2H, m), 1.37–1.77 (5H, m), 2.00–2.15 (2H, m), 2.26–2.44 (1H, m), 3.20 (2H, d, J=7.0 Hz), 3.39 (4H, s), 3.76 (2H, s), 7.60 (1H, dd, J=8.8, 2.0 Hz), 7.79 (1H, dd, J=8.6, 1.8 Hz), 7.89–7.98 (3H, m), 8.34 (1H, s).

IR (KBr): 2242, 1655, 1451, 1341, 1163, 700 cm$^{-1}$.

Reference Example 12
4-(tert-butoxycarbonyl)-1-(5-cyano-2-thienylmethyl)-2-piperazinone According to a similar method described in Reference Example 2, the title compound of colorless crystals was obtained from 4-(tert-butoxycarbonyl)-2-piperazinone and 5-cyano-2-thienylmethylbromide.

$^1$H-NMR (CDCl$_3$) δ: 1.47 (9H, s), 3.38 (2H, t, J=5.4 Hz), 3.65 (2H, t, J=5.4 Hz), 4.14 (2H, s), 4.74 (2H, s), 7.02 (1H, d, J=3.8 Hz), 7.50 (1H, d, J=3.8 Hz).

IR (KBr): 2218, 1703, 1649, 1425, 1337, 1186 cm$^{-1}$.

Reference Example 13
4-(6-chloronaphthalene-2-sulfonyl)-1-(5-cyano-2-thienylmethyl)-2-piperazinone According to a similar method described in Reference Example 11, the title compound of colorless crystals was obtained from 4-(tert-butoxycarbonyl)-1-(5-cyano-2-thienylmethyl)-2-piperazinone.

$^1$H-NMR (CDCl$_3$) δ: 3.35–3.50 (4H, m), 3.84 (2H, s), 4.66 (2H, s), 6.93 (1H, d, J=3.9 Hz), 7.42(1H, d, J=3.9 Hz), 7.61(1H, dd, J=8.9, 1.9 Hz), 7.77 (1H, dd, J=8.8, 1.8 Hz), 7.89–7.97(3H, m), 8.35(11H, s).

IR (KBr): 2218, 1663, 1346, 1165, 959, 694 cm$^{-1}$.

Reference Example 14
4-benzyloxycarbonyl-2-piperazinone

A mixture of 2-piperazinone (10 g), benzyl chlorocarbonate (20.5 g), sodium carbonate (31.8 g), ethyl acetate (200 ml) and water (200 ml) was stirred at room temperature for 2 hours. The organic layer was separated, washed with saturated brine, dried (MgSO$_4$) and concentrated. The resulting crystals was filtered, washed with ethyl acetate-ether and dried to give colorless crystals of the title compound (18.5 g.)

$^1$H-NMR (CDCl$_3$) δ: 3.35–3.47 (2H, m), 3.71 (2H, t, J=5.4 Hz), 4.17 (2H, s), 6.22–6.42 (1H, br), 7.37 (5H, s).

IR (KBr): 1711, 1663, 1412, 1337, 1287 cm$^{-1}$.

Reference Example 15
4-benzyloxycarbonyl-1-(4-bromobenzyl)-2-piperazinone

According to a similar method described in Reference Example 2, the title compound of colorless oil was obtained from 4-benzyloxycarbonyl-2-piperazinone and 4-bromobenzylbromide.

$^1$H-NMR (CDCl$_3$) δ: 3.26 (2H, t, J=5.4 Hz), 3.67 (2H, t, J=5.4 Hz), 4.23 (2H, s), 4.56 (2H, s), 5.15 (2H, s), 7.14 (2H, d, J=8.2 Hz), 7.35 (5H, s), 7.46 (2H, d, J=8.2 Hz).

IR (KBr): 1705, 1651, 1489, 1427, 1233, 1124 cm$^{-1}$.

Reference Example 16
4-benzyloxycarbonyl-1-[4-(4-pyridyl)benzyl]-2-piperazinone

A mixture of 4-benzyloxycarbonyl-1-(4-bromobenzyl)-2-piperazinone (807 mg), 4-pyridylboric acid (244 mg), tetrakis (triphenylphosphine)palladium (69 mg), 2M sodium carbonate solution (2 ml), toluene (8 ml) and ethanol (2 ml) was refluxed overnight. After the mixture was cooled, ethyl acetate was added to the reaction solution. The mixture was washed with water and saturated brine, dried (MgSO$_4$) and concentrated. The residue was purified with silica gel column chromatography (ethyl acetate) to give colorless crystals of the title compound (283 mg).

$^1$H-NMR (CDCl$_3$) δ: 3.32 (2H, t, J=5.1 Hz), 3.70 (2H, t, J=5.3 Hz), 4.27 (2H, s), 4.68 (2H, s), 5.16 (2H, s), 7.36 (5H, s), 7.38 (2H, d, J=8.7 Hz), 7.49 (2H, d, J=6.1 Hz), 7.62 (2H, d, J=8.7 Hz), 8.67 (2H, d, J=6.1 Hz).

IR (KBr): 1705, 1688, 1644, 1431, 1292, 1244 cm$^{-1}$.

Reference Example 17
4-benzyloxycarbonyl-1-[4-(tert-butoxycarbonylamino)benzyl]-2-piperazinone According to a similar method described in Reference Example 2, the title compound of pale yellow amorphous was obtained from 4-benzyloxycarbonyl-2-piperazinone and 4-(tert-butoxycarbonylamino)benzylbromide.

$^1$H-NMR (CDCl$_3$) δ: 1.51 (9H, s), 3.23 (2H, t, J=5.2 Hz), 3.63 (2H, t, J=5.3 Hz), 4.22 (2H, s), 4.55 (2H, s), 5.15 (2H, s), 7.10–7.40 (10H, m).

IR (KBr): 1707, 1655, 1530, 1235, 1163 cm$^{-1}$.

Reference Example 18
1-[4-(tert-butoxycarbonylamino)benzyl]-4-(6-chloronaphthalene-2-sulfonyl)-2-piperazinone In ethanol (15 ml) was dissolved 4-benzyloxy-carbonyl-1-[4-(tert-butoxycarbonylamino)benzyl]-2-piperazinone (401 mg), and to the solution was added 10% palladium on carbon (Pd—C) (160 mg). The mixture was vigorously stirred for 4 hours under hydrogen atmosphere, and the catalyst was removed. The solvent was evaporated, and to the residue was were added 6-chloronaphthalene-2-sulfonyl chloride (261 mg), sodium carbonate (212 mg), ethyl acetate (20 ml) and water (20 ml). The mixture was stirred at room temperature for 3 hours. The organic layer was separated, washed with saturated brine, dried (MgSO$_4$) and concentrated. The residue was purified with silica gel column chromatography (ethyl acetate:methanol=10:1) to give pale pink crystals of the title compound (340 mg).

¹H-NMR (CDCl₃) δ: 1.51 (9H, s), 3.29 (4H, m), 3.84 (2H, s), 4.47 (2H, s), 6.45 (1H, s), 7.07 (2H, d, J=8.6 Hz), 7.25 (2H, d, J=8.6 Hz), 7.60 (1H, dd, J=8.8, 2.0 Hz), 7.76 (1H, dd, J=8.7, 1.9 Hz), 7.88–7.97 (3H, m), 8.33 (1H, d, J=1.4 Hz).

IR (KBr): 1699, 1644, 1534, 1346, 1337, 1240, 1163 cm⁻¹.

Reference Example 19

1-(4-aminobenzyl)-4-(6-chloronaphthalene-2-sulfonyl)-2-piperazinone hydrochloride A solution of 4 N hydrochloric acid in ethyl acetate (10 ml) was added to a solution of 1-[4-(tert-butoxycarbonylamino)benzyl]-4-(6-chloronaphthalene-2-sulfonyl)-2-piperazinone (530 mg) in methanol (2 ml), and the mixture was stirred at room temperature for 3 hours. The reaction solution was concentrated, and the resulting crystals were filtered, washed with ethyl acetate-ether and dried to give the title compound (457 mg).

¹H-NMR (DMSO-d₆) δ: 3.22–3.45 (4H, m), 3.76 (2H, s), 4.47 (2H, s), 7.21 (4H, s), 7.73 (1H, dd, J=8.7, 2.1 Hz), 7.87 (1H, dd, J=8.7, 1.9 Hz), 8.18 (1H, d, J=8.6 Hz), 8.24–8.33 (2H, m), 8.59 (1H, d, J=1.8 Hz).

IR (KBr): 2934, 1651, 1493, 1348, 1337, 1161, 700 cm⁻¹.

Reference Example 20

4-benzyloxycarbonyl-1-[2-(1-tert-butoxycarbonyl-4-piperidyl)ethyl]-2-piperazinone According to a similar method described in Reference Example 2, oil of the title compound was obtained from 4-benzyloxycarbonyl-2-piperazinone and 1-tert-butoxycarbonyl-4-(2-methanesulfonyloxyethyl)piperidine.

¹H-NMR (CDCl₃) δ: 1.00–1.25 (2H, m), 1.45 (9H, s), 1.30–1.58 (3H, m), 1.58–1.70 (2H, m), 2.56–2.78 (2H, m), 3.33 (2H, t, J=5.2 Hz), 3.38–3.50 (2H, m), 3.71 (2H, t, J=5.3 Hz), 3.97–4.20 (2H, m), 4.14 (2H, s), 5.15 (2H, s), 7.26 (5H, s).

IR (KBr): 1694, 1657, 1426, 1236, 1163 cm⁻¹.

Reference Example 21

1-[2-(1-tert-butoxycarbonyl-4-piperidyl)ethyl]-4-(6-chloronaphthalene-2-sulfonyl)-2-piperazinone According to a similar method described in Reference Example 18, pale pink crystals of the title compound were obtained from 4-benzyloxycarbonyl-1-[2-(1-tert-butoxycarbonyl-4-piperidyl)ethyl]-2-piperazinone.

¹H-NMR (CDCl₃) δ: 0.93–1.20 (2H, m), 1.26–1.44 (3H, m), 1.44 (9H, s), 1.55–1.70 (2H, m), 2.54–2.64 (2H, m), 3.30–3.42 (2H, m), 3.39 (4H, s), 3.76 (2H, s), 3.94–4.16 (2H, m), 7.61 (1H, dd, J=8.8, 2.0 Hz), 7.79 (1H, dd, J=8.9, 1.7 Hz), 7.90–7.98 (3H, m), 8.36 (1H,

IR (KBr): 1690, 1649, 1418, 1339, 1167, 968, 700 cm⁻¹.

Reference Example 22

4-(6-chloronaphthalene-2-sulfonyl)-1-[2-(4-piperidyl)ethyl]-2-piperazinone Hydrochloride According to a similar method described in Reference Example 19, colorless crystals of the title compound were obtained from 1-[2-(1-tert-butoxycarbonyl-4-piperidyl)ethyl]-4-(6-chloronaphthalene-2-sulfonyl)-2-piperazinone.

¹H-NMR (DMSO-d₆) δ: 1.00–1.50 (5H, m), 1.60–1.80 (2H, m), 2.60–2.88 (2H, m), 3.20–3.43 (8H, m), 3.66 (2H, s), 7.74 (1H, dd, J=8.7, 2.1 Hz), 7.89 (1H, dd, J=8.8, 1.8 Hz), 8.18 (1H, d, J=8.8 Hz), 8.24–8.33 (2H, m), 8.59 (1H, s).

IR (KBr): 2936, 1651, 1345, 1163, 700 cm⁻¹.

Reference Example 23

4-benzyloxycarbonyl-1-[(1-tert-butoxycarbonyl-4-piperidyl)methyl]-2-piperazinone According to a similar method described in Reference Example 2, oil of the title compound was obtained from 4-benzyloxycarbonyl-2-piperazinone and 1-tert-butoxycarbonyl-4-methanesulfonyloxymethylpiperidine.

¹H-NMR (CDCl₃) δ: 1.04–1.41 (2H, m), 1.45 (9H, s), 1.52–1.68 (2H, m), 1.70–2.03 (1H, m), 2.57–2.77 (2H, m), 3.20–3.38 (2H, m), 3.36 (2H, t, J=5.3 Hz), 3.72 (2H, t, J=5.4 Hz), 4.02–4.20 (2H, m), 4.16 (2H, s), 5.16 (2H, s), 7.36 (5H, s).

IR (KBr): 1695, 1661, 1424, 1235, 1167 cm⁻¹.

Reference Example 24

1-[(1-tert-butoxycarbonyl-4-piperidyl)methyl]-4-(6-chloronaphthalene-2-sulfonyl)-2-piperazinone According to a similar method described in Reference Example 18, colorless crystals of the title compound were obtained from 4-benzyloxycarbonyl-1-[(1-tert-butoxycarbonyl-4-piperidyl)methyl]-2-piperazinone.

¹H-NMR (CDCl₃) δ: 0.98–1.21 (2H, m), 1.43 (9H, s), 1.38–1.58 (2H, m), 1.60–1.97 (1H, m), 2.50–2.70 (2H, m), 3.10–3.34 (2H, m), 3.34–3.48 (4H, m), 3.78 (2H, s), 3.95–4.16 (2H, m), 7.61 (1H, dd, J=9.0, 2.0 Hz), 7.80 (1H, dd, J=8.6, 1.8 Hz), 7.90–7.98 (3H, m), 7.36 (1H, s).

IR (KBr): 1678, 1657, 1350, 1167 cm⁻¹.

Reference Example 25

4-(6-chloronaphthalene-2-sulfonyl)-1-(4-piperidylmethyl)-2-piperazinone Hydrochloride According to a similar method described in Reference Example 19, colorless crystals of the title compound were obtained from 1-[(1-tert-butoxycarbonyl-4-piperidyl)methyl]-4-(6-chloronaphthalene-2-sulfonyl)-2-piperazinone.

¹H-NMR (DMSO-d₆) δ: 1.10–1.36 (2H, m), 1.48–1.65 (2H, m), 1.68–1.95 (1H, m), 2.57–2.82 (2H, m), 3.06–3.23 (4H, m), 3.36 (4H, s), 3.67 (2H, s), 7.72 (1H, dd, J=8.8, 2.2 Hz), 7.88 (1H, dd, J=8.7, 1.9 Hz), 8.18 (1H, d, J=8.8 Hz), 8.22–8.32 (2H, m), 8.58 (1H, s), 8.43–8.95 (2H, br).

IR (KBr): 2924, 1649, 1345, 1173, 961, 702 cm⁻¹.

Reference Example 26

4-benzyloxycarbonyl-1,2,3,4-tetrahydropyrazin-2-one

To a solution of N-benzyloxycarbonylglycine (10.5 g) and 2,2-diethoxyethylamine (7.33 g) in acetonitrile (50 ml) was added WSC hydrochloride (10.5 g) under ice-cooling, and the mixture was stirred at room temperature for 2 hours. The reaction solution was concentrated, and to the residue were added ethyl acetate and dilute hydrochloric acid. The organic layer was separated, washed with saturated and saturated brine, dried (MgSO₄) and concentrated. To the residue were added p-toluenesulfonic acid (951 mg) and toluene (150 ml), and the mixture was refluxed for 30 minutes. The mixture was cooled, and to the reaction solution was added ethyl acetate. The mixture was washed with saturated sodium bicarbonate solution and saturated brine, dried (MgSO₄) and concentrated. The resulting crystals were filtered, washed with ether and dried to give colorless crystals of the title compound (7.37 g).

¹H-NMR (CDCl₃) δ: 4.30 (2H, s), 5.22 (2H, s), 5.50–5.68 (1H, m), 6.29–6.48 (1H, m), 7.38 (5H, s), 7.50–8.00 (1H, br).

IR (KBr): 1698, 1649, 1410, 1321, 1107, 957, 760 cm⁻¹.

Reference Example 27

4-benzyloxycarbonyl-1-[trans-4-(1-tert-butoxycarbonylamino)cyclohexan-1-ylmethyl]-1,2,3,4-tetrahydropyrazine-2-one To a solution of 4-benzyloxycarbonyl-1,2,3,4-tetrahydropyrazine-2-one (813 mg) in DMF (30 ml) was added trans-4-(tert-butoxycarbonylamino)-1-methanesulfonyl-oxymethylcyclohexane which was prepared from trans-4-(1-tert-butoxycarbonylamino) cyclohexan-1-ylmethanol (803 mg) and methanesulfonyl chloride (0.298 ml). To the mixture were added potassium carbonate (967 mg) and potassium iodide (291 mg), and the mixture was stirred at 60 for 1 day, and then at 100° C. for 1 day. The reaction solution was concentrated under reduced pressure, and to the residue was water. The mixture was extracted with ethyl acetate. The extract was washed with saturated brine, dried ($MgSO_4$) and concentrated. The residue was purified with silica gel column chromatography (hexane:ethyl acetate=1:1) to give amorphous of the title compound (422 mg).

$^1$H-NMR ($CDCl_3$) δ: 0.97–1.14 (4H, m), 1.43 (9H, s), 1.54–1.88 (3H, m), 1.90–2.10 (2H, m), 3.26–3.50 (1H, m), 3.31 (2H, d, J=7.0 Hz), 4.30 (2H, s), 4.26–4.44 (1H, m), 5.21 (2H, s), 5.36–5.58 (1H, m), 6.26–6.47 (1H, m), 7.36 (5H, s).

IR (KBr): 1709, 1686, 1402, 1171 $cm^{-1}$.

Reference Example 28
1-[trans-4-(1-tert-butoxycarbonylamino)cyclohexan-1-ylmethyl]-4-(6-chloronaphthalene-2-sulfonyl)-2-piperazinone According to a similar method described in Reference Example 18, colorless crystals of the title compound were obtained from 4-benzyloxycarbonyl-1-[trans-4-(tert-butoxycarbonylamino)cyclohexan-1-ylmethyl]-1,2,3,4-tetrahydropyrazine-2-one.

1H-NMR ($CDCl_3$) δ: 0.85–1.13 (4H, in), 1.43 (9H, s), 1.48–1.70 (3H, in), 1.85–2.05 (2H, in), 3.16 (2H, d, J=7.0 Hz), 3.20–3.46 (5H, in), 3.77 (2H, s), 4.24–4.40 (1H, in), 7.60 (1H, dd, J=8.9, 1.9 Hz), 7.79 (1H, dd, J=8.8, 1.8 Hz), 7.89–7.98 (3H, in), 8.35 (1H, s).

IR(KBr): 1678, 1644, 1508, 1346, 1159 $cm^{-1}$.

Reference Example 29
1-(trans-4-aminocyclohexan-1-ylmethyl)-4-(6-chloronanhthalene-2-sulfonyl)-2-piperazinone hydrochloride According to a similar method described in Reference Example 19, colorless crystals of the title compound were obtained from 1-[trans-4-(1-tert-butoxycarbonyl-amino) cyclohexan-1-ylmethyl]-4-(6-chloronaphthalene-2-sulfonyl)-2-piperazinone.

1H-NMR (DMSO-d6) δ: 0.75–1.05 (2H, in), 1.05–1.34 (2H, in), 1.35–1.63 (3H, in), 1.78–1.94 (2H, in), 2.70–3.00 (1H, m), 3.08 (2H, d, J=6.4 Hz), 3.38–3.42 (4H, in), 3.65 (2H, s), 7.72 (1H, dd, J=8.7, 2.1 Hz), 7.88 (1H, dd, J=8.8, 1.8 Hz), 7.86–8.02 (3H, in), 8.18 (1H, d, J=8.8 Hz), 8.22–8.32 (2H, in), 8.58 (1H, s).

IR (KBr): 2934, 1649, 1345, 1163, 700 $cm^{-1}$.

Reference Example 30
2.2-dimethoxyethyl[4-(1H-imidazol-1-yl)benzyl]amine

To a solution of 2,2-dimethoxyethylamine (526 mg) and 4-(1H-imidazol-1-yl)benzaldehyde (861 mg) in methanol (25 ml) was added acetic acid (600 mg), and the mixture was stirred at room temperature for 1 hour. To the mixture was added, under ice-cooling, sodium triacetoxyborohydride (1.59 g), and the mixture was stirred at room temperature for 3 hours. The reaction solution was concentrated, and to the residue was added 1 N sodium hydroxide solution. The mixture was extracted with dichloromethane, dried and concentrated to give colorless oil of the title compound (1.21 g).

$^1$H-NMR ($CDCl_3$) δ: 2.76 (2H, d, J=5.6 Hz), 3.39 (6H, s), 3.86 (2H, s), 4.50 (1H, t, J=5.6 Hz), 7.20 (1H, s), 7.27 (1H, s), 7.34 (2H, d, J=8.8 Hz), 7.45 (2H, d, J=8.8 Hz), 7.84 (1H, s).

Working Example 1
1-(4-amidinobenzyl)-4-(naphthalene-2-sulfonyl)-2-piperazinone Hydrochloride A solution of ethanol (1 ml) and 4 N hydrochloric acid/dioxane (7 ml) was added to 1-(4-cyanobenzyl)-4-(naphthalene-2-sulfonyl)-2-piperazinone (405 mg), and the mixture was stirred at room temperature overnight. The solvent was concentrated, and to the residue was added 12% ammonia solution in methanol (5 ml). The mixture was stirred at room temperature for 4 days. The solvent was concentrated and purified with CHP20 column chromatography (water:acetonitrile:1 N hydrochloric acid=70:30:1) to give colorless amorphous of the title compound (207 mg).

$^1$H-NMR (DMSO-$d_6$) δ: 3.20–3.60 (4H, m), 3.81 (2H, s), 4.57 (2H, s), 7.35 (2H, d, J=8.3 Hz), 7.65–7.90 (5H, m), 8.05–8.28 (3H, m), 8.54 (1H, s), 9.14 (2H, brs), 9.33 (2H, brs).

IR (KBr): 3058, 1676, 1647, 1493, 1346, 1163 $cm^{-1}$.

Working Example 2
1-(4-amidinobenzyl)-4-(6-chloronaphthalene-2-sulfonyl)-2-piperazinone Hydrochloride To a solution of 4-(6-chloronaphthalene-2-sulfonyl)-1-(4-cyanobenzyl)-2-piperazinone (220 mg) in dioxane/ethanol (9/1) (10 ml), hydrogen chloride gas was bubbled for 2 minutes under ice-cooling, and the solution was allowed to stand at room temperature overnight. The solvent was concentrated, and to the residue was added 15% ammonia solution in ethanol (5 ml). The mixture was stirred at 60° C. for 2 hours. The solvent was concentrated and purified with CHP20 column chromatography (water:acetonitrile:1 N hydrochloric acid=70:30:1), and the resulting product was crystallized from ethanol-ethyl acetate to give colorless crystals of the title compound (173 mg).

$^1$H-NMR (DMSO-$d_6$) δ: 3.20–3.50 (4H, m), 3.81 (2H, s), 4.56 (2H, s), 7.35 (2H, d, J=8.4 Hz), 7.68 (2H, d, J=8.4 Hz), 7.74 (1H, dd, J=9.0, 2.2 Hz), 7.89 (1H, dd, J=8.6, 1.8 Hz), 8.18 (1H, d, J=8.6 Hz), 8.24–8.32 (2H, m), 8.59 (1H, s), 9.02 (2H, brs), 9.30 (2H, brs). IR (KBr): 3052, 1678, 1636, 1493, 1352, 1163, 698 $cm^{-1}$.

Working Example 3
1-(3-amidinobenzyl)-4-(6-chloronaphthalene-2-sulfonyl)-2-piperazinone Hydrochloride According to a similar method described in Working Example 2, colorless crystals of the title compound were obtained by using 4-(6-chloronaphthalene-2-sulfonyl)-1-(3-cyanobenzyl)-2-piperazinone instead of 4-(6-chloronaphthalene-2-sulfonyl)-1-(4-cyanobenzyl)-2-piperazinone.

$^1$H-NMR (DMSO-$d_6$) δ: 3.30–3.50 (4H, in), 3.79 (2H, s), 4.54 (2H, s), 7.47 (2H, d, J=5.0 Hz), 7.62 (1H, s), 7.64–7.71 (1H, in), 7.74 (1H, dd, J=8.8, 2.2 Hz), 7.89 (1H, dd, J=8.8, 1.8 Hz), 8.18 (1H, d, J=8.8 Hz), 8.25–8.33 (2H, in), 8.60 (1H, s), 9.16 (2H, brs), 9.38 (2H, brs).

IR(KBr): 3144, 1682, 1645, 1352, 1171, 774, 694 $cm^{-1}$.

Working Example 4
1-(trans-4-amidinocyclohexane-1-ylmethyl)-4-(6-chloronaphthalene-2-sulfonyl)2-piperazinone hydrochloride A solution of 28% hydrochloric acid in dioxane/ethanol (9/1) (10 ml) was added to 4-(6-chloronaphthalene-2-sulfonyl)-1-(trans-4-cyanocyclohexane-1-ylmethyl)-2-piperazinone (312 mg), and the mixture was allowed to stand at room temperature for 6 hours. The solvent was concentrated, and to the residue was added 15% ammonia solution in ethanol (10 ml). The mixture was stirred overnight. The solvent was concentrated and purified with CHP20 column chromatography (water:acetonitrile:1 N hydrochloric acid=70:30:1) to give colorless amorphous of the title compound (350 mg).

$^1$H-NMR (DMSO-d$_6$) δ: 0.70–0.95 (2H, m), 1.25–1.75 (7H, m), 2.20–2.39 (1H, m), 3.08 (2H, d, J=6.6 Hz), 3.3–3.4 (4H, m), 3.70 (2H, s), 7.72 (1H, dd, J=8.8, 2.2 Hz), 7.89 (1H, dd, J=8.8, 1.8 Hz), 8.19 (1H, d, J=8.8 Hz), 8.23–8.32 (2H, m), 8.60 (3H, brs), 8.78 (2H, brs).

IR (KBr): 3077, 1682, 1644, 1346, 1163, 698 cm$^{-1}$.

Working Example 5

1-(5-amidino-2-thienylmethyl)-4-(6-chloronaphthalene-2-sulfonyl)-2-piperazinone Hydrochloride According to a similar method described in Working Example 4, colorless crystals of the title compound were obtained by using 4-(6-chloronaphthalene-2-sulfonyl)-1-(5-cyano-2-thienylmethyl)-2-piperazinone instead of 4-(6-chloronaphthalene-2-sulfonyl)-1-(trans-4-cyanocyclohexane-1-ylmethyl)-2-piperazinone.

$^1$H-NMR (DMSO-d$_6$) δ: 3.39 (4H, s), 3.75 (2H, s), 4.68 (2H, s), 7.18 (1H, d, J=3.8 Hz), 7.73 (1H, dd, J=8.8, 1.2 Hz), 7.83–7.90 (2H, in), 8.15 (1H, d, J=8.8 Hz), 8.21–8.30 (2H, in), 8.57 (1H, s), 8.95 (2H, brs), 9.26 (2H, brs).

IR (KBr): 3005, 1659, 1636, 1499, 1350, 1167, 696 cm$^{-1}$.

Working Example 6

4-(6-chloronaphthalene-2-sulfonyl)-1-[4-(N-methylamidino)benzyl]-2-piperazinone hydrochloride A solution of 28% hydrochloric acid in dioxane/ethanol (9/1) (10 ml) was added to 4-(6-chloronaphthalene-2-sulfonyl)-1-(4-cyanobenzyl)-2-piperazinone (440 mg), and the mixture was allowed to stand at room temperature overnight. The solvent was concentrated, and to the residue was added 40% methylamine solution in methanol (10 ml). The mixture was stirred for 7 hours. The solvent was concentrated and purified with CHP2D column chromatography (water:acetonitrile:1 N hydrochloric acid=70:30:1) to give pale yellow amorphous of the title compound (173 mg).

$^1$H-NMR (DMSO-d$_6$) δ: 3.02 (3H, d, J=4.6 Hz), 3.20–3.55 (4H, m), 3.84 (2H, s), 4.55 (2H, s), 7.31 (2H, d, J=8.2 Hz), 7.65 (2H, d, J=8.2 Hz), 7.73 (1H, dd, J=8.8, 2.0 Hz), 7.88 (1H, dd, J=8.6, 1.8 Hz), 8.19 (1H, d, J=8.8 Hz), 8.24–8.32 (2H, m), 8.60 (1H, s), 9.05 (1H, brs), 9.51 (1H, brs), 9.96 (1H, d, J=1.6 Hz).

Working Example 7

4-(6-chloronaphthalene-2-sulfonyl)1-[4-(morpholino-iminomethyl)benzyl]-2-piperazinone Hydrochloride A solution of 28% hydrochloric acid dioxane/ethanol (9/1) (10 ml) was added to 4-(6-chloronaphthalene-2-sulfonyl)-1-(4-cyanobenzyl)-2-piperazinone (440 mg), and the mixture was allowed to stand at room temperature for 5 hours. The solvent was concentrated, and to the residue was added 10% morpholine solution in ethanol (10 ml). The mixture was stirred for 3 days. The solvent was concentrated and purified with CHP20 column chromatography (water:acetonitrile:1 N hydrochloric acid=70:30:1) to give colorless amorphous of the title compound (427 mg).

$^1$H-NMR (DMSO-d$_6$) δ: 3.20–3.50 (6H, m), 3.55–3.68 (2H, m), 3.70–3.95 (6H, m), 7.35 (2H, d, J=8.3 Hz), 7.47 (2H, d, J=8.3 Hz), 7.74 (1H, dd, J=8.7, 2.1 Hz), 7.89 (1H, dd, J=8.7, 1.7 Hz), 8.19 (1H, d, J=8.8 Hz), 8.25–8.32 (2H, m), 8.60 (1H, s), 9.40 (1H, brs), 9.53 (1H, brs).

IR (KBr): 3021, 1655, 1613, 1346, 1163, 1115, 698 cm$^{-1}$.

Working Example 8

1-[4-(N-aminoamidino)benzyl]-4-(6-chloronaphthalene-2-sulfonyl)-2-piperazinone Hydrochloride To 4-(6-chloronaphthalene-2-sulfonyl)-1-(4-cyanobenzyl)-2-piperazinone (220 mg) was added a solution of 28% hydrochloric acid in dioxane/ethanol (9/1) (10 ml), and the mixture was allowed to stand at room temperature for 7 hours. The solvent was concentrated, and to the residue was added a solution of hydrazine hydrate (125 mg) in ethanol (10 ml). The mixture was stirred overnight. The solvent was concentrated and purified with CHP20 column chromatography (water:acetonitrile:1 N hydrochloric acid=70:30:1) and LH20 (methanol) to give colorless amorphous of the title compound (100 mg).

$^1$H-NMR (DMSO-d$_6$) δ: 3.20–3.60 (4H, m), 3.82 (2H, s), 4.57 (2H, s), 7.36 (2H, d, J=8.3 Hz), 7.63 (2H, d, J=8.3 Hz), 7.76 (1H, dd, J=8.8, 2.1 Hz), 7.91 (1H, dd, J=8.8, 1.8 Hz), 8.21 (1H, d, J=8.8 Hz), 8.28–8.34 (2H, m), 8.62 (1H, s).

IR (KBr): 3065, 1647, 1346, 1163, 698 cm$^{-1}$.

Working Example 9

4-(6-chloronaphthalene-2-sulfonyl)-1-[4-(N-hydroxyamidino)benzyl]-2-piperazinone A mixture of 4-(6-chloronaphthalene-2-sulfonyl)-1-(4-cyanobenzyl)-2-piperazinone (440 mg), hydroxylamine hydrochloride (347 mg), sodium hydrogen carbonate (420 mg) and 80% ethanol (30 ml) was refluxed for 2 hours, and ethanol was evaporated. Precipitated crystals were washed with water, ethanol and ethyl acetate, and dried to give colorless crystals of the title compound (353 mg).

$^1$H-NMR (DMSO-d$_6$) δ: 3.20–3.45 (4H, m), 3.77 (2H, s), 4.47 (2H, s), 5.72 (2H, s), 7.14 (2H, d, J=8.3 Hz), 7.57 (2H, d, J=8.3 Hz), 7.71 (1H, dd, J=8.9, 2.1 Hz), 7.86 (1H, dd, J=8.7, 1.9 Hz), 8.20–8.30 (2H, m), 8.57 (1H, s), 9.60 (1H, s).

IR (KBr): 3243, 1634, 1348, 1171, 696 cm$^{-1}$.

Working Example 10

1-[4-(N-acetimidoylamino)benzyl]-4-(6-chloronaphthalene-2-sulfonyl)-2-piperazinone Hydrochloride To a solution of 1-(4-aminobenzyl)-4-(6-chloro-naphthalene-2-sulfonyl)-2-piperazinone hydrochloride (233 mg) in methanol (20 ml) were added ethyl acetimidate hydrochloride (618 mg) and triethylamine (0.836 ml), and the mixture was stirred at room temperature overnight. The solvent was concentrated and purified with CHP20 column chromatography (water:acetonitrile:1 N hydrochloric acid=70:30:1) to give pale yellow amorphous of the title compound (134 mg).

$^1$H-NMR (DMSO-d$_6$) δ: 2.33 (3H, s), 3.20–3.60 (4H, m), 3.79 (2H, s), 4.51 (2H, s), 7.15 (2H, d, J=8.6 Hz), 7.26 (2H, d, J=8.6 Hz), 7.73 (1H, dd, J=8.8, 2.2 Hz), 7.88 (1H, dd, J=8.8, 1.8 Hz), 8.18 (1H, d, J=8.8 Hz), 8.25–8.31 (2H, m), 8.47 (1H, brs), 8.59 (1H, s), 9.50 (1H, brs).

IR (KBr): 3044, 1632, 1348, 1161, 696, 583 cm$^{-1}$.

Working Example 11

1-[2-(1-amidino-4-piperidyl)ethyl]-4-(6-chloronaphthalene-2-sulfonyl)-2-piperazinone To a solution of 4-(6-chloronaphthalene-2-sulfonyl)-1-[2-(4-piperidyl)ethyl]-2-piperazinone Hydrochloride (118 mg) in methanol (10 ml) was added a solution of S-methylisothiourea hemisulfate (315 mg) and 28% sodium methoxide in methanol (482 mg), and the mixture was stirred at room temperature for 3 days. The solvent was concentrated and purified with CHP20 column chromatography (water:acetonitrile:1 N hydrochloric acid=70:30:1), and then purified with LH20 (methanol) to give colorless amorphous of the title compound (66 mg).

¹H-NMR (DMSO-d$_6$) δ: 0.80–1.50 (5H, m), 1.55–1.72 (2H, m), 2.77–2.95 (2H, m), 3.17–3.50 (6H, m), 3.67 (2H, s), 3.70–3.84 (2H, m), 7.37 (4H, brs), 7.73 (1H, dd, J=8.9, 2.1 Hz), 7.89 (1H, dd, J=8.6, 1.8 Hz), 8.18 (1H, d, J=8.9 Hz), 8.24–8.33 (2H, m), 8.59 (1H, s).

IR (KBr): 3152, 1649, 1346, 1163 cm$^{-1}$.

Working Example 12

1-[(1-acetimidoyl-4-piperidyl)methyl]-4-(6-chloronaphthalene-2-sulfonyl)-2-piperazinone According to a similar method described in Working Example 10, colorless amorphous of the title compound was obtained by using 4-(6-chloronaphthalene-2-sulfonyl)-1-(4-piperidylmethyl)-2-piperazinone hydrochloride instead of 1-(4-aminobenzyl)-4-(6-chloronaphthalene-2-sulfonyl)-2-piperazinone hydrochloride.

¹H-NMR (DMSO-d$_6$) δ: 1.00–1.25 (2H, m), 1.41–1.68 (2H, m), 1.75–2.02 (1H, m), 2.22 (3H, s), 2.84–3.12 (2H, m), 3.15 (2H, d, J=7.4 Hz), 3.37 (4H, brs), 3.68 (2H, s), 3.68–3.83 (1H, m), 3.95–4.10 (1H, m), 7.74 (1H, dd, J=8.8, 2.2 Hz), 7.89 (1H, dd, J=8.8, 1.8 Hz), 8.19 (1H, d, J=8.8 Hz), 8.25–8.33 (2H, m), 8.60 (1H, s), 8.61 (1H, brs), 9.19 (1H, brs).

IR (KBr): 3067, 1642, 1346, 1163, 698 cm$^{-1}$.

Working Example 13

1-[(1-amidino-4-piperidyl)methyl]-4-(6-chloronaphthalene-2-sulfonyl)-2-piperazinone Hydrochloride To a solution of 4-(6-chloronaphthalene-2-sulfonyl)-1-(4-piperidylmethyl)-2-piperazinone hydrochloride (230 mg) in DMF (10 ml) were added S-methylisothiourea hemisulfate (348 mg), triethylamine (0.418 ml) and water (2 ml), and the mixture was stirred at 50° C. overnight. To the mixture was added S-methylisothiourea hemisulfate (348 mg) and triethylamine (0.418 ml), and the mixture was additionally stirred at 50° C. overnight. The solvent was concentrated and purified with CHP20 column chromatography (water:acetonitrile:1 N hydrochloric acid=70:30:1) to give colorless amorphous of the title compound (160 mg).

¹H-NMR (DMSO-d$_6$) δ: 0.90–1.15 (2H, m), 1.43–1.60 (2H, m), 1.70–1.92 (1H, m), 2.76–2.94 (2H, m), 3.14 (2H, d, J=7.4 Hz), 3.37 (4H, brs), 3.67 (2H, s), 3.69–3.84 (2H, m), 7.37 (4H, brs), 7.73 (1H, dd, J=8.8, 2.2 Hz), 7.89 (1H, dd, J=8.8, 1.8 Hz), 8.19 (1H, d, J=8.8 Hz), 8.24–8.33 (2H, m), 8.60 (1H, s).

IR (KBr): 3098, 1638, 1613, 1352, 1171, 696 cm$^{-1}$.

Working Example 14

1-[trans-4-(N-acetimidoylamino)cyclohexane-1-ylmethyl]-4-(6-chloronaphthalene-2-sulfonyl)-2-piperazinone Hydrochloride According to a similar method described in Working Example 10, pale yellow amorphous of the title compound was obtained by using 1-(trans-4-aminocyclohexane-1-ylmethyl)-4-(6-chloronaphthalene-2-sulfonyl)-2-piperazinone hydrochloride instead of 1-(4-aminobenzyl)-4-(6-chloronaphthalene-2-sulfonyl)-2-piperazinone hydrochloride.

¹H-NMR (DMSO-d$_6$) δ: 0.77–1.23 (4H, m), 1.37–1.57 (3H, m), 1.66–1.81 (2H, m), 2.12 (3H, s), 3.08 (2H, d, J=7.0 Hz), 3.30–3.45 (5H, m), 3.69 (2H, s), 7.73 (1H, dd, J=8.8, 2.2 Hz), 7.89 (1H, dd, J=8.6, 1.8 Hz), 8.18 (1H, d, J=8.8 Hz), 8.24–8.33 (2H, m), 8.60 (2H, brs), 9.07 (1H, brs), 9.34 (1H, d, J=7.8 Hz).

IR (KBr): 3058, 1640, 1346, 1163, 698 cm$^{-1}$.

Working Example 15

4-(6-chloronaphthalene-2-sulfonyl)-1-[1-(4-pyridyl)-4-piperidylmethyl]-2-piperazinone In THF (100 ml) and DMF (100 ml) was dissolved 4-(benzyloxycarbonyl)-1,2,3,4-tetrahydropyrazine-2-one (3.48 g), and to the solution was added sodium hydride (270 mg; oil) at room temperature. The mixture was stirred for 30 minutes, and to the mixture was added 1-(4-pyridyl)-4-methylsulfonyloxymethylpiperidine (2.70 g). The mixture was stirred at 60° C. for 5 hours. The reaction solution was concentrated under reduced pressure, and to the residue was added ether. The mixture was extracted with dilute hydrochloric acid, and the extract was neutralized with sodium hydroxide solution. To the solution was added 10% sodium carbonate solution, and the solution was extracted with ethyl acetate-THF. The extract was washed with saturated brine, dried (MgSO$_4$) and concentrated. The residue was dissolved in ethanol (100 ml), and to the solution was added 10% palladium on carbon (Pd—C) (1.00 g). The mixture was vigorously stirred for 3 hours under hydrogen atmosphere. The catalyst was removed, and the solvent was evaporated. To the residue were added potassium carbonate (1.38 g), ethyl acetate (30 ml) and water (30 ml). Under ice-cooling, to the mixture was dropwise added a solution of 6-chloronaphthalene-2-sulfonyl chloride (2.61 g) in THF (30 ml), and the mixture was stirred at room temperature for 1 hour. The organic layer was separated, washed with saturated brine, dried (MgSO$_4$) and concentrated. The residue was crystallized from ethanol to give colorless crystals of the title compound (1.80 g).

¹H-NMR (CDCl$_3$) δ: 1.13–1.37 (2H, m), 1.52–1.70 (2H, m), 1.78–2.02 (1H, m), 2.67–2.83 (2H, m), 3.24 (2H, d, J=7.2 Hz), 3.43 (4H, s), 3.73–3.88 (2H, m), 3.80 (2H, s), 6.60 (2H, d, J=6.5 Hz), 7.62 (1H, dd, J=8.8, 1.8 Hz), 7.81 (1H, dd, J=8.8, 1.8 Hz), 7.92–7.99 (3H, m), 8.24 (2H, d, J=6.5 Hz), 8.36 (1H, s).

IR (KBr): 1655, 1599, 1345, 1159, 696, 586 cm$^{-1}$.

Working Example 16

4-(6-chloronaphthalene-2-sulfonyl)-1-[1-(4-pyridyl)-4-piperidylmethyl]-2-piperazinone Hydrochloride To 4-(6-chloronaphthalene-2-sulfonyl)-1-[1-(4-pyridyl)-4-piperidylmethyl]-2-piperazone (500 mg) obtained in Working Example 15 were added ethanol and 4 N hydrochloric acid in ethyl acetate to give a solution, which was concentrated under reduced pressure. The residue was crystallized from ethanol to give colorless crystals of the title compound (414 mg).

¹H-NMR (DMSO-d6) δ: 0.90–1.17 (2H, m), 1.46–1.62 (2H, m), 1.82–2.03 (1H, m), 2.90–3.10 (2H, m), 3.09 (2H, d, J=7.4 Hz), 3.37 (4H, s), 3.69 (2H, s), 4.00–4.17 (2H, m), 7.12 (2H, d, J=7.8 Hz), 7.74 (1H, dd, J=8.6, 2.0 Hz), 7.89 (1H, dd, J=8.5, 1.7 Hz), 8.13–8.32 (5H, in), 8.60 (1H, s).

IR(KBr): 2575, 1647, 1545, 1346, 1167 cm$^{-1}$.

Working Example 17

4-(6-chloronaphthalene-2-sulfonyl)-1-[4-(1H-imidazol-1-yl)benzyl]-2-piperazinone To a solution of N-(6-chloronaphthalene-2-sulfonyl) ethylenediamine hydrochloride (321 mg) and 4-(1H-imidazol-1-yl)benzaldehyde (172 mg) in methanol (10 ml) was added acetic acid (300 mg), and the mixture was stirred at room temperature for 1 hour. To the mixture was added, under ice-cooling, sodium triacetoxyborohydride (318 mg), and the mixture was stirred at room temperature for 5 hours. The reaction solution was concentrated, and the residue was dissolved in ethyl acetate. The solution was washed with sodium bicarbonate solution and brine, and dried, and to the solution was added triethylamine (700 mg) and then was added chloroacetyl chloride (300 mg). The mixture was stirred at room temperature for 30 minutes. The reaction solution was washed with sodium bicarbonate solution and brine, dried and concentrated. The residue was dissolved in DMF (20 ml), and to the solution was added potassium carbonate (150 mg). The mixture was stirred at 90 C for 2 hours. The reaction solution was concentrated, and the residue was dissolved in ethyl acetate, washed with water and brine, dried and concentrated. The residue was purified with column chromatography (ethyl acetate) and recrystallized from ethyl acetate to give colorless crystals of the title compound (177 mg).

$^1$H-NMR (CDCl$_3$) δ: 3.37 (4H, s), 3.87 (2H, s), 4.58 (2H, s), 7.20 (1H, s), 7.24 (1H, s), 7.29 (4H, s), 7.60 (1H, dd, J=2.2, 8.8 Hz), 7.74–7.83 (2H, m), 7.89–7.97 (3H, m), 8.35 (1H, s).

IR (KBr): 1665, 1520, 1487, 1337, 1165 cm$^{-1}$.

Working Example 18
4-[(E)-2-(4-chlorophenyl)ethenylsulfonyl)-1-[1-(4-pyridyl)-4-piperidylmethyl]-2-piperazinone Hydrochloride According to a method described in Working Example 15, 4-[(E)-2-(4-chlorophenyl)ethenylsulfonyl)-1-[1-(4-pyridyl)-4-piperidylmethyl]-2-piperazinone was obtained by using (E)-2-(4-chlorophenyl)ethenylsulfonyl chloride instead of 6-chloronaphthalene-2-sulfonyl chloride. A solution of 4-[(E)-2-(4-chlorophenyl)ethenylsulfonyl)-1-[1-(4-pyridyl)-4-piperidylmethyl]-2-piperazinone in ethanol and 4 N hydrochloric acid in ethyl acetate was concentrated under reduced pressure. The residue was treated with ether to give colorless amorphous of the title compound.

$^1$H-NMR (DMSO-d$_6$) δ: 1.02–1.25 (2H, m), 1.62–1.78 (2H, m), 1.95–2.18 (1H, m), 2.99–3.18 (2H, m), 3.24 (2H, d, J=7.2 Hz), 3.45 (4H, s), 3.79 (2H, s), 4.08–4.24 (2H, m), 7.15 (2H, d, J=7.6 Hz), 7.44 (1H, d, J=15.6 Hz), 7.52 (1H, d, J=15.6 Hz), 7.55 (2H, d, J=8.6 Hz), 7.82 (2H, d, J=8.6 Hz), 8.20 (2H, d, J=7.6 Hz).

IR (KBr): 2930, 1644, 1547, 1346, 1155 cm$^{-1}$.

Working Example 19
1-[1-(4-pyridyl)-4-piperidylmethyl]-4-(4-vinylphenylsulfonyl)-2-piperazinone Hydrochloride According to a method described in Working Example 15, 1-[1-(4-pyridyl)-4-piperidylmethyl]-4-(4-vinylphenylsulfonyl)-2-piperazinone was obtained by using 4-vinylphenylsulfonyl chloride instead of 6-chloronaphthalene-2-sulfonyl chloride. A solution of 1-[1-(4-pyridyl)-4-piperidylmethyl]-4-(4-vinylphenylsulfonyl)-2-piperazinone in ethanol and 4 N hydrochloric acid in ethyl acetate was concentrated under reduced pressure. The residue was crystallized from ethanol to give colorless crystals of the title compound.

$^1$H-NMR (DMSO-d$_6$) δ: 0.97–1.20 (2H, m), 1.52–1.68 (2H, m), 1.85–2.09 (1H, m), 2.98–3.15 (2H, m), 3.17 (2H, d, J=7.2 Hz), 3.35 (4H, s), 3.62 (2H, s), 4.08–4.26 (2H, m), 5.51 (1H, d, J=11.0 Hz), 6.08 (1H, d, J=17.6 Hz), 6.88 (1H, dd, J=17.6, 11.0 Hz), 7.15 (2H, d, J=7.6 Hz), 7.73–7.84 (4H, m), 8.20 (2H, d, J=7.6 Hz).

IR (KBr): 2917, 1651, 1530, 1345, 1161 cm$^{-1}$.

Reference Example 31
4-benzyloxycarbonyl-1-[4-hydroxy-1-(4-pyridyl)piperidin-4-ylmethyl]-2-oxo-1,2,3,4-tetrahydropyrazine A mixture of 4-hydroxypiperidine (30 g), 4-chloropyridine hydrochloride (45 g), sodium hydrogen carbonate (60 g) and isoamylalcohol (300 ml) was refluxed for 60 hours. The reaction solution was cooled, and insoluble materials were filtered off. The filtrate was concentrated, and the resulting crystals were washed with ether and dried to give 4-hydroxy-1-(4-pyridyl)piperidine (18 g).

$^1$H-NMR (CDCl$_3$) δ: 1.61 (2H, m), 1.96 (2H, m), 3.11 (2H, m), 3.72 (2H, m), 3.95 (1H, m), 6.66 (2H, d, J=6.6 Hz), 8.23 (2H, d, J=6.6 Hz).

To a suspension of pyridinium chlorochromate (24.1 g) and sodium acetate (18.3 g) in dichloromethane (500 ml) was added small portionwise 4-hydroxypiperidine (9.7 g), and the mixture was stirred at room temperature for 5 hours. To the reaction solution was added 1N sodium hydroxide solution, and insoluble materials were dissolved. The separated aqueous layer was extracted with dichloromethane, and combined dichloromethane solution was washed with brine, dried, concentrated and crystallized from toluene to give colorless crystals of 1-(4-pyridyl)-4-piperidinone (9.0 g).

$^1$H-NMR (CDCl$_3$) δ: 2.57 (4H, t, J=6.0 Hz), 3.75 (4H, t, J=6.0 Hz), 6.72 (2H, d, J=6.2 Hz), 8.33 (2H, d, J=6.2 Hz).

To a suspension of sodium hydride in oil (2.35 g) in dimethylsulfoxide (100 ml) was added portionwise, under ice-cooling, trimethylsulfoxonium iodide (13.5 g), and the mixture was stirred at room temperature for 30 minutes to give a uniform solution. To the reaction solution was added dropwise a solution of 1-(4-pyridyl)-4-piperidinone (9.0 g) in dimethylsulfoxide (20 ml), under ice-cooling, and the mixture was stirred at room temperature for 2 hours. To the reaction solution were added 4-benzyloxycarbonyl-2-oxo-1,2,3,4-tetrahydropyrazine (11.8 g), potassium t-butoxide (1.7 g) and t-butanol (200 ml), and the mixture was stirred at 80° C. for 15 hours. The reaction solution was concentrated, and to the residue was added water. The mixture was extracted with dichloromethane, washed with brine, dried and concentrated, and the resulting residue was purified with silica gel column chromatography (dichloromethane: methanol containing 10% ammonia solution=20:1) to give colorless amorphous of the title compound (6.93 g).

$^1$H-NMR (CDCl$_3$) δ: 1.50–1.70 (4H, m), 3.31 (2H, m), 3.56 (2H, s), 3.67 (2H, m), 4.36 (2H, s), 5.22 (2H, s), 5.59 (1H, m), 6.39 (1H, m), 6.66 (2H, d, J=6.6 Hz), 7.38 (5H, s), 8.23 (2H, d, J=6.6 Hz).

Reference Example 32
1-[4-hydroxy-1-(4-pyridyl)piperidin-4-ylmethyl]-2-piperazinone Hydrochloride To a solution of 4-benzyloxycarbonyl-1-[4-hydroxy-1-(4-pyridyl)piperidin-4-ylmethyl]-2-oxo-1,2,3,4-tetrahydropyrazine (6.93 g) in methanol (100 ml) were added 4N hydrochloric acid in ethyl acetate (4 ml) and 10% palladium on carbon (2.0 g), and the mixture was stirred, under hydrogen atmosphere, at room temperature for 15 hours. The catalyst was removed by filtration, and the filtrate was concentrated and dried under reduced pressure to give colorless syrup of the title compound (5.39 g).

$^1$H-NMR (CDCl$_3$+CD$_3$OD) δ: 1.55–1.90 (4H, m), 3.00–3.65 (10H, m), 3.91 (2H, m), 6.60 (2H, d, J=7.6 Hz), 8.09 (2H, d, J=7.6 Hz).

Working Example 20
4-(6-chloronaphthanlene-2-sulfonyl)-1-[4-hydroxy-1-(4-pyridyl)piperidin-4-ylmethyl]-2-piperazinone To a solution of 1-[4-hydroxy-1-(4-pyridyl)piperidin-4-ylmethyl]-2-piperazinone hydrochloride (1.0 g) and triethylamine (928 mg) in dichloromethane (30 ml) was added portionwise 6-chloronaphthanlene-2-sulfonyl chloride (800 mg), and the mixture was stirred at room temperature for 1 hour. The reaction solution washed with sodium hydroxide solution and brine, dried and concentrated, and the residue was purified with silica gel column chromatography (dichloromethane: methanol containing 10% ammonia solution=10:1) to give colorless solid of the title compound (1.32 g).

$^1$H-NMR (CDCl$_3$) δ: 1.40–1.65 (4H, m), 3.26 (2H, m), 3.39 (2H, s), 3.41 (2H, m), 3.52–3.68 (4H, m), 3.85 (2H, s), 6.62 (2H, d, J=6.6 Hz), 7.62 (1H, dd, J=2.0, 8.8 Hz), 7.80 (1H, dd, J=1.4, 8.8 Hz), 7.90–7.98 (3H, m), 8.19 (2H, d, J=6.6 Hz), 8.37 (1H, s).

IR (KBr): 1651, 1601, 1346, 1165 cm$^{-1}$.

Working Example 21

4-(6-chloronaphthanlene-2-sulfonyl)-1-F 4-hydroxy-1-(4-pyridyl)piperidin-4-ylmethyl]-2-piperazinone Hydrochloride To a solution of 4-(6-chloronaphthanlene-2-sulfonyl)-1-[4-hydroxy-1-(4-pyridyl)piperidin-4-ylmethyl]-2-piperazinone (500 mg) in ethyl acetate (30 ml) was added 4N hydrochloric acid in ethyl acetate (0.5 ml), and resulting precipitates were filtered, washed with ethyl acetate and dried to give colorless solid of the title compound (433 mg).

Working Example 22

4-(6-bromonaphthanlene-2-sulfonyl)-1-[4-hydroxy-1-(4-pyridyl)piperidin-4-yl]-2-piperazinone According to a method described in Working Example 20, colorless solid of the title compound (110 mg) was obtained from 1-[4-hydroxy-1-(4-pyridyl)piperidin-4-ylmethyl]-2-piperazinone hydrochloride (127 mg) and 6-bromonaphthanlene-2-sulfonyl chloride (119 mg).

$^1$H-NMR (CDCl$_3$) δ: 1.40–1.75 (4H, m), 3.18–3.80 (1OH, m), 3.85 (2H, s), 6.62 (2H, d, J=6.8 Hz), 7.75 (1H, dd, J=1.8, 8.8 Hz), 7.79 (1H, dd, J=1.8, 8.8 Hz), 7.88 (1H, d, J=8.8 Hz), 7.94 (1H, d, J=8.8 Hz), 8.14 (1H, s), 8.19 (2H, d, J=6.8 Hz), 8.35 (1H, s).

IR (KBr): 1651, 1601, 1514, 1346, 1165 cm$^{-1}$.

Working Example 23

1-[4-hydroxy-1-(4-pyridyl)piperidin-4-ylmethyl]-4-(4-vinylbenzenesulfonyl)-2-piperazinone According to a method described in Working Example 20, colorless solid of the title compound (714 mg) was obtained from 1-[4-hydroxy-1-(4-pyridyl)piperidin-4-ylmethyl]-2-piperazinone hydrochloride (750 mg) and 4-vinylbenzenesulfonyl chloride (512 mg).

$^1$H-NMR (CDCl$_3$) δ: 1.45–1.65 (4H, m), 3.20–3.40 (4H, m), 3.40 (2H, s), 3.50–3.70 (4H, m), 3.79 (2H, s), 5.50 (1H, d, J=11.0 Hz), 5.93 (1H, d, J=17.6 Hz), 6.64 (2H, d, J=6.6 Hz), 6.78 (1H, dd, J=11.0, 17.6 Hz), 7.59 (2H, d, J=8.6 Hz), 7.76 (2H, d, J=8.6 Hz), 8.22 (2H, d, J=6.6 Hz).

Working Example 24

1-[4-hydroxy-1-(4-pyridyl)piperidin-4-ylmethyl]-4-(4-vinylbenzenesulfonyl)-2-piperazinone Hydrochloride According to a method described in Working Example 21, colorless solid of the title compound (670 mg) was obtained by treating 1-[4-hydroxy-1-(4-pyridyl)piperidin-4-ylmethyl]-4-(4-vinylbenzenesulfonyl)-2-piperazinone (710 mg) with hydrochloric acid.

$^1$H-NMR (DMSO-d$_6$) δ: 1.46 (4H, m), 3.20–3.45 (6H, m), 3.56 (2H, m), 3.62 (2H, s), 3.88 (2H, m), 4.87 (1H, s), 5.49 (1H, d, J=10.6 Hz), 6.07 (1H, d, J=17.6 Hz), 6.87 (1H, dd, J=10.6, 17.6 Hz), 7.12 (2H, d, J=7.4 Hz), 7.77 (4H, s), 8.17 (2H, d, J=7.4 Hz).

Working Example 25

4-(7-chloro-2H-benzopyran-3-sulfonyl)-1-[4-hydroxy-1-(4-pyridyl)piperidin-4-ylmethyl]-2-piperazinone To a solution of 1-[1-(tert-butoxycarbonyl)-4-hydroxypiperidin-4-ylmethyl]-2-piperazinone (1.0 g) and triethylamine (991 mg) in dichloromethane (30 ml) was added portionwise, under ice-cooling, 7-chloro-4H-4-oxobenzopyran-3-sulfonyl chloride (900 mg), and the mixture was stirred at room temperature for 1 hour. The reaction solution was washed with water and brine, dried and concentrated, and the residue was purified with silica gel column chromatography (ethyl acetate) and crystallized from methanol to give colorless crystals of 1-[1-(tert-butoxycarbonyl)-4-hydroxypiperidin-4-ylmethyl]-4-(7-chloro-4H-4-oxobenzopyran-3-sulfonyl)-2-piperazinone (400 mg).

$^1$H-NMR (CDCl$_3$) δ: 1.45 (9H, s), 1.40–1.65 (4H, m), 3.12 (2H, m), 3.43 (2H, m), 3.57 (2H, m), 3.70–3.90 (4H, m), 4.06 (2H, s), 7.50 (1H, dd, J=1.8, 8.4 Hz), 7.60 (1H, d, J=1.8 Hz), 8.16 (1H, d, J=8.4 Hz), 8.67 (1H, s).

To a solution of 1-[1-(tert-butoxycarbonyl)-4-hydroxypiperidin-4-ylmethyl]-4-(7-chloro-4H-4-oxobenzopyran-3-sulfonyl)-2-piperazinone (400 mg) in methanol/THF (1:1, 20 ml) was added under ice-cooling sodium borohydride (41 mg), and the mixture was stirred at room temperature for 1 hour. The reaction solution was concentrated, and to the residue were added water and potassium hydrogensulfate solution. The mixture was extracted with ethyl acetate, washed with sodium bicarbonate solution and brine and dried with sodium sulfate. The solvent was concentrated, and the residue was dissolved in dichloromethane (20 ml). To the solution was added triethylamine (292 mg) and then was added at 0 C. methanesulfonyl chloride (100 mg), and the mixture was stirred at room temperature for 30 minutes. The reaction solution was washed with sodium bicarbonate solution, citric acid solution and brine, dried and concentrated, and the residue was purified with silica gel column chromatography (ethyl acetate) to give colorless solid of 1-[1-(tert-butoxycarbonyl)-4-hydroxypiperidin-4-ylmethyl]-4-(7-chloro-2H-benzopyran-3-sulfonyl)-2-piperazinone (150 mg).

$^1$H-NMR (CDCl$_3$) δ: 1.45 (9H, s), 1.40–1.70 (4H, m), 3.15 (2H, m), 3.35–3.70 (6H, m), 3.86 (2H, m), 3.94 (2H, s), 4.89 (2H, s), 6.93 (1H, d, J=1.8 Hz), 7.00 (1H, dd, J=1.8, 8.0 Hz), 7.14 (1H, d, J=8.0 Hz), 7.29 (1H, s).

IR (KBr): 3400, 1682, 1659, 1427, 1366, 1348, 1159 cm$^{-1}$.

To 1-[1-(tert-butoxycarbonyl)-4-hydroxypiperidin-4-ylmethyl]-4-(7-chloro-2H-benzopyran-3-sulfonyl)-2-piperazinone (150 mg) were added 4N hydrochloric acid in ethyl acetate (8 ml) and methanol (4 ml), and the mixture was stirred at room temperature for 30 minutes. The reaction solution was concentrated, and to the residue were added 4-chloropyridine hydrochloride (81 mg), triethylamine (81 mg) and ethanol (20 ml). The mixture was allowed to react in a sealed tube at 150° C. for 15 hours. The reaction solution was concentrated, and the residue was purified with silica gel column chromatography (dichloromethane: methanol containing 10% ammonia solution=10: 1) to give colorless solid of the title compound (63 mg).

$^1$H-NMR (CDCl$_3$) δ: 1.50–1.75 (4H, m), 3.22–3.39 (2H, m), 3.46 (2H, s), 3.52–3.73 (6H, m), 3.96 (2H, s), 4.89 (2H, d, J=1.2 Hz), 6.65 (2H, d, J=6.5 Hz), 6.94 (1H, d, J=2.0 Hz), 7.01 (1H, dd, J=2.0, 8.2 Hz), 7.15 (1H, d, J=8.2 Hz), 7.30 (1H, brs), 8.24 (2H, d, J=6.5 Hz).

Working Example 26

1-[4-acetoxy-1-(4-pyridyl)piperidin-4-ylmethyl]-4-(6-chloronaphthanlene-2-sulfonyl)-2-piperazinone To a solution of 4-(6-chloronaphthanlene-2-sulfonyl)-1-[4-hydroxy-1-(4-pyridyl)piperidin-4-ylmethyl]-2-piperazinone (800 mg) in dichloromethane (30 ml) were added triethylamine (785 mg) and acetic anhydride (476 mg), and the mixture was refluxed for 20 hours. The reaction solution washed with sodium bicarbonate solution and brine, dried and concentrated, and the residue was purified with silica gel column chromatography (dichloromethane: methanol containing 10% ammonia solution=20:1) and crystallized from ether to give colorless crystals of the title compound (800 mg).

$^1$H-NMR (CDCl$_3$) δ: 1.70 (2H, m), 2.06 (3H, s), 2.21 (2H, m), 3.02 (2H, m), 3.39 (2H, m), 3.49 (2H, m), 3.61 (2H, m), 3.83 (2H, s), 3.94 (2H, s), 6.65 (2H, d, J=6.2 Hz), 7.62 (1H, dd, J=1.8, 8.8 Hz), 7.80 (1H, dd, J=1.8, 8.8 Hz), 7.90–8.00 (3H, m), 8.25 (2H, d, J=6.2 Hz), 8.36 (1H, s).

IR (KBr): 1732, 1651, 1597, 1348, 1223, 1163 cm$^{-1}$.

Working Example 27
1-[4-acetoxy-1-(4-pyridyl)piperidin-4-ylmethyl]-4-(4-vinylbenzenesulfonyl)-2-piperazinone According to a method described in Working Example 26, 1-[4-hydroxy-1-(4-pyridyl)piperidin-4-ylmethyl]-4-(4-vinylbenzenesulfonyl)-2-piperazinone (780 mg) was subjected to acetylation to give colorless crystals of the title compound (696 mg).

$^1$H-NMR (CDCl$_3$) δ: 1.81 (2H, m), 2.11 (3H, s), 2.34 (2H, m), 3.20–3.40 (4H, m), 3.52 (2H, m), 3.75 (2H, s), 3.78 (2H, m), 3.97 (2H, s), 5.49 (1H, d, J=11.0 Hz), 5.92 (1H, d, J=17.6 Hz), 6.77 (2H, d, J=7.0 Hz), 6.78 (1H, dd, J=11.0, 17.6 Hz), 7.59 (2H, d, J=8.4 Hz), 7.75 (2H, d, J=8.4 Hz), 8.19 (2H, d, J=7.0 Hz).

IR (KBr): 1732, 1651, 1645, 1549, 1348, 1223, 1165 cm$^{-1}$.

Working Example 28
1-[4-acetoxy-1-(4-pyridyl)piperidin-4-ylmethyl]-4-(7-chloro-2H-benzopyran-3-sulfonyl)-2-piperazinone According to a method described in Working Example 26, 4-(7-chloro-2H-benzopyran-3-sulfonyl)-1-[4-hydroxy-1-(4-pyridyl)piperidin-4-ylmethyl]-2-piperazinone (467 mg) was subjected to acetylation to give colorless crystals of the title compound (327 mg).

$^1$H-NMR (CDCl$_3$) δ: 1.70–1.88 (2H, m), 2.08 (3H, s), 2.25–2.39 (2H, m), 3.01–3.18 (2H, m), 3.55 (4H, s), 3.60–3.76 (2H, m), 3.94 (2H, s), 4.03 (2H, s), 4.90 (2H, d, J=1.2 Hz), 6.68 (2H, brd, J=4.4 Hz), 6.93 (1H, d, J=2.0 Hz), 7.01 (1H, dd, J=2.0, 8.1 Hz), 7.15 (1H, d, J=8.1 Hz), 7.29 (1H, brs), 8.26 (2H, br).

Reference Example 33
4-(tert-butoxycarbonyl)-1-[4-(1H-imidazol-1-yl)benzyl]-2-piperazinone To a solution of N— (tert-butoxycarbonyl) ethylenediamine (5.0 g) and 4-(1H-imidazol-1-yl) benzaldehyde (5.35 g) in methanol (10 ml) was added acetic acid (300 mg), and the mixture was stirred at room temperature for 1 hour. To the mixture was added, under ice-cooling, sodium triacetoxyborohydride (318 mg), and the mixture was stirred at room temperature for 5 hours. The reaction solution was concentrated, and the residue was dissolved in ethyl acetate. The solution was extracted with water, and the aqueous layer was made alkaline with sodium hydroxide solution. The mixture was extracted with dichloromethane and dried with sodium sulfate, and sodium sulfate was filtered off. To the filtrate was added triethylamine (6.3 g) and then was added at 0° C. chloroacetyl chloride (3.53 g), and the mixture was stirred at room temperature for 30 minutes. The reaction solution washed with sodium bicarbonate solution and brine, dried and concentrated, and the residue was dissolved in DMF (100 ml). To the solution was added sodium hydride in oil (1.50 g), and the mixture was stirred at room temperature for 3 hours. The reaction solution was concentrated, and the residue was dissolved in ethyl acetate. The solution was washed with water and brine, dried and concentrated, and the residue was purified with column chromatography (ethyl acetate) to give colorless amorphous of the title compound (5.3 g).

$^1$H-NMR (CDCl$_3$) δ: 1.47 (9H, s), 3.31 (2H, t, J=5.3 Hz), 3.63 (2H, t, J=5.3 Hz), 4.18 (2H, s), 4.66 (2H, s), 7.21 (1H, t, J=1.2 Hz), 7.27 (1H, t, J=1.2 Hz), 7.38 (4H, s), 7.85 (1H, t, J=1.2 Hz).

Reference Example 34
1-[4-(1H-imidazol-1-yl)benzyl]-2-piperazinone Dihydrochloride To a solution of 4-(tert-butoxycarbonyl)-1-[4-(1H-imidazol-1-yl)benzyl]-2-piperazinone (1.5 g) in methanol (10 ml) was added 4N hydrochloric acid in ethyl acetate solution (50 ml), and the mixture was stirred at room temperature for 1 hour. The reaction solution was concentrated, and the residue was powdered with ethyl acetate, filtered and dried to give hygroscopic colorless solid of the title compound (1.12 g).

$^1$H-NMR (DMSO-d$_6$) δ: 3.58 (2H, m), 3.83 (2H, s), 4.10 (1H, s), 4.31 (1H, s), 4.70 (2H, s), 7.59 (2H, d, J=8.4 Hz), 7.80 (2H, d, J=8.4 Hz), 7.90 (1H, t, J=1.2 Hz), 8.31 (1H, dt, J=1.2, 9.2 Hz), 9.83 (1H, dt, J=1.2, 9.6 Hz), 9.97 (2H, brs).

Reference Example 35
1-(1-acetyl-4-methoxycarbonylpiperidin-4-ylmethyl)-2-piperazinone A mixture of methyl 1-acetyl-4-cyanoisonipecotate (3.95 g), Raney nickel (3 g), concentrated ammonia solution (15 ml) and methanol (100 ml) was stirred at 5 atms under hydrogen atmosphere for 2 hours, and the catalyst was filtered off. The reaction solution was concentrated to give light blue oil of methyl 1-acetyl-4-aminomethylisonipecotate. To a solution of the obtained methyl 1-acetyl-4-aminomethylisonipecotate and N-(2,2-diethoxyethyl)-Z-glycine (6.12 g) in acetonitrile (100 ml) was added WSC (6.12 g), and the mixture was stirred at room temperature for 15 hours. The reaction solution was concentrated, and to the residue were added ethyl acetate and water. The separated organic layer was washed with water, sodium bicarbonate solution, citric acid solution and brine, dried and concentrated, and the residue was dissolved in toluene (100 ml). To the solution was added p-toluene sulfonic acid hydrate (164 mg), and the mixture was stirred at 100° C. for 30 minutes. The reaction solution was washed with saturated sodium bicarbonate solution and brine, dried and concentrated, and the residue was purified with silica gel column chromatography (ethyl acetate: methanol=50:1) to give colorless oil of 1-(1-acetyl-4-methoxycarbonylpiperidin-4-ylmethyl)-4-benzyloxycarbonyl-2-oxo-1,2,3,4-tetrahydropyrazine (2.4 g).

$^1$H-NMR (CDCl$_3$) δ: 1.46 (2H, m), 2.07 (3H, s), 2.17 (2H, m), 2.67 (1H, m), 3.13 (1H, m), 3.57 (1H, m), 3.70 (2H, m), 3.73 (3H, s), 4.29 (2H, s), 4.40 (1H, m), 5.21 (2H, m), 5.35 (1H, m), 6.34 (1H, m), 7.38 (5H, s).

IR (KBr): 1715, 1688, 1644, 1447, 1422, 1402, 1229 cm$^{-1}$.

A solution of 1-(1-acetyl-4-methoxycarbonylpiperidin-4-ylmethyl)-4-benzyloxycarbonyl-2-oxo-1,2,3,4-tetrahydropyrazine (2.4 g) and 10% palladium on carbon (500 mg) in methanol (100 ml) was stirred at room temperature for 15 hours, under hydrogen atmosphere, and the catalyst was filtered off. The reaction solution was concentrated to give colorless oil of the title compound (1.40 g).

Reference Example 36
4-(6-chloronaphthanlene-2-sulfonyl)-1-(4-methoxycarbonylpiperidin-4-ylmethyl)-2-piperazinone hydrochloride To a solution of 1-(1-acetyl-4-methoxycarbonylpiperidin-4-ylmethyl)-2-piperazinone (850 mg) and triethylamine (435 mg) in dichloromethane (50 ml) was added 6-chloronaphthanlene-2-sulfonyl chloride (750 mg), and the mixture was stirred at room temperature for 30 minutes. The reaction solution was diluted with dichloromethane, washed with water, sodium bicarbonate solution and brine, dried and concentrated, and the residue was purified with silica gel column chromatography (ethyl acetate: methanol=30:1) to give colorless solid of 1-(1-acetyl-4-methoxycarbonylpiperidin-4-ylmethyl)-4-(6-chloronaphthanlene-2-sulfonyl)-2-piperazinone (1.11 g).

To a solution of 1-(1-acetyl-4-methoxycarbonylpiperidin-4-ylmethyl)-4-(6-chloronaphthanlene-2-sulfonyl)-2-piperazinone (1.25 g) in methanol (30 ml) was added concentrated hydrochloric acid (15 ml), and the mixture was refluxed for 5 hours. The reaction solution was concentrated, and to the residue were added ethyl acetate (50 ml) and saturated sodium hydrogen carbonate solution (50 ml). To the mixture was added di-tert-butyl bicarbonate (700 mg), and the mixture was stirred at room temperature for 30 minutes. The separated organic layer was washed with water and brine, dried and concentrated, and the resulting residue was purified with silica gel column chromatography (hexane:ethyl acetate=1:2) to give colorless solid of 1-[1-(tert-butoxycarbonyl)-4-methoxycarbonylpiperidin-4-ylmethyl]-4-(6-chloronaphthanlene-2-sulfonyl)-2-piperazinone (887 mg).

$^1$H-NMR (CDCl$_3$) δ: 1.37 (2H, m), 1.42 (9H, s), 1.98 (2H, m), 2.74 (2H, m), 3.35 (4H, s), 3.49 (2H, m), 3.69 (3H, s), 3.76 (2H, s), 3.87 (2H, m), 7.60 (1H, dd, J=1.8, 8.8 Hz), 7.77 (1H, dd, J=1.8, 8.8 Hz), 7.90–8.00 (3H, m), 8.33 (1H, s).

To 1-[1-(tert-butoxycarbonyl)-4-methoxycarbonylpiperidin-4-ylmethyl]-4-(6-chloronaphthanlene-2-sulfonyl)-2-piperazinone (500 mg) were added 4N hydrochloric acid in ethyl acetate (15 ml) and methanol (5 ml), and the mixture was stirred at room temperature for 30 minutes. The reaction solution was concentrated to give colorless solid of the title compound (457 mg).

$^1$H-NMR (DMSO-d$_6$) δ: 1.55 (2H, m), 1.90 (2H, m), 2.63 (2H, m), 3.10 (2H, m), 3.20–3.40 (4H, m), 3.44 (2H, s), 3.61 (3H, s), 3.70 (2H, s), 7.74 (1H, dd, J=1.8, 8.8 Hz), 7.87 (1H, dd, J=1.8, 8.8 Hz), 8.19 (1H, d, J=8.8 Hz), 8.25–8.32 (2H, m), 8.50 (2H, brs), 8.58 (1H, s).

Reference Example 37

1-(1-acetyl-4-methoxycarbonylpiperidin-4-ylmethyl)-4-(7-chloro-2H-benzopyran-3-sulfonyl)-2-piperazinone To a solution of 1-(1-acetyl-4-methoxycarbonylpiperidin-4-ylmethyl)-2-piperazinone (850 mg) and diisopropylethylamine (555 mg) in dichloromethane (15 ml) was gradually added dropwise at 0° C. a solution of 7-chloro-4-oxo-4H-benzopyran-3-sulfonyl chloride (960 mg) in dichloromethane (5 ml), and the mixture was stirred at 0° C. for 30 minutes. The reaction solution was diluted with dichloromethane, washed with water, citric acid solution, sodium bicarbonate solution and brine, dried and concentrated, and the residue was purified with silica gel column chromatography (ethyl acetate: methanol=10:1) to give pale yellow solid of 1-(1-acetyl-4-methoxycarbonylpiperidin-4-ylmethyl)-4-(7-chloro-4-oxo-4H-benzopyran-3-sulfonyl)-2-piperazinone (1.10 g).

To a solution of the obtained 1-(1-acetyl-4-methoxycarbonylpiperidin-4-ylmethyl)-4-(7-chloro-4-oxo-4H-benzopyran-3-sulfonyl)-2-piperazinone (1.10 g) in methanol (20 ml) was added sodium borohydride (116 mg), and the mixture was stirred at room temperature for 1 hour. The reaction solution was concentrated, and to the residue was added citric acid solution. The mixture was extracted with ethyl acetate, washed with brine, dried and concentrated, and the residue was dissolved in dichloromethane (20 ml). To the solution were added triethylamine (1.23 g) and methanesulfonyl chloride (420 mg), and the mixture was stirred at room temperature for 1 hour. The reaction solution was diluted with dichloromethane, washed with citric acid solution and brine, dried and concentrated, and the residue was purified with silica gel column chromatography (ethyl acetate:methanol=20:1) to give colorless solid of the title compound (790 mg).

$^1$H-NMR (CDCl$_3$) δ: 1.50 (2H, m), 2.06 (3H, s), 2.15 (2H, m), 2.67 (1H, m), 3.13 (1H, m), 3.30–3.80 (7H, m), 3.75 (3H, s), 3.89 (2H, s), 4.37 (1H, m), 4.88 (2H, s), 6.93 (1H, d, J=1.8 Hz), 7.00 (1H, dd, J=1.8, 8.2 Hz), 7.14 (1H, d, J=8.2 Hz), 7.27 (1H, s).

IR (KBr): 1726, 1644, 1634, 1601, 1485, 1451, 1348, 1325, 1161 cm$^{-1}$.

Reference Example 38

1-[1-(tert-butoxycarbonyl)-4-methoxycarbonylpiperidin-4-ylmethyl]-4-(7-chloro-2H-benzopyran-3-sulfonyl)-2-piperazinone To a solution of 1-(1-acetyl-4-methoxycarbonylpiperidin-4-ylmethyl)-4-(7-chloro-2H-benzopyran-3-sulfonyl)-2-piperazinone (790 mg) in methanol (30 ml) was added concentrated hydrochloric acid (15 ml), and the mixture was refluxed for 5 hours. The reaction solution was concentrated, and to the residue were added ethyl acetate (30 ml) and saturated sodium hydrogen carbonate solution (30 ml) and then was added di-tert-butyl bicarbonate (500 mg), and the mixture was stirred at room temperature for 30 minutes. The organic layer was separated, washed with water and brine, dried and concentrated, and the resulting residue was purified with silica gel column chromatography (hexane:ethyl acetate=1:2) to give colorless solid of the title compound (260 mg).

$^1$H-NMR (CDCl$_3$) δ: 1.44 (9H, s), 1.30–1.60 (2H, m), 2.08 (2H, m), 2.79 (2H, m), 3.35–3.65 (6H, m), 3.73 (3H, s), 3.89 (2H, s), 3.92 (2H, m), 4.88 (2H, s), 6.93 (1H, d, J=1.8 Hz), 6.99 (1H, dd, J=1.8, 8.2 Hz), 7.14 (1H, d, J=8.2 Hz), 7.27 (1H, s).

IR (KBr): 1730, 1682, 1660, 1427, 1161 cm$^{-1}$.

Reference Example 39

4-(5-bromo-2-thiophenesulfonyl)-1-[1-(tert-butoxycarbonyl)piperidin-4-ylmethyl]-2-piperazinone To a solution of 1-[1-(tert-butoxycarbonyl)piperidin-4-ylmethyl]-2-piperazinone (500 mg) in ethyl acetate (15 ml) and sodium bicarbonate solution (10 ml) was added at 0° C. 5-bromo-2-thiophenesulfonyl chloride (440 mg), and the mixture was stirred at room temperature for 30 minutes. The organic layer was separated, washed with brine, dried and concentrated, and the residue was purified with silica gel column chromatography (hexane:ethyl acetate=2:3) to give colorless solid of the title compound (430 mg).

$^1$H-NMR (CDCl$_3$) δ: 1.17 (2H, m), 1.45 (9H, s), 1.40–1.65 (2H, m), 1.83 (1H, m), 2.65 (2H, m), 3.26 (2H, m), 3.38 (2H, m), 3.47 (2H, m), 3.78 (2H, s), 4.10 (2H, m), 7.17 (1H, d, J=4.0 Hz), 7.36 (1H, d, J=4.0 Hz).

IR (KBr): 1686, 1659, 1427, 1402, 1366, 1242, 1165 cm$^{-1}$.

Reference Example 40

4-[4-(1H-imidazol-1-ylmethyl)benzenesulfonyl]-1-(piperidin-4-ylmethyl)-2-piperazinone Dihydrochloride To a solution of 1-[1-(tert-butoxycarbonyl)piperidin-4-ylmethyl]-2-piperazinone (500 mg) in ethyl acetate (15 ml)

and sodium bicarbonate solution (10 ml) was added at 0° C. 4-(bromomethyl)benzenesulfonyl chloride (453 mg), and the mixture was stirred at room temperature for 30 minutes. The organic layer was separated, washed with brine, dried and concentrated, and the residue was purified with silica gel column chromatography (hexane: ethyl acetate=2:3) to give colorless crystals of 4-[4-(bromomethyl)benzenesulfonyl]-1-[1-(tert-butoxycarbonyl)piperidin-4-ylmethyl]-2-piperazinone (437 mg).

$^1$H-NMR (CDCl$_3$) δ: 1.16 (2H, m), 1.44 (9H, s), 1.40–1.60 (2H, m), 1.80 (1H, m), 2.64 (2H, m), 3.23 (2H, d, J=5.4 Hz), 3.34 (2H, m), 3.42 (2H, m), 3.72 (2H, s), 4.08 (2H, m), 4.51 (2H, s), 7.60 (2H, d, J=8.4 Hz), 7.78 (2H, d, J=8.4 Hz).

IR (KBr): 1684, 1659, 1427, 1350, 1242, 1169 cm$^{-1}$.

A mixture of 4-[4-(bromomethyl)benzenesulfonyl]-1-[1-(tert-butoxycarbonyl)piperidin-4-ylmethyl]-2-piperazinone (430 mg), potassium carbonate (112 mg) and imidazole (83 mg) in DMF (15 ml) was stirred at 70° C. for 1 hour. The reaction solution was concentrated, and to the residue was added water. The mixture was extracted with ethyl acetate, washed with water, sodium bicarbonate solution and brine, dried and concentrated, and the residue was recrystallized from ethyl acetate/hexane to give colorless crystals of 4-[4-(1H-imidazol-1-ylmethyl)benzenesulfonyl]-1-[1-(tert-butoxycarbonyl)piperidin-4-ylmethyl]-2-piperazinone (421 mg).

$^1$H-NMR (CDCl$_3$) δ: 1.16 (2H, m), 1.44 (9H, s), 1.40–1.90 (3H, m), 2.64 (2H, m), 3.22 (2H, m), 3.32 (2H, m), 3.42 (2H, m), 3.69 (2H, s), 4.08 (2H, m), 5.24 (2H, s), 6.93 (1H, s), 7.16 (1H, s), 7.30 (2H, d, J=8.4 Hz), 7.59 (1H, s), 7.78 (2H, d, J=8.4 Hz).

IR (KBr): 1686, 1661, 1427, 1348, 1242, 1167 cm$^{-1}$.

To 4-[4-(1H-imidazol-1-ylmethyl)benzenesulfonyl]-1-[1-(tert-butoxycarbonyl)piperidin-4-ylmethyl]-2-piperazinone (420 mg) was added 4N hydrochloric acid in ethyl acetate (15 ml) and methanol (4 ml), and the mixture was stirred at room temperature for 30 minutes. The reaction solution was concentrated to give amorphous of the title compound (442 mg).

$^1$H-NMR (DMSO-d$_6$) δ: 1.28 (2H, m), 1.61 (2H, m), 1.84 (1H, m), 2.73 (2H, m), 3.00–3.70 (10H, m), 5.60 (2H, s), 7.67 (2H, d, J=8.2 Hz), 7.75 (1H, s), 7.84 (1H, s), 8.80 (1H, brs), 9.02 (1H, brs), 9.39 (1H, s).

IR (KBr): 3335, 2951, 1640, 1348, 1169 cm$^{-1}$.

Working Example 29
4-(6-chloronaphthanlene-2-sulfonyl)-1-[4-(1H-imidazol-1-yl)benzyl]-1,2,3,4-tetrahydropyrazine-2-one 1) To a solution of Fmoc-glycine (300 mg) and HOBt (192 mg) in DMF (20 ml) was added WSC (240 mg), and the mixture was stirred at room temperature for 10 minutes. To the mixture was added a solution of 2,2-dimethoxyethyl[4-(1H-imidazol-1-yl)benzyl]amine (261 mg) in DMF (2 ml), and the mixture was stirred at room temperature for 2 hours. The reaction solution was concentrated, and the residue was dissolved in ethyl acetate. The solution was washed with sodium bicarbonate solution and brine, dried and concentrated, and the residue was dissolved in dichloromethane (10 ml). To the solution was added piperidine (2 ml), and the mixture was stirred at room temperature for 10 minutes. The reaction solution was concentrated, and the residue was dissolved in dichloromethane (10 ml). To the solution were added triethylamine (202 mg) and 6-chloronaphthanlene-2-sulfonyl chloride (261 mg), and the mixture was stirred was stirred at room temperature for 1 hour. The reaction solution was concentrated, and the residue was purified with column chromatography (ethyl acetate) to give colorless crystals of N-(2,2-dimethoxyethyl)-N-[4-(1H-imidazol-1-yl)benzyl]-N$^\alpha$-(6-chloronaphthanlene-2-sulfonyl)glycinamide.

$^1$H-NMR (CDCl$_3$) 3.17 (3/5×2H, d, J=4.8 Hz), 3.24 (3/5×6H, s), 3.31 (2/5×6H, s), 3.37 (2/5×2H, d, J=5.0 Hz), 3.82 (2/5×2H, s), 4.02 (3/5×2H, s), 4.18 (3/5×1H, t, J=4.8 Hz), 4.36 (2/5×1H, t, J=5.0 Hz), 4.50 (215×2H, s), 4.57 (3/5×211, s), 5.83 (1H, brs), 6.94–7.29 (6H, in), 7.49 (2/5×1H, dd, J=2.0, 8.8 Hz), 7.58 (3/5×1H, dd, J=2.0, 8.8 Hz), 7.78–7.98 (5H, in), 8.33 (2/5×1H, s), 8.45 (3/5×1H, s).

2) To a solution of the above obtained N-(2,2-dimethoxyethyl)-N-[4-(1H-imidazol -1-yl)benzyl]N$^\alpha$-(6-chloronaphthanlene-2-sulfonyl)glycinamide in dichioroethane (20 ml) was added p-toluene sulfonic acid (230 mg), and the mixture was refluxed for 30 minutes. The reaction solution was concentrated, and the residue was dissolved in ethyl acetate. The solution was washed with water and brine, dried and concentrated, and the residue was purified with column chromatography (ethyl acetate) and recrystallized form dichioromethane/ether to give colorless crystals of the title compound (144 mg).

1H-NMR (CDCl$_3$) δ: 4.28 (2H, s), 4.51 (2H, s), 5.66 (1H, d, J=5.6 Hz), 6.30 (1H, d, J=5.6 Hz), 6.89 (2H, d, J=8.4 Hz), 6.98 (2H, d, J=8.4 Hz), 7.17 (1H, s), 7.22 (1H, s), 7.57 (1H, dd, J=1.8, 8.8 Hz), 7.74–7.96 (5H, in), 8.36 (1H, s).

IR (KBr): 1682, 1524, 1352, 1167, 706 cm$^{-1}$.

Working Example 30
4-(6-chloronaphthanlene-2-sulfonyl)-1-[4-(1H-imidazol-1-yl)benzyl]-2-piperazinone To 4-(tert-butoxycarbonyl)-1-[4-(1H-imidazol-1-yl)benzyl]-2-piperazinone (5.3 g) was added trifluoroacetic acid (40 ml), and the mixture was allowed to stand at room temperature for 1 hour. The reaction solution was concentrated, and the residue was dissolved in dichloromethane (50 ml). To the solution were added triethylamine (9.01 g) and 6-chloronaphthanlene-2-sulfonyl chloride (4.0 g), and the mixture was stirred at room temperature for 1 hour. The reaction solution was separated, and the organic layer was washed with brine, dried and concentrated. The residue was purified with silica gel column chromatography (ethyl acetate) and recrystallized from ethyl acetate to give colorless crystals of the title compound (4.93 g).

Working Example 31
4-(6-bromonaphthanlene-2-sulfonyl)-1-[4-(1H-imidazol-1-yl)benzyl]-2-piperazinone To a solution of 1-[4-(1H-imidazol-1-yl)benzyl]-2-piperazinone dihydrochloride (200 mg) in ethyl acetate (10 ml) and sodium bicarbonate solution (10 ml) was added 6-bromonaphthanlene-2-sulfonyl chloride (186 mg), and the mixture was stirred at room temperature for 1 hour. The reaction solution was separated, and the organic layer was washed with brine, dried and concentrated. The residue was purified with silica gel column chromatography (ethyl acetate) to give colorless crystals of the title compound (104 mg).

$^1$H-NMR (CDCl$_3$)δ: 3.37 (4H, s), 3.87 (2H, s), 4.58 (2H, s), 7.21 (1H, s), 7.24 (1H, t, J=1.2 Hz), 7.29 (4H, s), 7.73 (1H, dd, J=1.8, 8.8 Hz), 7.78–7.95 (4H, m), 8.11 (1H, s), 8.34 (1H, s).

IR (KBr): 1653, 1524, 1346, 1165 cm$^{-1}$.

Working Example 32
4-(6-fluoronaphthanlene-2-sulfonyl)-1-[4-(1H-imidazol-1-yl)benzyl]-2-piperazinone According to a method described in Working Example 31, colorless crystals of the title compound (86 mg) were obtained from 1-[4-(1H-imidazol-1-yl)benzyl]-2-piperazinone dihydrochloride (200 mg) and 6-fluoronaphthanlene-2-sulfonyl chloride (150 mg).

$^1$H-NMR (CDCl$_3$) δ: 3.38 (4H, s), 3.86 (2H, s), 4.59 (2H, s), 7.21 (1H, t, J=0.8 Hz), 7.24 (1H, t, J=1.2 Hz), 7.30 (4H, s), 7.45 (1H, dt, J=2.6, 8.8 Hz), 7.55 (1H, dd, J=2.2, 8.6 Hz), 7.74–7.84 (2H, m), 7.96 (1H, d, J=8.6 Hz), 8.01 (1H, dd, J=5.4, 8.8 Hz), 8.38 (1H, s).

IR (KBr): 1653, 1524, 1348, 1163 cm$^{-1}$.

Working Example 33

4-(6-methylphthanlene-2-sulfonyl)-1-[4-(1H-imidazol-1-yl)benzyl]-2-piperazinone

According to a method described in Working Example 31, colorless crystals of the title compound (59 mg) were obtained from 1-[4-(1H-imidazol-1-yl)benzyl]-2-piperazinone dihydrochloride (200 mg) and 6-methylnaphthanlene-2-sulfonyl chloride (147 mg).

$^1$H-NMR (CDCl$_3$) δ: 2.57 (3H, s), 3.36 (4H, s), 3.87 (2H, s), 4.57 (2H, s), 7.20 (1H, s), 7.23 (1H, s), 7.26 (4H, s), 7.48 (1H, dd, J=1.8, 8.8 Hz), 7.68–7.75 (2H, m), 7.80 (1H, s), 7.88 (1H, d, J=8.8 Hz), 7.90 (1H, d, J=8.8 Hz), 8.32 (1H, s).

IR (KBr): 1651, 1524, 1346, 1163 cm$^{-1}$.

Working Example 34

4-(6-chloronaphthanlene-2-sulfonyl)-1-[4-(2-methyl-1H-imidazol-1-yl)benzyl]-2-piperazinone To a solution of N-(tert-butoxycarbonyl)ethylenediamine (431 mg) and 4-(2-methyl-1H-imidazol-1-yl)benzaldehyde (500 mg) in dichloromethane (10 ml) was added acetic acid (323 mg), and the mixture was stirred at room temperature for 1 hour. To the mixture was added, under ice-cooling, sodium triacetoxyborohydride (855 mg), and the mixture was stirred at room temperature for 15 hours. The reaction solution was concentrated, and the residue was dissolved in ethyl acetate. The solution was extracted with water, and the aqueous layer was made alkaline with sodium hydroxide solution. The mixture was extracted with dichloromethane and dried with sodium sulfate, and sodium sulfate was filtered of f. To the filtrate was added triethylamine (543 mg) and then was added at 0° C. chloroacetyl chloride (455 mg), and the mixture was stirred at room temperature for 30 minutes. The reaction solution was washed with sodium bicarbonate solution and brine, dried and concentrated, and the residue was dissolved in DMF (15 ml). To the solution was added sodium hydride in oil (129 mg), and the mixture was stirred at room temperature for 3 hours. The reaction solution was concentrated, and the residue was dissolved in ethyl acetate. The solution was washed with water and brine, dried and concentrated, and the residue was purified with column chromatography (ethyl acetate) to give 4-(tert-butoxycarbonyl)-1-[4-(2-methyl-1H-imidazol-1-yl)benzyl]-2-piperazinone. To the obtained 4-(tert-butoxycarbonyl)-1-[4-(2-methyl-1H-imidazol-1-yl)benzyl]-2-piperazinone was added trifluoroacetic acid (8 ml), and the mixture was stirred at room temperature for 1 hour and concentrated. The residue was dissolved in dichloromethane (20 ml). To the solution was added triethylamine (1.58 g) and then was added 6-chloronaphthanlene-2-sulfonyl chloride (700 mg), and the mixture was stirred at room temperature for 1 hour. The reaction solution was separated, and the organic layer was washed with brine, dried and concentrated. The residue was purified with silica gel column chromatography (ethyl acetate) to give colorless crystals of the title compound (70 mg).

$^1$H-NMR (CDCl$_3$) δ: 2.34 (3H, s), 3.40 (4H, s), 3.87 (2H, s), 4.60 (2H, s), 6.95 (1H, d, J=1.4 Hz), 7.02 (1H, d, J=1.4 Hz), 7.20 (2H, d, J=8.8 Hz), 7.29 (2H, d, J=8.8 Hz), 7.60 (1H, dd, J=1.8, 8.8 Hz), 7.79 (1H, dd, J=1.8, 8.8 Hz), 7.90–7.98 (3H, m), 8.35 (1H, s).

Working Example 35

1-(1-acetimidoyl-4-methoxycarbonylpiperidin-4-ylmethyl)-4-(6-chloronaphthanlene-2-sulfonyl)-2-piperazinone Hydrochloride To a solution of 4-(6-chloronaphthanlene-2-sulfonyl)-1-(4-methoxycarbonylpiperidin-4-ylmethyl)-2-piperazinone hydrochloride (100 mg) and triethylamine (294 mg) in methanol (15 ml) was added ethyl acetimidate (240 mg), and the mixture was stirred at room temperature for 15 hours. The reaction solution was concentrated, and the residue was dissolved in dichloromethane. The solution was washed with 1N sodium hydroxide solution, dried and concentrated, and the residue was dissolved in ethyl acetate. To the solution was added a solution of hydrochloric acid in ethyl acetate, and precipitated hydrochloride salt was filtered and dried to give colorless solid of the title compound (129 mg).

$^1$H-NMR (DMSO-d$_6$) δ: 1.51 (2H, m), 1.91 (2H, m), 2.20 (3H, s), 3.00 (2H, m), 3.20–3.40 (4H, m), 3.44 (2H, s), 3.60 (3H, s), 3.69 (2H, s), 3.79 (2H, m), 7.75 (1H, dd, J=1.8, 8.8 Hz), 7.88 (1H, dd, J=1.8, 8.8 Hz), 8.20 (1H, d, J=8.8 Hz), 8.25–8.33 (2H, m), 8.58 (1H, s), 9.04 (2H, brs).

Working Example 36

4-(6-chloronaphthanlene-2-sulfonyl)-1-[4-methoxycarbonyl-1-(4-pyridyl)piperidin-4-ylmethyl]-2-piperazinone Hydrochloride A solution of 4-(6-chloronaphthanlene-2-sulfonyl)-1-(4-methoxycarbonylpiperidin-4-ylmethyl)-2-piperazinone hydrochloride (237 mg), chloropyridine hydrochloride (89 mg) and triethylamine (200 mg) in ethanol (20 ml) was allowed to react in a sealed tube at 150° C. for 15 hours. The reaction solution was concentrated, and the residue was dissolved in dichloromethane. The solution was washed with 1N sodium hydroxide solution, dried and concentrated, and the residue was purified with silica gel column chromatography (dichloromethane:methanol containing 10% ammonia solution=20:1) to give colorless solid of 4-(6-chloronaphthanlene-2-sulfonyl)-1-[4-methoxycarbonyl-1-(4-pyridyl)piperidin-4-ylmethyl]-2-piperazinone (180 mg).

$^1$H-NMR (CDCl$_3$) δ: 1.51 (2H, m), 2.10 (2H, m), 2.84 (2H, m), 3.37 (4H, s), 3.52 (2H, s), 3.67 (2H, m), 3.71 (3H, s), 3.79 (2H, s), 6.58 (2H, d, J=6.6 Hz), 7.61 (1H, dd, J=2.0, 8.8 Hz), 7.79 (1H, dd, J=1.8, 8.0 Hz), 7.90–8.00 (3H, m), 8.23 (2H, d, J=6.6 Hz), 8.35 (1H, s).

IR (KBr): 1728, 1661, 1595, 1348, 1165 cm$^{-1}$.

To the obtained 4-(6-chloronaphthanlene-2-sulfonyl)-1-[4-methoxycarbonyl-1-(4-pyridyl)piperidin-4-ylmethyl]-2-piperazinone (180 mg) was added a solution of hydrochloric acid in ethyl acetate to give colorless solid of the title compound (150 mg) as hydrochloride salt.

$^1$H-NMR (DMSO-d$_6$) δ: 1.45 (2H, m), 1.93 (2H, m), 3.06 (2H, m), 3.20–3.50 (6H,), 3.61 (3H, s), 3.70 (2H, s), 3.98 (2H, m), 7.12 (2H, d, J=7.4 Hz), 7.75 (1H, dd, J=2.0, 8.8 Hz), 7.88 (1H, dd, J=1.8, 8.8 Hz), 8.16–8.34 (5H, m), 8.59 (1H, s).

Working Example 37

4-(7-chloro-2H-benzopyran-3-sulfonyl)-1-[4-methoxycarbonyl-1-(4-pyridyl)piperidin-4-ylmethyl]-2-piperazinone To 1-[1-(tert-butoxycarbonyl)-4-methoxycarbonylpiperidin-4-ylmethyl]-4-(7-chloro-2H-benzopyran-3-sulfonyl)-2-piperazinone (260 mg) was added 4N hydrochloric acid in ethyl acetate (10 ml) and methanol (4 ml), and the mixture was stirred at room temperature for 30 minutes. The reaction solution was concentrated to give colorless solid of 4-(7-chloro-2H-benzopyran-3-sulfonyl)-1-(4-methoxycarbonylpiperidin-4-ylmethyl)-2-piperazinone hydrochloride (228 mg). A solution of 4-(7-chloro-2H-benzopyran-3-sulfonyl)-1-(4-methoxycarbonylpiperidin-4-ylmethyl)-2-piperazinone hydrochloride (228 mg), chloropyridine hydrochloride (80 mg) and triethylamine (225 mg) in ethanol (14 ml) was allowed to react in a sealed tube at 150% for 15 hours. The reaction solution was concentrated, and the residue was dissolved in dichloromethane. The solution was washed with 1N sodium hydroxide solution, dried and concentrated, and the residue was purified with silica gel column chromatography (dichloromethane:methanol containing 10% ammonia solution=20:1) to give colorless solid of the title compound (126 mg).

$^1$H-NMR (CDCl$_3$) δ: 1.60 (2H, m), 2.20 (2H, m), 2.91 (2H, m), 3.37–3.56 (4H, m), 3.60 (2H, s), 3.64–3.80 (4H, m), 3.75 (3H, s), 3.90 (2H, s), 4.89 (2H, s), 6.62 (2H, d, J=6.6 Hz), 6.93 (1H, d, J=1.8 Hz), 7.00 (1H, dd, J=1.8, 8.0 Hz), 7.14 (1H, d, J=8.0 Hz), 7.27 (1H, s), 8.25 (2H, d, J=6.6 Hz).

IR (KBr): 1728, 1661, 1597, 1348, 1159 cm$^{-1}$.

Working Example 38

4-(6-chloronaphthanlene-2-sulfonyl)-1-[4-hydroxymethyl-1-(4-pyridyl)piperidin-4-ylmethyl]-2-piperazinone To a solution of 4-(6-chloronaphthanlene-2-sulfonyl)-1-[4-methoxycarbonyl-1-(4-pyridyl)piperidin-4-ylmethyl]-2-piperazinone (95 mg) in tetrahydrofuran (20 ml) was added lithium borohydride (89 mg), and the mixture was stirred at room temperature for 15 hours. To the reaction solution was added 1N hydrochloric acid (0.1 ml), and the mixture was concentrated. The residue was dissolved in dichloromethane, and the solution was washed with 1N sodium hydroxide solution, dried and concentrated. The residue was purified with silica gel column chromatography (dichloromethane: methanol containing 10% ammonia solution=20:1) to give colorless solid of the title compound (32 mg).

$^1$H-NMR (CDCl$_3$) δ: 1.47–1.75 (4H, m), 2.60–3.00 (4H, m), 3.20–3.60 (6H, m), 3.65 (2H, s), 3.84 (2H, t, J=4.8 Hz), 6.59 (2H, d, J=6.6 Hz), 7.58 (1H, dd, J=1.8, 8.8 Hz), 7.80 (1H, dd, J=1.8, 8.8 Hz), 7.86–7.96 (3H, m), 8.04 (2H, d, J=6.6 Hz), 8.35 (1H, s).

IR (KBr): 1634, 1534, 1333, 1157, 1105 cm$^{-1}$.

Working Example 39

4-{[4-(6-chloro-2-naphthanlenesulfonyl)-2-oxo-1-piperazinyl]methyl}-1-(4-pyridyl)isonipecotic Acid To a solution of 4-(6-chloronaphthanlene-2-sulfonyl)-1-[4-methoxycarbonyl-1-(4-pyridyl)piperidin-4-ylmethyl]-2-piperazinone (200 mg) in acetic acid (4 ml) was added 6N hydrochloric acid (2 ml), and the mixture was refluxed for 8 hours. The reaction solution was concentrated, and the residue was purified with CHP column chromatography (20% acetonitrile/water) to give colorless crystals of the title compound (163 mg).

$^1$H-NMR (DMSO-d$_6$) δ: 1.52 (2H, m), 2.02 (2H, m), 2.95–3.15 (4H, m), 3.41 (2H, m), 3.50–3.77 (6H, m), 7.04 (2H, d, J=7.2 Hz), 7.63 (1H, dd, J=2.2, 8.8 Hz), 7.82 (1H, dd, J=1.8, 8.8 Hz), 7.96–8.18 (5H, m), 8.44 (1H, s).

IR (KBr): 1647, 1593, 1541, 1387, 1337, 1155 cm$^{-1}$.

Working Example 40

N,N-dimethyl 4-{[4-(6-chloro-2-naphthanlenesulfonyl)-2-oxo-1-piperazinyl]methyl}-1-(4-pyridyl)isonipecotamide To a solution of 4-{[4-(6-chloro-2-naphthanlenesulfonyl)-2-oxo-1-piperazinyl]methyl}-1-(4-pyridyl)isonipecotic acid (100 mg), dimethylamine hydrochloride (23 mg), HOBt (42 mg) and diisopropylethylamine (48 mg) in DMF (10 ml) was added WSC (71 mg), and the mixture was stirred at room temperature for 15 hours. The reaction solution was concentrated, and to the residue was added 1N sodium hydroxide solution. The mixture was extracted with dichloromethane, dried and concentrated, and the residue was purified with silica gel column chromatography (dichloromethane:methanol containing 10% ammonia solution=20:1) to give colorless solid of the title compound (45 mg).

$^1$H-NMR (CDCl$_3$) δ: 1.80–2.20 (4H, m), 2.80 (3H, s), 3.04 (3H, s), 3.20–3.45 (6H, m), 3.60–3.80 (4H, m), 4.32 (2H, s), 6.67 (2H, d, J=6.6 Hz), 7.54 (1H, dd, J=2.0, 8.8 Hz), 7.80–7.98 (4H, m), 8.26 (2H, d, J=6.6 Hz), 8.38 (1H, s).

IR (KBr): 1736, 1663, 1597, 1510, 1337, 1155 cm$^{-1}$.

Working Example 41

N-methyl 4-{[4-(6-chloro-2-naphthanlenesulfonyl)-2-oxo-1-piperazinyl]methyl}-1-(4-pyridyl)isonipecotamide According to a method described in Working Example 40, colorless solid of the title compound (48 mg) was obtained from 4-{[4-(6-chloro-2-naphthanlenesulfonyl)-2-oxo-1-piperazinyl]methyl}-1-(4-pyridyl)isonipecotic acid (125 mg), methylamine hydrochloride (31 mg).

$^1$H-NMR (CDCl$_3$) δ: 1.90–2.25 (4H, m), 2.88 (3H, d, J=4.2 Hz), 3.35–3.50 (8H, m), 3.74 (2H, s), 3.76 (2H, m), 6.70 (2H, d, J=6.6 Hz), 7.55 (1H, br), 7.60 (1H, dd, J=2.0, 8.8 Hz), 7.79 (1H, dd, J=1.8, 8.8 Hz), 7.90–7.98 (3H, m), 8.27 (2H, d, J=6.6 Hz), 8.39 (1H, s).

IR (KBr): 1732, 1651, 1597, 1543, 1337, 1159 cm$^{-1}$.

Working Example 42

4-{[4-(6-chloro-2-naphthanlenesulfonyl)-2-oxo-1-piperazinyl]methyl}-1-(4-pyridyl)isonipecotamide According to a method described in Working Example 40, colorless solid of the title compound (45 mg) was obtained from 4-{[4-(6-chloro-2-naphthanlenesulfonyl)-2-oxo-1-piperazinyl]methyl}-1-(4-pyridyl)isonipecotic acid (125 mg) and ammonium chloride (37 mg).

$^1$H-NMR (CDCl$_3$) δ: 1.90–2.20 (4H, m), 3.20–3.80 (10H, m), 3.79 (2H, s), 5.67 (1H, brs), 6.57 (2H, d, J=6.6 Hz), 7.57 (1H, brs), 7.59 (1H, dd, J=1.8, 8.8 Hz), 7.80 (1H, dd, J=1.8, 8.8 Hz), 7.88–7.98 (3H, in), 8.25 (2H, d, J=6.6 Hz), 8.40 (1H, s).

IR(KBr): 3364, 3185, 1730, 1690, 1597, 1514, 1348, 1248, 1161 cm$^{-1}$.

Working Example 43

4-{4-[4-(6-chloronaphthanlene-2-sulfonyl)-2-oxo-1-piperazinylmethyl]-4-hydroxy-1-piperidinyl}-1-pyridine 1-oxide To a solution of 4-(6-chloronaphthanlene-2-sulfonyl)-1-[4-hydroxy-1-(4-pyridyl)piperidin-4-ylmethyl]-2-piperazinone (100 mg) in dichloromethane (15 ml) was added m-chloroperbenzoic acid (48 mg), and the mixture was stirred at room temperature for 15 hours. The reaction solution was diluted with dichloromethane, washed with 1N sodium hydroxide solution, dried and concentrated, and the residue was purified with silica gel column chromatography (dichloromethane: methanol containing 10% ammonia solution=20:1) to give colorless solid of the title compound (30 mg).

$^1$H-NMR (CDCl$_3$) δ: 1.40–1.70 (4H, m), 3.18–3.65 (10H, m), 3.84 (2H, s), 6.62 (2H, d, J=7.6 Hz), 7.62 (1H, dd, J=1.8, 8.8 Hz), 7.80 (1H, dd, J=1.8, 8.8 Hz), 7.86–8.00 (5 H, m), 8.37 (1H, s).

Working Example 44

4-{4-[4-(6-chloronaphthanlene-2-sulfonyl)-2-oxo-1-piperazinylmethyl]-4-methoxycarbonyl-1-piperidinyl}-1-pyridine 1-oxide To a solution of 4-(6-chloronaphthanlene-2-sulfonyl)-1-[4-methoxycarbonyl-1-(4-pyridyl)piperidin-4-ylmethyl]-2- piperazinone (100 mg) in dichloromethane (15 ml) was added m-chloroperbenzoic acid (62 mg), and the mixture was stirred at room temperature for 15 hours. The reaction solution was diluted with dichloromethane, washed with 1N sodium hydroxide solution, dried and concentrated, and the residue was purified with silica gel column chromatography (dichloromethane:methanol containing 10% ammonia solution=20:1) to give colorless solid of the title compound (26 mg).

$^1$H-NMR (CDCl$_3$) δ: 1.55 (2H, m), 2.11 (2H, m), 2.89 (2H, m), 3.74 (4H, s), 3.55 (2H, s), 3.57 (2H, m), 3.73 (3H, s), 3.79 (2H, s), 6.59 (2H, d, J=7.8 Hz), 7.61 (1H, dd, J=1.8, 8.8 Hz), 7.79 (1H, dd, J=1.8, 8.8 Hz), 7.90–8.00 (5H, m), 8.35 (1H, s).

IR (KBr): 1728, 1661, 1495, 1346, 1165 cm$^{-1}$.

Working Example 45

4-(6-chloronaphthanlene-2-sulfonyl)-1-{[1-(4-pyridyl)-4-peridinyl]cyanomethyl}-2-piperazinone To a suspension of N-(tert-butoxycarbonyl)isonipecotic acid aldehyde (1.59 g), N-(6-chloronaphthanlene-2-sulfonyl)ethylenediamine hydrochloride (2.0 g) and sodium hydrogen sulfite (1.94 g) in ethanol (15 ml) was added a solution of potassium cyanide (609 mg) in water (6 ml), and the mixture was stirred at 50° C. for 20 hours The reaction solution was concentrated, and to the residue were added dichloromethane and water. Insoluble materials were filtered off, and the separated organic layer was washed with brine, dried and concentrated. The residue was purified with silica gel column chromatography (hexane:ethyl acetate=1:1) to give colorless syrup of N-{[1-(tert-butoxycarbonyl)-4-piperidinyl]cyanomethyl}-N'-(6-chloronaphthanlene-2-sulfonyl)ethylenediamine (710 mg).

$^1$H-NMR (CDCl$_3$) δ: 1.20–1.40 (2H, m), 1.47 (9H, s), 1.60–1.85 (3H, m), 2.53–2.80 (3H, m), 2.90–3.20 (3H, m), 3.24 (1H, d, J=6.2 Hz), 4.18 (2H, m), 4.94 (1H, m), 7.58 (1H, dd, J=1.8, 8.8 Hz), 7.80–7.95 (4H, m), 8.43 (1H, s).

To a solution of N-{[1-(tert-butoxycarbonyl)-4-piperidinyl]cyanomethyl}-N'-(6-chloronaphthanlene-2-sulfonyl)ethylenediamine (652 mg) and triethylamine (260 mg) in dichloromethane (20 ml) was added chloroacetyl chloride (175 mg), and the mixture was stirred at room temperature for 30 minutes. To the reaction solution was added DBU (400 mg), and the mixture was stirred at room temperature for 1 hour. The reaction solution was diluted with dichloromethane, washed with 10% citric acid solution, dried and concentrated, and the residue was purified with silica gel column chromatography (hexane: ethyl acetate=1:1) to give colorless crystals of 1-{[1-(tert-butoxycarbonyl)-4-piperidinyl]cyanomethyl}-4-(6-chloronaphthanlene-2-sulfonyl)-2-piperazinone (512 mg).

$^1$H-NMR (CDCl$_3$) δ: 1.05–1.40 (2H, m), 1.44 (9H, s), 1.91 (2H, m), 2.64 (2H, m), 3.28 (1H, m), 3.40–3.80 (5H, m), 4.00–4.30 (3H, m), 5.33 (1H, d, J=10.2 Hz), 7.62 (1H, dd, J=1.8, 8.8 Hz), 7.79 (1H, dd, J=1.8, 8.8 Hz), 7.90–8.00 (3H, m), 8.36 (1H, s).

IR (KBr): 2251, 1682, 1427, 1348, 1167 cm$^{-1}$.

To 1-{[1-(tert-butoxycarbonyl)-4-piperidinyl]cyanomethyl}-4-(6-chloronaphthanlene-2-sulfonyl)-2-piperazinone (512 mg) was added a solution of 4N hydrochloric acid in ethyl acetate (10 ml) and methanol (10 ml), and the mixture was stirred at room temperature for 30 minutes. The reaction solution was concentrated to give colorless crystals of 4-(6-chloronaphthanlene-2-sulfonyl)-1-[(4-piperidinyl)cyanomethyl]-2-piperazinone hydrochloride (430 mg).

A solution of 4-(6-chloronaphthanlene-2-sulfonyl)-1-[(4-piperidinyl)cyanomethyl]-2-piperazinone hydrochloride (430 mg), chloropyridine hydrochloride (169 mg) and triethylamine (452 mg) in ethanol (26 ml) was allowed to react in a sealed tube at 150° C. for 15 hours. The reaction solution was concentrated, and the residue was dissolved in dichloromethane. The solution was washed with 1N sodium hydroxide solution, dried and concentrated, and the residue was purified with silica gel column chromatography (dichloromethane: methanol containing 10% ammonia solution=20: 1) to give colorless solid of the title compound (37 mg).

$^1$H-NMR (CDCl$_3$) δ: 1.27 (2H, m), 1.50 (2H, m), 2.03 (1H, m), 2.73 (1H, m), 2.87 (1H, m), 3.26 (1H, m), 3.26 (1H, m), 3.40–4.00 (6H, m), 4.11 (1H, d, J=16.8 Hz), 5.35 (1H, d, J=10.2 Hz), 6.63 (2H, d, J=6.6 Hz), 7.63 (1H, dd, J=2.2, 8.8 Hz), 7.80 (1H, dd, J=2.0, 8.8 Hz), 7.90–8.00 (3H, m), 8.27 (2H, d, J=6.6 Hz), 8.37 (1H, s).

IR (KBr): 1667, 1595, 1346, 1165 cm$^{-1}$.

Working Example 46

4-(6-chloronaphthanlene-2-sulfonyl)-1-[1-[4-(1H-imidazol-1-yl)phenyl]ethyl]-2-piperazinone To a solution of 1-[4-(1H-imidazol-1-yl)phenyl]ethanol (280 mg) in dichloromethane (6 ml) was added thionyl chloride (1 ml), and the mixture was stirred at room temperature for 30 minutes. The reaction solution was concentrated to give 1-(1-chloroethyl)-4-(1H-imidazol-1-yl) benzene. To a solution of 4-(tert-butoxycarbonyl)-2-piperazinone (300 mg) in DMF (20 ml) was added sodium hydride (57 mg) in oil, and the mixture was stirred at room temperature for 30 minutes. To the mixture was added the above obtained 1-(1-chloroethyl)-4-(1H-imidazol-1-yl) benzene, and the mixture was stirred at room temperature for 15 hours. The reaction solution was concentrated, and to the residue were added ethyl acetate and water. The organic layer was washed with water and brine, dried and concentrated, and the residue was purified with silica gel column chromatography (ethyl acetate) to give colorless amorphous of 4-(tert-butoxycarbonyl)-1-[1-[4-(1H-imidazol-1-yl)phenyl]ethyl]-2-piperazinone.

To 4-(tert-butoxycarbonyl)-1-[1-[4-(1H-imidazol-1-yl) phenyl]ethyl]-2-piperazinone was added trifluoroacetic acid (10 ml), and the mixture was stirred at room temperature for 30 minutes. The reaction solution was concentrated, and the residue was dissolved in dichloromethane (15 ml). To the solution were added triethylamine (700 mg) and 6-chloronaphthanlene-2-sulfonyl chloride (400 mg), and the mixture was stirred at room temperature for 1 hour. The reaction solution was concentrated, and to the residue was ethyl acetate and water. The organic layer was washed with water, sodium bicarbonate solution and brine, dried and concentrated, and the residue was purified with silica gel column chromatography (ethyl acetate) to give colorless solid of the title compound (99 mg).

$^1$H-NMR (CDCl$_3$) δ: 1.49 (3H, d, J=7.4 Hz), 2.90–3.15 (2H, m), 3.25–3.55 (2H, m), 3.76 (1H, d, J=16.8 Hz), 3.99 (1H, d, J=16.8 Hz), 6.02 (1H, q, J=7.4 Hz), 7.21 (1H, s), 7.24 (1H, s), 7.30 (4H, s), 7.60 (1H, dd, J=1.8, 8.8 Hz), 7.78 (1H, dd, J=1.8, 8.8 Hz), 7.82 (1H, s), 7.88–7.98 (3H, m), 8.33 (1H, s).

Working Example 47

4-(6-chloronaphthanlene-2-sulfonyl)-1-[4-(1H-1,2,4-triazole-1-yl)benzyl]-2-piperazinone According to a method described in Working Example 46, colorless solid of the title compound was obtained from 4-(1H-1,2,4-triazol-1-yl)benzylalcohol instead of 1-[4-(1H-imidazol-1-yl)phenyl]ethanol.

¹H-NMR (CDCl₃) δ: 3.37 (4H, s), 3.87 (2H, s), 4.59 (2H, s), 7.31 (2H, d, J=8.6 Hz), 7.53–7.64 (3H, m), 7.78 (1H, dd, J=11.8, 8.6 Hz), 7.88–7.97 (3H, m), 8.10 (1H, s), 8.34 (1H, s), 8.52 (1H, s).

IR (KBr): 1651, 1522, 1493, 1346, 1279, 1165 cm⁻¹.

Working Example 48

4-(6-chloronaphthanlene-2-sulfonyl)-1-[trans-4-(4H-1,2,4-triazole-4-yl)cyclohexylmethyl]-2-piperazinone To a solution of methyl tranexamate hydrochloride (2.07 g), N-(2,2-diethoxyethyl)-Z-glycine (3.13 g) and HOBt (1.53 g) in acetonitrile (40 ml) was added WSC (2.29 g), and the mixture was stirred at room temperature for 15 hours. The reaction solution was concentrated, and to the residue were added ethyl acetate and water. The organic layer washed with water, sodium bicarbonate solution, citric acid solution and brine, dried and concentrated, and the residue was dissolved in toluene (30 ml). To the solution was added p-toluene sulfonic acid hydrate (190 mg), and the mixture was stirred at 100 C. for 20 minutes. The reaction solution was washed with saturated sodium bicarbonate solution and brine, dried and concentrated, and the residue was purified with silica gel column chromatography (hexane:ethyl acetate=2:1) to give colorless oil of 1-(trans-4-methoxycarbonylcyclohexylmethyl)-4-benzyloxycarbonyl-2-oxo-1,2,3,4-tetrahydropyrazine (2.0 g).

A solution of 1-(trans-4-methoxycarbonylcyclohexylmethyl)-4-benzyloxycarbonyl-2-oxo-1,2,3,4-tetrahydropyrazine (2.0 g) and 10% palladium on carbon (400 mg) in methanol (80 ml) was stirred at room temperature for 15 hours, under hydrogen atmosphere, and the catalyst was filtered off. The reaction solution was concentrated to give colorless oil of 1-(trans-4-methoxycarbonylcyclohexylmethyl)-2-piperazinone. To the obtained 1-(trans-4-methoxycarbonylcyclohexylmethyl)-2-piperazinone were added ethyl acetate (20 ml) and sodium bicarbonate solution (20 ml), and then was added 6-chloro-2-naphthanlenesulfonyl chloride (1.5 g), and the mixture was stirred at room temperature for 5 hours. The separated organic layer was washed with water and brine, dried and concentrated, and the residue was crystallized from ethyl acetate to give colorless crystals of 4-(6-chloro-2-naphthanlenesulfonyl)-1-(trans-4-methoxycarbonylcyclohexylmethyl)-2-piperazinone (1.4 g).

¹H-NMR (CDCl₃) δ: 0.97 (2H, m), 1.30 (2H, m), 1.35–1.70 (3H, m), 1.92 (2H, m), 2.19 (1H, m), 3.19 (2H, d, J=7.0 Hz), 3.39 (4H, s), 3.65 (3H, s), 3.78 (2H, s), 7.60 (1H, dd, J=2.2, 8.8 Hz), 7.79 (1H, dd, J=1.8, 8.8 Hz), 7.90–7.97 (3H, m), 8.35 (1H, s).

To a solution of 4-(6-chloro-2-naphthanlenesulfonyl)-1-(trans-4-methoxycarbonylcyclohexylmethyl)-2-piperazinone (1.33 g) in methanol (10 ml) and THF (30 ml) was added 1N sodium hydroxide solution (10 ml), and the mixture was stirred at room temperature for 2 hours. The reaction solution was concentrated, and the residue was dissolved in water. To the solution was added 1N hydrochloric acid (10 ml), and the resulting precipitates were filtered, washed with water, dried and concentrated to give 4-(6-chloro-2-naphthanlenesulfonyl)-1-(trans-4-carboxycyclohexylmethyl)-2-piperazinone (1.22 g). The obtained 4-(6-chloro-2-naphthanlenesulfonyl)-1-(trans-4-carboxycyclohexylmethyl)-2-piperazinone (1.0 g) was suspended in DMF (25 ml). To the suspension were added diphenylphosphoryl azide (651 mg) and triethylamine (326 mg), and the mixture was stirred at room temperature for 3 hours. The reaction solution was concentrated, and to the residue was ethyl acetate. The mixture was washed with water, dried and concentrated, and to the residue was added toluene (25 ml). The mixture was refluxed for 3 hours. To the mixture were added pyridine (1 ml) and t-butanol (10 ml), and the mixture was refluxed for 3 hours. The reaction solution was concentrated, and to the residue was ethyl acetate. The mixture was washed with water, dried and concentrated, and the residue was purified with silica gel column chromatography (hexane:ethyl acetate:dichloromethane=2:1:1) to give colorless crystals of 1-[trans-4-(tert-butoxycarbonylamino)cyclohexylmethyl]-4-(6-chloronaphthanlene-2-sulfonyl)-2-piperazinone (265 mg).

¹H-NMR (CDCl₃) δ: 0.90–1.10 (4H, m), 1.43 (9H, s), 1.50–1.70 (3H, m), 1.97 (2H, m), 3.16 (2H, d, J=7.0 Hz), 3.37 (1H, m), 3.39 (4H, s), 3.77 (2H, s), 4.86 (1H, d, J=6.4 Hz), 7.60 (1H, dd, J=2.2, 8.8 Hz), 7.79 (1H, dd, J=1.8, 8.8 Hz), 7.90–7.98 (3H, m), 8.35 (1H, s).

To 1-[trans-4-(tert-butoxycarbonylamino)cyclohexylmethyl]-4-(6-chloronaphthanlene-2-sulfonyl)-2-piperazinone (265 mg) was added a solution of 4N hydrochloric acid in ethyl acetate (10 ml) and methanol (10 ml), and the mixture was stirred at room temperature for 30 minutes. The reaction solution was concentrated to give crude crystals of 1-[trans-4-aminocyclohexylmethyl]-4-(6-chloronaphthanlene-2-sulfonyl)-2-piperazinone hydrochloride. The mixture of the obtained 1-[trans-4-aminocyclohexylmethyl]-4-(6-chloronaphthanlene-2-sulfonyl)-2-piperazinonehydrochloride, N,N-dimethylformamide azine dihydrochloride (106 mg) and pyridine (10 ml) was stirred at 115% for 4 days. The reaction solution was concentrated, and the residue was dissolved in dichloromethane. The solution was washed with water and brine, dried and concentrated, and the residue was purified with silica gel column chromatography (dichloromethane:methanol containing 10% ammonia solution=10:1) to give colorless solid of the title compound (101 mg).

¹H-NMR (CDCl₃) δ: 1.22 (2H, m), 1.50–1.90 (5H, m), 2.17 (2H, m), 3.27 (2H, d, J=6.8 Hz), 3.42 (4H, s), 3.72 (2H, s), 3.98 (1H, m), 7.61 (1H, dd, J=1.8, 8.8 Hz), 7.80 (1H, dd, J=1.8, 8.8 Hz), 7.90–8.00 (3H, m), 8.17 (2H, s), 8.35 (1H, s).

IR (KBr): 1651, 1495, 1456, 1346, 1184, 1165 cm⁻¹.

Working Example 49

4-(6-chloro-2-naphthanlenesulfonyl)-1-(4-thioureidobenzyl)-2-piperazinone

To a solution of 4-(tert-butoxycarbonyl)-2-piperazinone (600 mg) in DMF (9 ml) was added sodium hydride in oil (120 mg), and the mixture was stirred at room temperature for 1 hour. To the mixture was added dropwise a solution of 4-nitrobenzyl bromide (648 mg) in THF (5 ml) at ° C., and the mixture was stirred for 30 minutes. The reaction solution was diluted with water, extracted with ethyl acetate, washed with water and brine, dried and concentrated, and the residue was crystallized from diisopropylether to give colorless crystals of 4-(tert-butoxycarbonyl)-1-(4-nitrobenzyl)-2-piperazinone (755 mg).

¹H-NMR (CDCl₃) δ: 1.47 (9H, s), 3.30 (2H, m), 3.64 (2H, m), 4.19 (2H, s), 4.71 (2H, s), 7.44 (2H, d, J=8.6 Hz), 8.21 (2H, d, J=8.6 Hz).

To 4-(tert-butoxycarbonyl)-1-(4-nitrobenzyl)-2-piperazinone (335 mg) was added a solution of 4N hydrochloric acid in ethyl acetate (10 ml), and the mixture was stirred at room temperature for 30 minutes. The reaction solution was concentrated, and to the residue were added ethyl acetate (10 ml) and sodium bicarbonate solution (10 ml), and then was added 6-chloro-2-naphthanlenesulfonyl chloride (522 mg). The mixture was stirred at room temperature for 1 hour. The separated organic layer was washed with water and brine, dried and concentrated, and the residue was crystallized from diisopropylether to give colorless crystals of 4-(6-chloro-2-naphthanlenesulfonyl)-1-(4-nitrobenzyl)-2-piperazinone (870 mg).

The mixture of 4-(6-chloro-2-naphthanlenesulfonyl)-1-(4-nitrobenzyl)-2-piperazinone (800 mg), 10% palladium on carbon (240 mg), methanol (4 ml) and THF (16 ml) was stirred under hydrogen atmosphere at room temperature, until starting materials disappeared, and the catalyst was filtered off. The solvent was concentrated to give colorless solid of 1-(4-aminobenzyl)-4-(6-chloro-2-naphthanlenesulfonyl)-2-piperazinone.

$^1$H-NMR (CDCl$_3$) δ: 3.29 (4H, s), 3.81 (2H, s), 4.41 (2H, s), 6.63 (2H, d, J=8.4 Hz), 6.95 (2H, d, J=8.4 Hz), 7.60 (1H, dd, J=2.0, 8.8 Hz), 7.76 (1H, dd, J=1.8, 8.8 Hz), 7.90–8.03 (3H, m), 8.34 (1H, s).

The obtained 1-(4-aminobenzyl)-4-(6-chloro-2-naphthanlenesulfonyl)-2-piperazinone was dissolved in acetone (8 ml) and THF (8 ml), and to the solution was added benzoyl isocyanate (300 mg). The mixture was stirred at room temperature for 1 hour. To the mixture was added 1N sodium hydroxide solution (2 ml), and the mixture was stirred at room temperature for 1 hour. The reaction solution was concentrated, and to the residue was added hydrous ethanol. Precipitated crystals were filtered, washed with ethanol and ether to give colorless crystals of the title compound (922 mg).

$^1$H-NMR (DMSO-d$_6$) δ: 3.10–3.45 (4H, m), 3.76 (2H, s), 4.42 (2H, s), 7.08 (2H, d, J=8.2 Hz), 7.29 (2H, d, J=8.2 Hz), 7.40 (2H, br), 8.17 (1H, d, J=8.8 Hz), 8.20–8.35 (2H, m), 8.39 (1H, s), 8.66 (1H, s).

Working Example 50

1-[4-(2-aminoimidazol-1-yl)benzy]-4-(6-chloronaphthanlene-2-sulfonyl)-2-piperazinone hydrochloride To a solution of 4-(6-chloro-2-naphthanlenesulfonyl)-1-(4-thioureidobenzyl)-2-piperazinone (520 mg) in DMF (5 ml) was added methyl iodide (1 ml), and the mixture was stirred at room temperature for 3 days. The reaction solution was concentrated, and to the residue were added 2,2-dimethoxyethylamine (335 mg) and ethanol (4 ml). The mixture was refluxed for 24 hours, and the reaction solution was concentrated. To the residue were added ethanol (2 ml) and concentrated hydrochloric acid (6 ml), and the mixture was stirred 50° C. for 1 hour. The reaction solution was concentrated, and to the residue were added dichloromethane (2 ml) and triethylamine (6 ml), and then was added di-tert-butyl dicarbonate (335 mg), and the mixture was stirred at room temperature for 1 hour, diluted with dichloromethane, washed with brine, dried and concentrated. The residue was purified with silica gel column chromatography (dichloromethane:methanol containing 10% ammonia solution=50:1→20:1) to give colorless solid of 1-{4-[1-(tert-butoxycarbonyl)-2-imidazolylamino]benzyl}-4-(6-chloro-2-naphthanlenesulfonyl)-2-piperazinone (104 mg) and colorless amorphous of 1-[4-(2-aminoimidazol-1-yl)benzyl]-4-(6-chloronaphthanlene-2-sulfonyl)-2-piperazinone (159 mg).

$^1$H-NMR (CDCl$_3$) δ: 3.41 (4H, s), 3.49 (2H, s), 3.86 (2H, s), 4.59 (2H, s), 6.64 (1H, d, J=2.2 Hz), 6.76 (1H, d, J=2.2 Hz), 7.33 (4H, s), 7.60 (1H, dd, J=1.8, 8.8 Hz), 7.79 (1H, dd, J=1.8, 8.8 Hz), 7.90–8.00 (3H, m), 8.36 (1H, s).

The obtained 1-[4-(2-aminoimidazol-1-yl)benzyl]-4-(6-chloronaphthanlene-2-sulfonyl)-2-piperazinone (159 mg) was converted to hydrochloride in a solution of hydrochloric acid in ethyl acetate to give colorless solid of the title compound (91 mg).

$^1$H-NMR (DMSO-d$_6$) δ: 3.33 (4H, m), 3.81 (2H, s), 4.54 (2H, s), 6.95 (1H, d, J=2.2 Hz), 7.00–7.08 (3H, m), 7.28 (2H, d, J=8.8 Hz), 7.34 (2H, d, J=8.8 Hz), 7.73 (1H, dd, J=2.2, 8.8 Hz), 7.89 (1H, dd, J=1.8, 8.8 Hz), 8.15–8.33 (3H, m), 8.60 (1H, s).

IR (KBr): 3077, 1655, 1346, 1163 cm$^{-1}$.

Working Example 51

1-[4-(2-imidazolylamino)benzyl]-4-(6-chloronaphthanlene-2-sulfonyl)-2-piperazinone 1-{4-[1-(tert-butoxycarbonyl)-2-imidazolylamino]benzyl}-4-(6-chloro-2-naphthanlenesulfonyl)-2-piperazinone obtained in Working Example 50

$^1$H-NMR (CDCl$_3$) δ: 1.63 (9H, s), 3.28 (4H, s), 3.84 (2H, s), 4.48 (2H, s), 6.67 (1H, d, J=1.8 Hz), 6.92 (1H, d, J=1.8 Hz), 7.08 (2H, d, J=8.4 Hz), 7.48–7.62 (2H, m), 7.76 (1H, dd, J=1.8, 8.8 Hz), 7.86–7.96 (3H, m), 8.32 (1H, s), 9.01 (1H, s).

To 1-{4-[1-(tert-butoxycarbonyl)-2-imidazolylamino]benzyl}-4-(6-chloro-2-naphthanlenesulfonyl)-2-piperazinone (104 g) were added 4N hydrochloric acid in ethyl acetate (6 ml) and methanol (4 ml), and the mixture was stirred at room temperature for 3 hours. The reaction solution was concentrated, and to the residue was added 1N sodium hydroxide solution. The mixture was extracted with dichloromethane, dried and concentrated, and the residue was purified with silica gel column chromatography (dichloromethane:methanol containing 10% ammonia solution=20:1) to give colorless crystals of the title compound (36 mg).

$^1$H-NMR (CDCl$_3$+CD$_3$OD) δ: 3.32 (4H, s), 3.82 (2H, s), 4.45 (2H, s), 6.72 (2H, s), 7.06 (4H, s), 7.60 (1H, dd, J=1.8, 8.8 Hz), 7.77 (1H, dd, J=1.8, 8.8 Hz), 7.88–8.00 (3H, m), 8.34 (1H, s).

IR (KBr): 3231, 1640, 1576, 1514, 1341, 1163 cm$^{-1}$.

Working Example 52

4-(6-chloronaphthanlene-2-sulfonyl)-1-[4-(4H-1,2,4-triazole-4-yl)benzyl]-2-piperazinone A mixture of 1-(4-aminobenzyl)-4-(6-chloronaphthanlene-2-sulfonyl)-2-piperazinone hydrochloride (150 mg), N,N-dimethylformamide azine dihydrochloride (85 mg) and pyridine (10 ml) was refluxed for 15 hours. The reaction solution was concentrated, and the residue was dissolved in dichloromethane. The solution was washed with water and brine, dried and concentrated, and the residue was purified with silica gel column chromatography (ethyl acetate: methanol=10: 1) to give colorless solid of the title compound (109 mg).

$^1$H-NMR (CDCl$_3$) δ: 3.39 (4H, s), 3.86 (2H, s), 4.61 (2H, s), 7.31 (2H, d, J=8.8 Hz), 7.38 (2H, d, J=8.8 Hz), 7.61 (1H, dd, J=1.8, 8.8 Hz), 7.79 (1H, dd, J=1.8, 8.8 Hz), 7.90–7.98 (3H, m), 8.36 (1H, s), 8.44 (2H, s).

IR (KBr): 1651, 1528, 1495, 1346, 1165 cm$^{-1}$.

Working Example 53

4-(7-chloro-2H-benzopyran-3-sulfonyl)-1-[1-(4-pyridyl)piperidin-4-ylmethyl]-2-piperazinone Hydrochloride To a solution of 1-[1-(tert-butoxycarbonyl)piperidin-4-ylmethyl]-2-piperazinone (5.0 g) and triethylamine (6.792 g) in dichloromethane (80 ml) was added dropwise at 0° C. a solution of 2-chloroethanesulfonyl chloride (4.11 g) in dichloromethane (20 ml), and the mixture was stirred at 0 for 30 minutes. The reaction solution was diluted with dichloromethane, washed with water, citric acid solution, sodium bicarbonate solution and brine, dried and concentrated, and the residue was purified with silica gel column chromatography (ethyl acetate) to give colorless amorphous of 1-[1-(tert-butoxycarbonyl)piperidin-4-ylmethyl]-4-vinylsulfonyl-2-piperazinone (3.99 g).

$^1$H-NMR (CDCl$_3$) δ: 1.20 (2H, m), 1.45 (9H, s), 1.60 (2H, m), 1.85 (1H, m), 2.67 (2H, m), 3.30 (2H, br), 3.46 (4H, s), 3.83 (2H, s), 4.10 (2H, m), 6.15 (2H, d, J=1.0, 8.8 Hz), 6.34 (1H, dd, J=1.0, 16.4 Hz), 6.46 (1H, dd, J=8.8, 16.4 Hz).

IR (KBr): 1686, 1659, 1427, 1348, 1161 cm$^{-1}$.

To a solution of the obtained 1-[1-(tert-butoxycarbonyl) piperidin-4-ylmethyl]-4-vinylsulfonyl-2-piperazinone (3.99 g) and 4-chlorosalicylaldehyde (1.61 g) in tert-butanol (35 ml) was added potassium t-butoxide (446 mg), and the mixture was refluxed for 4 days. The reaction solution was concentrated, and the residue was partitioned with ethyl acetate/water. The organic layer was washed with brine, dried and concentrated, and the residue was purified with silica gel column chromatography (hexane:ethyl acetate= 1:4) to give colorless solid of 1-[1-(tert-butoxycarbonyl) piperidin-4-ylmethyl]-4-(7-chloro-2H-benzopyran-3-sulfonyl)-2-piperazinone (1.856 g).

$^1$H-NMR (CDCl$_3$) δ: 1.19 (2H, m), 1.45 (9H, s), 1.59 (2H, m), 1.86 (1H, m), 2.66 (2H, m), 3.29 (2H, br), 3.40–3.60 (4H, m), 3.89 (2H, s), 4.10 (2H, m), 4.88 (2H, d, J=1.0 Hz), 6.93 (1H, d, J=1.8 Hz), 7.00 (1H, dd, J=1.8, 8.0 Hz), 7.14 (1H, d, J=8.0 Hz), 7.28 (1H, s).

IR (KBr): 1686, 1659, 1426, 1348, 1163 cm$^{-1}$.

To 1-[1-(tert-butoxycarbonyl)piperidin-4-ylmethyl]-4-(7-chloro-2H-benzopyran-3-sulfonyl)-2-piperazinone (1.856 g) were added 4N hydrochloric acid in ethyl acetate (40 ml) and methanol (25 ml), and the mixture was stirred at room temperature for 30 minutes. The reaction solution was concentrated to give colorless crystals of 4-(7-chloro-2H-benzopyran-3-sulfonyl)-1-(piperidin-4-ylmethyl)-2-piperazinone hydrochloride (1.618 g).

$^1$H-NMR (DMSO-d$_6$) δ: 1.32 (2H, m), 1.70 (2H, m), 1.91 (1H, m), 2.78 (2H, m), 3.15–3.60 (8H, m), 3.77 (2H, s), 4.98 (2H, d, J=0.8 Hz), 7.06 (1H, d, J=1.8 Hz), 7.11 (1H, dd, J=1.8, 8.0 Hz), 7.48 (1H, d, J=8.0 Hz), 7.50 (1H, s), 8.42 (1H, brs), 8.69 (1H, brs).

IR (KBr): 2944, 1649, 1601, 1348, 1165 cm$^{-1}$.

To sodium bicarbonate solution were added 4-(7-chloro-2H-benzopyran-3-sulfonyl)-1-(piperidin-4-ylmethyl)-2-piperazinone hydrochloride (1.4 g) and chloropyridine hydrochloride (1.02 g), and the mixture was extracted with dichloromethane (twice), dried and concentrated. To the residue was added isoamylalcohol (50 ml), and the mixture was allowed to react at 130° C. for 15 hours. The reaction solution was concentrated, and the residue was dissolved in dichloromethane. The solution was washed with 1 N sodium hydroxide solution, dried and concentrated, and the residue was purified with silica gel column chromatography (dichloromethane: methanol containing 10% ammonia solution=20: 1) to give colorless solid 4-(7-chloro-2H-benzopyran-3-sulfonyl)-1-[1-(4-pyridyl)piperidin-4-ylmethyl]-2-piperazinone (608 mg).

$^1$H-NMR (CDCl$_3$) δ: 1.31 (2H, m), 1.72 (2H, m), 1.98 (1H, m), 2.82 (2H, m), 3.32 (2H, d, J=7.2 Hz), 3.40–3.60 (4H, m), 3.87 (2H, m), 3.91 (2H, s), 4.89 (2H, s), 6.63 (2H, d, J=6.4 Hz), 6.93 (1H, d, J=1.8 Hz), 7.00 (1H, dd, J=1.8, 8.4 Hz), 7.14 (1H, d, J=8.0 Hz), 7.29 (1H, s), 8.24 (2H, d, J=6.4 Hz).

To the obtained 4-(7-chloro-2H-benzopyran-3-sulfonyl)-1-[1-(4-pyridyl)piperidin-4-ylmethyl]-2-piperazinone (608 mg) was added a solution of hydrochloric acid in ethyl acetate to give colorless solid of the title compound (480 mg) as hydrochloride salt.

$^1$H-NMR (DMSO-d$_6$) δ: 1.18 (2H, m), 1.72 (2H, m), 2.09 (1H, m), 3.11 (2H, m), 3.24 (2H, d, J=6.6 Hz), 3.35–3.60 (4H, m), 3.78 (2H, s), 4.19 (2H, m), 4.99 (2H, s), 7.05–7.20 (4H, m), 7.48 (1H, d, J=8.0 Hz), 7.50 (1H, s), 8.18 (2H, m).

IR (KBr): 3023, 1645, 1599, 1547, 1348, 1159 cm$^{-1}$.

Working Example 54

1-(1-acetimidoylpiperidin-4-ylmethyl)-4-(7-chloro-2H-benzopyran-3-sulfonyl)-2-piperazinone Hydrochloride According to a similar method described in Working Example 10, colorless solid of the title compound was obtained from 4-(7-chloro-2H-benzopyran-3-sulfonyl)-1-(piperidin-4-ylmethyl)-2-piperazinone hydrochloride.

$^1$H-NMR (DMSO-d$_6$) δ: 1.20 (2H, m), 1.69 (2H, m), 1.99 (1H, m), 2.25 (3H, s), 3.06 (2H, m), 3.25 (2H, d, J=7.4 Hz), 3.42 (2H, m), 3.50 (2H, m), 3.78 (2H, s), 3.96 (2H, m), 4.98 (2H, s), 7.07 (1H, d, J=2.2 Hz), 7.11 (1H, dd, J=2.2, 8.0 Hz), 7.48 (1H, d, J=8.0 Hz), 7.50 (1H, s), 8.91 (2H, brs).

IR (KBr): 3069, 1640, 1601, 1333, 1157 cm$^{-1}$.

Working Example 55

4-(5-chlorobenzofuran-2-sulfonyl)-1-[1-(4-pyridyl)piperidin-4-ylmethyl]-2-piperazinone Hydrochloride To a solution of 1-[1-(tert-butoxycarbonyl)piperidin-4-ylmethyl]-2-piperazinone (2.5 g) and triethylamine (1.7 g) in dichloromethane (35 ml) was added at 0° C. a solution of chloromethanesulfonyl chloride (1.26 g) in dichloromethane (2 ml), and the mixture was stirred at room temperature for 30 minutes. The reaction solution was washed with water, 10% citric acid solution and brine, dried and concentrated, and the residue was purified with silica gel column chromatography (ethyl acetate) to give colorless syrup of 1-[1-(tert-butoxycarbonyl)piperidin-4-ylmethyl]-4-(chloromethanesulfonyl)-2-piperazinone (2.47 g).

$^1$H-NMR (CDCl$_3$) δ: 1.20 (2H, m), 1.45 (9H, s), 1.60 (2H, m), 1.90 (1H, m), 2.69 (2H, m), 3.32 (2H, m), 3.46 (2H, m), 3.75 (2H, m), 4.00–4.20 (4H, m), 4.58 (2H, s).

IR (KBr): 1682, 1651, 1427, 1354, 1167 cm$^{-1}$.

A mixture of 1-[1-(tert-butoxycarbonyl)piperidin-4-ylmethyl]-4-(chloromethanesulfonyl)-2-piperazinone (2.47 g), 5-chlorosalicylaldehyde (917 mg), potassium carbonate (810 mg) and DMF (30 ml) was stirred at 100° C. for 2 days, and the reaction solution was concentrated. To the residue was added water, and the mixture was extracted with ethyl acetate, washed with water and brine, dried and concentrated. The residue was purified with silica gel column chromatography (hexane:ethyl acetate=1:4) to give colorless solid of 1-[1-(tert-butoxycarbonyl)piperidin-4-ylmethyl]-4-(5-chlorobenzofuran-2-sulfonyl)-2-piperazinone (272 mg).

$^1$H-NMR (CDCl$_3$) δ: 1.14 (2H, m), 1.44 (9H, s), 1.58 (2H, m), 1.78 (1H, m), 2.60 (2H, m), 3.24 (2H, m), 3.44 (2H, m), 3.61 (2H, m), 3.99 (2H, s), 4.07 (2H, m), 7.39 (1H, d, J=0.8 Hz), 7.45 (1H, dd, J=1.8, 8.4 Hz), 7.51 (1H, d, J=8.4 Hz), 7.69 (1H, dd, J=0.8, 1.8 Hz).

IR (KBr): 1682, 1661, 1427, 1368, 1165 cm$^{-1}$.

To 1-[1-(tert-butoxycarbonyl)piperidin-4-ylmethyl]-4-(5-chlorobenzofuran-2-sulfonyl)-2-piperazinone (270 mg) were added 4N hydrochloric acid in ethyl acetate (8 ml) and methanol (2 ml), and the mixture was stirred at room temperature for 30 minutes. The reaction solution was concentrated to give 4-(5-chlorobenzofuran-2-sulfonyl)-1-(piperidin-4-ylmethyl)-2-piperazinone hydrochloride (229 mg).

$^1$H-NMR (DMSO-d$_6$) δ: 1.24 (2H, m), 1.59 (2H, m), 1.83 (1H, m), 2.70 (2H, m), 3.05–3.40 (6H, m), 3.57 (2H, m), 3.86 (2H, s), 7.59 (1H, dd, J=11.2, 8.4 Hz), 7.74 (1H, s), 7.81 (1H, d, J=8.4 Hz), 7.91 (1H, d, J=1.2 Hz), 8.31 (1H, brs), 8.62 (1H, brs).

To sodium bicarbonate solution were added 4-(5-chlorobenzofuran-2-sulfonyl)-1-(piperidin-4-ylmethyl)-2- piperazinone hydrochloride (215 mg) and chloropyridine hydrochloride (144 mg), and the mixture was extracted with dichloromethane (twice), dried and concentrated. To the residue was added isoamylalcohol (15 ml), and the mixture was allowed to react at 130° C. for 15 hours. The reaction solution was concentrated, and the residue was dissolved in dichloromethane. The solution was washed with 1N sodium hydroxide solution, dried and concentrated, and the residue was purified with silica gel column chromatography (dichloromethane:methanol containing 10% ammonia solution 15:1) to give colorless solid of 4-(5-chlorobenzofuran-2-sulfonyl)-1-[1-(4-pyridyl)piperidin-4-ylmethyl]-2-piperazinone (87 mg), which was treated with hydrochloric acid to give colorless solid of the title compound (80 mg) as hydrochloride salt.

$^1$H-NMR (DMSO-d$_6$) δ: 1.08 (2H, m), 1.58 (2H, m), 1.96 (1H, m), 3.02 (2H, m), 3.17 (2H, d, J=7.4 Hz), 3.30 (2H, m), 3.60 (2H, m), 3.88 (2H, s), 4.11 (2H, m), 7.13 (2H, d, J=7.6 Hz), 7.61 (1H, dd, J=2.2, 8.8 Hz), 7.74 (1H, s), 7.82 (1H, d, J=8.8 Hz), 7.93 (1H, d, J=2.2 Hz), 8.18 (2H, d, J=7.6 Hz).

Working Example 56
4-[5-(4-chlorophenyl)-2-thiophenesulfonyl]-1-[1-(4-pyridyl)piperidin-4-ylmethyl]-2-piperazinone A mixture of 4-(5-bromo-2-thiophenesulfonyl)-1-[1-(tert-butoxycarbonyl)piperidin-4-ylmethyl]-2-piperazinone (115 mg), 4-chlorophenylboronic acid (52 mg), tetrakistriphenylphosphine palladium (25 mg), 2M sodium carbonate solution (0.25 ml) and dimethoxyethane (10 ml) was refluxed for 15 hours. The reaction solution was concentrated, and to the residue was sodium bicarbonate solution. The mixture was extracted with ethyl acetate, washed with brine, dried, and concentrated, and the residue was purified with silica gel column chromatography (hexane:ethyl acetate=1:3) to give colorless solid of 1-[1-(tert-butoxycarbonyl)piperidin-4-ylmethyl]-4-[5-(4-chlorophenyl)-2-thiophenesulfonyl]-2-piperazinone (113 mg).

$^1$H-NMR (CDCl$_3$) δ: 1.16 (2H, m), 1.44 (9H, s), 1.63 (2H, m), 1.83 (1H, m), 2.64 (2H, m), 3.26 (2H, br), 3.40 (2H, m), 3.46 (2H, m), 3.82 (2H, s), 4.07 (2H, m), 7.31 (1H, d, J=4.2 Hz), 7.41 (2H, d, J=8.8 Hz), 7.53 (2H, d, J=8.8 Hz), 7.56 (1H, d, J=4.2 Hz).

IR (KBr): 1682, 1661, 1489, 1429, 1366, 1242, 1165 cm$^{-1}$.

To 1-[1-(tert-butoxycarbonyl)piperidin-4-ylmethyl]-4-[5-(4-chlorophenyl)-2-thiophenesulfonyl]-2-piperazinone (115 mg) were added 4N hydrochloric acid in ethyl acetate (10 ml) and methanol (4 ml), and the mixture was stirred at room temperature for 30 minutes. The reaction solution was concentrated to give crude crystals of 4-[5-(4-chlorophenyl)-2-thiophenesulfonyl]-1-(piperidin-4-ylmethyl)-2-piperazinone hydrochloride. A mixture of the obtained 4-[5-(4-chlorophenyl)-2-thiophenesulfonyl]-1-(piperidin-4-ylmethyl)-2-piperazinone hydrochloride and chloropyridine hydrochloride (85 mg) was added to sodium bicarbonate solution, and the mixture was extracted with dichloromethane (twice), dried and concentrated. To the residue was added isoamylalcohol (10 ml), and the mixture was stirred at 130° C. for 15 hours. The reaction solution was concentrated, and the residue was dissolved in dichloromethane. The solution was washed with 1 N sodium hydroxide solution, dried and concentrated, and the residue was purified with silica gel column chromatography (dichloromethane: methanol containing 10% ammonia solution 10:1) to give colorless solid of the title compound (42 mg).

$^1$H-NMR (CDCl$_3$) δ: 1.30 (2H, m), 1.70 (2H, m), 1.96 (1H, m), 2.82 (2H, m), 3.30 (2H, d, J=7.4 Hz), 3.38–3.55 (4H, m), 3.85 (2H, s), 3.87 (2H, m), 6.62 (2H, d, J=6.0 Hz), 7.32 (1H, d, J=4.0 Hz), 7.43 (2H, d, J=8.8 Hz), 7.54 (2H, d, J=8.8 Hz), 7.57 (1H, d, J=4.0 Hz), 8.22 (2H, d, J=6.0 Hz).

IR (KBr): 1651, 1595, 1489, 1431, 1352, 1163 cm$^{-1}$.

Working Example 57
1-[1-(4-pyridyl)piperidin-4-ylmethyl]-4-(5-vinylthiophene-2-sulfonyl)-2-piperazinone Hydrochloride A mixture of 4-(5-bromo-2-thiophenesulfonyl)-1-[1-(tert-butoxycarbonyl)piperidin-4-ylmethyl]-2-piperazinone (200 mg), vinyltributyltin (365 mg), lithium chloride (50 mg), tetrakistriphenylphosphine palladium (50 mg) and dioxane (15 ml) was refluxed for 2 hours. The reaction solution was concentrated, and the residue was purified with silica gel column chromatography (hexane: ethyl acetate=1:2) to give colorless solid of 1-[1-(tert-butoxycarbonyl)piperidin-4-ylmethyl]-4-(5-vinyl-2-thiophenesulfonyl)-2-piperazinone (209 mg).

$^1$H-NMR (CDCl$_3$) δ: 1.15 (2H, m), 1.44 (9H, s), 1.56 (2H, m), 1.84 (1H, m), 2.64 (2H, m), 3.25 (2H, m), 3.38 (2H, m), 3.43 (2H, m), 3.79 (2H, s), 4.08 (2H, m), 5.38 (1H, d, J=11.0 Hz), 5.73 (1H, d, J=17.6 Hz), 6.78 (1H, dd, J=11.0, 17.6 Hz), 7.01 (1H, d, J=4.2 Hz), 7.45 (1H, d, J=4.2 Hz).

IR (KBr): 1682, 1661, 1427, 1366, 1242, 1165 cm$^{-1}$.

According to a similar method described in Working Example 56, colorless solid of the title compound (9 mg) was obtained from 1-[1-(tert-butoxycarbonyl)piperidin-4-ylmethyl]-4-(5-vinyl-2-thiophenesulfonyl)-2-piperazinone instead of 1-[1-(tert-butoxycarbonyl)piperidin-4-ylmethyl]-4-[5-(4-chlorophenyl)-2-thiophenesulfonyl]-2-piperazinone. Free form of the title compound was obtained and then it was treated with hydrochloric acid to give hydrochloride.

$^1$H-NMR (DMSO-d$_6$) δ: 1.08 (2H, m), 1.64 (2H, m), 1.99 (1H, m), 3.00–3.65 (8H, m), 3.67 (2H, s), 4.17 (2H, m), 5.42 (1H, d, J=11.0 Hz), 5.83 (1H, d, J=17.6 Hz), 6.97 (1H, dd, J=11.0, 17.6 Hz), 7.16 (2H, d, J=7.6 Hz), 7.33 (1H, d, J=4.2 Hz), 7.66 (1H, d, J=4.2 Hz), 8.18 (2H, m).

Working Example 58
1-(1-acetimidoylpiperidin-4-ylmethyl)-4-(6-chloro-3,4-dihydronaphthanlene-2-sulfonyl)-2-piperazinone Hydrochloride To a solution of 1-[1-(tert-butoxycarbonyl)piperidin-4-ylmethyl]-2-piperazinone (50 mg) in ethyl acetate (10 ml) and sodium bicarbonate solution (10 ml) was added at 0° C. 6-chloro-3,4-dihydronaphthanlene-2-sulfonyl chloride (40 mg), and the mixture was stirred at room temperature for 30 minutes. The organic layer was separated, washed with brine, dried and concentrated, and the residue was purified with silica gel column chromatography (hexane:ethyl acetate=1:4) to give colorless wax of 1-[1-(tert-butoxycarbonyl)piperidin-4-ylmethyl]-4-(6-chloro-3,4-dihydronaphthanlene-2-sulfonyl)-2-piperazinone (48 mg).

$^1$H-NMR (CDCl$_3$) δ: 1.17 (2H, m), 1.45 (9H, s), 1.60 (2H, m), 1.86 (1H, m), 2.50–2.75 (4H, m), 2.94 (2H, m), 3.28 (2H, m), 3.40–3.60 (4H, m), 3.86 (2H, s), 4.08 (2H, m), 7.14–7.27 (3H, m), 7.34 (1H, s).

IR (KBr): 1682, 1661, 1427, 1366, 1346, 1315, 1161 cm$^{-1}$.

To 1-[1-(tert-butoxycarbonyl)piperidin-4-ylmethyl]-4-(6-chloro-3,4-dihydronaphthanlene-2-sulfonyl)-2-piperazinone (43 mg) was added 4N hydrochloric acid in ethyl acetate (6 ml) and the mixture was stirred at room temperature for 30 minutes. The reaction solution was concentrated to give crude crystals of 4-(6-chloro-3,4-dihydronaphthanlene-2-sulfonyl)-1-(piperidin-4-ylmethyl)-2-piperazinone hydrochloride. To a solution of the obtained 4-(6-chloro-3,4-dihydronaphthanlene-2-sulfonyl)-1-(piperidin-4-ylmethyl)-2-piperazinone hydrochloride and triethylamine (125 mg) in methanol (10 ml) was added ethyl acetimidate (101 mg), and the mixture was stirred at room temperature for 15 hours. The reaction solution was concentrated, and the residue was dissolved in dichloromethane. The solution was washed with 1N sodium hydroxide solution, dried and concentrated, and the residue was dissolved in ethyl acetate. To the solution was added a solution of hydrochloric acid in ethyl acetate, and precipitated hydrochloride salt was filtered and dried to give colorless solid of the title compound (26 mg).

$^1$H-NMR (DMSO-d$_6$) δ: 1.19 (2H, m), 1.68 (2H, m), 2.00 (1H, m), 2.24 (3H, s), 2.55 (2H, m), 2.88–3.55 (10H, m), 3.73 (2H, s), 3.85 (1H, m), 4.05 (1H, m), 7.30–7.53 (4H, m), 8.61 (1H, brs), 9.19 (1H, brs).

Working Example 59
4-(6-chloro-3,4-dihydronaphthanlene-2-sulfonyl)-1-[1-(4-pryridyl)piperidin-4-ylmethyl]-2-piperazinone According to a similar method described in Working Example 15, colorless solid of the title compound was obtained from 6-chloro-3,4-dihydronaphthanlene-2-sulfonyl chloride instead of 6-chloronaphthanlene-2-sulfonyl chloride.

$^1$H-NMR (CDCl$_3$) δ: 1.30 (2H, m), 1.73 (2H, m), 1.97 (1H, m), 2.60 (2H, m), 2.83 (2H, m), 2.95 (2H, m), 3.32 (2H, d, J=7.4 Hz), 3.40–3.60 (4H, m), 3.80–3.95 (4H, m), 6.63 (2H, d, J=6.0 Hz), 7.14–7.27 (3H, m), 7.35 (1H, s), 8.24 (2H, d, J=6.0 Hz).

IR (KBr): 1651, 1597, 1345, 1155 cm$^{-1}$.

Working Example 60
4-(6-bromonaphthanlene-2-sulfonyl)-1-[1-(4-pyridyl)piperidin-4-ylmethyl]-2-piperazinone Hydrochloride According to a similar method described in Working Example 15, colorless solid of the title compound was obtained from 6-bromonaphthanlene-2-sulfonyl chloride instead of 6-chloronaphthanlene-2-sulfonyl chloride.

$^1$H-NMR (DMSO-d$_6$) δ: 1.04 (2H, m), 1.50 (2H, m), 1.91 (1H, m), 2.96 (2H, m), 3.09 (2H, d, J=7.4 Hz), 3.34 (4H, s), 3.70 (2H, s), 4.04 (2H, m), 7.09 (2H, d, J=7.4 Hz), 7.80–7.95 (2H, m), 8.14–8.25 (4H, m), 8.45 (1H, s), 8.60 (1H, s).

Working Example 61
4-(6-fluoronaphthanlene-2-sulfonyl)-1-[1-(4-pyridyl)piperidin-4-ylmethyl]-2-piperazinone Hydrochloride According to a similar method described in Working Example 15, colorless solid of the title compound was obtained from 6-fluoronaphthanlene-2-sulfonyl chloride instead of 6-chloronaphthanlene-2-sulfonyl chloride.

$^1$H-NMR (DMSO-d$_6$) δ: 1.05 (2H, m), 1.55 (2H, m), 1.91 (1H, m), 3.00 (2H, m), 3.09 (2H, d, J=7.4 Hz), 3.34 (4H, s), 3.68 (2H, s), 4.10 (2H, m), 7.12 (2H, d, J=7.6 Hz), 7.66 (1H, dt, J=2.8, 8.8 Hz), 7.80–8.00 (2H, m), 8.15–8.23 (3H, in), 8.36 (1H, dd, J=5.4, 8.8 Hz), 8.61 (1H, s).

Working Example 62
4-(6-methylnaphthanlene-2-sulfonyl)-1-[1-(4-pyridyl)piperidin-4-ylmethyl]-2-piperazinone According to a similar method described in Working Example 15, colorless solid of the title compound was obtained from 6-methylnaphthanlene-2-sulfonyl chloride instead of 6-chloronaphthanlene-2-sulfonyl chloride.

1H-NMR (CDCl$_3$) δ: 1.25 (2H, m), 1.59 (2H, m), 1.88 (1H, m), 2.58 (3H, s), 2.73 (2H, m), 3.23 (2H, d, J=7.2 Hz), 3.41 (4H, s), 3.78 (2H, m), 3.81 (2H, s), 6.59 (2H, d, J=6.6 Hz), 7.50 (1H, dd, J=1.8, 8.6 Hz), 7.70–7.78 (2H, m), 7.90 (1H, d, J=8.0 Hz), 7.92 (1H, d, J=8.6 Hz), 8.23 (2H, d, J=6.6 Hz), 8.34 (1H, brs).

IR(KBr): 1651, 1597, 1345, 1163 cm$^{-1}$.

Working Example 63
1-(1-acetimidoyl-4-hydroxypiperidin-4-ylmethyl)-4-(6-chloronaphthanlene-2-sulfonyl)-2-piperazinone hydrochloride According to a similar method described in Working Example 10, colorless solid of the title compound was obtained from 4-(6-chloronaphthanlene-2-sulfonyl)-1-(4-hydroxypiperidin-4-ylmethyl)-2-piperazinone hydrochloride.

$^1$H-NMR (DMSO-d$_6$) δ: 1.30–1.60 (4H, m), 2.21 (3H, s), 3.10–3.50 (6H, m), 3.56 (2H, m), 3.69 (2H, s), 3.81 (2H, m), 4.91 (1H, brs), 7.74 (1H, dd, J=1.8, 8.8 Hz), 7.89 (1H, dd, J=1.8, 8.8 Hz), 8.19 (1H, d, J=8.8 Hz), 8.27 (1H, s), 8.29 (1H, d, J=8.8 Hz), 8.60 (2H, s), 9.17 (1H, brs).

Working Example 64
1-[1-acetimidoyl-4-hydroxypiperidin-4-ylmethyl]-4-(7-bromo-2H-benzopyran-3-sulfonyl)piperazin-2-one Hydrochloride According to a similar method described in Working Example 10, colorless crystals of the title compound were obtained from 4-(7-bromo-2H-benzopyran-3-sulfonyl)-1-(4-hydroxypiperidin-4-ylmethyl)-2-piperazinone hydrochloride instead of 1-(4-aminobenzyl)-4-(6-chloronaphthanlene-2-sulfonyl)-2-piperazinone hydrochloride.

$^1$H-NMR (DMSO-d$_6$) δ: 1.50–1.70 (4H, m), 2.45 (3H, s), 2.82–3.10 (4H, m), 3.24–3.64 (6H, m), 3.80 (2H, s), 4.99 (2H, s), 7.20 (1H, d, J=1.8 Hz), 7.41 (1H, d, J=8.2 Hz), 7.48 (1H, s), 8.56 (1H, br s), 9.12 (1H, br s). IR (KBr): 3350, 2978, 1647, 1595, 1561, 1495, 1481, 1416 cm$^{-1}$.

Working Example 65
1-[1-acetimidoyl-4-hydroxypiperidin-4-ylmethyl]-4-(7-chloro-6-fluoro-2H-benzopyran-3-sulfonyl)piperazin-2-one Hydrochloride According to a similar method described in Working Example 10, colorless crystals of the title compound were obtained from 4-(7-chloro-6-fluoro-2H-benzopyran-3-sulfonyl)-1-(4-hydroxypiperidin-4-ylmethyl)-2-piperazinone hydrochloride instead of 1-(4-aminobenzyl)-4-(6-chloronaphthanlene-2-sulfonyl)-2-piperazinone hydrochloride.

$^1$H-NMR (DMSO-d$_6$) δ:1.50–1.70 (4H, m), 2.25 (3H, s), 2.80–3.02 (4H, m), 3.34–3.70 (6H, m), 3.81 (2H, s), 4.99 (2H, s), 7.26 (1H, d, J=6.2 Hz), 7.47 (1H, s), 7.59 (1H, d, J=9.0 Hz), 8.52–8.70 (1H, br), 9.12–9.25 (1H, br). IR (KBr): 3320, 2677, 2492, 1668, 1634, 1574, 1483, 1418 cm$^{-1}$.

Working Example 66
4-(7-bromo-2H-benzopyran-3-sulfonyl)-1-[4-hydroxy-1-(4-pyridyl)piperidin-4-ylmethyl]piperazin-2-one Hydrochloride According to a similar method described in Working Example 25, colorless crystals of the title compound were obtained from 7-bromo-4H-4-oxobenzopyran-3-sulfonyl chloride instead of 7-chloro-4H-4-oxobenzopyran-3-sulfonyl chloride.

$^1$H-NMR (DMSO-d$_6$) δ: 1.50–1.70 (4H, m), 3.27–3.64 (8H, m), 3.80 (2H, s), 3.90–4.03 (2H, m), 4.99 (2H, s), 7.17 (2H, d, J=6.4 Hz), 7.21 (1H, d, J=1.8 Hz), 7.26 (1H, dd, J=8.0, 1.8 Hz), 7.41 (1H, d, J=8.0 Hz), 7.48 (1H, s), 8.20 (2H, d, J=6.4 Hz), 13.20–13.40 (1H, br). IR (KBr): 3350, 3069, 2928, 1645, 1595, 1549, 1481, 1456, 1416 cm$^{-1}$.

Working Example 67
4-(7-chloro-6-fluoro-2H-benzopyran-3-sulfonyl)-1-[1-(4-pyridyl)-4-hydroxypiperidin-4-ylmethyl]piperazin-2-one Hydrochloride According to a similar method described in Working Example 25, colorless crystals of the title compound were obtained from 7-chloro-6-fluoro-4H-4-oxobenzopyran-3-sulfonyl chloride instead of 7-chloro-4H-4-oxobenzopyran-3-sulfonyl chloride.

$^1$H-NMR (DMSO-d$_6$) δ: 1.58–1.65 (4H, m), 3.37–3.64 (8H, m), 3.80 (2H, s), 3.90–4.09 (2H, m), 4.99 (2H, s), 7.22 (2H, d, J=6.6 Hz), 7.27 (1H, d, J=6.8 Hz), 7.47 (1H, s), 7.59 (1H, d, J=9.4 Hz), 8.20 (2H, d, J=6.6 Hz), 13.25–13.51 (1H, br). IR (KBr): 3320, 3196, 2934, 1645, 1549, 1485, 1418 cm$^{-1}$.

Working Example 68
4-(7-chloro-4-hydroxycourmarin-3-sulfonyl)-1-[1-(4-pyridyl)piperidin-4-ylmethyl]piperazin-2-one 1) To a suspension of 7-chloro-4-hydroxycourmarin (4.10 g) in 1,4-dioxane was added dropwise chlorosulfonic acid (2.8 ml), and the mixture was stirred at room temperature overnight. Precipitates were filtered off, and the filtrate was washed with dioxane and diisopropylether, and dried to give colorless crystals of 7-chloro-4-hydroxycourmarin-3-sulfonic acid (3.62 g).

$^1$H-NMR (DMSO-d$_6$) δ: 7.44 (1H, dd, J=8.4, 2.0 Hz), 7.57 (1H, d, J=2.0 Hz), 7.87 (1H, d, J=8.4 Hz), 13.90–14.30 (1H, br).

IR(KBr): 3085, 1740, 1713, 1634, 1605, 1559, 1491, 1447 cm$^{-1}$.

2) To thionyl chloride(13 ml) was added 7-chloro-4-hydroxycourmarin-3-sulfonic acid (3.55 g), and the mixture was refluxed for 2 hours. Under reduced pressure, the reaction solution was concentrated, and the residue was recrystallized from toluene to give 7-chloro-4-hydroxycourmarin-3-sulfonyl chloride (2.44 g).

3) To a solution of 1-[1-(4-pyridyl)piperidin-4-ylmethyl]piperazin-2-one (274 mg) and diisopropylethylamine (388 mg) in dichloromethane (5 ml) was added dropwise, under ice-cooling, a suspension of 7-chloro-4-hydroxycoumarin-3-sulfonyl chloride (325 mg) in dichloromethane (15 ml), and the mixture was stirred at room temperature overnight. The reaction solution was washed with 0.5N hydrochloric acid and saturated brine, dried and concentrated, and the residue was purified with silica gel column chromatography (eluent:methanol/dichloromethane=1/3) and crystallized from ethyl acetate and ethanol to give colorless crystals of the title compound (0.108 g). 1H-NMR (DMSO-d6) δ: 1.02–1.12 (2H, m), 1.58–1.70 (2l1, m), 1.80–2.05 (1H, br), 2.82–2.86 (2l1, m), 3.19 (2l1, d, J=8.2 Hz), 3.27–3.47 (4H, m), 3.86 (2l1, s), 3.95–4.03 (2l1, m), 6.97 (2H, d, J=6.8 Hz), 7.23 (1H, dd, J=8.2, 2.0 Hz), 7.28 (1H, d, J=2.0 Hz), 7.81 (1H, d, J=8.2 Hz), 8.16 (2H, d, J=6.8 Hz).

IR(KBr): 2928, 1682, 1645, 1605, 1549, 1497, 1451, 1424 cm$^{-1}$.

Working Example 69
4-(7-chloro-4-hydroxycoumarin-3-sulfonyl)-1-[4-(1-imidazolyl)benzyl]piperazin-2-one According to a similar method described in Working Example 68, colorless crystals of the title compound were obtained from 1-[4-(1-imidazolyl)benzyl]piperazin-2-one instead of 1-[1-(4-pyridyl)piperidin-4-ylmethyl]piperazin-2-one.

$^1$H-NMR (DMSO-d$_6$) δ: 3.18–3.47 (4H, s), 3.96 (2H, s), 4.56 (2H, s), 7.19 (1H, dd, J=8.4, 1.8 Hz), 7.26 (1H, d, J=1.8 Hz), 7.32–7.80 (3H, m), 7.55 (2H, d, J=8.8 Hz), 7.77–7.84 (2H, m), 8.60 (1H, s).

IR (KBr): 3412, 1645, 1605, 1560, 1541, 1524, 1497, 1424 cm$^{-1}$.

Working Example 70
4-(7-chlorocourmarin-3-sulfonyl)-1-[4-(1-imidazolyl)benzyl]piperazin-2-one 1) To a solution of 1-[4-(1-imidazolyl)benzyl]piperazin-2-one (586 mg) and diisopropylethylamine (388 mg) in dichloromethane (10 ml) was added dropwise, under ice-cooling, a solution of methyl chlorosulfonylacetate (380 mg) in dichloromethane (10 ml), and the mixture was stirred at room temperature overnight. The reaction solution was washed with 0.5N hydrochloric acid and saturated brine, dried and concentrated, and the residue was purified with silica gel column chromatography (eluent: methanol/dichloromethane=1/10) to give colorless oil of 1-[4-(1-imidazolyl)benzyl]-4-methoxycarbonylmethylsulfonyl-2-oxopiperazine (0.170 g).

$^1$H-NMR (CDCl$_3$) δ: 3.38–3.43 (2H, m), 3.61–3.66 (2H, m), 3.80 (2H, s), 4.08 (2H, s), 4.14 (2H, s), 7.20 (1H, s), 7.30 (1H, s), 7.40 (4H, s), 7.87 (1H, s).

IR(KBr): 3119, 2928, 1746, 1651, 1615, 1522, 1489, 1435 cm$^{-1}$.

2) To ethanol (5 ml) were added 1-[4-(1-imidazolyl)benzyl]-4-methoxycarbonylmethylsulfonyl-2-oxopiperazine (0.164 g), 4-chlorosalicylaldehyde (66 mg) and piperidine (11 mg), and the mixture was refluxed for 3 hours and cooled to room temperature. Precipitates were filtered off, and the filtrate was washed with ethanol and dried to give colorless crystals of the title compound (166 mg).

$^1$H-NMR (CDCl$_3$) δ: 3.39–3.44 (2H, m), 3.78–3.83 (2H, m), 4.08 (2H, s), 4.65 (2H, s), 7.23 (1H, s), 7.28 (1H, s), 7.38–7.42 (6H, m), 7.61 (1H, d, J=9.0 Hz), 7.87 (1H, s), 8.53 (1H, s).

IR (KBr): 2919, 1755, 1746, 1644, 1603, 1553, 1524, 1487, 1422 cm$^{-1}$.

Working Example 71
4-(7-chlorocourmarin-3-sulfonyl)-1-[1-(4-pyridyl)piperidin-4-ylmethyl]piperazin-2-one According to a similar method described in Working Example 70, colorless crystals of the title compound were obtained from 1-[1-(4-pyridyl)piperidin-4-ylmethyl]piperazin-2-one instead of 1-[4-(1-imidazolyl)benzyl]piperazin-2-one.

$^1$H-NMR (CDCl$_3$) δ: 1.21–1.41 (2H, m), 1.71–2.15 (3H, m), 2.79–2.90 (2H, m), 3.32 (2H, d, J=7.2 Hz), 3.46–3.52 (2H, m), 3.78–3.93 (4H, m), 3.98 (2H, s), 6.64 (2H, d, J=6.4 Hz), 7.38–7.44 (2H, m), 7.62 (1H, d, J=8.0 Hz), 8.24 (2H, d, J=6.4 Hz), 8.54 (1H, s).

IR (KBr): 2928, 2855, 1744, 1647, 1603, 1547, 1510, 1501 cm$^{-1}$.

Working Example 72
methyl 3-[4-(6-chloronaphthanlene-2-sulfonyl)-2-oxopiperazine-1-yl]-3-[1-(4-pyridyl)piperidin-4-yl]propionate 1) A solution of 1-benzyloxycarbonyl-4-piperidinealdehyde (10.70 g) and methyl triphenylphosphoranilideneacetate (14.38 g) in toluene (100 ml) was refluxed for 2 hours and cooled to room temperature. Under reduced pressure, the reaction solution was concentrated, and the residue was purified with silica gel column chromatography (eluent:ethyl acetate/hexane=1/3) and crystallized from a mixture of ethyl acetate and ethanol to give colorless crystals of methyl 3-(1-benzyloxycarbonylpiperidin-4-yl)acrylate (8.78 g).

$^1$H-NMR (CDCl$_3$) δ: 1.32–1.47 (2H, m), 1.72–1.78 (2H, m), 2.25–2.37 (1H, m), 2.78–2.91 (2H, m), 3.74 (3H, s), 4.17–4.24 (2H, m), 5.13 (2H, s), 5.81 (1H, dd, J=16.0, 1.6 Hz), 6.90 (1H, dd, J=16.0, 6.6 Hz), 7.30–7.38 (5H, m).

IR (KBr): 2948, 2855, 1730, 1698, 1653, 1497, 1470, 1435 cm$^{-1}$.

2) To a solution of methyl 3-(1-benzyloxycarbonylpiperidin-4-yl)acrylate (5.55 g) and 4-(tert-butoxycarbonyl)-2-piperazinone (3.66 g) in tetrahydrofuran (50 ml) was added potassium tert-butoxide (0.56 g), and the mixture was stirred under nitrogen atmosphere at room temperature for 3 days. The reaction solution was diluted with ethyl acetate (50 ml), washed with 0.5N hydrochloric acid and saturated brine, dried and concentrated, and the residue was purified with silica gel column chromatography (eluent:acetone/hexane=1/2) to give colorless amorphous of methyl 3-(1-benzyloxycarbonylpiperidin-4-yl)-3-[4-(tert-butoxycarbonyl)-2-oxopiperazine-1-yl]propionate (5.51 g).

3) To a solution of methyl 3-(1-benzyloxycarbonylpiperidin-4-yl)-3-[4-(tert-butoxycarbonyl)-2-oxopiperazine-1-yl] propionate (4.78 g) in ethyl acetate (15 ml) was added 4N hydrochloric acid in ethyl acetate (15 ml) and the mixture was stirred at room temperature for 4 hours. The reaction solution was concentrated, and the residue was diluted with water, made basic with saturated sodium hydrogen carbonate solution and extracted with dichloromethane. The extract was washed with saturated brine, dried and concentrated to give pale yellow amorphous of methyl 3-(1-benzyloxycarbonylpiperidin-4-yl)-3-(2-oxopiperazine-1-yl) propionate (2.34 g).

4) To a solution of methyl 3-(1-benzyloxycarbonylpiperidin-4-yl)-3-(2-oxopiperazine-1-yl)propionate (1.01 g) and triethylamine (0.51 g) in dichloromethane (10 ml) was added, under ice-cooling, 6-chloronaphthanlene-2-sulfonyl chloride (0.78 g), and the mixture was stirred at room temperature for 6 hours. The reaction solution was washed with 0.05N sodium hydrogen carbonate solution and saturated brine, dried and concentrated, and the residue was purified with silica gel column chromatography (eluent:acetone/hexane=1/3) to give colorless amorphous of methyl 3-(1-benzyloxycarbonylpiperidin-4-yl)-3-[4-(6-chloronaphthanlene-2-sulfonyl)-2-oxopiperazine-1-yl] propionate (1.21 g).

5) A mixture of methyl 3-(1-benzyloxycarbonylpiperidin-4-yl)-3-[4-(6-chloronaphthanlene-2-sulfonyl)-2-oxopiperazine-1-yl]propionate (628 mg), triethylsilane (465 mg), triethylamine (30 mg) and palladium chloride (18 mg) was refluxed under nitrogen atmosphere for 3 hours. The reaction solution was cooled to room temperature. To the solution was added methanol (10 ml), and the mixture was stirred at room temperature for 30 minutes. Insoluble materials were filtered off, and the filtrate was concentrated. To the residue were added 4-chloropyridine hydrochloride (221 mg), triethylamine (405 mg) and ethanol (15 ml), and the mixture was allowed to react in a sealed tube at 150 for 15 hours. The reaction solution was concentrated, and the residue was purified with silica gel column chromatography (dichloromethane: methanol containing 10% ammonia solution=20: 1) and crystallized from a mixture of ethanol and diethylether to give colorless crystals of the title compound (115 mg).

$^1$H-NMR (CDCl$_3$) δ: 1.13–1.29 (2H, m), 1.41–1.50 (1H, m), 1.68–1.75 (1H, m), 1.90–2.15 (1H, br), 2.57–2.84 (4H, m), 3.34–3.48 (4H, m), 3.57 (3H, s), 3.64–3.94 (5H, m), 6.58 (2H, d, J=6.6 Hz), 7.69–7.80 (2H, m), 7.95–8.06 (3H, m), 8.25 (2H, d, J=6.6 Hz), 8.39 (1H, d, J=0.8 Hz).

IR(KBr): 2944, 1732, 1651, 1595, 1539, 1514, 1506, 1487, 1456, 1435 cm$^{-1}$.

Working Example 73

1-[4-hydroxy-1-(4-pyrimidinyl)piperidin-4-ylmethyl]-4-(6-chloronaphthanlene-2-sulfonyl)piperazin-2-one 1) To a solution of 1,4-dioxa-8-azaspiro[4,5]decane (9.02 g) and diisopropylethylamine (9.77 g) in ethanol (30 ml) was added 4,6-dichloropyrimidine (9.88 g), and the mixture was stirred at room temperature for 1 hour. The reaction solution was concentrated, and the residue was diluted with dichloromethane (150 ml). The mixture was washed with 0.3N sodium hydroxide solution and saturated brine, dried and concentrated, and the residue was crystallized from diethylether to give colorless crystals of 8-(6-chloropyrimidine-4-yl)-1,4-dioxa-8-azaspiro[4,5]decane (15.84 g).

$^1$H-NMR (CDCl$_3$) δ: 1.72–1.78 (4H, m), 3.73–3.79 (4H, m), 4.01 (4H, s), 6.54 (1H, d, J=0.8 Hz), 8.37 (1H, d, J=0.8 Hz).

2) To a solution of 8-(6-chloropyrimidine-4-yl)-1,4-dioxa-8-azaspiro[4,5]decane (12.79 g) in acetone (50 ml) was added 4N hydrochloric acid (50 ml), and the mixture was stirred at 50° C. for 1 hour. Under reduced pressure, acetone was removed, and the residue was neutralized with 2N sodium hydroxide solution and was extracted with ethyl acetate. The extract was washed with saturated brine, dried and concentrated, and the residue was crystallized from diethylether to give colorless crystals of 1-(6-chloropyrimidine-4-yl)piperidin-4-one (10.09 g).

$^1$H-NMR (CDCl$_3$) δ: 2.28 (4H, t, J=6.2 Hz), 3.98 (4H, t, J=6.2 Hz), 6.61 (1H, d, J=1.0 Hz), 8.45 (1H, d, J=1.0 Hz).

3) To a solution of trimethylsulfoxonium iodide (10.56 g) in dimethylsulfoxide (50 ml) was added 60% sodium hydride (1.84 g) in oil, and the mixture was stirred at room temperature for 1 hour. To the mixture was added, under ice-cooling, 1-(6-chloropyrimidine-4-yl)piperidin-4-one (8.50 g), and the mixture was stirred at room temperature for 3 hours. The reaction solution was poured into ice-water, and the mixture was extracted with ethyl acetate. The extract was washed with saturated brine, dried and concentrated, and the residue was crystallized from diethylether to give colorless crystals of 6-(6-chloropyrimidine-4-yl)-1-oxa-6-azaspiro[2,5]octane (5.67 g).

$^1$H-NMR (CDCl$_3$) δ: 1.47–1.58 (2H, m), 1.86–2.01 (2H, m), 2.76 (2H, s), 3.54–3.68 (2H, m), 4.00–4.11 (2H, m), 6.56 (1H, d, J=1.0 Hz), 8.38 (1H, d, J=1.0 Hz).

4) To a solution of 6-(6-chloropyrimidine-4-yl)-1-oxa-6-azaspiro[2,5]octane (4.00 g) and 4-(tert-butoxycarbonyl)-2-piperazinone (3.38 g) in tert-butylalcohol (50 ml) was added potassium tert-butoxide (0.57 g), and the mixture was stirred at 80° C. overnight. The reaction solution was concentrated, and the residue was diluted with ethyl acetate (100 ml), washed with 0.5N hydrochloric acid and saturated brine, dried and concentrated. The residue was purified with silica gel column chromatography (eluent: ethyl acetate) and crystallized from a mixture of ethyl acetate and diethylether to give colorless crystals of 4-(tert-butoxycarbonyl)-1-[1-(6-chloro-4-pyrimidinyl)-4-hydroxypiperidin-4-ylmethyl] piperazin-2-one (5.51 g).

$^1$H-NMR (CDCl$_3$) δ: 1.48 (9H, s), 1.51–1.75 (4H, m), 3.32–3.48 (6H, m), 3.64–3.69 (2H, m), 4.16 (2H, s), 4.16–4.28 (2H, m), 6.52 (1H, d, J=0.6 Hz), 8.36 (1H, d, J=0.6 Hz).

IR (KBr): 3350, 2976, 2930, 1690, 1682, 1651, 1576, 1520, 1495, 1418 cm$^{-1}$.

5) In ethanol (30 ml) was dissolved 4-(tert-butoxycarbonyl)-1-[1-(6-chloro-4-pyrimidinyl)-4-hydroxypiperidin-4-ylmethyl]piperazin-2-one (808 mg), and to the solution was added 10% palladium on carbon (containing 50% water, 242 mg). Under hydrogen atmosphere, the mixture was vigorously stirred overnight, and the catalyst was removed. The solvent was evaporated under reduced pressure, and the residue was purified with silica gel column chromatography (eluent:methanol/ethyl acetate=1/10) to give colorless amorphous of 4-(tert-butoxycarbonyl)-1-[4-hydroxy-1-(4-pyrimidinyl)piperidin-4-ylmethyl]piperazin-2-one (527 mg).

$^1$H-NMR (CDCl$_3$) δ: 1.48 (9H, s), 1.50–1.75 (4H, m), 3.30–3.4 (7H, m), 3.64–3.69 (2H, m), 4.16 (2H, s), 4.18–4.25 (2H, m), 6.52 (1H, dd, J=6.4, 1.0 Hz), 8.17 (1H, d, J=6.4 Hz), 8.58 (1H, d, J=1.0 Hz).

5) To a solution of 4-(tert-butoxycarbonyl)-1-[4-hydroxy-1-(4-pyrimidinyl)piperidin-4-ylmethyl]piperazin-2-one (516 mg) in tetrahydrofuran (4 ml) was added a solution of 4N hydrochloric acid in ethyl acetate (4 ml), and the mixture was stirred at room temperature for 4 hours. The reaction solution was concentrated, and the residue was crystallized from tetrahydrofuran to give colorless crystals of 1-[4-hydroxy-1-(4-pyrimidinyl)piperidin-4-ylmethyl]piperazin-2-one hydrochloride (435 mg).

6) To a solution of 1-[4-hydroxy-1-(4-pyrimidinyl)piperidin-4-ylmethyl]piperazin-2-one hydrochloride (197 mg) and triethylamine (182 mg) in dichloromethane (10 ml) was added, under ice-cooling, 6-chloronaphthanlene-2-sulfonyl chloride (188 mg), and the mixture was stirred at room temperature for 3 hours. The reaction solution was washed with 0.05N sodium hydrogen carbonate solution and saturated brine, dried and concentrated, and the residue was purified with silica gel column chromatography (eluent:methanol/ethyl acetate=1/10) and crystallized from a mixture of ethanol and diethylether to give colorless crystals of the title compound (154 mg).

$^1$H-NMR (CDCl$_3$) δ: 1.40–1.62 (4H, m), 3.22–3.30 (2H, m), 3.35–3.44 (4H, m), 3.54–3.59 (2H, m), 3.85 (2H, s), 4.13 (2H, br d, J=13.4 Hz), 6.48 (1H, d, J=7.2 Hz), 7.62 (1H, dd, J=8.8, 1.8 Hz), 7.80 (1H, dd, J=8.8, 1.8 Hz), 7.96 (2H, d, J=8.8 Hz), 7.96 (1H, d, J=1.8 Hz), 8.16 (1H, d, J=7.2 Hz), 8.37 (1H, d, J=1.8 Hz), 8.56 (1H, s).

IR (KBr): 2919, 1651, 1593, 1539, 1495, 1456, 1429 cm$^{-1}$.

Working Example 74
1-[1-(6-chloropyrimidine-4-yl)-4-hydroxypiperidin-4-ylmethyl]-4-(6-chloronaphthanlene-2-sulfonyl)piperazin-2-one According to a similar method described in Working Example 73, colorless crystals of the title compound were obtained from 1-[1-(6-chloropyrimidine-4-yl)-4-hydroxypiperidin-4-ylmethyl]piperazin-2-one hydrochloride instead of 1-[4-hydroxy-1-(4-pyrimidinyl)piperidin-4-ylmethyl]piperazin-2-one hydrochloride.

$^1$H-NMR (CDCl$_3$) δ: 1.35–1.59 (4H, m), 3.24–3.30 (2H, m), 3.37–3.44 (4H, m), 3.53–3.58 (2H, m), 3.85 (2H, s), 3.95–4.20 (3H, br), 6.48 (1H, s), 7.63 (1H, dd, J=8.8, 1.8 Hz), 7.80 (1H, dd, J=8.8, 1.8 Hz), 7.96 (2H, d, J=8.8 Hz), 7.96 (1H, d, J=1.8 Hz), 8.34 (1H, s), 8.37 (1H, d, J-1.8 Hz).

IR (KBr): 2926, 1645, 1580, 1526, 1495, 1456, 1424 cm$^{-1}$.

Working Example 75
1-[1-(2-chloropyrimidine-4-yl)-4-hydroxypiperidin-4-ylmethyl]-4-(6-chloronaphthanlene-2-sulfonyl)piperazin-2-one According to a similar method described in Working Example 73, colorless crystals of the title compound were obtained from 1-[1-(2-chloropyrimidine-4-yl)-4-hydroxypiperidin-4-ylmethyl]piperazin-2-one hydrochloride instead of 1-[4-hydroxy-1-(4-pyrimidinyl)piperidin-4-ylmethyl]piperazin-2-one hydrochloride.

$^1$H-NMR (CDCl$_3$) δ: 1.35–1.58 (4H, m), 3.24–3.58 (8H, m), 3.85 (2H, s), 3.95–4.25 (2H, br), 6.36 (1H, d, J=6.2 Hz), 7.62 (1H, dd, J=8.4, 1.6 Hz), 7.94 (1H, dd, J=8.4, 1.6 Hz), 7.95 (2H, d, J=8.4 Hz), 7.96 (1H, d, J=1.6 Hz), 8.00 (1H, d, J=6.2 Hz), 8.36 (1H, d, J=1.6 Hz).

IR (KBr): 2928, 1651, 1590, 1537, 1495, 1456, 1429 cm$^{-1}$.

Working Example 76
1-[1-(6-benzylaminopyrimidine-4-yl)-4-hydroxypiperidin-4-ylmethyl]-4-(6-chloronaphthanlene-2-sulfonyl)piperazin-2-one According to a similar method described in Working Example 73, colorless crystals of the title compound were obtained from 1-[1-(6-benzylaminopyrimidine-4-yl)-4-hydroxypiperidin-4-ylmethyl]piperazin-2-one hydrochloride instead of 1-[4-hydroxy-1-(4-pyrimidinyl)piperidin-4-ylmethyl]piperazin-2-one hydrochloride.

$^1$H-NMR (CDCl$_3$) δ: 1.35–1.60 (4H, m), 3.12–3.26 (2H, m), 3.35 (2H, s), 3.37–3.42 (2H, m), 3.52–3.57 (2H, m), 3.83 (2H, s), 3.96 (2H, br d, J=13.2 Hz), 4.44 (2H, d, J=5.4 Hz), 5.07 (1H, br t, J=5.4 Hz), 5.39 (1H, s), 7.31–7.35 (5H, m), 7.61 (1H, dd, J=8.8, 1.4 Hz), 7.79 (1H, dd, J=8.8, 1.4 Hz), 7.94 (2H, d, J=8.4 Hz), 7.95 (1H, d, J=1.4 Hz), 8.15 (1H, s), 8.35 (1H, d, J=1.4 Hz).

IR (KBr): 3320, 2926, 1645, 1595, 1549, 1495, 1454, 1429 cm$^{-1}$.

Working Example 77
1-[4-hydroxy-1-(4-pyrimidinyl)piperidin-4-ylmethyl]-4-(4-vinylbenzenesulfonyl)piperazin-2-one According to a similar method described in Working Example 73, colorless crystals of the title compound were obtained from 4-vinylbenzenesulfonyl chloride instead of 6-chloronaphthanlene-2-sulfonyl chloride.

$^1$H-NMR (CDCl$_3$) δ: 1.43–1.65 (4H, m), 3.25–3.39 (3H, m), 3.40 (2H, s), 3.54–3.59 (2H, m), 3.78 (2H, s), 4.15 (2H, br d, J=12.8 Hz), 4.60–4.80 (1H, br), 5.50 (1H, d, J=11.0 Hz), 5.93 (1H, d, J=16.6 Hz), 6.49 (1H, dd, J=6.2, 1.0 Hz), 6.78 (1H, dd, J=16.0, 11.0 Hz), 7.59 (2H, d, J=8.4 Hz), 7.76 (2H, d, J=8.4 Hz), 8.15 (1H, d, J=6.2 Hz), 8.55 (1H, d, J=1.0 Hz).

IR (KBr): 3320, 2928, 1651, 1593, 1539, 1504, 1497, 1429 cm$^{-1}$.

Working Example 78
1-(1-acetimidoylpiperidin-4-ylmethyl)-4-[4-(1H-imidazol-1-ylmethyl)benzenesulfonyl]-2-piperazinone Hydrochloride According to a similar method described in Working Example 10, colorless solid of the title compound was obtained from 4-[4-(1H-imidazol-1-ylmethyl)benzenesulfonyl]-1-(piperidin-4-ylmethyl)-2-piperazinone hydrochloride.

$^1$H-NMR (DMSO-d$_6$) δ: 1.13 (2H, m), 1.60 (2H, m), 1.91 (1H, m), 2.24 (3H, s), 2.90–3.40 (8H, m), 3.58 (2H, s), 3.85 (1H, m), 4.02 (1H, m), 5.43 (2H, s), 7.22 (1H, s), 7.44 (1H, s), 7.55 (2H, d, J=8.4 Hz), 7.84 (2H, d, J=8.4 Hz), 8.32 (1H, s), 8.59 (1H, brs), 9.14 (1H, brs).

IR (KBr): 3098, 1636, 1499, 1348, 1165 cm$^{-1}$.

Working Example 79
4-[4-(1H-imidazol-1-ylmethyl)benzenesulfonyl]-1-[1-(4-pyridyl)piperidin-4-ylmethyl]-2-piperazinone Hydrochloride A mixture of 4-[4-(1H-imidazol-1-ylmethyl)benzenesulfonyl]-1-(piperidin-4-ylmethyl)-2-piperazinone dihydrochloride (209 mg) and chloropyridine hydrochloride (93 mg) was added to sodium bicarbonate solution, and the mixture was extracted with dichloromethane (twice), dried and concentrated. To the residue was added isoamylalcohol (10 ml), and the mixture was stirred at 130% for 15 hours. The reaction solution was concentrated, and the residue was dissolved in dichloromethane. The solution was washed with 1N sodium hydroxide solution, dried and concentrated, and the residue was purified with silica gel column chromatography (dichloromethane:methanol containing 10% ammonia solution=7:1) to give colorless solid of 4-[4-(1H-imidazol-1-ylmethyl)benzenesulfonyl]-1-[1-(4-pyridyl)piperidin-4-ylmethyl]-2-piperazinone (102 mg). The obtained 4-[4-(1H-imidazol-1-ylmethyl)benzenesulfonyl]-1-[1-(4-pyridyl)piperidin-4-ylmethyl]-2-piperazinone was dissolved in ethyl acetate (5 ml), and to the solution was added a solution of 4N hydrochloric acid in ethyl acetate. Precipitates were filtered, washed with ethyl acetate and dried to give colorless solid of the title compound (103 mg).

$^1$H-NMR (DMSO-d$_6$) δ: 1.10 (2H, m), 1.65 (2H, m), 3.00–3.50 (8H, m), 3.59 (2H, s), 4.18 (2H, m), 5.60 (2H, s), 7.17 (2H, d, J=7.2 Hz), 7.69 (2H, d, J=8.4 Hz), 7.74 (1H, t, J=1.6 Hz), 7.84 (1H, t, J=1.6 Hz), 7.88 (2H, d, J=8.4 Hz), 8.19 (2H, d, J=7.2 Hz), 9.38 (1H, s).

Working Example 80

(S)-4-(6-chloronaphthanlene-2-sulfonyl)-1-[4-(4-pyridyl)benzyl]-2-piperazinone

In ethanol (15 ml) was dissolved (S)-4-benzyloxycarbonyl-1-[4-(4-pyridyl)benzyl]-2-piperazinone (401 mg), and to the solution was added 10% palladium on carbon (160 mg). The mixture was vigorously stirred under hydrogen stream for 4 hours, and the catalyst was removed. The solvent was evaporated under reduced pressure, and to the residue were added 6-chloronaphthanlene-2-sulfonyl chloride (261 mg), sodium carbonate (212 mg), ethyl acetate (20 ml) and water (20 ml). The mixture was stirred at room temperature for 3 hours, and the separated organic layer was washed with saturated brine, dried and concentrated. The residue was purified with silica gel column chromatography (ethyl acetate:methanol=10:1) to give pale pink crystals of the title compound (340 mg).

$^1$H-NMR (CDCl$_3$) δ: 3.37 (4H, s), 3.89 (2H, s), 4.60 (2H, s), 7.27 (2H, d, J=8.3 Hz), 7.45 (2H, d, J=6.2 Hz), 8.53 (2H, d, J=8.3 Hz), 7.60 (1H, dd, J=8.9, 1.9 Hz), 7.79 (1H, dd, J=8.8, 1.8 Hz), 7.88–7.98 (3H, m), 8.36 (1H, d, J=1.6 Hz), 8.66 (2H, d, J=6.2 Hz).

IR (KBr): 1651, 1346, 1167, 964, 696, 588 cm$^{-1}$.

Working Example 81

(S)-3-benzyloxymethyl-4-(6-chloronaphthanlene-2-sulfonyl)-1-[4-(1H-imidazol-1-yl)benzyl]-2-piperazinone To (S)-3-benzyloxymethyl-4-(tert-butoxycarbonyl)-1-[4-(1H-imidazol-1-yl)benzyl]-2-piperazinone (477 mg) were added 4N hydrochloric acid in ethyl acetate (15 ml) and ethanol (5 ml), and the mixture was stirred at room temperature for 1 hour. The reaction solution was concentrated, and to the residue were added THF (15 ml), triethylamine (0.558 ml), N,N-dimethylaminopyridine (catalytic amount) and 6-chloronaphthanlene-2-sulfonyl chloride (392 mg). The mixture was stirred at room temperature for 2 hours. The reaction solution was concentrated under reduced pressure, and to the residue was added saturated sodium hydrogen carbonate solution. The mixture was extracted with ethyl acetate. The extract was washed with saturated brine, dried and concentrated, and the residue was purified with silica gel column chromatography (ethyl acetate) to give amorphous of the title compound (216 mg).

$^1$H-NMR (CDCl$_3$) δ: 3.05 (1H, dt, J=12.0, 3.0 Hz), 3.18–3.35 (1H, m), 3.85–3.98 (3H, m), 4.05 (1H, d, J=15.2 Hz), 4.27 (1H, dd, J=9.5, 3.1 Hz), 4.42 (2H, s), 4.66 (1H, t, J=2.6 Hz), 5.01 (1H, d, J=15.2 Hz), 6.98 (2H, d, J=8.6 Hz), 7.12 (2H, t, J=8.6 Hz), 7.16–7.33 (7H, m), 7.58 (1H, dd, J=8.9, 2.1 Hz), 7.50 (1H, t, J=1.0 Hz), 7.81–7.92 (4H, m), 8.41 (1H, s).

IR (KBr): 1651, 1522, 1337, 1161, 698 cm$^{-1}$.

Working Example 82

(S)-3-benzyl-4-(6-chloronaphthanlene-2-sulfonyl)-1-[4-(1H-imidazol-1-yl)benzyl]-2-piperazinone To a solution of (S)-3-benzyl-4-(benzyloxycarbonyl)-1-[4-(1H-imidazol-1-yl)benzyl]-5,6-dehydro-2-piperazinone (479 mg) in ethanol (30 ml) was added 10% palladium on carbon (200 mg), and the mixture was vigorously stirred under hydrogen stream for 1 hour. The catalyst was removed, and the solvent was evaporated under reduced pressure. To the residue were added THF (20 ml), triethylamine (0.279 ml), N,N-dimethylaminopyridine (catalytic amount) and 6-chloronaphthanlene-2-sulfonyl chloride (313 mg), and the mixture was stirred at room temperature for 5 hours. The reaction solution was concentrated under reduced pressure, and to the residue was added saturated sodium hydrogen carbonate solution. The mixture was extracted with ethyl acetate, and the extract was washed with saturated brine, dried and concentrated. The residue was purified with silica gel column chromatography (ethyl acetate) to give amorphous of the title compound (367 mg).

$^1$H-NMR (CDCl$_3$) δ: 2.74–2.85 (1H, m), 2.97–3.30 (2H, m), 3.30 (2H, d, J=6.0 Hz), 3.63–3.77 (1H, m), 4.45 (1H, d, J=14.8 Hz), 4.59 (1H, d, J=14.8 Hz), 4.74 (1H, t, J=5.3 Hz), 7.07–7.25 (11H, m), 7.48–7.60 (2H, m), 7.72 (1H, d, J=8.8 Hz), 7.80–7.88 (3H, m), 8.23 (1H, s).

IR (KBr): 1649, 1524, 1489, 1331, 1157, 698 cm$^{-1}$.

Working Example 83

(S)-4-(6-chloronaphthanlene-2-sulfonyl)-1-[4-(1H-imidazol-1-yl)benzyl]-3-isopropyl-2-piperazinone According to a similar method described in Working Example 18, amorphous of the title compound was obtained from (S)-4-(benzyloxycarbonyl)-1-[4-(1H-imidazol-1-yl)benzyl]-3-isopropyl-5,6-dehydro-2-piperazinone instead of (S)-3-benzyl-4-(benzyloxycarbonyl)-1-[4-(1H-imidazol-1-yl)benzyl]-5,6-dehydro-2-piperazinone.

$^1$H-NMR (CDCl$_3$) δ: 1.07 (3H, d, J=6.8 Hz), 1.14 (3H, d, J=6.8 Hz), 2.21–2.40 (1H, m), 2.98–3.08 (2H, m), 3.48–3.65 (1H, m), 3.76–3.90 (1H, m), 4.22–4.33 (2H, m), 4.42 (1H, d, J=14.8 Hz), 6.90–7.11 (4H, m), 7.18 (1H, t, J=1.3 Hz), 7.23 (1H, t, J=1.1 Hz), 7.57 (1H, dd, J=8.7, 2.1 Hz), 7.77 (1H, t, J=1.2 Hz), 7.81–7.94 (4H, m), 8.39 (1H, s).

IR (KBr): 1647, 1524, 1337, 1161, 698 cm$^{-1}$.

Reference Example 41

(S)-3-benzyloxymethyl-4-(tert-butoxycarbonyl)-1-[4-(1H-imidazol-1-yl)benzyl]-2-oxo-1,2,3,4-tetrahydropyrazine To a solution of N-tert-butoxycarbonyl-O-benzyl-L-serine (1.48 g) and 2,2-dimethoxyethyl[4-(1H-imidazol-1-yl)benzyl]amine (1.31 g) in acetonitrile (50 ml) were added HOBt (842 mg) and WSC hydrochloride (1.05 g), under ice-cooling, and the mixture was stirred at room temperature for 2 hours. To the mixture was added N,N-dimethylaminopyridine (catalytic amount), and the mixture was stirred overnight. The reaction solution was concentrated, and to the residue were added ethyl acetate and water. The organic layer was separated, washed with saturated brine, dried and concentrated, and the residue was purified with silica gel column chromatography (ethyl acetate methanol=20:1). To the obtained product were added p-toluene sulfonic acid (856 mg) and toluene (60 ml), and the mixture was refluxed for 30 minutes and cooled. To the reaction solution was added ethyl acetate, and the mixture was washed with saturated sodium bicarbonate solution and saturated brine, dried and concentrated. The residue was purified with silica gel column chromatography (ethyl acetate:methanol=20:1) to give amorphous of the title compound (1.14 g).

$^1$H-NMR (CDCl$_3$) δ: 1.46 and 1.50 (total 9H, s), 3.62–3.86 (1H, m), 3.90–4.07 (1H, m), 4.39–4.58 (3H, m), 4.90–5.14 (2H, m), 5.30–5.50 (1H, m), 6.31–6.53 (1H, m), 7.11 (2H, d, J=7.0 Hz), 7.17–7.22 (2H, m), 7.24–7.37 (7H, m), 7.76 (1H, s).

IR (KBr): 1705, 1680, 1524, 1670, 1125 cm$^{-1}$.

Reference Example 42
(S)-3-benzyloxymethyl-4-(tert-butoxycarbonyl)-1-[4-(1H-imidazol-1-yl)benzyl]-2-piperazinone In ethanol (80 ml) was dissolved (S)-3-benzyloxymethyl-4-(tert-butoxycarbonyl)-1-[4-(1H-imidazol-1-yl)benzyl]-2-oxo-1,2,3,4-tetrahydropyrazine (1.13 g), and to the solution was added 10% palladium on carbon (1 g). The mixture was subjected to catalytic reduction for 9 hours with medium pressure reduction apparatus, and the catalyst was removed. The solvent was evaporated under reduced pressure to give colorless amorphous of the title compound (1.02 g).

$^1$H-NMR (CDCl$_3$) δ: 1.46 (9H, s), 3.08–3.23 (1H, m), 3.30–4.35 (7H, m), 4.54 (2H, s), 4.55–4.80 (1H, m), 5.15–5.43 (1H, m), 7.07 (2H, d, J=8.4 Hz), 7.20 (2H, s), 7.26–7.40 (7H, m), 7.79 (1H, s).

IR (KBr): 1698, 1655, 1524, 1414, 1167 cm$^{-1}$.

Reference Example 43
(S)-3-benzyl-4-(benzyloxycarbonyl)-1-[4-(1H-imidazol-1-yl)benzyl]-2-oxo-1,2,3,4-tetrahydropyrazine According to a similar method described in Reference Example 41, colorless amorphous of the title compound was obtained from N-benzyloxycarbonyl-L-phenylalanine and 2,2-dimethoxyethyl[4-(1H-imidazol-1-yl)benzyl]amine.

$^1$H-NMR (CDCl$_3$) δ: 2.91–3.10 (2H, m), 4.43–5.23 (5H, m), 5.29–5.64 (1H, m), 6.17–6.48 (1H, m), 7.05–7.40 (16H, m), 7.84 (1H, s).

IR (KBr): 1713, 1678, 1524, 1445, 1420, 1304 cm$^{-1}$.

Reference Example 44
(S)-4-(benzyloxycarbonyl)-1-[4-(1H-imidazol-1-yl)benzyl]-3-isopropyl-2-oxo-1,2,3,4-tetrahydropyrazine According to a similar method described in Reference Example 41, colorless amorphous of the title compound was obtained from N-benzyloxycarbonyl-L-valine and 2,2-dimethoxyethyl[4-(1H-imidazol-1-yl)benzyl]amine.

$^1$H-NMR (CDCl$_3$) δ: 0.86–1.06 (6H, m), 1.90–2.20 (1H, m), 4.48–4.84 (3H, m), 5.17–5.23 (2H, m), 5.48–5.67 (1H, m), 6.29–6.48 (1H, m), 7.21 (1H, s), 7.27 (1H, s), 7.37 (9H, s), 7.85 (1H, s).

IR (KBr): 1709, 1680, 1524, 1420, 1399, 1277, 1256 cm$^{-1}$.

Reference Example 45
4-[(E)-2-(4-chlorophenyl)ethenylsulfonyl]-1-(4-cyanobenzyl)-2-piperazinone According to a similar method described in Reference Example 6, colorless crystals of the title compound were obtained from (E)-2-(4-chlorophenyl)ethenylsulfonyl chloride instead of 6-chloronaphthanlene-2-sulfonyl chloride.

$^1$H-NMR (CDCl$_3$) δ: 3.36–3.44 (2H, m), 3.45–3.53 (2H, m), 3.97 (2H, s), 4.66 (2H, s), 6.64 (1H, d, J=15.6 Hz), 7.36 (2H, d, J=8.1 Hz), 7.43 (4H, s), 7.50 (1H, d, J=15.6 Hz), 7.62 (2H, d, J=8.1 Hz).

Reference Example 46
1-(4-cyanobenzyl)-4-(4-vinylbenzenesulfonyl)-2-piperazinone According to a similar method described in Reference Example 6, colorless crystals of the title compound were obtained from 4-vinylbenzenesulfonyl chloride instead of 6-chloronaphthanlene-2-sulfonyl chloride.

$^1$H-NMR (CDCl$_3$) δ: 3.32 (4H, s), 3.81 (2H, s), 4.60 (2H, s), 5.50 (1H, d, J=11.0 Hz), 5.92 (1H, d, J=17.7 Hz), 6.72 (1H, dd, J=17.7, 11.0 Hz), 7.30 (2H, d, J=8.2 Hz), 7.54–7.65 (4H, m), 7.75 (2H, d, J=8.4 Hz).

Reference Example 47
4-(6-chloronaphthanlene-2-sulfonyl)-1-(5-cyano-2-pyridylmethyl)-2-piperazinone According to a similar method described in Reference Example 2, colorless crystals of 4-(tert-butoxycarbonyl)-1-(5-cyano-2-pyridylmethyl)-2-piperazinone 4-(tert-butoxycarbonyl)-2-piperazinone and 2-chloromethyl-5-cyanopyridine.

$^1$H-NMR (CDCl$_3$) δ: 1.48 (9H, s), 3.46–3.54 (2H, m), 3.64–3.72 (2H, m), 4.16 (2H, s), 4.76 (2H, s), 7.46 (1H, d, J=8.2 Hz), 7.95 (1H, dd, J=8.2, 2.2 Hz), 8.82 (1H, d, J=2.2 Hz).

According to a similar method described in Reference Example 11, colorless crystals of the title compound were obtained from 4-(tert-butoxycarbonyl)-1-(5-cyano-2-pyridylmethyl)-2-piperazinone.

$^1$H-NMR (CDCl$_3$) δ: 3.38–3.47 (2H, m), 3.58–3.65 (2H, m), 3.84 (2H, s), 4.67 (2H, s), 7.37 (1H, d, J=8.1 Hz), 7.62 (1H, dd, J=8.9, 1.9 Hz), 7.79 (1H, dd, J=8.7, 1.9 Hz), 7.85–7.98 (4H, m), 8.36 (1H, s), 8.71–8.74 (1H, m).

Reference Example 48
4-(6-chloronaphthanlene-2-sulfonyl)-1-(7-cyano-2-naphthylmethyl)-2-piperazinone According to a similar method described in Reference Example 47, colorless crystals of the title compound were obtained from 4-(tert-butoxycarbonyl)-2-piperazinone and 2-bromomethyl-7-cyanonaphthanlene.

$^1$H-NMR (CDCl$_3$) δ: 3.37 (4H, m), 3.90 (2H, s), 4.72 (2H, s), 7.44 (1H, dd, J=8.4, 1.6 Hz), 7.56–7.65 (2H, m), 7.68 (1H, s) 7.75–7.82 (2H, m), 7.83–7.96 (4H, m), 8.15 (1H, s), 8.34 (1H, s).

Reference Example 49
4-(7-chloro-2H-benzopyran-3-sulfonyl)-1-(4-cyanobenzyl)-2-piperazinone To a solution of 1-(4-cyanobenzyl)-2-piperazinone hydrochloride (3.85 g) and triethylamine (12.5 ml) in dichloromethane (50 ml) was added dropwise a solution of 2-chloroethanesulfonyl chloride (4.08 g) in dichloromethane (10 ml) at 0° C., and the mixture was stirred at 0° C. for 4 hours. The reaction solution was diluted with dichloromethane, washed with sodium bicarbonate solution and saturated brine, dried (MgSO$_4$) and concentrated, and the residue was purified with silica gel column chromatography (ethyl acetate) to give colorless crystals of 1-(4-cyanobenzyl)-4-vinylsulfonyl-2-piperazinone (3.15 g).

$^1$H-NMR (CDCl$_3$) δ: 3.35–3.49 (4H, m), 3.92 (2H, s), 4.67 (2H, s), 6.15 (1H, dd, J=8.6, 1.0 Hz), 6.34 (1H, dd, J=16.4, 1.0 Hz), 6.46 (1H, dd, J=16.4, 8.6 Hz), 7.38 (2H, d, J=8.7 Hz), 7.66 (2H, d, J=8.7 Hz).

To a solution of 1-(4-cyanobenzyl)-4-vinylsulfonyl-2-piperazinone (1.53 g) and 4-chlorosalicylaldehyde (0.94 g) in tert-butanol (20 ml) was added potassium tert-butoxide (187 mg), and the mixture was refluxed for 4 days. The reaction solution was concentrated under reduced pressure, and precipitated crystals were washed with acetone-ethanol to give pale brown crystals of the title compound (0.88 g).

$^1$H-NMR (CDCl$_3$) δ: 3.35–3.45 (2H, m), 3.50–3.60 (2H, m), 3.98 (2H, s), 4.67 (2H, s), 4.87 (1H, d, J=1.6 Hz), 6.93

(1H, d, J=1.8 Hz), 7.00 (1H, dd, J=8.2, 1.8 Hz), 7.14 (2H, d, J=8.2 Hz), 7.30 (1H, s), 7.37 (2H, d, J=8.4 Hz), 7.64 (2H, d, J=8.4 Hz).

Reference Example 50
4-(5-chlorobenzofuran-2-sulfonyl)-1-(4-cyanobenzyl)-2-piperazinone To a solution of 1-(4-cyanobenzyl)-2-piperazinone hydrochloride (3.78 g) and triethylamine (6.27 ml) in dichloromethane (50 ml) was added a solution of chloromethanesulfonyl chloride (2.68 g) in dichloromethane (10 ml) at 0° C. and the mixture was stirred at 0° C. for 1 hour. The reaction solution was diluted with dichloromethane, washed with sodium bicarbonate solution and saturated brine, dried (MgSO$_4$) and concentrated, and the residue was purified with silica gel column chromatography (hexane:ethyl acetate=1:2) to give colorless crystals of 4-chloromethylsulfonyl-1-(4-cyanobenzyl)-2-piperazinone (4.01 g).

$^1$H-NMR (CDCl$_3$) δ: 3.38 (2H, t, J=5.3 Hz), 3.73 (2H, t, J=5.3 Hz), 4.20 (2H, s), 4.57 (2H, s), 4.67 (2H, s), 7.38 (1H, d, J=8.1 Hz), 7.65 (1H, d, J=8.1 Hz).

A mixture of 4-chloromethylsulfonyl-1-(4-cyanobenzyl)-2-piperazinone (3.20 g), 5-chlorosalicylaldehyde (2.29 g), potassium carbonate (1.48 g), potassium iodide (1.62 g) and DMF (80 ml) was stirred at 80° C. for 2 days. The reaction solution was concentrated under reduced pressure, and to the residue was added ethyl acetate. The mixture was washed with water and saturated brine, dried (MgSO$_4$) and concentrated, and the residue was purified with silica gel column chromatography (hexane:ethyl acetate=1:1) to give colorless crystals of the title compound (384 mg).

$^1$H-NMR (CDCl$_3$) δ: 3.33–3.41 (2H, m), 3.55–3.63 (2H, m), 4.07 (2H, s), 4.61 (2H, s), 7.30 (2H, d, J=8.2 Hz), 7.39 (1H, s), 7.47–7.49 (2H, m), 7.58 (2H, d, J=8.2 Hz), 7.68–7.72 (1H, m).

Reference Example 51
4-[4-[N-(tert-butoxycarbonyl)-N-(4-pyridyl)aminomethyl]benzenesulfonyl]-1-(4-cyanobenzyl)-2-piperazinone To a solution of 4-[N-(tert-butoxycarbonyl)amino]pyridine (971 mg) in DMF (20 ml) was added sodium hydride (200 mg), and the mixture was stirred at room temperature for 1.5 hours. To the mixture was added a solution of 4-[4-(bromomethyl)benzenesulfonyl]-1-(4-cyanobenzyl)-2-piperazinone (1.79 g), which was obtained from 1-(4-cyanobenzyl)-2-piperazinone hydrochloride and 4-(bromomethyl)benzenesulfonyl chloride according to a method described in Reference Example 6, in DMF (10 ml), and the mixture was stirred for 4 hours. The reaction solution was concentrated under reduced pressure, and to the residue was added ethyl acetate. The mixture was washed with water and saturated brine, dried and concentrated, and the residue was purified with silica gel column chromatography (ethyl acetate:methanol=90:10) to give colorless amorphous of the title compound (734 mg).

$^1$H-NMR (CDCl$_3$) δ: 1.47 (9H, s), 3.25–3.40 (4H, m), 3.79 (2H, s), 4.61 (2H, s), 5.01 (2H, s), 7.18 (2H, d, J=6.2 Hz), 7.32 (2H, d, J=8.4 Hz), 7.42 (2H, d, J=8.2 Hz), 7.63 (2H, d, J=8.4 Hz), 7.76 (2H, d, J=8.2 Hz), 8.50 (2H, d, J=6.2 Hz).

Reference Example 52
1-[1-(tert-butoxycarbonyl)-4-piperidyl]-4-(6-chloronaphthanlene-2-sulfonyl)-2-piperazinone To a solution of N-(6-chloronaphthanlene-2-sulfonyl)ethylenediamine (4.51 g) and 1-(tert-butoxycarbonyl)-4-piperidone (2.59 g) in THF (110 ml) was added acetic acid (1.48 ml), and the mixture was stirred at room temperature for 30 minutes. To the mixture was added sodium triacetoxyborohydride (2.86 g), and the mixture was stirred at room temperature for 5 hours. The reaction solution was concentrated under reduced pressure, and to the residue was added ethyl acetate. The mixture was washed with sodium bicarbonate solution and saturated brine, dried and concentrated, and the residue was purified with column chromatography (ethyl acetate:methanol=9:1) to give amorphous of 1-(tert-butoxycarbonyl)-4-[N-[2-[N-(6-chloronaphthanlene-2-sulfonyl)amino]ethyl]amino]piperidine (5.78 g).

In THF (10 ml) was dissolved 1-(tert-butoxycarbonyl)-4-[N-[2-[N-(6-chloronaphthanlene-2-sulfonyl)amino]ethyl]amino]piperidine (468 mg), and to the solution was added dropwise at 0° C. a solution of chloroacetyl chloride (136 mg) in THF (1 ml) and then was added a solution of triethylamine (152 mg) in THF (1 ml). The mixture was stirred at 0° C. for 2 hours, and to the mixture were added a solution of 1,8-diazabicyclo[5.4.0]-7-undecene (457 mg) in THF (1 ml) and DMF (5 ml). The mixture was stirred at room temperature for 1 week. The reaction solution was concentrated under reduced pressure, and to the residue was added ethyl acetate. The mixture was washed with water and saturated brine, dried and concentrated, and the residue was crystallized form ethanol to give the title compound (366 mg).

$^1$H-NMR (CDCl$_3$) δ: 1.44 (9H, s), 1.40–1.56 (4H, m), 2.64–2.83 (2H, m), 3.27–3.48 (4H, m), 3.79 (2H, s), 4.09–4.26 (2H, m), 4.43–4.65 (2H, m), 7.61 (1H, dd, J=8.9, 1.9 Hz), 7.79 (1H, dd, J=8.8, 1.8 Hz), 7.90–7.97 (3H, m), 8.35 (1H, s).

Reference Example 53
4-(6-chloronaphthanlene-2-sulfonyl)-1-1-(tert-butoxycarbonyl)-3-pyrrolidinylmethyl]-2-piperazinone According to a similar method described in Reference Example 27, pale yellow green oil of 4-benzyloxycarbonyl-1-[1-(tert-butoxycarbonyl)-3-pyrrolidinylmethyl]-1,2,3,4-tetrahydropyrazine-2-one was obtained from 1-(tert-butoxycarbonyl)pyrrolidine-3-ylmethanol instead of trans-4-(1-tert-butoxycarbonylamino)cyclohexane-1-ylmethanol.

$^1$H-NMR (CDCl$_3$) δ: 1.45 (9H, s), 1.50–1.70 (1H, m), 1.85–2.08 (1H, m), 2.40–2.60 (1H, m), 2.92–3.15 (1H, m), 3.20–3.80 (5H, m), 4.32 (2H, s), 5.22 (2H, s), 5.40–5.58 (1H, m), 6.19–6.50 (1H, m), 7.38 (5H, m).

According to a similar method described in Reference Example 18, pale pink crystals of the title compound were obtained from 4-benzyloxycarbonyl-1-[1-(tert-butoxycarbonyl)-3-pyrrolidinylmethyl]-1,2,3,4-tetrahydropyrazine-2-one.

$^1$H-NMR (CDCl$_3$) δ: 1.45 (9H, s), 1.47–1.65 (1H, m), 1.72–1.97 (1H, m), 2.32–2.56 (1H, m), 2.86–3.62 (10H, m), 3.77 (2H, s), 7.61 (1H, dd, J=8.9, 1.9 Hz), 7.79 (1H, dd, J=8.7, 1.7 Hz), 7.91–7.98 (3H, m), 8.36 (1H, s).

Reference Example 54
4-(3-bromobenzenesulfonyl)-1-[1-(tert-butoxycarbonyl)-4-piperidylmethyl]-2-piperazinone To a mixture of 1-[1-(tert-butoxycarbonyl)-4-piperidylmethyl]-2-piperazinone (1.19 g), sodium carbonate (848 mg), ethyl acetate (40 ml) and water (20 ml) was added 3-bromobenzenesulfonyl chloride (1.02 g), and the mixture was stirred at room temperature for 1 hour. The organic layer was separated, washed with saturated brine, dried and concentrated, and the residue was purified with silica gel column chromatography (hexane:ethyl acetate=1:2) to give colorless crystals of the title compound (1.05 g).

¹H-NMR (CDCl₃) δ: 1.00–1.28 (2H, m), 1.44 (9H, s), 1.43–1.62 (2H, m), 1.70–1.93 (1H, m), 2.55–2.75 (2H, m), 3.10–3.50 (6H, m), 3.74 (2H, s), 4.00–4.18 (2H, m), 7.41–7.52 (1H, m), 7.70–7.82 (2H, m), 7.94 (1H, t, J=1.8 Hz).

Reference Example 55
1-[1-(tert-butoxycarbonyl)-4-piperidylmethyl]-4-[4-[(E)-2-chloroethenyl]benzenesulfonyl]-2-piperazinone To a solution of 4-[4-(bromomethyl)benzenesulfonyl]-1-[1-(tert-butoxycarbonyl)-4-piperidylmethyl]-2-piperazinone (2.85 g) in DMF (30 ml) was added potassium acetate (1.58 g), and the mixture was stirred at 60° C. for 4 hours. The reaction solution was concentrated under reduced pressure, and to the residue was added ethyl acetate. The mixture was washed with water and saturated brine, dried and concentrated, and the residue was dissolved in methanol (50 ml). To the solution was added sodium methoxide (28% methanol solution, 290 mg), and the mixture was stirred at room temperature for 2 hours. The reaction solution was concentrated under reduced pressure, and to the residue was added ethyl acetate. The mixture was washed with water and saturated brine, dried (MgSO₄) and concentrated. The residual crystals were washed with ether to give colorless crystals of 1-[1-(tert-butoxycarbonyl)-4-piperidylmethyl]-4-[4-(hydroxymethyl)benzenesulfonyl]-2-piperazinone (2.02 g).

¹H-NMR (CDCl₃) δ: 0.95–1.20 (2H, m), 1.44 (9H, s), 1.38–1.58 (2H, m), 1.65–1.90 (1H, m), 2.25–2.75 (3H, m), 3.10–3.47 (6H, m), 3.72 (2H, s), 3.95–4.15 (2H, m), 4.82 (2H, d, J=4.8 Hz), 7.57 (2H, d, J=8.5 Hz), 7.77 (2H, d, J=8.5 Hz).

To a solution of oxalyl chloride (0.70 ml) in dichloromethane (60 ml) was added dropwise at −70° C. a solution of dimethylsulfoxide (0.85 ml) in dichloromethane (10 ml). Ten minutes later, to the mixture was added dropwise a solution of 1-[1-(tert-butoxycarbonyl)-4-piperidylmethyl]-4-[4-(hydroxymethyl)benzenesulfonyl]-2-piperazinone (1.87 g) in dichloromethane (20 ml), and the mixture was stirred at about −65° C. for 1 hour. To the mixture was added triethylamine (2.79 ml), and the mixture was stirred at −60° C. to −30° C. for 2 hours. The reaction solution was diluted with dichloromethane, washed with water and saturated brine, dried and concentrated, and the the residue was purified with silica gel column chromatography (ethyl acetate). Precipitated crystals were washed with ether to give colorless crystals of 1-[1-(tert-butoxycarbonyl)-4-piperidylmethyl]-4-[4-formylbenzenesulfonyl]-2-piperazinone (2.02 g).

¹H-NMR (CDCl₃) δ: 1.00–1.30 (2H, m), 1.44 (9H, s), 1.45–1.60 (2H, m), 1.70–1.95 (1H, m), 2.53–2.73 (2H, m), 3.12–3.50 (6H, m), 3.76 (2H, s), 3.98–4.18 (2H, m), 7.98 (2H, d, J=8.5 Hz), 8.10 (2H, d, J=8.5 Hz), 10.14 (1H, s).

To a suspension of chromiun (II) chloride (737 mg) in THF (10 ml) was added a solution of 1-[1-(tert-butoxycarbonyl)-4-piperidylmethyl]-4-[4-formylbenzenesulfonyl]-2-piperazinone (466 mg) and chloroform (0.160 ml) in THF (7 ml), and the mixture was refluxed for 1 hour. To the reaction solution was added ethyl acetate, and the mixture was washed with water and saturated brine, dried and concentrated, and the residue was purified with silica gel column chromatography (hexane:ethyl acetate=1:2) to give colorless crystals of the title compound (235 m g).

¹H-NMR (CDCl₃) δ: 0.97–1.30 (2H, m), 1.44 (9H, s), 1.35–1.57 (2H, m), 1.66–1.89 (1H, m), 2.55–2.73 (2H, m), 3.08–3.48 (6H, m), 3.71 (2H, s), 3.99–4.16 (2H, m), 6.82 (2H, d, J=13.8 Hz), 6.90 (1H, d, J=13.8 Hz), 7.48 (2H, d, J=8.6 Hz), 7.75 (2H, d, J=8.6 Hz).

Reference Example 56
1-(tert-butoxycarbonyl)-4-methoxy-4-piperidinecarbaldehyde

To a solution of 6-(tert-butoxycarbonyl)-1-oxa-6-azaspiro[2,5]octane (17.5 g) in methanol (250 ml) was added p-toluene sulfonic acid hydrate (285 mg), and the mixture was stirred at room temperature for 2 hours. The reaction solution was concentrated under reduced pressure, and to the residue was added ethyl acetate. The mixture was washed with sodium bicarbonate solution and saturated brine, dried and concentrated, and the residue was crystallized from ice-cooled hexane to give colorless solid of 1-(tert-butoxycarbonyl)-4-methoxy-4-piperidinemethanol (9.32 g).

¹H-NMR (CDCl₃) δ: 1.46 (9H, s), 1.30–1.87 (4H, m), 3.05–3.23 (2H, m), 3.24 (3H, s), 3.51 (2H, d, J=6.0 Hz), 3.68–3.83 (2H, m).

To a solution of oxalyl chloride (4.36 ml) in dichloromethane (220 ml) was added dropwise at −70% a solution of dimethylsulfoxide (5.32 ml) in dichloromethane (20 ml), and 30 minutes later, to the mixture was added dropwise a solution of 1-(tert-butoxycarbonyl)-4-methoxy-4-piperidinemethanol (6.13 g) in dichloromethane (60 ml). The mixture was stirred around −65° C. for 1 hour. To the mixture was added triethylamine (17.4 ml), and the mixture was stirred between the temperature ranging from −60° C. to 0° C. for 2 hours. The reaction solution was washed with water and saturated brine, dried and concentrated, and the residue was purified with silica gel column chromatography (hexane:ethyl acetate=3:1) to give colorless solid of the title compound (6.32 g).

¹H-NMR (CDCl₃) δ: 1.46 (9H, s), 1.65–1.80 (4H, m), 3.10–3.27 (2H, m), 3.32 (3H, s), 3.71–3.88 (2H, m), 9.57 (1H, s).

Reference Example 57
4-benzyloxycarbonyl-1-[1-(tert-butoxycarbonyl)-4-methoxy-4-piperidylmethyl]-2-piperazinone To a solution of 1-(benzyloxycarbonyl)ethylenediamine (1.94 g) and 1-(tert-butoxycarbonyl)-4-methoxy-4-piperidinecarbaldehyde (2.43 g) in THF (50 ml) was added acetic acid (0.572 ml), and the mixture was stirred at room temperature for 1 hour. To the mixture was added sodium triacetoxyborohydride (2.12 g), and the mixture was stirred at room temperature for 4 hours. To the reaction solution was added ethyl acetate, and the mixture was washed with sodium bicarbonate solution and saturated brine, dried and concentrated. The residue was dissolved in ethyl acetate (40 ml) and THF (20 ml), and to the solution was added triethylamine (2.09 ml). To the mixture was added dropwise at 0° C. a solution of chloroacetyl chloride (0.796 ml) in ethyl acetate (5 ml), and the mixture was stirred at 0° C. for 2 hours. To the reaction solution was added ethyl acetate, and the mixture was washed with water and saturated brine, dried and concentrated. The residue was purified with column chromatography (hexane:ethyl acetate=1:1→0:1), and the obtained amorphous solid (3.81 g) was dissolved in DMF (50 ml). To the solution was added, under ice-cooling, sodium hydride (306 mg), and the mixture was stirred at room temperature for 3 hours. The reaction solution was concentrated under reduced pressure, and to the residue was added ethyl acetate. The mixture was washed with water and saturated brine, dried and concentrated, and the residue was purified with silica gel column chromatography (hexane:ethyl acetate=1:2) to give pale yellow syrup of the title compound (2.84 g).

¹H-NMR (CDCl₃) δ: 1.30–1.80 (4H, m), 1.45 (9H, s), 3.00–3.20 (2H, m), 3.22 (3H, s), 3.35–3.90 (8H, m), 4.18 (2H, s), 5.16 (2H, s), 7.36 (5H, m).

Reference Example 58
1-[1-(tert-butoxycarbonyl)-4-methoxy-4-piperidylmethyl]-4-(6-chloronaphthanlene-2-sulfonyl)-2-piperazinone According to a similar method described in Reference Example 18, colorless crystals of the title compound were obtained from 4-benzyloxycarbonyl-1-[(1-tert-butoxycarbonyl-4-methoxy-4-piperidyl)methyl]-2-piperazinone.

$^1$H-NMR (CDCl$_3$) δ: 1.25–1.70 (4H, m), 1.42 (9H, s), 2.94–3.13 (2H, m), 3.17 (3H, s), 3.30–3.82 (8H, m), 3.79 (2H, s), 7.60 (1H, dd, J=8.8, 2.0 Hz), 7.79 (1H, dd, J=8.6, 1.8 Hz), 7.90–7.98 (3H, m), 8.35 (1H, d, J=1.8 Hz).

Reference Example 59
4-benzyloxycarbonyl-1-[1-(tert-butoxycarbonyl)-4-methanesulfonylamino-4-piperidylmethyl]-1,2,3,4-tetrahydropyrazine-2-one To a solution of 4-aminomethyl-1-benzyl-4-methanesulfonylaminopiperidine (2.97 g) and N-(2,2-diethoxyethyl)-Z-glycine (3.90 g) in acetonitrile (50 ml) was added WSC (2.30 g), and the mixture was stirred at room temperature. The reaction solution was concentrated, and to the residue were added ethyl acetate and water. The separated organic layer was washed with water, sodium bicarbonate solution, citric acid solution and brine, dried and concentrated, and the residue was purified with silica gel column chromatography (ethyl acetate:methanol=95:5) to give syrup of 1-benzyl-4-[N-[N-(2,2-diethoxyethyl)-Z-glycyl]aminomethyl]-4-methanesulfonylaminopiperidine (4.44 g). In 1,2-dichloroethane (90 ml) was dissolved 1-benzyl-4-[N-[N-(2,2-diethoxyethyl)-Z-glycyl]aminomethyl]-4-methanesulfonylaminopiperidine (3.49 g), and to the solution was added p-toluenesulfonic acid hydrate (1.10 g). The mixture was stirred at 80° C. for 6 hours. The reaction solution was concentrated under reduced pressure, and to the residue was added ethyl acetate. The mixture was washed with washed with saturated sodium bicarbonate solution and brine, dried and concentrated, and the residue was purified with silica gel column chromatography (ethyl acetate:ethanol=20:1) to give amorphous of 4-benzyloxycarbonyl-1-(1-benzyl-4-methanesulfonylamino-4-piperidylmethyl)-1,2,3,4-tetrahydropyrazine-2-one (2.02 g).

$^1$H-NMR (CDCl$_3$) δ: 1.80–1.90 (4H, m), 2.27–2.44 (2H, m), 2.55–2.70 (2H, m), 3.05 (3H, s), 3.51 (2H, s), 3.91 (2H, s), 4.31 (2H, s), 5.20 (2H, s), 5.87–6.02 (1H, m), 6.31–6.49 (1H, m), 7.20–7.42 (10H, m).

To a solution of 4-benzyloxycarbonyl-1-(1-benzyl-4-methanesulfonylamino-4-piperidylmethyl)-1,2,3,4-tetrahydropyrazine-2-one (1.97 g) in 1,2-dichloroethane (20 ml) was added 1-chloroethyl chlorocarbonate (0.432 ml), and the mixture was stirred at 80° C. for 15 minutes. The reaction solution was concentrated, and to the residue was added methanol (0.20 ml). The mixture was stirred at 80° C. for 30 minutes. The reaction solution was concentrated, and to the residue were added ethyl acetate (20 ml), saturated sodium bicarbonate solution (20 ml) and di-tert-butyl dicarbonate (1.00 g). The mixture was stirred at room temperature, and the separated organic layer was washed with saturated brine, dried and concentrated. The residue was purified with silica gel column chromatography (hexane:ethyl acetate=1:2) to give amorphous of the title compound (1.28 g).

$^1$H-NMR (CDCl$_3$) δ: 1.45 (9H, s), 1.70–1.93 (4H, m), 3.07 (3H, s), 3.20–3.40 (2H, m), 3.62–3.80 (2H, m), 3.91 (2H, brs), 4.32 (2H, s), 4.25–4.40 (1H, m), 5.21 (2H, s), 5.87–6.03 (1H, m), 6.33–6.51 (1H, m), 7.38 (5H, m).

Reference Example 60
1-[1-(tert-butoxycarbonyl)-4-methanesulfonylamino-4-piperidylmethyl]-4-(6-chloronaphthanlene-2-sulfonyl)-2-piperazinone According to a similar method described in Reference Example 18, amorphous of the title compound was obtained from 4-benzyloxycarbonyl-1-[1-(tert-butoxycarbonyl)-4-methanesulfonylamino-4-piperidylmethyl]-1,2,3,4-tetrahydropyrazine-2-one.

$^1$H-NMR (CDCl$_3$) δ: 1.44 (9H, s), 1.60–1.90 (4H, m), 3.04 (3H, s), 3.15–3.90 (12H, m), 4.35 (1H, s), 7.60 (1H, dd, J=8.7, 2.1 Hz), 7.80 (1H, dd, J=8.8, 1.8 Hz), 7.90–8.00 (3H, m), 8.36 (1H, d, J=1.6 Hz).

Reference Example 61
1-[1-(tert-butoxycarbonyl)-4-methanesulfonylamino-4-piperidylmethyl]-4-(7-chloro-2H-benzopyran-3-sulfonyl)-2-piperazinone In ethanol (20 ml) was dissolved 4-benzyloxycarbonyl-1-[1-(tert-butoxycarbonyl)-4-methanesulfonylamino-4-piperidylmethyl]-1,2,3,4-tetrahydropyrazine-2-one (1.20 g). To the solution was added 10% palladium on carbon (240 mg), and the mixture was vigorously stirred overnight, under hydrogen stream. The catalyst was removed, and the solvent was evaporated under reduced pressure. The residue was dissolved in dichloromethane (30 ml), and to the solution was added N-ethyldiisopropylamine (0.600 ml). To the mixture was added portionwise, under ice-cooling, a solution of 7-chloro-4H-4-oxobenzopyran-3-sulfonyl chloride (961 mg) in dichloromethane (15 ml), and the mixture was stirred at 0° C. for 1 hour. The reaction solution was washed with sodium bicarbonate solution and saturated brine, dried and concentrated, and the residue was purified with silica gel column chromatography (ethyl acetate) to give amorphous (1.01 g), which was dissolved in methanol/THF (1:1, 40 ml). To the solution was added, under ice-cooling, sodium borohydride (91 mg), and the mixture was stirred at 0° C. for 2 hours. The reaction solution was concentrated, and to the residue were added water and a little amount of acetic acid. The mixture was extracted with ethyl acetate, washed with saturated brine and dried, and the solvent was concentrated. The residue was dissolved in THF (20 ml), and to the solution was added triethylamine (1.60 ml) and then was added at 0° C. a solution of methanesulfonyl chloride (0.267 ml) in THF (3 ml). The mixture was stirred at room temperature overnight, and to the reaction solution was added ethyl acetate. The mixture was washed with 5% potassium hydrogensulfate solution and brine, dried and concentrated, and the residue was purified with silica gel column chromatography (ethyl acetate) to give amorphous of the title compound (765 mg).

$^1$H-NMR (CDCl$_3$) δ: 1.45 (9H, s), 1.68–1.90 (4H, m), 3.06 (3H, s), 3.22–3.40 (2H, m), 3.50–3.90 (8H, m), 3.96 (2H, s), 4.48 (1H, s), 4.89 (2H, s), 6.93 (1H, d, J=1.9 Hz), 7.01 (1H, dd, J=8.1, 1.9 Hz), 7.16 (1H, d, J=8.1 Hz), 7.30 (1H, s).

Reference Example 62
1-(tert-butoxycarbonyl)-4-[4-(6-chloro-2-naphthanlenesulfonyl)-2-oxo-1-piperazinylmethyl]isonipecotic Acid To a solution of tert-butyl 4-aminomethyl-1-(tert-butoxycarbonyl)isonipecotate (9.8 g) and N-(2,2-diethoxyethyl)-Z-glycine (9.76 g) in acetonitrile (100 ml) was added WSC (6.33 g), and the mixture was stirred at room temperature for 7 hours. The reaction solution was concentrated, and to the residue were added ethyl acetate and water. The separated organic layer was washed with water, sodium bicarbonate solution, citric acid solution and brine, dried and concentrated, and the residue was purified with silica gel column chromatography (hexane:ethyl acetate=1:1) to give syrup of tert-butyl 1-(tert-butoxycarbonyl)-4-[N-[N-(2,2-diethoxyethyl)-Z-glycyl]aminomethyl]isonipecotate (12.1 g).

In toluene (180 ml) was dissolved tert-butyl 1-(tert-butoxycarbonyl)-4-[N-[N-(2,2-diethoxyethyl)-Z-glycyl]aminomethyl]isonipecotate (12.0 g). To the solution was added p-toluene sulfonic acid hydrate (270 mg), and the mixture was stirred at 110° C. for 6 hours. To the reaction solution was added ethyl acetate, and the mixture was washed with saturated sodium bicarbonate solution and brine, dried and concentrated. The residue was purified with silica gel column chromatography (hexane:ethyl acetate=1:1) to give 4-benzyloxycarbonyl-1-[1,4-bis(tert-butoxycarbonyl)-4-piperidylmethyl]-1,2,3,4-tetrahydropyrazine-2-one (5.12 g).

$^1$H-NMR (CDCl$_3$) δ: 1.20–1.50 (2H, m), 1.44, (9H, s), 1.46 (9H, s), 1.90–2.10 (2H, m), 2.73–2.95 (2H, m), 3.63 (2H, br), 3.83–4.06 (2H, m), 4.30 (2H, s), 5.21 (2H, s), 5.39–5.55 (1H, m), 6.23–6.44 (1H, m), 7.37 (5H, m).

According to a similar method described in Reference Example 18, amorphous of 1-[1,4-bis(tert-butoxycarbonyl)-4-piperidylmethyl]-4-(6-chloronaphthanlene-2-sulfonyl)-2-piperazinone (4.21 g) was obtained from 4-benzyloxycarbonyl-1-[1,4-bis(tert-butoxycarbonyl)-4-piperidylmethyl]-1,2,3,4-tetrahydropyrazine-2-one (5.10 g).

$^1$H-NMR (CDCl$_3$) δ: 1.25–1.50 (2H, m), 1.42 (9H, s), 1.44 (9H, s), 1.80–2.00 (2H, m), 2.68–2.90 (2H, m), 3.26–3.70 (6H, m), 3.77 (2H, s), 3.70–4.00 (2H, m), 7.61 (1H, dd, J=8.9, 1.9 Hz), 7.78 (1H, dd, J=8.6, 1.8 Hz), 7.91–7.98 (3H, m), 8.34 (1H, d, J=1.4 Hz).

To a solution of 1-[1,4-bis(tert-butoxycarbonyl)-4-piperidylmethyl]-4-(6-chloronaphthanlene-2-sulfonyl)-2-piperazinone (3.11 g) in toluene (15 ml) was added trifluoroacetic acid (10 ml), and the mixture was stirred at room temperature for 2.5 hours The reaction solution was concentrated, and to the residue were added THF (20 ml), water (20 ml), sodium carbonate (1.59 g) and di-tert-butyl dicarbonate (2.18 g). The mixture was stirred at room temperature for 2.5 hours. The reaction solution was concentrated under reduced pressure, and to the residue were added water and ether. To the separated aqueous layer was added 10% citric acid solution to make the solution acidic, and the solution was extracted with ethyl acetate. The organic layer was washed with saturated brine, dried and concentrated. Precipitated crystals were washed with ether to give colorless crystals of the title compound (2.26 g).

$^1$H-NMR (CDCl$_3$) δ: 1.20–1.50 (2H, m), 1.44 (9H, s), 1.90–2.08 (2H, m), 2.65–2.95 (2H, m), 3.30–3.70 (6H, m), 3.75–4.10 (2H, m), 3.82 (2H, s), 7.58 (1H, dd, J=8.8, 2.0 Hz), 7.80 (1H, dd, J=8.6, 1.6 Hz), 7.86–8.00 (3H, m), 8.39 (1H, s).

Reference Example 63

1-[4-benzyloxycarbonylamino-1-(tert-butoxycarbonyl)-4-piperidylmethyl]-4-(6-chloronaphthanlene-2-sulfonyl)-2-piperazinone To a solution of 1-(tert-butoxycarbonyl)-4-[4-(6-chloro-2-naphthanlenesulfonyl)-2-oxo-1-piperazinylmethyl]isonipecotic acid (5.66 g) in toluene (100 ml) were added triethylamine (1.67 ml) and diphenylphosphoryl azide (2.59 ml), and the mixture was stirred at room temperature for 1 hour, and then at 100° C. for 30 minutes. To the reaction solution was added benzylalcohol (1.57 ml), and the mixture was stirred at 100 C. overnight. The reaction solution was concentrated, and the residue was purified with silica gel column chromatography (hexane:ethyl acetate=1:1) to give amorphous of the title compound (7.42 g).

$^1$H-NMR (CDCl$_3$) δ: 1.42 (9H, s), 1.35–2.00 (4H, m), 2.77–2.95 (2H, m), 3.05–3.35 (4H, m), 3.55–3.90 (6H, m), 4.47 (1H, s), 5.02 (2H, s), 7.30–7.45 (5H, m), 7.60 (1H, dd, J=8.8, 1.8 Hz), 7.75 (1H, dd, J=8.8, 1.8 Hz), 7.88–7.98 (3H, m), 8.32 (1H, s).

Reference Example 64

Methyl 2-[4-(6-chloronaphthanlene-2-sulfonyl)-2-oxo-1-piperazinyl]-2-(4-cyanophenyl)acetate A mixture of 4-bromophenylacetic acid (2.15 g), carbon tetrachloride (2 ml) and thionyl chloride (2.88 ml) was stirred at 65° C. for 30 minutes. To the mixture were added N-bromosuccinimide (2.14 g), carbon tetrachloride (10 ml) and 48% hydrobromic acid (2 drops), and the mixture was stirred at 80° C. for 2 hours. The reaction solution was concentrated, and to the residue was methanol (20 ml). The mixture was stirred at room temperature for 2 hours. The reaction solution was concentrated under reduced pressure, and to the residue was added ethyl acetate. The mixture was washed with sodium bicarbonate solution and saturated brine, dried and concentrated to give yellow oil of methyl 2-bromo-2-(4-bromophenyl)acetate (2.91 g).

$^1$H-NMR (CDCl$_3$) δ: 3.79 (3H, s), 5.30 (1H, s), 7.42 (2H, d, J=8.8 Hz), 7.51 (2H, d, J=8.8 Hz).

To a mixture of 1-(tert-butoxycarbonyl)ethylenediamine (881 mg), potassium carbonate (1.17 g) and acetonitrile (18 ml) was added a solution of methyl 2-bromo-2-(4-bromophenyl)acetate (1.39 g) in acetonitrile (7 ml), and the mixture was stirred at room temperature overnight. To the reaction solution was added ethyl acetate, and the mixture was washed with sodium bicarbonate solution and saturated brine, dried and concentrated. The residue was purified with silica gel column chromatography (hexane:ethyl acetate=1:1) to give yellow syrup (1.66 g), which was dissolved in THF (20 ml). To the solution was added triethylamine (0.896 ml), and then was added dropwise at 0° C. a solution of chloroacetyl chloride (0.408 ml) in THF (5 ml), and the mixture was stirred at 0° C. for 20 minutes. To the reaction solution was added ethyl acetate, and the mixture was washed with water and saturated brine, dried and concentrated. The residue was purified with column chromatography (hexane:ethyl acetate=2:1) to give syrup (1.83 g), which was dissolved in DMF (20 ml). To the solution was added sodium hydride (160 mg), and the mixture was stirred at room temperature overnight. The reaction solution was concentrated under reduced pressure, and to the residue was added ethyl acetate. The mixture was washed with water and saturated brine, dried and concentrated, and the residue was purified with silica gel column chromatography (hexane:ethyl acetate=1:1) to give methyl 2-(4-bromophenyl)-2-[4-(tert-butoxycarbonyl)-2-oxo-1-piperazinyl]acetate (1.28 g).

$^1$H-NMR (CDCl$_3$) δ: 1.44 (9H, s), 3.16 (1H, d, J=15.0 Hz), 3.20–3.50 (3H, m), 3.63 (1H, d, J=15.0 Hz), 3.88 (3H, s), 5.37 (1H, br), 7.18 (2H, d, J=8.6 Hz), 7.55 (2H, d, J=8.6 Hz).

A mixture of methyl 2-(4-bromophenyl)-2-[4-(tert-butoxycarbonyl)-2-oxo-1-piperazinyl]acetate (1.28 g), zinc cyanide (211 mg), tetrakis (triphenylphosphine)palladium (139 mg) and DMF (10 ml) was stirred at 80° C. for 6 hours and cooled. To the reaction solution were added ethyl acetate, water and a little amount of ammonia solution. The organic layer was separated, washed with saturated brine, dried and concentrated, and the residue was purified with silica gel column chromatography (hexane:ethyl acetate=1:1) to give yellow syrup of methyl 2-[4-(tert-butoxycarbonyl)-2-oxo-1-piperazinyl]-2-(4-cyanophenyl) acetate (1.01 g).

$^1$H-NMR (CDCl$_3$) δ: 1.44 (9H, s), 3.13 (1H, d, J=15.0 Hz), 3.24–3.52 (4H, m), 3.69 (1H, d, J=15.0 Hz), 3.90 (3H, s), 5.31 (1H, br), 7.44 (2H, d, J=8.7 Hz), 7.72 (2H, d, J=8.7 Hz).

According to a similar method described in Reference Example 11, amorphous of the title compound (673 mg) was obtained from methyl 2-[4-(tert-butoxycarbonyl)-2-oxo-1-piperazinyl]-2-(4-cyanophenyl)acetate (1.01 g).

$^1$H-NMR (CDCl$_3$) δ: 3.12 (1H, d, J=15.0 Hz), 3.24–3.48 (4H, m), 3.62 (1H, d, J=15.0 Hz), 3.84 (3H, s), 6.06–6.16 (1H, m), 7.36 (2H, d, J=8.4 Hz), 7.57 (1H, dd, J=8.8, 1.8 Hz), 7.67 (2H, d, J=8.4 Hz), 7.85–7.94 (4H, m), 8.40 (1H, s).

Reference Example 65

4-(6-chloronaphthanlene-2-sulfonyl)-2.6-piperazinedione

To a solution of diethyl iminodiacetate (1.89 g) and triethylamine (2.09 ml) in DMF (20 ml)-THF (20 ml) was added 6-chloronaphthanlene-2-sulfonyl chloride (2.87 g), and the mixture was stirred at room temperature overnight. The reaction solution was concentrated under reduced pressure, and to the residue was added ethyl acetate. The mixture was washed with water and saturated brine, dried and concentrated, and the residue was purified with silica gel column chromatography (hexane: ethyl acetate=2: 1) to give colorless crystals of diethyl N-(6-chloronaphthanlene-2-sulfonyl)iminodiacetate (5.99 g).

$^1$H-NMR (CDCl$_3$) δ: 1.17 (6H, t, J=7.2 Hz), 4.08 (4H, q, J=7.2 Hz), 4.26 (4H, s), 7.55 (1H, dd, J=8.8, 2.0 Hz), 7.83–7.95 (4H, m), 8.41 (1H, s).

In methanol (30 ml) was dissolved diethyl N-(6-chloronaphthanlene-2-sulfonyl)iminodiacetate (5.99 g). To the solution was added 1N sodium hydroxide (24 ml), and the mixture was stirred at room temperature overnight. The reaction solution was concentrated under reduced pressure, and to the residue was added 1N hydrochloric acid to make the mixture acidic. The mixture was extracted with ethyl acetate, and the organic layer was washed with water and saturated brine, dried and concentrated to give colorless crystals of N-(6-chloronaphthanlene-2-sulfonyl) iminodiacetatic acid (2.00 g)

$^1$H-NMR (CDCl$_3$) δ: 4.12 (4H, s), 7.68 (1H, dd, J=8.8, 2.2 Hz), 7.88 (1H, dd, J=8.8, 1.8 Hz), 8.08 (1H, d, J=8.8 Hz), 8.16–8.25 (2H, m), 8.54 (1H, s).

To a solution of N-(6-chloronaphthanlene-2-sulfonyl) iminodiacetatic acid (358 mg) and triethylamine (0.153 ml) in acetonitrile (10 ml) was added isobutyl chlorocarbonate (0.130 ml), and the mixture was stirred at 0° C. for 30 minutes. To the mixture was added ammonia solution (0.5 ml), and the mixture was stirred for 30 minutes. To the mixture was added 1N hydrochloric acid (10 ml), and precipitated crystals were washed with water to give pale yellow solid of N-(6-chloronaphthanlene-2-sulfonyl) iminodiacetatic acid monoamide (286 mg).

$^1$H-NMR (CDCl$_3$) δ: 3.94 (2H, s), 4.12 (2H, s), 7.27 (1H, brs), 7.63 (1H, brs), 7.69 (1H, dd, J=8.6, 2.0 Hz), 7.89 (1H, dd, J=8.6, 1.8 Hz), 8.11 (1H, d, J=8.6 Hz), 8.16–8.26 (2H, m), 8.55 (1H, s).

To a solution of the N-(6-chloronanhthalane-2-sulfonyl) iminodiacetatic acid monoamide (286 mg) in THF (10 ml) was added at 0° C. a solution of N,N'-carbonyldiimidazole (114 mg) in THF (2 ml), and the mixture was refluxed for 6 hours. The reaction solution was concentrated under reduced pressure, and to the residue was added ethyl acetate. The mixture was washed with water and saturated brine, dried and concentrated, and the residue was purified with silica gel column chromatography (hexane: ethyl acetate=1:1) to give colorless crystals of the title compound (175 mg).

1H-NMR (CDCl$_3$) δ: 4.16 (4H, s), 7.57–7.67 (2H, m), 7.77 (1H, dd, J=8.8, 1.8 Hz), 7.91–7.90 (3H, m), 8.37 (1H, s).

4-(6-chloronaphthanlene-2-sulfonyl)-1-(4-cyanobenzyl)-1,4-diazepan-2-one

According to a similar method described in Reference Example 52, colorless crystals of the title compound were obtained from N-(6-chloronaphthanlene-2-sulfonyl) propylenediamine hydrochloride and 4-cyanobenzaldehyde.

$^1$H-NMR (CDCl$_3$) δ: 1.68–1.84 (2H, m), 3.30–3.38 (2H, m), 3.56 (2H, t, J=5.8 Hz), 4.16 (2H, s), 4.47 (2H, s), 7.22 (2H, d, J=8.4 Hz), 7.52 (2H, d, J=8.4 Hz), 7.59 (1H, dd, J=8.9, 1.9 Hz), 7.82 (1H, dd, J=8.7, 1.7 Hz), 7.87–7.97 (3H, m), 8.41 (1H, s).

Reference Example 67

4-[1-(tert-butoxycarbonyl)-4-piperidylmethyl]-1-(6-chloronaphthanlene-2-sulfonyl)-1.4-diazepan-5-one A solution of 2,2-diethoxyethylamine (2.66 g), 1-(tert-butoxycarbonyl)-4-piperidinecarbaldehyde (4.27 g) and acetic acid (1.14 ml) in THF (100 ml) was stirred at room temperature for 1 hour. To the solution was added sodium triacetoxyborohydride (4.24 g), and the mixture was stirred at room temperature for 5 hours. To the mixture was added sodium triacetoxyborohydride (4.24 g), and the mixture was stirred overnight. To the reaction solution was added ethyl acetate, and the mixture was washed with sodium bicarbonate solution and saturated brine, dried and concentrated. The obtained yellow oil (6.64 g) was dissolved in acetonitrile (120 ml), and to the solution were added Z-β-alanine (6.63 g) and WSC (2.78 g). The mixture was stirred at room temperature overnight. The reaction solution was concentrated under reduced pressure, and to the residue was added ethyl acetate. The mixture was washed with water and saturated brine, dried and concentrated, and the residue was purified with silica gel column chromatography (hexane:ethyl acetate=1:2) to give pale yellow oil (6.31 g). A part of the oil (5.53 g) was dissolved in toluene (100 ml). To the solution was added p-toluenesulfonic acid hydrate (95 mg), and the mixture was stirred at 110° C. overnight. To the reaction solution was added ethyl acetate, and the mixture was washed with saturated sodium bicarbonate solution and saturated brine, dried and concentrated. The residue was purified with silica gel column chromatography (hexane:ethyl acetate=1:1) to give 1-benzyloxycarbonyl-4-[1-(tert-butoxycarbonyl)-4-piperidylmethyl]-1,4,6,7-tetrahydro-5H-1,4-diazepin-5-one (1.82 g).

$^1$H-NMR (CDCl$_3$) δ: 1.00–1.33 (2H, m), 1.44, (9H, s), 1.50–1.67 (2H, m), 1.67–1.95 (1H, m), 2.50–2.85 (4H, m), 3.20–3.60 (2H, m), 3.90–4.20 (4H, m), 4.95–5.25 (1H, m), 5.21 (2H, s), 6.35–6.60 (1H, m), 7.38 (5H, m).

According to a similar method described in Reference Example 18, amorphous of the title compound was obtained from 1-benzyloxycarbonyl-4-[1-(tert-butoxycarbonyl)-4-piperidylmethyl]-1,4,6,7-tetrahydro-5H-1,4-diazepin-5-one.

$^1$H-NMR (CDCl$_3$) δ: 0.95–1.80 (5H, m), 1.43 (9H, s), 2.52–2.72 (2H, m), 2.72–2.85 (2H, m), 3.05–3.45 (6H, m), 3.45–3.60 (2H, m), 3.95–4.15 (2H, m), 7.59 (1H, dd, J=8.8, 2.0 Hz), 7.74 (1H, dd, J=8.6, 1.8 Hz), 7.87–7.96 (3H, m), 8.32 (1H, s).

Working Example 84

1-(4-amidinobenzyl)-4-[(E)-2-(4-chlorophenyl) ethenylsulfonyl)-2-piperazinone Hydrochloride According to a similar method described in Working Example 4, colorless crystals of the title compound were obtained from 4-[(E)-2-(4-chlorophenyl)ethenylsulfonyl]-1-(4-cyanobenzyl)-2-piperazinone.

$^1$H-NMR (DMSO-d$_6$) δ: 3.38–3.50 (4H, m), 3.90 (2H, s), 4.65 (2H, s), 7.43–7.57 (6H, m), 7.73–7.85 (4H, m), 9.10 (2H, brs), 9.35 (2H, brs).

Working Example 85

1-(4-amidinobenzyl)-4-(4-vinylbenzenesulfonyl)-2-piperazinone Hydrochloride

According to a similar method described in Working Example 4, colorless crystals of the title compound were obtained from 1-(4-cyanobenzyl)-4-(4-vinylbenzenesulfonyl)-2-piperazinone.

$^1$H-NMR (DMSO-d$_6$) δ: 3.23–3.40 (4H, m), 3.73 (2H, s), 4.59 (2H, s), 5.50 (1H, d, J=11.1 Hz), 6.07 (1H, d, J=17.5 Hz), 6.87 (1H, dd, J=17.5, 11.1 Hz), 7.39 (2H, d, J=8.4 Hz), 7.72–7.85 (6H, m), 9.11 (2H, brs), 9.35 (2H, brs).

Working Example 86

1-(5-amidino-2-pyridylmethyl)-4-(6-chloronaphthanlene-2-sulfonyl)-2-piperazinone Dihydrochloride According to a similar method described in Working Example 4, powder of the title compound was obtained from 4-(6-chloronaphthanlene-2-sulfonyl)-1-(5-cyano-2-pyridylmethyl)-2-piperazinone.

$^1$H-NMR (DMSO-d$_6$) δ: 3.46 (4H, brs), 3.77 (2H, s), 4.64 (2H, s), 7.42 (1H, d, J=8.4 Hz), 7.74 (1H, dd, J=8.9, 2.1 Hz), 7.90 (1H, dd, J=8.6, 1.8 Hz), 8.07 (1H, dd, J=8.4, 2.2 Hz), 8.20 (1H, d, J=8.9 Hz), 8.25–8.34 (3H, m), 8.61 (1H, s), 8.83 (1H, d, J=2.2 Hz), 9.20 (2H, brs), 9.49 (2H, brs).

Working Example 87

1-(7-amidino-2-naphthylmethyl)-4-(6-chloronaphthanlene-2-sulfonyl)-2-piperazinone Hydrochloride According to a similar method described in Working Example 4, colorless crystals of the title compound were obtained from 4-(6-chloronaphthanlene-2-sulfonyl)-1-(7-cyano-2-naphthylmethyl)-2-piperazinone.

$^1$H-NMR (DMSO-d$_6$) δ: 3.23–3.50 (4H, m), 3.84 (2H, s), 4.68 (2H, s), 7.44 (1H, dd, J=8.4, 1.6 Hz), 7.69–7.93 (5H, m), 8.09 (1H, dd, J=8.4 Hz), 8.15 (1H, dd, J=8.8 Hz), 8.20–8.31 (2H, m), 8.42 (1H, s), 8.60 (1H, s), 9.00–9.70 (4H, br).

Working Example 88

1-(4-amidinobenzyl)-4-(7-chloro-2H-benzopyran-3-sulfonyl)-2-piperazinone Hydrochloride According to a similar method described in Working Example 4, colorless crystals of the title compound were obtained from 4-(7-chloro-2H-benzopyran-3-sulfonyl)-1-(4-cyanobenzyl)-2-piperazinone.

$^1$H-NMR (DMSO-d$_6$) δ: 3.32–3.42 (2H, m), 3.48–3.58 (2H, m), 3.90 (2H, s), 4.65 (2H, s), 4.99 (2H, s), 7.07 (1H, d, J=1.9 Hz), 7.12 (1H, dd, J=8.0, 1.9 Hz), 7.43–7.52 (4H, m), 7.78 (2H, d, J=8.2 Hz), 9.14 (2H, brs), 9.36 (2H, brs).

Working Example 89

1-(4-amidinobenzyl)-4-(5-chlorobenzofuran-2-sulfonyl)-2-piperazinone Hydrochloride According to a similar method described in Working Example 4, colorless crystals of the title compound were obtained from 4-(5-chlorobenzofuran-2-sulfonyl)-1-(4-cyanobenzyl)-2-piperazinone.

$^1$H-NMR (DMSO-d) δ: 3.26–3.40 (2H, m), 3.55–3.66 (2H, m), 3.99 (2H, s), 4.58 (2H, s), 7.39 (2H, d, J=8.4 Hz), 7.60 (1H, dd, J=8.8, 2.2 Hz), 7.71 (2H, d, J=8.4 Hz), 7.76 (1H, d, J=0.6 Hz), 7.82 (1H, d, J=8.8 Hz), 7.94 (1H, d, J=2.2 Hz), 9.09 (2H, brs), 9.33 (2H, brs).

Working Example 90

1-(4-amidinobenzyl)-4-[3-(1H-imidazol-1-ylmethyl)benzenesulfonyl]-2-Diperazinone Dihydrochloride A solution of 4-[3-(bromomethyl)benzenesulfonyl]-1-(4-cyanobenzyl)-2-piperazinone (1.21 g) obtained from 1-(4-cyanobenzyl)-2-piperazinone hydrochloride and 3-(bromomethyl)benzenesulfonyl chloride according to a method described in Reference Example 6 and imidazole (613 mg) in DMF (20 ml) was stirred at room temperature overnight. The reaction solution was concentrated under reduced pressure, and to the residue was added ethyl acetate. The mixture was washed with sodium bicarbonate solution and saturated brine, dried (MgSO$_4$) and concentrated, and the residue was purified with silica gel column chromatography (ethyl acetate: methanol containing 10% ammonia solution=85: 15) to give pale yellow amorphous of 1-(4-cyanobenzyl)-4-[3-(1H-imidazol-1-ylmethyl)benzenesulfonyl]-2-piperazinone (734 mg).

$^1$H-NMR (CDCl$_3$) δ: 3.23–3.39 (4H, m), 3.78 (2H, s), 4.60 (2H, s), 5.23 (2H, s), 6.93 (1H, s), 7.14 (1H, s), 7.32 (2H, d, J=8.2 Hz), 7.39 (1H, d, J=7.8 Hz), 7.53–7.66 (5H, m), 7.76 (1H, d, J=7.8 Hz).

According to a similar method described in Working Example 4, pale yellow amorphous of the title compound was obtained from 1-(4-cyanobenzyl)-4-[3-(1H-imidazol-1-ylmethyl)benzenesulfonyl]-2-piperazinone.

$^1$H-NMR (DMSO-d$_6$) δ: 3.20–3.40 (4H, 3), 3.77 (2H, s), 4.56 (2H, s), 5.61 (2H, s), 7.35 (2H, d, J=8.4 Hz), 7.65–7.94 (7H, m), 8.01 (1H, s), 9.33 (2H, brs), 9.43 (1H, s), 9.51 (2H, brs).

Working Example 91

1-(4-amidinobenzyl)-4-[4-(1H-imidazol-1-ylmethyl)benzenesulfonyl]-2-piperazinone Dihydrochloride According to a similar method described in Working Example 90, colorless crystals of the title compound were obtained from 1-(4-cyanobenzyl)-2-piperazinone hydrochloride and 4-(bromomethyl)benzenesulfonyl chloride.

$^1$H-NMR (DMSO-d$_6$) δ: 3.33 (4H, br), 3.73 (2H, s), 4.57 (2H, s), 5.63 (2H, s), 7.41 (2H, d, J=8.2 Hz), 7.68–7.93 (8H, m), 9.28 (2H, brs), 9.42 (1H, s), 9.47 (2H, brs).

Working Example 92

1-(4-amidinobenzyl)-4-[4-[N-(4-pyridyl)aminomethyl]benzenesulfonyl]-2-piperazinone Dihydrochloride According to a similar method described in Working Example 4, pale yellow amorphous of the title compound was obtained from 4-[4-[N-(tert-butoxycarbonyl)-N-(4-pyridyl)aminomethyl]benzenesulfonyl]-1-(4-cyanobenzyl)-2-piperazinone.

$^1$H-NMR (DMSO-d$_6$) δ: 3.33 (4H, br), 3.71 (2H, s), 4.57 (2H, s), 4.70 (2H, d, J=6.0 Hz), 6.82–6.92 (1H, m), 7.02–7.12 (1H, m), 7.40 (2H, d, J=8.4 Hz), 7.65 (2H, d, J=8.0 Hz), 7.79 (2H, d, J=8.4 Hz), 7.84 (2H, d, J=8.0 Hz), 8.10–8.28 (2H, m), 9.17 (2H, brs), 9.33–9.50 (3H, m).

Working Example 93

4-(7-chloro-2H-benzopyran-3-sulfonyl)-1-[4-(N-methoxycarbonylamidino)benzyl]-2-piperazinone To a solution of 1-(4-amidinobenzyl)-4-(7-chloro-2H-benzopyran-3-sulfonyl)-2-piperazinone hydrochloride (99 mg) and triethylamine (0.084 ml) in dichloromethane (10 ml) was added dropwise a solution of methyl chlorocarbonate (0.023 g) in dichloromethane (2 ml) at 0 C., and the mixture was stirred at 0° C. for 1 hour. The reaction solution was diluted with dichloromethane, washed with sodium bicarbonate solution and saturated brine, dried (MgSO$_4$) and concentrated. Precipitated crystals were washed with ether to give colorless crystals of the title compound (95 mg).

$^1$H-NMR (DMSO-d$_6$) δ: 3.25–3.40 (2H, m), 3.47–3.56 (2H, m), 3.62 (3H, s), 3.89 (2H, s), 4.61 (2H, s), 4.97 (2H, s), 7.06 (1H, d, J=1.9 Hz), 7.11 (1H, dd, J=8.1, 1.9 Hz), 7.34 (2H, d, J=8.2 Hz), 7.47 (2H, d, J=8.1 Hz), 7.49 (1H, s), 7.94 (2H, d, J=8.2 Hz), 9.05 (2H, br).

Working Example 94
1-[4-[N-(1-acetoxyethoxycarbonyl)amidino]benzyl]-4-(7-chloro-2H-benzopyran-3-sulfonyl)-2-piperazinone A solution of 1-(4-amidinobenzyl)-4-(7-chloro-2H-benzopyran-3-sulfonyl)-2-piperazinone hydrochloride (99 mg), O-(1-acetoxyethoxycarbonyl)-4-nitrophenol (54 mg), diisopropylethylamine (39 mg) in DMF (5 ml) was stirred at 80° C. for 1 hour. The reaction solution was concentrated under reduced pressure, and to the residue was added ethyl acetate. The mixture was washed with sodium bicarbonate solution and saturated brine, dried (MgSO$_4$) and concentrated. Precipitated crystals were washed with ether to give colorless crystals of the title compound (49 mg).

$^1$H-NMR (CDCl$_3$) δ: 1.55 (3H, s), 2.08 (3H, s), 3.30–3.40 (2H, m), 3.45–3.55 (2H, m), 3.98 (2H, s), 4.67 (2H, s), 4.86 (2H, s), 6.35–6.70 (1H, br), 6.91–7.03 (2H, m), 7.13 (1H, d, J=8.2 Hz), 7.28 (1H, s), 7.34 (2H, d, J=8.2 Hz), 7.85 (2H, d, J=8.2 Hz).

Working Example 95
4-(7-chloro-2H-benzopyran-3-sulfonyl)-1-[4-(N-pivaloyloxymethoxycarbonylamidino)benzyl]-2-piperazinone According to a method described in Working Example 94, colorless crystals of the title compound were obtained from O-(pivaloyloxymethoxycarbonyl)-4-nitrophenol instead of O-(1-acetoxyethoxycarbonyl)-4-nitrophenol.

$^1$H-NMR (CDCl$_3$) δ: 1.22 (9H, s), 3.32–3.42 (2H, m), 3.46–3.56 (2H, m), 3.98 (2H, s), 4.67 (2H, s), 4.86 (2H, d, J=1.0 Hz), 5.87 (2H, s), 6.93 (1H, d, J=1.8 Hz), 7.00 (1H, dd, J=8.0, 1.8 Hz), 7.14 (1H, d, J=8.0 Hz), 7.28 (1H, s), 7.34 (2H, d, J=8.5 Hz), 7.86 (2H, d, J=8.5 Hz).

Working Example 96
4-(7-chloro-2H-benzopyran-3-sulfonyl)-1-[4-[N-(5-methyl-2-oxo-1,3-dioxol-4-ylmethoxycarbonyl)amidino]benzyl]-2-piperazinone According to a method described in Working Example 94, colorless crystals of the title compound were obtained from O-(5-methyl-2-oxo-1,3-dioxol-4-ylmethoxycarbonyl)-4-nitrophenol instead of O-(1-acetoxyethoxycarbonyl)-4-nitrophenol.

$^1$H-NMR (CDCl$_3$) δ: 2.20 (3H, s), 3.32–3.42 (2H, m), 3.46–3.56 (2H, m), 3.98 (2H, s), 4.67 (2H, s), 4.86 (2H, d, J=1.2 Hz), 4.93 (2H, s), 6.92 (1H, d, J=2.2 Hz), 7.00 (1H, dd, J=8.0, 2.2 Hz), 7.13 (1H, d, J=8.0 Hz), 7.28 (1H, s), 7.34 (2H, d, J=8.4 Hz), 7.85 (2H, d, J=8.4 Hz).

Working Example 97
4-(6-chloronaphthanlene-2-sulfonyl)-1-[2-[1-(4-pyridyl)-4-piperidyl]ethyl]-2-piperazinone Hydrochloride According to a similar method described in Working Example 15, 4-(6-chloronaphthanlene-2-sulfonyl)-1-[2-[1-(4-pyridyl)-4-piperidyl]ethyl]-2-piperazinone was obtained from 1-(4-pyridyl)-4-[2-(methylsulfonyloxy)ethyl]piperidine instead of 1-(4-pyridyl)-4-methylsulfonyloxymethylpiperidine. The obtained product was dissolved in ethanol and 4N hydrochloric acid in ethyl acetate, and the solution was concentrated under reduced pressure to give colorless crystals of the title compound.

$^1$H-NMR (DMSO-d$_6$) δ: 0.87–1.24 (4H, m), 1.30–1.60 (1H, m), 1.64–1.80 (2H, m), 2.94–3.13 (2H, m), 3.16–3.48 (6H, m), 3.69 (2H, s), 4.06–4.22 (2H, m), 7.16 (2H, d, J=7.8 Hz), 7.72 (1H, dd, J=8.7, 2.1 Hz), 7.90 (1H, dd, J=8.6, 1.8 Hz), 8.15–8.31 (5H, m), 8.60 (1H, s).

Working Example 98
4-(6-chloronaphthanlene-2-sulfonyl)-1-[1-(4-pyridyl)-4-piperidyl]-2-piperazinone Hydrochloride To 1-[1-(tert-butoxycarbonyl)-4-piperidyl]-4-(6-chloronaphthanlene-2-sulfonyl)-2-piperazinone (3.71 g) were added 4N hydrochloric acid in ethyl acetate (20 ml) and ethanol (10 ml), and the mixture was stirred at room temperature for 30 minutes. The reaction solution was concentrated to give colorless crystals of 4-(6-chloronaphthanlene-2-sulfonyl)-1-(4-piperidyl)-2-piperazinone hydrochloride (3.11 g).

To a solution of 10% sodium carbonate were added 4-(6-chloronaphthanlene-2-sulfonyl)-1-(4-piperidyl)-2-piperazinone hydrochloride (800 mg) and bromopyridine hydrochloride (1.05 g), and the mixture was extracted with ethyl acetate, dried and concentrated. To the residue was added isoamylalcohol (30 ml), and the mixture was allowed to react at 130° C. for 12 hours. The reaction solution was concentrated under reduced pressure, and to the residue was added 10% sodium carbonate solution. The mixture was extracted with admixture of ethyl acetate-THF, and the extract was washed with saturated brine, dried (MgSO$_4$) and concentrated. To the residue was added ethanol to give colorless crystals of 4-(6-chloronaphthanlene-2-sulfonyl)-1-[1-(4-pyridyl)-4-piperidyl-2-piperazinone (289 mg). Apart of the crystals were treated with hydrochloric acid to give colorless solid of the title compound (185 mg) as hydrochloride.

$^1$H-NMR (DMSO-d$_6$) δ: 1.50–1.67 (4H, m), 3.08–3.40 (6H, m), 3.67 (2H, s), 4.20–4.60 (3H, m), 7.19 (2H, d, J=7.8 Hz), 7.74 (1H, dd, J=8.8, 2.0 Hz), 7.88 (1H, dd, J=8.8, 1.8 Hz), 8.15–8.33 (5H, m), 8.59 (1H, s).

Working Example 99
4-(6-chloronaphthanlene-2-sulfonyl)-1-[1-(4-pyridyl)-3-pyrrolidinylmethyl]-2-piperazinone Hydrochloride According to a similar method described in Working Example 98, amorphous of the title compound was obtained from 1-[1-(tert-butoxycarbonyl)-3-pyrrolidinylmethyl]-4-(6-chloronaphthanlene-2-sulfonyl)-2-piperazinone.

$^1$H-NMR (DMSO-d$_6$) δ: 1.52–1.78 (1H, m), 1.87–2.08 (1H, m), 2.38–2.64 (1H, m), 3.02–3.60 (10H, m), 3.71 (2H, s), 6.76 (2H, br), 7.72 (1H, dd, J=8.9, 2.1 Hz), 7.91 (1H, dd, J=8.5, 1.7 Hz), 8.14–8.34 (5H, m), 8.62 (1H, s).

Working Example 100
1-[1-acetimidoyl-3-pyrrolidinylmethyl]-4-(6-chloronaphthanlene-2-sulfonyl)-2-piperazinone Hydrochloride According to a similar method described in Working Example 10, colorless crystals of the title compound were obtained from 4-(6-chloronaphthanlene-2-sulfonyl)-1-(3-pyrrolidinylmethyl)-2-piperazinone hydrochloride.

$^1$H-NMR (DMSO-d$_6$) δ: 1.50–1.70 (1H, m), 1.80–2.02 (1H, m), 2.15 and 2.20 (total 3H, each s), 2.42–2.63 (1H, m), 2.90–3.08 (1H, m), 3.14–3.70 (9H, m), 3.67 (2H, s), 7.74 (1H, dd, J=8.7, 2.1 Hz), 7.90 (1H, dd, J=8.6, 1.8 Hz), 8.16–8.34 (4H, m), 8.61 (1H, s), 9.04–9.14 (1H, m).

Working Example 101
4-(6-chloronaphthanlene-2-sulfonyl)-1-1-(4-pyridyl)-3-piperidylmethyl]-2-piperazinone Hydrochloride According to a similar method described in Working Example 15, 4-(6-chloronaphthanlene-2-sulfonyl)-1-[1-(4- pyridyl)-3-piperidylmethyl]-2-piperazinone was obtained from 1-(4-pyridyl)-3-methylsulfonyloxymethylpiperidine instead of 1-(4-pyridyl)-4-methylsulfonyloxymethylpiperidine. The obtained product was dissolved in ethanol and 4N hydrochloric acid in ethyl acetate, and the solution was concentrated under reduced pressure to give colorless amorphous of the title compound.

$^1$H-NMR (DMSO-d$_6$) δ: 1.00–2.00 (5H, m), 2.85–3.60 (8H, m), 3.73 (2H, s), 3.80–4.07 (2H, m), 7.13 (2H, d, J=7.8 Hz), 7.74 (1H, dd, J=8.9, 1.9 Hz), 7.91 (1H, dd, J=8.7, 1.7 Hz), 8.13–8.34 (5H, m), 8.62 (1H, s).

Working Example 102

4-(4-isopropenylbenzenesulfonyl)-1-[1-(4-pyridyl)-4-piperidylmethyl]-2-piperazinone Hydrochloride To a solution of 1-[1-(4-pyridyl)-4-piperidylmethyl]-2-piperazinone (549 mg) and triethylamine (0.836 ml) in dichloromethane (10 ml) was added dropwise a solution of 4-(2-bromo-1-methylethyl)benzenesulfonyl chloride (893 mg) in dichloromethane (2 ml) at 0° C., and the mixture was stirred at 0 for 1 hour and then at room temperature for 6 hours. The reaction solution was diluted with dichloromethane, washed with water and saturated brine, dried (MgSO$_4$) and concentrated. The residue was dissolved in ethanol (20 ml), and to the solution was added 1 N sodium hydroxide (2 ml). The mixture was stirred at 80° C. for 30 minutes, and to the reaction solution was added ethyl acetate. The mixture was washed with water and saturated brine, dried (MgSO$_4$) and concentrated, and the residue was purified with silica gel column chromatography (acetone:methanol=9:1→1:1) and washed with water to give colorless crystals of 4-(4-isopropenylbenzenesulfonyl)-1-[1-(4-pyridyl)-4-piperidylmethyl]-2-piperazinone (155 mg).

$^1$H-NMR (CDCl$_3$) δ: 1.15–1.40 (2H, m), 1.60–2.02 (3H, m), 2.19 (3H, s), 2.70–2.90 (2H, m), 3.26 (2H, d, J=7.4 Hz), 3.30–3.40 (2H, m), 3.40–3.50 (2H, m), 3.73 (2H, s), 3.78–3.93 (2H, m), 5.28 (1H, s), 5.51 (1H, s), 6.62 (2H, d, J=6.4 Hz), 7.63 (2H, d, J=8.5 Hz), 7.75 (2H, d, J=8.5 Hz), 8.24 (2H, d, J=6.4 Hz).

The obtained product was dissolved in ethanol and 4N hydrochloric acid in ethyl acetate, and the solution was concentrated under reduced pressure to give colorless amorphous of the title compound.

Working Example 103

4-[4-[(E)-1-propenyl]benzenesulfonyl]-1-[1-(4-pyridyl)-4-piperidylmethyl]-2-piperazinone Hydrochloride According to a similar method described in Working Example 102, colorless crystals of 4-[4-[(E)-1-propenyl]benzenesulfonyl]-1-[1-(4-pyridyl)-4-piperidylmethyl]-2-piperazinone was obtained from 4-(2-bromopropyl)benzenesulfonyl chloride instead of 4-(2-bromo-1-methylethyl)benzenesulfonyl chloride.

$^1$H-NMR (CDCl$_3$) δ: 1.14–1.40 (2H, m), 1.57–1.74 (2H, m), 1.80–2.02 (4H, m), 2.70–2.90 (2H, m), 3.25 (2H, d, J=7.8 Hz), 3.27–3.38 (2H, m), 3.38–3.50 (2H, m), 3.73 (2H, s), 3.78–3.94 (2H, m), 6.41–6.48 (2H, m), 6.62 (2H, d, J=6.0 Hz), 7.49 (2H, d, J=8.4 Hz), 7.71 (2H, d, J=8.4 Hz), 8.24 (2H, d, J=6.0 Hz).

The obtained product was dissolved in ethanol and 4N hydrochloric acid in ethyl acetate, and the solution was concentrated under reduced pressure to give colorless amorphous of the title compound.

Working Example 104

4-(4-iodobenzenesulfonyl)-1-[1-(4-pyridyl)-4-piperidylmethyl]-2-piperazinone Hydrochloride To a mixture of 1-[1-(4-pyridyl)-4-piperidylmethyl]-2-piperazinone (549 mg), sodium bicarbonate solution (5 ml), ethyl acetate (10 ml) and THF (5 ml) was added dropwise, under ice-cooling, a solution of 4-iodobenzenesulfonyl chloride (1.21 g) in THF (10 ml), and the mixture was stirred at 0° C. for 1 hour. The separated organic layer was washed with saturated brine, dried (MgSO$_4$) and concentrated, and the residue was purified with silica gel column chromatography (acetone:methanol=9: 1→1:1) and washed with water to give colorless crystals of 4-(4-iodobenzenesulfonyl)-1-[1-(4-pyridyl)-4-piperidylmethyl]-2-piperazinone (155 mg). A part of the crystals were treated with hydrochloric acid to give colorless crystals of the title compound as hydrochloride.

$^1$H-NMR (DMSO-d$_6$) δ: 0.95–1.30 (2H, m), 1.50–1.75 (2H, m), 1.80–2.15 (1H, m), 2.95–3.55 (8H, m), 3.61 (2H, s), 4.08–4.28 (2H, m), 7.17 (2H, d, J=7.5 Hz), 7.59 (2H, d, J=8.6 Hz), 8.06 (2H, d, J=8.6 Hz), 8.19 (2H, d, J=7.5 Hz).

Working Example 105

4-(3-bromobenzenesulfonyl)-1-[1-(4-pyridyl)-4-piperidylmethyl]-2-piperazinone Hydrochloride To a solution of 1-[1-(4-pyridyl)-4-piperidylmethyl]-2-piperazinone (2.74 g) and triethylamine (1.67 ml) in dichloromethane (50 ml) was added dropwise at 0° C. 3-bromobenzenesulfonyl chloride (2.56 g), and the mixture was stirred at 0° C. for 1 hour. The reaction solution was diluted with dichloromethane, was washed with water and saturated brine, dried (MgSO$_4$) and concentrated, and the residue was purified with silica gel column chromatography (acetone methanol=9:1=>1:1) and washed with water to give colorless crystals of 4-(3-bromobenzenesulfonyl)-1-[1-(4-pyridyl)-4-piperidylmethyl]-2-piperazinone (1.28 g). A part of the crystals were treated with hydrochloric acid to give colorless crystals of the title compound as hydrochloride.

1H-NMR (DMSO-d$_6$) δ: 0.95–1.22 (2H, m), 1.51–1.72 (2H, m), 1.85–2.12 (1H, m), 2.97–3.25 (4H, m), 3.30–3.48 (4H, m), 3.67 (2H, s), 4.08–4.28 (2H, m), 7.17 (2H, d, J=7.2 Hz), 7.59–7.70 (1H, m), 7.81–7.89 (1H, m), 7.95–8.04 (2H, m), 8.20 (2H, d, J=7.2 Hz).

Working Example 106

4-(coumarin-6-sulfonyl)-1-[1-(4-pyridyl)-4-piperidylmethyl]-2-piperazinone hydrochloride According to a similar method described in Working Example 105, 4-(coumarin-6-sulfonyl)-1-[1-(4-pyridyl)-4-piperidylmethyl]-2-piperazinone was obtained from 1-[1-(4-pyridyl)-4-piperidylmethyl]-2-piperazinone and coumarin-6-sulfonyl chloride.

$^1$H-NMR (CDCl$_3$): 1.17–1.42 (2H, m), 1.62–1.78 (2H, m), 1.80–2.09 (114, m), 2.73–2.92 (2H, m), 3.28 (2H, d, J=7.4 Hz), 3.33–3.43 (214, m), 3.43–3.53 (2H, m), 3.75 (2H, s), 3.80–3.95 (2H, m), 6.55–6.68 (3H, m), 7.51 (1H, d, J=8.6 Hz), 7.78 (1H, d, J=9.8 Hz), 7.92 (1H, dd, J=8.6, 2.1 Hz), 7.98 (1H, d, J=2.1 Hz), 8.24 (2H, d, J=6.5 Hz).

A part of the product was treated with hydrochloric acid to give colorless amorphous of the title compound as hydrochloride.

Working Example 107

4-(7-chloro-4H-4-oxobenzopyran-3-sulfonyl)-1-[1-(4-pyridyl)-4-piperidylmethyl]-2-piperazinone Hydrochloride According to a similar method described in Working Example 105, powder of 4-(7-chloro-4H-4-oxobenzopyran-3-sulfonyl)-1-[1-(4-pyridyl)-4-piperidylmethyl]-2-piperazinone was obtained from 1-[1-(4-pyridyl)-4-piperidylmethyl]-2-piperazinone and 7-chloro-4H-4-oxobenzopyran-3-sulfonyl chloride.

$^1$H-NMR (CDCl$_3$) δ: 1.17–1.43 (2H, m), 1.60–2.20 (3H, m), 2.75–2.95 (2H, m), 3.31 (2H, d, J=7.4 Hz), 3.43–3.58

(2H, m), 3.80–4.00 (4H, m), 3.99 (2H, s), 6.66 (2H, br), 7.51 (1H, dd, J=8.2, 1.8 Hz), 7.62 (1H, d, J=1.8 Hz), 8.17 (1H, d, J=8.2 Hz), 8.19 (2H, br), 8.67 (1H, s).

A part of the obtained product was treated with hydrochloric acid to give amorphous of the title compound as hydrochloride salt.

Working Example 108
4-[(1,1'-biphenyl)-4-ylsulfonyl]-1-[1-(4-pyridyl)-4-piperidylmethyl]-2-piperazinone Hydrochloride A mixture of 4-(4-iodobenzenesulfonyl)-1-[1-(4-pyridyl)-4-piperidylmethyl)-2-piperazinone (216 mg), phenylboronic acid (98 mg), tetrakis(triphenylphosphine)palladium (46 mg), 1M sodium carbonate solution (1.2 ml) and dimethoxyethane (10 ml) was refluxed for 2 hours and cooled, and to the reaction solution was added ethyl acetate. The mixture was washed with water and saturated brine, dried and concentrated, and the residue was purified with silica gel column chromatography (acetone:methanol=9:1→1:1) and washed with water to give colorless crystals of 4-[(1,1'-biphenyl)-4-ylsulfonyl]-1-[1-(4-pyridyl)-4-piperidylmethyl]-2-piperazinone (115 mg), which were dissolved in ethanol and a solution of 4N hydrochloric acid in ethyl acetate. The solution was concentrated under reduced pressure to give amorphous of the title compound.

$^1$H-NMR (DMSO-$d_6$) δ: 0.95–1.20 (2H, m), 1.50–1.70 (2H, m), 1.80–2.10 (1H, m), 2.90–3.25 (4H, m), 3.38 (4H, brs), 3.67 (2H, s), 4.00–4.20 (2H, m), 7.09 (2H, d, J=7.5 Hz), 7.46–7.61 (3H, m), 7.78–7.85 (2H, m), 7.91 (2H, d, J=8.7 Hz), 8.00 (2H, d, J=8.7 Hz), 8.18 (2H, d, J=7.5 Hz).

Working Example 109
4-[(1,1'-biphenyl)-3-ylsulfonyl]-1-[1-(4-pyridyl)-4-piperidylmethyl]-2-piperazinone Hydrochloride According to a similar method described in Working Example 108, amorphous of the title compound was obtained from 4-(3-bromobenzenesulfonyl)-1-[1-(4-pyridyl)-4-piperidylmethyl]-2-piperazinone and phenylboronic acid.

$^1$H-NMR (DMSO-$d_6$) δ: 0.90–1.20 (2H, m), 1.45–1.68 (2H, m), 1.80–2.10 (1H, m), 2.90–3.25 (4H, m), 3.25–3.55 (4H, m), 3.71 (2H, s), 4.03–4.23 (2H, m), 7.11 (2H, d, J=7.4 Hz), 7.27–7.61 (3H, m), 7.73–7.89 (4H, m), 7.98–8.13 (2H, m), 8.18 (2H, d, J=7.4 Hz).

Working Example 110
4-[3'-chloro(1,1'-biphenyl)-3-ylsulfonyl]-1-[1-(4-pyridyl)-4-piperidylmethyl]-2-piperazinone Hydrochloride According to a similar method described in Working Example 108, colorless crystals of the title compound were obtained from 4-(3-bromobenzenesulfonyl)-1-[1-(4-pyridyl)-4-piperidylmethyl]-2-piperazinone and 3-chlorophenylboronic acid.

$^1$H-NMR (DMSO-$d_6$) δ: 0.93–1.20 (2H, m), 1.50–1.70 (2H, m), 1.85–2.10 (1H, m), 2.95–3.20 (4H, m), 3.28–3.48 (4H, m), 3.70 (2H, s), 4.06–4.24 (2H, m), 7.14 (2H, d, J=7.3 Hz), 7.46–7.61 (2H, m), 7.70–7.80 (4H, m), 8.01–8.22 (4H, m).

Working Example 111
4-(4-ethynylbenzenesulfonyl)-1-[1-(4-pyridyl)-4-piperidylmethyl]-2-piperazinone Hydrochloride To a solution of 1-[1-(tert-butoxycarbonyl)-4-(4-iodobenzenesulfonyl)-4-piperidylmethyl]-2-piperazinone (1.13 g), which was produced according to a method described in Reference Example 54 using 1-[1-(tert-butoxycarbonyl)-4-piperidylmethyl]-2-piperazinone and 4-iodobenzenesulfonyl chloride, in diethylamine (20 ml)-DMF (5 ml) were added trimethylsilylacetylene (244 mg), bis(triphenylphosphine)palladium chloride (II) (69 mg) and copper iodide (2 ml), and the mixture was stirred at room temperature for 5 hours. The reaction solution was concentrated, and the residue was purified with silica gel column chromatography (hexane:acetone=1:1) to give brown crystals of 1-[1-(tert-butoxycarbonyl)-4-piperidylmethyl]-4-[4-[2-(trimethylsilyl)ethynyl]benzenesulfonyl]-2-piperazinone (825 mg). To a solution of 1-[1-(tert-butoxycarbonyl)-4-piperidylmethyl]-4-[4-[2-(trimethylsilyl)ethynyl]benzenesulfonyl]-2-piperazinone (534 mg) in toluene (10 ml) was added trifluoroacetic acid (5 ml), and the mixture was stirred for 1 hour. The reaction solution was concentrated, and the residue was dissolved in ethanol (20 ml). To the solution was added 1N sodium hydroxide (2 ml), and the mixture was stirred at room temperature for 1 hour. To the reaction solution was added ethyl acetate, and the mixture was washed with 10% sodium carbonate solution and saturated brine, dried (MgSO$_4$) and concentrated. Precipitated crystals were washed with ethanol-ether to give brown crystals of 4-(4-ethynylbenzenesulfonyl)-1-[4-piperidylmethyl]-2-piperazinone (450 mg). To 10% sodium carbonate solution was added bromopyridine hydrochloride (272 mg), and the mixture was extracted with ethyl acetate, dried and concentrated. To the residue were added 4-(4-ethynylbenzenesulfonyl)-1-[4-piperidylmethyl]-2-piperazinone (289 mg) and isoamylalcohol (10 ml), and the mixture was allowed to react at 130% overnight. The reaction solution was concentrated under reduced pressure, and to the residue was added 10% sodium carbonate solution. The mixture was extracted with ethyl acetate-THF, and the extract was washed with saturated brine, dried and concentrated. The residue was purified with silica gel column chromatography (acetone:methanol=9:1→1:1), washed with water, and precipitated crystals were washed with acetone-ether to give powder of 4-(4-ethynylbenzenesulfonyl)-1-[1-(4-pyridyl)-4-piperidylmethyl]-2-piperazinone (85 mg).

$^1$H-NMR (CDCl$_3$) δ: 1.15–1.40 (2H, m), 1.57–1.73 (2H, m), 1.80–2.02 (1H, m), 2.70–2.90 (2H, m), 3.26 (2H, d, J=7.4 Hz), 3.34 (1H, s), 3.30–3.40 (2H, m), 3.40–3.50 (2H, m), 3.74 (2H, s), 3.80–3.94 (2H, m), 6.63 (2H, d, J=6.0 Hz), 7.67 (2H, d, J=8.5 Hz), 7.77 (2H, d, J=8.5 Hz), 8.24 (2H, d, J=6.0 Hz).

A part of the product was treated with hydrochloric acid to give powder of the title compound as hydrochloride.

Working Example 112
4-(3-ethynylbenzenesulfonyl)-1-[1-(4-pyridyl)-4-piperidylmethyl]-2-piperazinone Hydrochloride According to a similar method described in Working Example 111, powder of 4-(3-ethynylbenzenesulfonyl)-1-[1-(4-pyridyl)-4-piperidylmethyl]-2-piperazinone was obtained from 4-(3-bromobenzenesulfonyl)-1-[1-(tert-butoxycarbonyl)-4-piperidylmethyl]-2-piperazinone instead of 1-[1-(tert-butoxycarbonyl)-4-(4-iodobenzenesulfonyl)-4-piperidylmethyl]-2-piperazinone.

$^1$H-NMR (CDCl$_3$) δ: 1.16–1.40 (2H, m), 1.60–1.75 (2H, m), 1.82–2.03 (1H, m), 2.72–2.90 (2H, m), 3.22–3.50 (7H, m), 3.74 (2H, s), 3.80–3.93 (2H, m), 6.63 (2H, d, J=5.2 Hz), 7.50–7.60 (1H, m), 7.70–7.83 (2H, m), 7.88–7.92 (1H, m), 8.23 (2H, br).

A part of the product was treated with hydrochloric acid to give colorless amorphous of the title compound as hydrochloride.

Working Example 113
4-[4-[(E)-2-chloroethenyl]benzenesulfonyl]-1-[1-(4-pyridyl)-4-piperidylmethyl]-2-piperazinone Hydrochloride According to a similar method described in Working Example 98, amorphous of 4-[4-[(E)-2-chloroethenyl]benzenesulfonyl]-1-[1-(4-pyridyl)-4-piperidylmethyl]-2-piperazinone was obtained from 1-[1-(tert-butoxycarbonyl)-4-piperidylmethyl]-4-[4-[(E)-2-chloroethenyl]benzenesulfonyl]-2-piperazinone.

$^1$H-NMR (CDCl$_3$) δ: 1.15–1.42 (2H, m), 1.60–1.76 (2H, m), 1.82–2.08 (1H, m), 2.73–2.92 (2H, m), 3.27 (2H, d, J=7.4 Hz), 3.28–3.50 (4H, m), 3.73 (2H, s), 3.80–3.95 (2H, m), 6.64 (2H, d, J=4.8 Hz), 6.79–6.94 (2H, m), 7.48 (2H, d, J=8.5 Hz), 7.75 (2H, d, J=8.5 Hz), 8.22 (2H, br).

A part of the product was treated with hydrochloric acid to give colorless amorphous of the title compound as hydrochloride.

Working Example 114
4-(4-ethylbenzenesulfonyl)-1-[1-(4-pyridyl)-4-piperidylmethyl]-2-piperazinone Hydrochloride In ethanol (10 ml) was dissolved 1-[1-(4-pyridyl)-4-piperidylmethyl]-4-(4-vinylbenzenesulfonyl)-2-piperazinone (88 mg), and to the solution was added 10% palladium on carbon (30 mg). The mixture was vigorously stirred under hydrogen stream for 3 hours, and the catalyst was removed. The solvent was evaporated under reduced pressure, and to the residue were added ethanol and 4N hydrochloric acid in ethyl acetate. The mixture was concentrated under reduced pressure to give colorless amorphous of the title compound (100 mg).

$^1$H-NMR (DMSO-d$_6$) δ: 0.96–1.23 (2H, m), 1.22 (3H, t, J=7.5 Hz), 1.55–1.73 (2H, m), 1.88–2.12 (1H, m), 2.73 (2H, q, J=7.5 Hz), 3.00–3.23 (4H, m), 3.25–3.50 (4H, m), 3.57 (2H, s), 4.10–4.27 (2H, m), 7.17 (2H, d, J=7.4 Hz), 7.52 (2H, d, J=8.1 Hz), 7.74 (2H, d, J=8.1 Hz), 8.19 (2H, d, J=7.4 Hz).

Working Example 115
1-[1-(4-pyridyl)-4-piperidylmethyl]-4-(3-vinylbenzenesulfonyl)-2-piperazinone Hydrochloride In ethanol (10 ml) was dissolved 4-(3-ethynylbenzenesulfonyl)-1-[1-(4-pyridyl)-4-piperidylmethyl]-2-piperazinone (40 mg), and to the solution was added Lindlar catalyst (40 mg). The mixture was vigorously stirred under hydrogen stream for 5 days, and the catalyst was removed. The solvent was evaporated under reduced pressure, and precipitated crystals were washed with acetone-ether.

A part of the crystals were treated with hydrochloric acid to give colorless amorphous of the title compound (35 mg) as hydrochloride.

$^1$H-NMR (DMSO-d$_6$) δ: 0.93–1.20 (2H, m), 1.50–1.70 (2H, m), 1.82–2.08 (1H, m), 2.96–3.20 (4H, m), 3.35 (4H, s), 3.65 (2H, s), 4.08–4.25 (2H, m), 5.45 (1H, d, J=11.0 Hz), 6.04 (1H, d, J=17.6 Hz), 6.90 (1H, dd, J=17.6, 11.0 Hz), 7.16 (2H, d, J=6.9 Hz), 7.58–7.78 (2H, m), 7.82–8.03 (2H, m), 8.19 (2H, d, J=6.9 Hz).

Working Example 116
1-(1-acetimidoyl-4-hydroxy-4-piperidylmethyl)-4-(7-chloro-2H-benzopyran-3-sulfonyl)-2-piperazinone Hydrochloride According to a similar method described in Working Example 10, colorless amorphous of the title compound was obtained from 4-(7-chloro-2H-benzopyran-3-sulfonyl)-1-(4-hydroxy-4-piperidylmethyl)-2-piperazinone hydrochloride.

$^1$H-NMR (DMSO-d$_6$) δ: 1.45–1.75 (4H, m), 2.25 (3H, s), 3.15–4.40 (12H, m), 5.50 (2H, s), 7.07 (1H, d, J=2.0 Hz), 7.21 (1H, dd, J=8.1, 2.0 Hz), 7.49 (1H, d, J=8.1 Hz), 7.50 (1H, s), 8.67 (1H, brs), 9.24 (1H, brs).

Working Example 117
1-(1-amidino-4-hydroxy-4-piperidylmethyl)-4-(7-chloro-2H-benzopyran-3-sulfonyl)-2-piperazinone hydrochloride According to a similar method described in Working Example 13, colorless amorphous of the title compound was obtained from 4-(7-chloro-2H-benzopyran-3-sulfonyl)-1-(4-hydroxy-4-piperidylmethyl)-2-piperazinone hydrochloride.

$^1$H-NMR (DMSO-d$_6$) δ: 1.43–1.57 (4H, m), 3.10–3.70 (1OH, m), 3.79 (2H, s), 4.99 (2H, s), 7.07 (1H, d, J=2.2 Hz), 7.12 (1H, dd, J=8.0, 2.2 Hz), 7.25–7.40 (4H, m), 7.48 (1H, d, J=8.0 Hz), 7.49 (1H, s).

Working Example 118
4-(7-chloro-2H-benzopyran-3-sulfonyl)-1-[4-propionyloxy-1-(4-pyridyl)piperidin-4-ylmethyl]-2-piperazinone According to a similar method described in Working Example 26, colorless crystals of the title compound were obtained from 4-(7-chloro-2H-benzopyran-3-sulfonyl)-1-[4-hydroxy-1-(4-pyridyl)-4-piperidylmethyl]-2-piperazinone and propionic anhydride.

$^1$H-NMR (CDCl$_3$) δ: 1.14 (3H, t, J=7.6 Hz), 1.67–1.86 (2H, m), 2.24–2.40 (2H, m), 2.35 (2H, q, J=7.6 Hz), 2.94–3.11 (2H, m), 3.53 (4H, s), 3.58–3.72 (2H, m), 3.93 (2H, s), 4.03 (2H, s), 4.89 (2H, d, J=1.2 Hz), 6.65 (2H, d, J=6.6 Hz), 6.93 (1H, d, J=2.0 Hz), 7.01 (1H, dd, J=8.1, 2.0 Hz), 7.15 (1H, d, J=8.1 Hz), 7.29 (1H, s), 8.28 (2H, d, J=6.6 Hz).

Working Example 119
4-(6-chloronaphthanlene-2-sulfonyl)-1-[4-methoxy-1-(4-pyridyl)-4-piperidylmethyl]-2-piperazinone To 1-[1-(tert-butoxycarbonyl)-4-methoxy-4-piperidylmethyl]-4-(6-chloronaphthanlene-2-sulfonyl)-2-piperazinone (1.15 g) were added 4N hydrochloric acid in ethyl acetate (10 ml) and ethanol (1 ml), and the mixture was stirred at room temperature for 1 hour. The reaction solution was concentrated, and the resulting crystals were filtered, washed with ethyl acetate-ethanol and dried to give 4-(6-chloronaphthanlene-2-sulfonyl)-1-[4-methoxy-4-piperidylmethyl]-2-piperazinone hydrochloride (980 mg). A solution of 4-(6-chloronaphthanlene-2-sulfonyl)-1-[4-methoxy-4-piperidylmethyl]-2-piperazinone hydrochloride (488 mg), chloropyridine hydrochloride (180 mg) and triethylamine (0.558 ml) in ethanol (10 ml) was allowed to react in a sealed tube 150° C. for 10 hours, and to the reaction solution was added ethyl acetate. The mixture was washed with 5% sodium carbonate solution and saturated brine, dried and concentrated, and the residue was purified with silica gel column chromatography (ethyl acetate-:methanol containing 10% ammonia solution=85:15) Precipitated crystals were washed-with ethanol-ether to give colorless crystals of the title compound (363 mg).

$^1$H-NMR (CDCl$_3$) δ: 1.40–1.60 (2H, m), 1.61–1.77 (2H, m), 3.02–3.18 (2H, m), 3.20 (3H, s), 3.35–3.56 (6H, m), 3.56–3.66 (2H, m), 3.81 (2H, s), 6.59 (2H, d, J=6.7 Hz), 7.61 (1H, dd, J=9.0, 2.0 Hz), 7.80 (1H, dd, J=8.8, 1.8 Hz), 7.90–7.99 (3H, m), 8.23 (2H, d, J=6.7 Hz), 8.36 (1H, d, J=1.4 Hz).

Working Example 120
4-(6-chloronaphthanlene-2-sulfonyl)-1-[4-methanesulfonylamino-1-(4-pyridyl)-4-piperidylmethyl]-2-piperazinone According to a similar method described in Working Example 119, colorless crystals of the title compound were obtained from 1-[1-(tert-butoxycarbonyl)-4-methanesulfonylamino-4-piperidylmethyl]-4-(6-chloronaphthanlene-2-sulfonyl)-2-piperazinone.

$^1$H-NMR (CDCl$_3$) δ: 1.36–1.60 (2H, m), 1.70–1.88 (2H, m), 3.02 (3H, s), 3.00–3.75 (12H, m), 6.74 (2H, d, J=6.2 Hz), 7.01 (1H, s), 7.74 (1H, d, J=8.2 Hz), 7.90 (1H, d, J=8.2 Hz), 8.06–8.34 (5H, m), 8.60 (1H, s).

Working Example 121

4-(7-chloro-2H-benzopyran-3-sulfonyl)-1-[4-methanesulfonylamino-1-(4-pyridyl)-4-piperidylmethyl]-2-piperazinone According to a similar method described in Working Example 119, powder of the title compound was obtained from 1-[1-(tert-butoxycarbonyl)-4-methanesulfonylamino-4-piperidylmethyl]-4-(7-chloro-2H-benzopyran-3-sulfonyl)-2-piperazinone.

$^1$H-NMR (DMSO-$d_6$) δ: 1.50–1.73 (2H, m), 1.80–2.00 (2H, m), 3.06 (3H, s), 3.11–3.75 (10H, m), 3.80 (2H, s), 4.99 (2H, s), 6.79 (2H, d, J=6.4 Hz), 7.07 (1H, d, J=2.2 Hz), 7.11 (1H, brs), 7.12 (1H, dd, J=8.0, 2.2 Hz), 7.48 (1H, d, J=8.0 Hz), 7.49 (1H, s), 8.13 (2H, d, J=6.4 Hz).

Working Example 122

1-(1-acetimidoyl-4-methanesulfonylamino-4-piperidylmethyl)-4-(7-chloro-2H-benzopyran-3-sulfonyl)-2-piperazinone hydrochloride According to a similar method described in Working Example 10, colorless crystals of the title compound were obtained from 4-(7-chloro-2H-benzopyran-3-sulfonyl)-1-(4-methanesulfonylamino-4-piperidylmethyl)-2-piperazinone hydrochloride.

$^1$H-NMR (DMSO-$d_6$) δ: 1.55–2.10 (4H, m), 2.25 (3H, s), 3.08 (3H, s), 3.30–3.95 (12H, m), 4.99 (2H, s), 7.08 (1H, d, J=2.0 Hz), 7.12 (1H, dd, J=8.1, 2.0 Hz), 7.26 (1H, s), 7.49 (1H, d, J=8.1 Hz), 7.50 (1H, s), 8.59 (1H, brs), 9.18 (1H, brs).

Working Example 123

2-[N-[4-[4-(6-chloro-2-naphthanlenesulfonyl)-2-oxo-1-piperazinylmethyl]-1-(4-pyridyl)isonipecotyl]amino]ethyl Acetate Hydrochloride To a solution of 1-(tert-butoxycarbonyl)-4-[4-(6-chloro-2-naphthanlenesulfonyl)-2-oxo-1-piperazinylmethyl]isonipecotic acid (679 mg), glycine methylester hydrochloride (188 mg) and triethylamine (0.209 ml) in acetonitrile (20 ml) was added WSC (288 mg), and the mixture was stirred at room temperature overnight. The reaction solution was concentrated under reduced pressure, and to the residue was added ethyl acetate. The mixture was washed with water and saturated brine, dried and concentrated, and the residue was purified with silica gel column chromatography (ethyl acetate) to give colorless crystals of methyl 2-[N-[1-(tert-butoxycarbonyl)-4-[4-(6-chloro-2-naphthanlenesulfonyl)-2-oxo-1-piperazinylmethyl]isonipecotyl]amino]acetate (574 mg).

According to a similar method described in Working Example 119, 2-[N-[4-[4-(6-chloro-2-naphthanlenesulfonyl)-2-oxo-1-piperazinylmethyl]-1-(4-pyridyl)isonipecotyl]amino]ethyl acetate was obtained using thus obtained methyl 2-[N-[1-(tert-butoxycarbonyl)-4-[4-(6-chloro-2-naphthanlenesulfonyl)-2-oxo-1-piperazinylmethyl]isonipecotyl]amino]acetate.

$^1$H-NMR (CDCl$_3$) δ: 1.22 (3H, t, J=7.1 Hz), 1.55–1.78 (2H, m), 1.95–2.15 (2H, m), 3.00–3.18 (2H, m), 3.32–3.50 (4H, m), 3.52–3.68 (4H, m), 3.78 (2H, s), 3.96 (2H, d, J=5.4 Hz), 4.07 (2H, q, J=7.1 Hz), 6.58 (2H, d, J=6.2 Hz), 6.77 (1H, br), 7.61 (1H, dd, J=8.8, 1.8 Hz), 7.79 (1H, dd, J=8.7, 1.7 Hz), 7.90–8.00 (3H, m), 8.21 (2H, d, J=6.2 Hz), 8.36 (1H, s).

A part of the product was treated with hydrochloric acid to give amorphous of the title compound as hydrochloride.

Working Example 124

Ethyl 3-[N-[4-[4-(6-chloro-2-naphthanlenesulfonyl)-2-oxo-1-piperazinylmethyl]-1-(4-pyridyl)isonipecotyl]amino]propionate According to a similar method described in Working Example 123, colorless crystals of the title compound were obtained from β-alanine ethylester hydrochloride instead of glycine methylester hydrochloride.

$^1$H-NMR (CDCl$_3$) δ: 1.21 (3H, t, J=7.2 Hz), 1.55–1.75 (2H, m), 1.90–2.05 (2H, m), 2.51 (2H, t, J=5.9 Hz), 2.94–3.10 (2H, m), 3.30–3.65 (10H, m), 3.78 (2H, s), 4.08 (2H, q, J=7.2 Hz), 6.59 (2H, d, J=6.6 Hz), 6.66 (1H, t, J=5.7 Hz), 7.62 (1H, dd, J=8.9, 1.9 Hz), 7.79 (1H, dd, J=8.8, 1.8 Hz), 7.92–8.00 (3H, m), 8.24 (2H, d, J=6.6 Hz), 8.36 (1H, d, J=1.4 Hz).

Working Example 125

Ethyl 4-[N-[4-[4-(6-chloro-2-naphthanlenesulfonyl)-2-oxo-1-piperazinylmethyl]-1-(4-pyridyl)isonipecotyl]amino]butyrate According to a similar method described in Working Example 123, colorless crystals of the title compound were obtained from ethyl 4-aminobutyrate hydrochloride instead of glycine methylester hydrochloride.

$^1$H-NMR (CDCl$_3$) δ: 1.24 (3H, t, J=7.2 Hz), 1.55–1.90 (4H, m), 1.92–2.10 (2H, m), 2.38 (2H, t, J=6.7 Hz), 2.98–3.14 (2H, m), 3.20–3.48 (6H, m), 3.55 (2H, s), 3.50–3.66 (2H, m), 3.77 (2H, s), 4.10 (2H, q, J=7.2 Hz), 6.60 (2H, d, J=6.6 Hz), 6.70 (1H, t, J=4.9 Hz), 7.61 (1H, dd, J=8.8, 2.0 Hz), 7.79 (1H, dd, J=8.6, 1.8 Hz), 7.91–7.99 (3H, m), 8.24 (2H, d, J=6.6 Hz), 8.35 (1H, d, J=1.4 Hz).

Working Example 126

2-[N-[4-[4-(6-chloro-2-naphthanlenesulfonyl)-2-oxo-1-piperazinylmethyl]-1-(4-pyridyl)isonipecotyl]amino]acetic acid To a solution of ethyl 2-[N-[4-[4-(6-chloro-2-naphthanlenesulfonyl)-2-oxo-1-piperazinylmethyl]-1-(4-pyridyl)isonipecotyl]amino]acetate hydrochloride (199 mg) in ethanol (5 ml) was added 1N sodium hydroxide (0.6 ml), and the mixture was stirred at room temperature for 2 hours. To the reaction solution was added 1N hydrochloric acid, and the neutralized solution was concentrated. The residue was purified with CHP20 column chromatography (water:acetonitrile=70:30) to give amorphous of the title compound (156 mg).

$^1$H-NMR (DMSO-$d_6$) δ: 1.20–1.40 (2H, m), 1.77–1.95 (2H, m), 2.75–2.93 (2H, m), 3.20–3.45 (6H, m), 3.45–3.75 (4H, m), 6.72 (2H, d, J=6.2 Hz), 7.75 (1H, dd, J=8.8, 2.2 Hz), 7.88 (1H, dd, J=8.8, 1.8 Hz), 8.04–8.15 (3H, m), 8.20 (1H, d, J=8.8 Hz), 8.26–8.35 (2H, m), 8.59 (1H, s).

Working Example 127

3-[N-[4-[4-(6-chloro-2-naphthanlenesulfonyl)-2-oxo-1-piperazinylmethyl]-1-(4-pyridyl)isonipecotyl]amino]propionic Acid According to a similar method described in Working Example 126, amorphous of the title compound was obtained from ethyl 3-[N-[4-[4-(6-chloro-2-naphthanlenesulfonyl)-2-oxo-1-piperazinylmethyl]-1-(4-pyridyl)isonipecotyl]amino]propionate.

$^1$H-NMR (DMSO-$d_6$) δ: 1.20–1.42 (2H, m), 1.80–2.00 (2H, m), 2.39 (2H, t, J=6.7 Hz), 2.65–2.85 (2H, m), 3.15–3.40 (8H, m), 3.50–3.70 (4H, m), 6.73 (2H, d, J=6.5 Hz), 7.75 (1H, dd, J=8.8, 2.2 Hz), 7.84–7.96 (2H, m), 8.10 (2H, d, J=6.5 Hz), 8.20 (1H, d, J=8.8 Hz), 8.25–8.34 (2H, m), 8.59 (1H, s).

Working Example 128

4-[N-[4-[4-(6-chloro-2-naphthanlenesulfonyl)-2-oxo-1-piperazinylmethyl]-1-(4-pyridyl)isonipecotyl]amino]butyric acid According to a similar method described in Working Example 126, amorphous of the title compound was obtained from ethyl 4-[N-[4-[4-(6-chloro-2-naphthanlenesulfonyl)-2-oxo-1-piperazinylmethyl]-1-(4-pyridyl)isonipecotyl]amino]butyrate.

$^1$H-NMR (DMSO-d$_6$) δ: 1.20–1.46 (2H, m), 1.50–1.75 (2H, m), 1.80–2.05 (2H, m), 2.20 (2H, t, J=7.1 Hz), 2.70–2.90 (2H, m), 2.95–3.80 (12H, m), 6.79 (2H, d, J=6.0 Hz), 7.76 (1H, dd, J=8.9, 1.9 Hz), 7.82–7.94 (2H, m), 8.12 (2H, br), 8.21 (1H, d, J=8.6 Hz), 8.25–8.37 (2H, m), 8.60 (1H, s).

Working Example 129

1-[4-benzyloxycarbonylamino-1-(4-pyridyl)-4-piperidylmethyl]-4-(6-chloronaphthanlene-2-sulfonyl)-2-piperazinone According to a similar method described in Working Example 119, amorphous of the title compound was obtained from 1-[4-benzyloxycarbonylamino-1-(tert-butoxycarbonyl)-4-piperidylmethyl]-4-(6-chloronaphthanlene-2-sulfonyl)-2-piperazinone.

$^1$H-NMR (CDCl$_3$) δ: 1.55–1.80 (2H, m), 1.80–2.05 (2H, m), 2.85–3.05 (2H, m), 3.15–3.33 (4H, m), 3.45–3.62 (2H, m), 3.66 (2H, s), 3.77 (2H, s), 4.60 (1H, s), 5.04 (2H, s), 6.60 (2H, d, J=6.3 Hz), 7.30–7.45 (5H, m), 7.61 (1H, dd, J=8.9, 1.9 Hz), 7.76 (1H, dd, J=8.7, 1.7 Hz), 7.88–7.98 (3H, m), 8.25 (2H, d, J=6.3 Hz), 8.34 (1H, s).

Working Example 130

Methyl 2-(4-amidinophenyl)-2-[4-(6-chloronaphthanlene-2-sulfonyl)-2-oxo-1-piperazinyl]acetate Hydrochloride According to a similar method described in Working Example 4, colorless crystals of the title compound were obtained from methyl 2-[4-(6-chloronaphthanlene-2-sulfonyl)-2-oxo-1-piperazinyl]-2-(4-cyanophenyl)acetate.

$^1$H-NMR (DMSO-d$_6$) δ: 2.80–3.80 (10H, m), 7.45–8.05 (6H, m), 8.05–8.30 (3H, m), 8.40 (1H, s), 9.19 (2H, brs), 9.44 (2H, brs).

Working Example 131

4-(6-chloronaphthanlene-2-sulfonyl)-1-[4-(1H-imidazol-1-yl)benzyl]-2,6-piperazinedione To a solution of 4-(6-chloronaphthanlene-2-sulfonyl)-2,6-piperazinedione (136 mg), 4-(1H-imidazol-1-yl)benzylalcohol (70 mg) and triphenylphosphine (157 mg) in THF (10 ml) was added dropwise at 0° C. a solution of diethyl azodicarboxylate (104 mg) in THF (2 ml), and the mixture was stirred at 0° C. for 2 hours. The reaction solution was concentrated under reduced pressure, and precipitated crystals were washed with water and ether to give colorless crystals of the title compound (175 mg).

1H-NMR (CDCl$_3$) δ: 4.19 (414, s), 4.58 (214, s), 7.16–7.25 (4H, m), 7.33 (214, d, J=8.4 Hz), 7.62 (1H, dd, J=9.2, 2.2 Hz), 7.73–7.82 (214, m), 7.87–7.99 (3H, m), 8.34 (1H, s).

1-(4-amidinobenzyl)-4-(6-chloronaphthanlene-2-sulfonyl).1,4-diazepan-2-one hydrochloride According to a similar method described in Working Example 4, colorless crystals of the title compound were obtained from 4-(6-chloronaphthanlene-2-sulfonyl)-1-(4-cyanobenzyl)-1,4-diazepan-2-one.

$^1$H-NMR (DMSO-d$_6$) δ: 1.64 (2H, br), 3.35–3.50 (4H, m), 4.16 (2H, s), 4.54 (2H, s), 7.38 (2H, d, J=8.2 Hz), 7.68–7.78 (3H, m), 7.86 (1H, dd, J=8.8, 1.8 Hz), 8.17 (1H, d, J=8.8 Hz), 8.22–8.31 (2H, m), 8.57 (1H, brs), 9.04 (2H, brs), 9.32 (2H, brs).

Working Example 133

4-(6-chloronaphthanlene-2-sulfonyl)-1-[4-(1H-imidazol-1-yl)benzyl]-1,4-diazepan-2-one According to a similar method described in Working Example 17, colorless crystals of the title compound were obtained from N-(6-chloronaphthanlene-2-sulfonyl)propylenediamine hydrochloride and 4-(1H-imidazol-1-yl)benzaldehyde.

$^1$H-NMR (CDCl$_3$) δ: 1.65–1.80 (2H, m), 3.31–3.40 (2H, m), 3.57 (2H, t, J=6.0 Hz), 4.19 (2H, s), 4.46 (2H, s), 7.17–7.25 (6H, m), 7.59 (1H, dd, J=8.8, 2.2 Hz), 7.79–7.90 (5H, m), 8.43 (1H, s).

Working Example 134

1-(6-chloronaphthanlene-2-sulfonyl)-4-[1-(4-pyridyl)-4-piperidylmethyl]-1,4-diazepan-5-one Hydrochloride According to a similar method described in Working Example 119, 1-(6-chloronaphthanlene-2-sulfonyl)-4-[1-(4-pyridyl)-4-piperidylmethyl]-1,4-diazepan-5-one was obtained from 4-[1-(tert-butoxycarbonyl)-4-piperidylmethyl]-1-(6-chloronaphthanlene-2-sulfonyl)-1,4-diazepan-5-one. A part of the product was treated with hydrochloric acid to give amorphous of the title compound as hydrochloride.

$^1$H-NMR (DMSO-d$_6$) δ: 0.95–1.23 (2H, m), 1.55–1.75 (2H, m), 1.80–2.05 (1H, m), 2.63–2.76 (2H, m), 2.97–3.20 (4H, m), 3.20–3.35 (4H, m), 3.50–3.65 (2H, m), 4.05–4.25 (2H, m), 7.16 (2H, d, J=7.6 Hz), 7.73 (1H, dd, J=8.9, 1.9 Hz), 7.83 (1H, dd, J=8.7, 1.9 Hz), 8.13–8.32 (5H, m), 8.52 (1H, d, J=1.4 Hz).

Working Example 135

4-(1-acetimidoyl-4-piperidylmethyl)-1-(6-chloronaphthanlene-2-sulfonyl)-1,4-diazepin-5-one Hydrochloride According to a similar method described in Working Example 10, amorphous of the title compound was obtained from 1-(6-chloronaphthanlene-2-sulfonyl)-4-(4-piperidylmethyl)-1,4-diazepin-5-one hydrochloride.

$^1$H-NMR (DMSO-d$_6$) δ: 0.95–1.30 (2H, m), 1.53–1.73 (2H, m), 1.73–1.95 (1H, m), 2.23 (3H, s), 2.63–2.74 (2H, m), 2.90–3.20 (4H, m), 3.20–3.33 (4H, m), 3.44–3.61 (2H, m), 3.70–4.10 (2H, m), 7.73 (1H, dd, J=8.9, 2.1 Hz), 7.83 (1H, dd, J=8.7, 1.9 Hz), 8.17 (1H, d, J=8.8 Hz), 8.23–8.30 (2H, m), 8.51 (1H, d, J=1.4 Hz), 8.59 (1H, brs), 9.17 (1H, brs).

Formulation Example 1

For example, FXa inhibitor (e.g., a pharmaceutical composition for treating deep vein thrombosis, cerebral infarction due to atrial fibrillation or auricular fibrillation, etc.) of the present invention, which comprises a compound of the formula (I) or a salt thereof as an active ingredient, can be produced according to the following formulations:

1. Capsule

| | |
|---|---|
| (1) Compound obtained in Working Example 16 | 40 mg |
| (2) lactose | 70 mg |

-continued

| | |
|---|---|
| (3) fine crystalline cellulose | 9 mg |
| (4) magnesium stearate | 1 mg |
| 1 capsule | 120 mg |

(1), (2), (3) and ½ of (4) are mixed and then granulated. To the granules is added the remainder of (4), and the whole is filled into a gelatin capsule.

2. Tablet

| | |
|---|---|
| (1) Compound obtained in Working Example 16 | 40 mg |
| (2) lactose | 58 mg |
| (3) corn starch | 18 mg |
| (3) fine crystalline cellulose | 3.5 mg |
| (5) magnesium stearate | 0.5 mg |
| 1 tablet | 120 mg |

(1), (2), (3), ¾ of (4) and ½ of (5) are mixed and then granulated. To the granules are added the remainders of (4) and (5), followed by subjecting the mixture to compression molding.

Formulation Example 2

Compound obtained in Working Example 16 (50 mg) is dissolved in distilled water for injection (Japanese Pharmacopoeia) 50 ml, and to the solution is added the distilled water to make the whole volume 100 ml. The solution is filtered under sterile conditions. Each 1 ml of the solution is filled into a vial for injection under sterile conditions, subjected to freeze-drying and kept airtight.

Experimental Example 1

(1) Inhibitory Effect on Human Activated Coagulation Factor X (FXa)
Method:

In 0.05M Tris-HCl buffer solution (pH 8.3) 225 µl containing 0.145 M sodium chloride and 2 mM calcium chloride, test compound dissolved in dimethylsulfoxide 5 µl and human FXa (0.3 unit/ml) 10 µl were reacted at 37° C. for 10 minutes. To the reaction solution was added substrate (3 mM, S-2765) 10 µl and the mixture was further reacted at 37° C. for 10 minutes. To the reaction solution was added 50% acetic acid aqueous solution 25 µl to stop the reaction.

$IC_{50}$ values (concentration of the test compound which inhibits 50% of FXa activity) were calculated by measuring change of absorbance at 405 nm with microplate reader.

(2) Measurement of in vitro Blood Coagulation Time
(2-1) Measurement of Prothrombin Time (PT):

Using PT-Test Wako (Wako Pure Chemical), coagulation time was measured with automatic measuring apparatus of coagulation time (STA compact, DIAGNOSTICA STAGO). To human normal plasma (fresh human plasma: FFP; Sekisui Kagaku Kogyou) 97 µl was added test compound dissolved in dimethylsulfoxide (DMSO) 3 µl, and the mixture was heated at 37 C. for 4 minutes. To the above plasma 50 µl was added thromboplastin derived from rabbit brain 100 µl, and coagulation time was measured.

Concentration required to double coagulation time was calculated based on coagulation time when DMSO was added instead of test compound.

(2-2) Measurement of Activated Partial Thromboplastin Time (APTT):

Using a clinical assay kit, STA-APTT-LT (DIAGNOSTICA STAGO), coagulation time was measured with automatic measuring apparatus of coagulation time (STA compact, DIAGNOSTICA STAGO). To human normal plasma (fresh human plasma: FFP; Sekisui Kagaku Kogyou) 97 µl was added test compound dissolved in dimethylsulfoxide (DMSO) 3 µl and further added activated partial thromboplastin 50 µl per plasma 50 µl, and the mixture was heated at 37° C. for 4 minutes. To the mixture was added 20 mmol/l $CaCl_2$ solution 50 µl, and coagulation time was measured.

Concentration required to double coagulation time was calculated based on coagulation time when DMSO was added instead of test compound.

(2-3) Measurement of Thrombin Time (TT):

Coagulation time was measured with automatic measuring apparatus of coagulation time (Biomatic B10, Sarstedt). Thrombin derived from human plasma (Sigma) was dissolved in distilled water to give a 2.3 NIH units/ml solution. To human normal plasma (fresh human plasma: FFP; Sekisui Kagaku Kogyou) 97 µl was added test compound dissolved in dimethyl-sulfoxide (DMSO) 3 µl, and the mixture was heated at 37° C. for 3 minutes. To the above plasma 100 µl was added thrombin solution 200 µl, and coagulation time was measured.

Concentration required to double coagulation time was calculated based on coagulation time when DMSO was added instead of test compound.

(3) Measurement Ex Vivo Blood Coagulation Time (Mouse)
(3-1) Intravenous Administration:

Male ICR mice (25–35 g, Slc) were employed. Test compounds 5 ml/kg were administered once to these animals through tail vein, under anesthesia with sodium pentobarbital (50 mg/kg, i.p.). Five minutes after administration, blood 0.8 ml was collected from abdominal aorta using 3.8% trisodium citrate (whole blood:trisodium citrate solution= 9:1 by volume). The trisodium citrate supplemented blood was centrifuged at 3000 rpm for 15 minutes to obtain plasma. To the plasma 50 µl was added thromboplastin derived from rabbit brain 100 µl, and coagulation time was measured with automatic measuring apparatus of coagulation time (STA compact, DIAGNOSTICA STAGO), using PT-Test Wako (Wako Pure Chemical).

Test compounds were dissolved in physiological saline, and as control, physiological saline was administered instead of test compounds. Activity of each test compound was shown in ratio (%) determined by comparing coagulation time of test compound group with that of control group.

(3-2) Oral Administration:

Male ICR mice (25–35 g, Slc) fasting for more than 12 hours were employed.

Test compounds 5 ml/kg were orally administered to these animals. One hour after administration, blood was collected from abdominal aorta under anesthesia with sodium pentobarbital (50 mg/kg, i.p.).

Test compounds were suspended in 0.5% methylcellulose, and as control, 0.5% methylcellulose was administered instead of test compounds. The other conditions are the same as the above described experiment (Intravenous Administration).

(4) In Vivo Antithrombotic Activity Measurement
(4-1) Arteriovenous Shunt Method (Rat):

Method of Umetsu et al. (Thromb. Haemostas., 39: 74–83, 1978) was carried out. Usingmale SD rats, under anesthesia with sodium pentobarbital (50 mg/kg, i.p.), extracorporeal circulation system made of polyethylene tube to which silk thread was inserted was prepared between the right carotid artery and the left jugular vein. In order to prevent the blood from coagulating, a physiological saline containing heparin (50 U/ml) was filled in the tube. The blood was circulated for 15 minutes, and wet weight of thrombus attached to the silk thread was measured. Test compounds were orally or intravenously administered to these animals. When administered orally, Test compounds were suspended in 0.5% methyl-cellulose and Test compounds 5 ml/kg were orally administered to fasting animals 2 hours before starting the experiment, and as control, 0.5% methylcellulose was administered instead of test compounds. When administered intravenously, Test compounds 1 ml/kg volume were administered through tail vein 5 minutes before starting circulation. Test compounds were dissolved in physiological saline, and as control, physiological saline was administered instead of test compounds. Antithrombotic activity (%) of each test compound was determined by comparing wet weight of thrombus of test compound group with that of control group.

(4-2) Rat Abdominal Cava Partial Ligation Model

Male Sprague-Dawley rats (250–400 g, Nippon Clea) were employed. Abdominal thrombus model was carried out with modifying method of Finkle et al. (Thromb. Haemostas., 79, 431–438, 1998). Under anesthesia with sodium pentobarbital (50 mg/kg, i.p.), abdominal cava of the rat was carefully detached. Thereafter, all of the bifurcatios between bifurcation of the renal vein of abdominal cava and 1 cm downstream therefrom was ligated with threads. Balloon catheter (Fogarty 2F, Baxter) was inserted from left femoral vein, and the portion between two threads was injured thrice with balloon containing 200–300 ml of air. Balloon catheter was removed, and thread on bifurcation of the renal vein were tied together with 26G needle and the needle was removed to prepare partial ligation. Another thread was tied 30 minutes later, and thrombus formed between these two threads was carefully extracted. Wet weight of thrombus was measured with analytical balance having windshield (BP110S, Satorius). In addition, from abdominal cava blood 2 ml was collected with using 1/10 volume of 3.8% sodium citrate (Citral, Yamanouchi Pharmaceutical Co., Ltd.) and centrifuged at 3000 rpm for 10 minutes to give poor platelet plasma (PPP). Test compounds were orally or intravenously administered to these animals. When administered orally, Test compounds were suspended in 0.5% methyl-cellulose and Test compounds 5 ml/kg were orally administered to fasting animals 2 hours before starting the experiment, and as control, 0.5% methylcellulose was administered instead of test compounds. When administered intravenously, Test compounds 1 ml/kg volume were administered through tail vein 5 minutes before starting partial ligation. Test compounds were dissolved in physiological saline, and as control, physiological saline was administered instead of test compounds. Activity (%, inhibition rate of thrombus formation) of each test compound was determined by comparing wet weight of thrombus of test compound group with that of control group.

(4-3) Rat Deep Vein Thrombosis (DVT) Model

Male SD rats (body weight: 250–350 g) were employed. Under anesthesia with sodium pentobarbital (50 mg/kg, i.p.), polyethylene tube was inserted to left femoral vein. To the polyethylene tube, silk thread (length: 5 cm) connected with guide wire was previously inserted. In order to prevent the blood from coagulating, a physiological saline containing heparin (50 U/ml) was filled in the tube. The polyethylene tube was inserted until it reached abdominal cava and silk thread was installed in abdominal cava with using guide wire. Thirty minutes after installing silk thread, heparin (200 U/kg) was intravenously administered through tail vein. After the rat was bled by cutting brachial artery, abdominal part was opened. The silk thread was taken out and wet weight of thrombus attached to silk thread (including weight of silk thread) was measured. Test compounds were intravenously administered to these animals with 1 ml/kg volume through tail vein 5 minutes before installing silk thread. Test compounds were dissolved in physiological saline, and as control, physiological saline was administered instead of test compounds. Wet weight of thrombus alone was calculated by the formula:

(wet weight of thrombus attached to silk thread)–(wet weight (11.6±0.2 mg) measured by soaking silk thread with vein blood collected with heparin)

Experimental Results $IC_{50}$ is shown in Table 1. As is clear therefrom, the compounds of the present invention shows superior FXa inhibitory activity.

TABLE 1

| Working Example No. | IC50 ($\mu$M) |
|---|---|
| 2 | 0.050 |

INDUSTRIAL APPLICABILITY

Compound (I) or a salt thereof of the present invention has superior FXa inhibitory activity, shows less side effect such as bleeding, and is useful as anti-coagulant which is absorbable when orally administered, and therefore, it is advantageously used for the prevention or treatment of various diseases based on thrombus and infarction.

What is claimed is:

1. A compound of the formula:

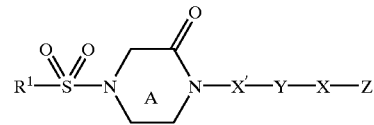

wherein $R^1$ is an unsubstituted or substituted heterocyclic group;

ring A may be further substituted;

X' is a chemical bond or an unsubstituted or substituted alkylene chain;

Y is an unsubstituted or substituted divalent cyclic group;

X is a chemical bond or an unsubstituted or substituted alkylene chain; and

Z is an unsubstituted or substituted nitrogen-containing heterocyclic group;

or a salt thereof.

2. A compound according to claim 1, wherein $R^1$ is a benzopyranyl group unsubstituted or substituted with a halogen atom.

3. A compound according to claim 1, wherein X' is an alkylene chain unsubstituted or substituted with 1- to 3 substituents selected from the group consisting of an unsubstituted or substituted lower alkyl group, an unsubstituted or substituted carbamoyl group, cyano group, hydroxy group and an unesterified or esterified carboxyl group.

4. A compound according to claim 1, wherein Y is an unsubstituted or substituted divalent cyclic hydrocarbon group.

5. A compound according to claim 1, wherein Y is an unsubstituted or substituted divalent heterocyclic group.

6. A compound according to claim 1, wherein Y is an unsubstituted or substituted phenylene.

7. A compound according to claim 1, wherein Y is an unsubstituted or substituted piperidine residue.

8. A pharmaceutical composition comprising the compound as claimed in claim 1 or a salt thereof; and an excipient, a binder, a disintegrating agent, a lubricant, a sweetener, a surfactant, a suspending agent or an emulsifier.

9. A composition of claim 8, which is an anti-coagulant.

10. A composition of claim 8, which is an inhibitor of activated coagulation factor X.

11. A composition of claim 8, which is for the treatment of myocardial infarction, cerebral thrombosis or deep vein thrombosis.

12. A method of using the compound as claimed in claim 1 or a salt thereof for manufacturing an anti-coagulant.

13. A method of using the compound as claimed in claim 1 or a salt thereof for manufacturing an inhibitor of activated coagulation factor X.

14. A method of using the compound as claimed in claim 1 or a salt thereof for manufacturing a pharmaceutical composition for the treatment of myocardial infarction, cerebral thrombosis or deep vein thrombosis.

15. A method for inhibiting coagulation in a mammal which comprises administering to said mammal an effective amount of the compound as claimed in claim 1 or a salt thereof.

16. A method for inhibiting activated coagulation factor X in a mammal which comprises administering to said mammal an effective amount of the compound as claimed in claim 1 or a salt thereof.

17. A method for treating cardiac infarction, cerebral thrombosis or deep vein thrombosis in a mammal which comprises administering to said mammal an effective amount of the compound as claimed in claim 1 or a salt thereof.

18. A method for producing the compound as claimed in claim 1 or a salt thereof by reacting a compound of the formula: $R^1SO_2Q$ wherein Q is a halogen atom, and $R^1$ is as defined in claim 1 or a salt thereof;
with a compound of the formula:

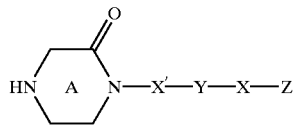

wherein A, X', Y, X and Z are as defined in claim 1 or a salt thereof;
producing the compound as claimed in claim 1 or a salt thereof by reacting a compound or a salt thereof represented by the formula:

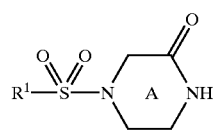

wherein $R^1$ and A are as defined in claim 1; with a compound or a salt thereof represented by the formula:

wherein $Q^1$ is a halogen atom or a group of the formula: $R^2$—$SO_2$—O—; wherein $R^2$ is a lower alkyl group unsubstituted or substituted with a halogen atom or an optionally unsubstituted or substituted phenyl group,
and X', Y, X and Z are as defined in claim 1;
producing a compound or a salt thereof as claimed in claim 1 represented by the formula:

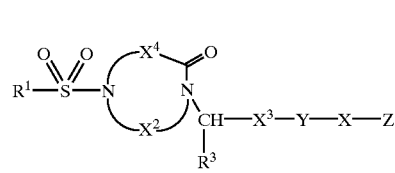

wherein $X^2$ is ethylene, $X^4$ is methylene, $X^3$ is a chemical bond or an unsubstituted or substituted alkylene chain, $R^3$ is a hydrogen atom or an unsubstituted or substituted hydrocarbon group, and $R^1$, Y, X and Z are as defined in claim 1;

by subjecting a compound or a salt thereof represented by the formula:

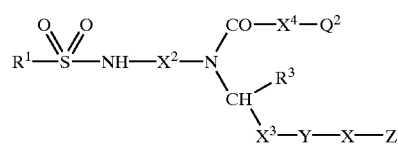

wherein $Q^2$ is a halogen atom or a group of the formula: $R^4$—$SO_2$—O—; wherein $R^4$ is a lower alkyl group unsubstituted or substituted with a halogen atom or an unsubstituted or substituted phenyl group, $X^2$, $X^3$, $X^4$ and $R^3$ are as defined above, and $R^1$, Y, X and Z are as defined in claim 1, to ring closure reaction;

producing a compound or a salt thereof as claimed in claim 1 represented by the formula:

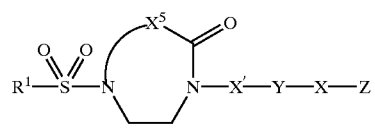

$X^5$ is methylene, and $R^1$, X', Y, X and Z are as defined in claim 1, by subjecting a compound or a salt thereof represented by the formula:

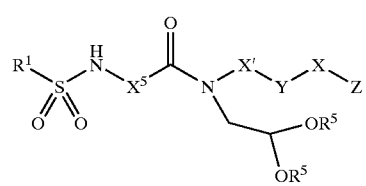

wherein $R^5$ is a lower alkyl group, $X^5$ is as defined above, and $R^1$, X', Y, X and Z are as defined in claim 1 to ring closure reaction, and if desired, subjecting the obtained product to reduction; or producing the compound as claimed in claim 1 or a salt thereof by reacting a compound or a salt thereof represented by the formula:

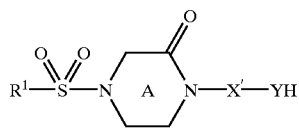

wherein $R^1$, A, X' and Y are as defined in claim 1,
with a compound or a salt thereof represented by the formula:

$$Z\text{—}X\text{—}Q^3$$

$Q^3$ is a halogen atom or a group of the formula: $R^6$—$SO_2$—O—; wherein $R^6$ is a lower alkyl group unsubstituted or substituted with a halogen atom or an unsubstituted or substituted phenyl group, and X and Z are as defined in claim 1.

19. A compound selected from the group consisting of 4-(7-chloro-2H-benzopyran-3-sulfonyl)-1-[4-hydroxy-1-(4-pyridyl)piperidin-4-ylmethyl]-2-piperazinone 4-(7-chloro-2H-benzopyran-3-sulfonyl)-1-[1-(4-pyridyl)piperidin-4-ylmethyl]-2-piperazinone and pharmaceutically acceptable salts thereof.

20. A pharmaceutical composition comprising
a compound of claim 19 or a salt thereof;
and an excipient, a binder, a disintegrating agent, a lubricant, a sweetener, a surfactant, a suspending agent or an emulsifier.

21. A method of using a compound of claim 19 or a salt thereof for manufacturing an anti-coagulant.

22. A method of using a compound of claim 19 or a salt thereof for manufacturing an inhibitor of activated coagulation factor X.

23. A method of using a compound of claim 19 or a salt thereof for manufacturing a pharmaceutical composition for the treatment of myocardial infarction, cerebral thrombosis or deep vein thrombosis.

24. A method for inhibiting coagulation in a mammal which comprises administering to said mammal an effective amount of a compound of claim 19 or a salt thereof.

25. A method for inhibiting activated coagulation factor X in a mammal which comprises administering to said mammal an effective amount of a compound of claim 19 or a salt thereof.

26. A method for treating myocardial infarction, cerebral thrombosis or deep vein thrombosis in a mammal comprising administering to said mammal an effective amount of a compound as claimed in claim 19 or a salt thereof.

* * * * *